(12) United States Patent
Schiffer-Mannioui et al.

(10) Patent No.: US 11,690,873 B2
(45) Date of Patent: Jul. 4, 2023

(54) UNIVERSAL CHIMERIC ANTIGEN RECEPTOR T CELLS SPECIFIC FOR CD22

(71) Applicant: CELLECTIS SA, Paris (FR)

(72) Inventors: Cecile Schiffer-Mannioui, Villiers sur Marne (FR); Philippe Duchateau, Draveil (FR); Anne-Sophie Gautron, Etréchy (FR)

(73) Assignee: CELLECTIS SA, Paris (FR)

( * ) Notice: Subject to any disclaimer, the term of this patent is extended or adjusted under 35 U.S.C. 154(b) by 583 days.

(21) Appl. No.: 16/498,276

(22) PCT Filed: Mar. 30, 2018

(86) PCT No.: PCT/EP2018/058368
§ 371 (c)(1),
(2) Date: Sep. 26, 2019

(87) PCT Pub. No.: WO2018/178378
PCT Pub. Date: Oct. 4, 2018

(65) Prior Publication Data
US 2021/0100839 A1 Apr. 8, 2021

(30) Foreign Application Priority Data

Mar. 31, 2017 (DK) .............................. PA201770239
Mar. 31, 2017 (DK) .............................. PA201770240
Jun. 30, 2017 (DK) .............................. PA201770542
Oct. 19, 2017 (WO) ................. PCT/EP2017/076800

(51) Int. Cl.
| | | |
|---|---|---|
| C07K 14/705 | (2006.01) | |
| C07K 19/00 | (2006.01) | |
| A61P 35/00 | (2006.01) | |
| A61K 39/395 | (2006.01) | |
| A61K 35/17 | (2015.01) | |
| C07K 14/725 | (2006.01) | |
| C07K 16/28 | (2006.01) | |
| A61P 35/02 | (2006.01) | |
| A61K 31/365 | (2006.01) | |

(52) U.S. Cl.
CPC ............ *A61K 35/17* (2013.01); *A61K 31/365* (2013.01); *A61K 39/39558* (2013.01); *A61P 35/02* (2018.01); *C07K 14/7051* (2013.01); *C07K 14/70517* (2013.01); *C07K 14/70578* (2013.01); *C07K 16/2803* (2013.01); *C07K 2317/34* (2013.01); *C07K 2317/53* (2013.01); *C07K 2317/622* (2013.01)

(58) Field of Classification Search
CPC ................ C07K 16/2803; C07K 19/00; C07K 2317/622
See application file for complete search history.

(56) References Cited

U.S. PATENT DOCUMENTS

| | | |
|---|---|---|
| 4,683,195 A | 7/1987 | Mullis et al. |
| 5,037,743 A | 8/1991 | Welch et al. |
| 5,143,830 A | 9/1992 | Holland et al. |
| 5,858,358 A | 1/1999 | June et al. |
| 5,883,223 A | 3/1999 | Gray |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 8,846,387 B2 | 9/2014 | Russell et al. |
| 2006/0121005 A1 | 6/2006 | Berenson et al. |

FOREIGN PATENT DOCUMENTS

| | | |
|---|---|---|
| EP | 2737904 A2 | 6/2014 |
| WO | WO 1997/034598 A1 | 9/1997 |
| WO | WO 2001/040214 A1 | 6/2001 |
| WO | WO 2008/102199 A1 | 8/2008 |
| WO | WO 2012/138927 A2 | 10/2012 |
| WO | WO 2013/123061 A1 | 8/2013 |
| WO | WO 2013/126720 A2 | 8/2013 |
| WO | WO 2013/153391 A1 | 10/2013 |
| WO | WO 2013/176915 A1 | 11/2013 |
| WO | WO 2014/065961 A1 | 5/2014 |
| WO | WO 2014/191128 A1 | 12/2014 |
| WO | WO 2015/075195 A1 | 5/2015 |
| WO | WO 2015/121454 A1 | 8/2015 |
| WO | WO 2015/136001 A1 | 9/2015 |
| WO | WO 2016/120216 A1 | 8/2016 |
| WO | WO 2016/149578 A1 | 9/2016 |
| WO | WO 2016/201047 A1 | 12/2016 |
| WO | WO 2018/007263 A1 | 1/2018 |

(Continued)

OTHER PUBLICATIONS

Brudno et al (2018 Nature Reviews Clinical Oncology. 15:31-46).*
Jayaraman et al, 2020. EBioMedicine. 58: 102931; pp. 1-12 as printed.*
Tokuriki et al, 2009, Current Opinion in Structural Biology. 19: 596-604.*

(Continued)

*Primary Examiner* — Zachary C Howard
(74) *Attorney, Agent, or Firm* — Casimir Jones, S.C.; Peter J. Schlueter

(57) ABSTRACT

The present invention relates to new CD22 Chimeric Antigen Receptors (CD22 CAR), an engineered immune cell endowed with said new CD22 CAR and comprising at least inactivated TRAC gene for use in therapy. The engineered immune cells endowed with such CARs are particularly suited for treating relapsed refractory CD22 expressing cancers.

20 Claims, 13 Drawing Sheets

Specification includes a Sequence Listing.

(56) References Cited

FOREIGN PATENT DOCUMENTS

| WO | WO 2018/073391 A1 | 4/2018 |
|----|-------------------|--------|
| WO | WO 2018/073394 A1 | 4/2018 |

OTHER PUBLICATIONS

Bhattacharya et al, 2017. Plos One. 12(3): e0171355, pp. 1-22 as printed.*

International Search Report and Written Opinion for PCT/EP2018/058368, dated Jul. 25, 2018. 12 pages.

Abelson et al., Methods in Enzymology. Academic Press, Inc. vol. 154. 1987. TOC only. 8 pages.

Abelson et al., Methods in Enzymology. Academic Press, Inc. vol. 155. 1987. TOC only. 8 pages.

Abelson et al., Methods in Enzymology. Academic Press, Inc. vol. 185. 1990. TOC only. 10 pages.

Andris-Widhopf et al., Generation of human scFv antibody libraries: PCR amplification and assembly of light- and heavy-chain coding sequences. Cold Spring Harb Protoc. Sep. 1, 2011;2011(9):pdb.prot065573. 13 pages.

Arimondo et al., Exploring the cellular activity of camptothecin-triple-helix-forming oligonucleotide conjugates. Mol Cell Biol. Jan. 2006;26(1):324-33.

Atkins et al., A case for "StopGo": reprogramming translation to augment codon meaning of GGN by promoting unconventional termination (Stop) after addition of glycine and then allowing continued translation (Go). RNA. Jun. 2007;13(6):803-10.

Ausubel. Current Protocols in Molecular Biology. 2000, Wiley and son Inc, Library of Congress, USA. TOC only. 19 Pages.

Bierer et al., Cyclosporin A and FK506: molecular mechanisms of immunosuppression and probes for transplantation biology. Curr Opin Immunol. Oct. 1993;5(5):763-73.

Boch et al., Breaking the code of DNA binding specificity of TAL-type III effectors. Science. Dec. 11, 2009;326(5959):1509-12.

Brentjens et al., CD19-targeted T cells rapidly induce molecular remissions in adults with chemotherapy-refractory acute lymphoblastic leukemia. Sci Transl Med. Mar. 20, 2013;5(177):177ra38. 19 pages.

Choulika et al., Induction of homologous recombination in mammalian chromosomes by using the I-Scel system of *Saccharomyces cerevisiae*. Mol Cell Biol. Apr. 1995;15(4):1968-73.

Christian et al., Targeting DNA double-strand breaks with TAL effector nucleases. Genetics. Oct. 2010;186(2):757-61.

Cong et al., Multiplex genome engineering using CRISPR/Cas systems. Science. Feb. 15, 2013;339(6121):819-23.

Cros et al., Problems related to resistance to cytarabine in acute myeloid leukemia. Leuk Lymphoma. Jun. 2004;45(6):1123-32.

Deltcheva et al., CRISPR RNA maturation by trans-encoded small RNA and host factor RNase III. Nature. Mar. 31, 2011;471(7340):602-7.

Donnelly et al., Nuclear localization and shuttling of herpes simplex virus tegument protein VP13/14. J Virol. Mar. 2001;75(6):2566-74.

Doronina et al., Site-specific release of nascent chains from ribosomes at a sense codon. Mol Cell Biol. Jul. 2008;28(13):4227-39.

Eisenschmidt et al., Developing a programmed restriction endonuclease for highly specific DNA cleavage. Nucleic Acids Res. Dec. 14, 2005;33(22):7039-47.

Eyquem et al., Targeting a CAR to the TRAC locus with CRISPR/Cas9 enhances tumour rejection. Nature. Mar. 2, 2017;543(7643):113-117.

Faderl et al., Augmented hyper-CVAD based on dose-intensified vincristine, dexamethasone, and asparaginase in adult acute lymphoblastic leukemia salvage therapy. Clin Lymphoma Myeloma Leuk. Feb. 2011;11(1):54-9.

Fielding et al., Outcome of 609 adults after relapse of acute lymphoblastic leukemia (ALL); an MRC UKALL12/ECOG 2993 study. Blood. Feb. 1, 2007;109(3):944-50.

Gardin et al. Postremission treatment of elderly patients with acute myeloid leukemia in first complete remission after intensive induction chemotherapy: results of the multicenter randomized Acute Leukemia French Association (ALFA) 9803 trial. Blood. Jun. 15, 2007;109(12):5129-35.

Garneau et al., The CRISPR/Cas bacterial immune system cleaves bacteriophage and plasmid DNA. Nature. Nov. 4, 2010;468(7320):67-71.

Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86.

Greenlee et al., Cancer statistics, 2000. CA Cancer J Clin. Jan.-Feb. 2000;50(1):7-33.

Grupp et al., Chimeric antigen receptor-modified T cells for acute lymphoid leukemia. N Engl J Med. Apr. 18, 2013;368(16):1509-1518.

Haso et al., Anti-CD22-chimeric antigen receptors targeting B-cell precursor acute lymphoblastic leukemia. Blood. Feb. 14, 2013;121(7):1165-74.

Henderson et al., Comparison of the effects of FK-506, cyclosporin A and rapamycin on IL-2 production. Immunology. Jul. 1991;73(3):316-21.

Ho et al., Isolation of anti-CD22 Fv with high affinity by Fv display on human cells. Proc Natl Acad Sci U S A. Jun. 20, 2006;103(25):9637-42.

Inaba et al., Acute lymphoblastic leukaemia. Lancet. Jun. 1, 2013;381(9881):1943-55.

James et al., Antigen sensitivity of CD22-specific chimeric TCR is modulated by target epitope distance from the cell membrane. J Immunol. May 15, 2008;180(10):7028-38.

Jena et al., Redirecting T-cell specificity by introducing a tumor-specific chimeric antigen receptor. Blood. Aug. 19, 2010;116(7):1035-44.

Jinek et al., A programmable dual-RNA-guided DNA endonuclease in adaptive bacterial immunity. Science. Aug. 17, 2012;337(6096):816-21.

Juillerat et al., An oxygen sensitive self-decision making engineered CAR T-cell. Sci Rep. Jan. 20, 2017;7:39833. 8 pages.

Kalish et al., Targeted genome modification via triple helix formation. Ann N Y Acad Sci. Nov. 2005;1058:151-61.

Kalos et al., T cells with chimeric antigen receptors have potent antitumor effects and can establish memory in patients with advanced leukemia. Sci Transl Med. Aug. 10, 2011;3(95):95ra73. 21 pages.

Kebriaei et al., Phase I trials using Sleeping Beauty to generate CD19-specific CAR T cells. J Clin Invest. Sep. 1, 2016;126(9):3363-76.

Kochenderfer et al., Chemotherapy-refractory diffuse large B-cell lymphoma and indolent B-cell malignancies can be effectively treated with autologous T cells expressing an anti-CD19 chimeric antigen receptor. J Clin Oncol. Feb. 20, 2015;33(6):540-9.

Kochenderfer et al., Eradication of B-lineage cells and regression of lymphoma in a patient treated with autologous T cells genetically engineered to recognize CD19. Blood. Nov. 18, 2010;116(20):4099-102.

Kuhn et al., Inducible gene targeting in mice. Science. Sep. 8, 1995;269(5229):1427-9.

Lee et al., T cells expressing CD19 chimeric antigen receptors for acute lymphoblastic leukaemia in children and young adults: a phase 1 dose-escalation trial. Lancet. Feb. 7, 2015;385(9967):517-528.

Li et al., TAL nucleases (TALNs): hybrid proteins composed of TAL effectors and FokI DNA-cleavage domain. Nucleic Acids Res. Jan. 2011;39(1):359-72.

Liu et al., Inhibition of T cell signaling by immunophilin-ligand complexes correlates with loss of calcineurin phosphatase activity. Biochemistry. Apr. 28, 1992;31(16):3896-901.

Long et al., Lessons learned from a highly-active CD22-specific chimeric antigen receptor. Oncoimmunology. Apr. 1, 2013;2(4):e23621. 3 pages.

Lonial et al., Treatment options for relapsed and refractory multiple myeloma. Clin Cancer Res. Mar. 15, 2011;17(6):1264-77.

(56) References Cited

OTHER PUBLICATIONS

Macleod et al., Integration of a CD19 CAR into the TCR Alpha Chain Locus Streamlines Production of Allogeneic Gene-Edited CAR T Cells. Mol Ther. Apr. 5, 2017;25(4):949-961.

Mai et al., Phase III trial of bortezomib, cyclophosphamide and dexamethasone (VCD) versus bortezomib, doxorubicin and dexamethasone (PAd) in newly diagnosed myeloma. Leukemia. Aug. 2015;29(8):1721-9.

Mali et al., RNA-guided human genome engineering via Cas9. Science. Feb. 15, 2013;339(6121):823-6.

Maude et al., CD19-targeted chimeric antigen receptor T-cell therapy for acute lymphoblastic leukemia. Blood. Jun. 25, 2015;125(26):4017-23.

Miller et al., Gene Transfer Vectors For Mammalian Cells,. H. Miller and M. P. Calos eds., 1987, Cold Spring Harbor Laboratory. TOC only. 5 pages.

Moscou et al., A simple cipher governs DNA recognition by TAL effectors. Science. Dec. 11, 2009;326(5959):1501.

Mullighan. Genome sequencing of lymphoid malignancies. Blood. Dec. 5, 2013;122(24):3899-907.

Mullighan. Genomic characterization of childhood acute lymphoblastic leukemia. Semin Hematol. Oct. 2013;50(4):314-24.

Oriol et al., Outcome after relapse of acute lymphoblastic leukemia in adult patients included in four consecutive risk-adapted trials by the Pethema Study Group. Haematologica. Apr. 2010:95(4):589-96.

Paques et al., Meganucleases and DNA double-strand break-induced recombination: perspectives for gene therapy. Curr Gene Ther. Feb. 2007;7(1):49-66.

Park et al., CD19-targeted CAR T-cell therapeutics for hematologic malignancies: interpreting clinical outcomes to date. Blood. Jun. 30, 2016;127(26):3312-20.

Park et al., Treating cancer with genetically engineered T cells. Trends Biotechnol. Nov. 2011;29(11):550-7.

Peipp et al., Efficient eukaryotic expression of fluorescent scFv fusion proteins directed against CD antigens for FACS applications. J Immunol Methods. Feb. 15, 2004;285(2):265-80.

Perbal, A Practical Guide To Molecular Cloning. 1984. TOC only. 11 pages.

Perrin et al., Asymmetrical recognition and activity of the I-Scel endonuclease on its site and on intron-exon junctions. EMBO J. Jul. 1993;12(7):2939-47.

Pingoud et al., Precision genome surgery. Nat Biotechnol. Jul. 2007;25(7):743-4.

Porter et al., Chimeric antigen receptor-modified T cells in chronic lymphoid leukemia. N Engl J Med. Aug. 25, 2011;365(8):725-33.

Porteus et al., Gene targeting using zinc finger nucleases. Nat Biotechnol. Aug. 2005;23(8):967-73.

Qin et al., Preclinical development of Bispecific Chimeric Antigen Receptor Targeting both CD19 and CD22. Blood, vol. 126 No. 23, Dec. 3, 2015. p. 4427. 5 pages.

Raulf-Heimsoth. T cell—primary culture from peripheral blood. Methods Mol Med. 2008;138:17-30.

Rouet et al., Introduction of double-strand breaks into the genome of mouse cells by expression of a rare-cutting endonuolease. Mol Cell Biol. Dec. 1994;14(12):8096-106.

Sambrook et al, Molecular Cloning: A Laboratory Manual, Third Edition. 2001, Cold Spring Harbor, New York: Cold Spring Harbor Laboratory Press. TOC only. 23 pages.

Sblattero et al., Exploiting recombination in single bacteria to make large phage antibody libraries. Nat Biotechnol. Jan. 2000;18(1):75-80.

Shah et al., Anti-CD22 CAR T-cell therapy induces reponses in relapsed, refractory ALL, ASH annual meeting and esposition Dec. 3-6, 2016. Dec. 6, 2016, xp002781456. 3 pages.

Shen et al., Engineering peptide linkers for scFv immunosensors. Anal Chem. Mar. 15, 2008;80(6):1910-7.

Sorek et al., CRISPR-mediated adaptive immune systems in bacteria and archaea. Annu Rev Biochem. 2013;82:237-66.

Stoddard. Homing endonuclease structure and function. Q Rev Biophys. Feb. 2005;38(1):49-95.

Tavernier et al., Outcome of treatment after first relapse in adults with acute lymphoblastic leukemia initially treated by the LALA-94 trial. Leukemia. Sep. 2007;21(9):1907-14.

Valton et al., A Multidrug-resistant Engineered CAR T Cell for Allogeneic Combination Immunotherapy. Mol Ther. Sep. 2015;23(9):1507-18.

Van De Donk et al., Monoclonal antibody-based therapy as a new treatment strategy in multiple myeloma. Leukemia. Feb. 2012;26(2):199-213.

Van Meir et al., Exciting new advances in neuro-oncology: the avenue to a cure for malignant glioma. CA Cancer J Clin. May-Jun. 2010;60(3):166-93.

Varterasian et al., Phase II trial of bryostatin 1 in patients with relapsed low-grade non-Hodgkin's lymphoma and chronic lymphocytic leukemia. Clin Cancer Res. Mar. 2000;6(3):825-8.

Wells et al., Pre-Clinical Activity of Allogeneic Anti-CD22 CAR-T cells for the treatment of B-cell acute lymphoblastic leukemia, Blood, American Society of Hematology, us. vol. 130 suppl. 1, Dec. 7, 2017, p. 808, 6 pages.

Wells et al., pre-clinical activity of allogeneic anti-cd22 car-t cells for the treatment of b-cell acute lymphoblastic leukemia. ASH 2017 Atlanta, Feb. 7, 2017, xp002781137, 17 pages.

Wender et al., The practical synthesis of a novel and highly potent analogue of bryostatin. J Am Chem Soc. Nov. 20, 2002;124(46):13648-9.

Xiao et al., Identification and characterization of fully human anti-CD22 monoclonal antibodies. MAbs. May-Jun. 2009;1(3):297-303.

* cited by examiner

SEQUENCE LISTING

```
<160> NUMBER OF SEQ ID NOS: 144

<210> SEQ ID NO 1
<211> LENGTH: 21
<212> TYPE: PRT
<213> ORGANISM: homo sapiens
<220> FEATURE:
<221> NAME/KEY: MISC_FEATURE
<223> OTHER INFORMATION: CD8alpha signal peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 20
<212> TYPE: PRT
<213> ORGANISM: homo sapiens
<220> FEATURE:
<221> NAME/KEY: misc_feature
<223> OTHER INFORMATION: signal peptide

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 16
<212> TYPE: PRT
<213> ORGANISM: homo sapiens
```

-continued

```
<220> FEATURE:
<221> NAME/KEY: misc_feature
<223> OTHER INFORMATION: FcgRIIIa hinge

<400> SEQUENCE: 3

Gly Leu Ala Val Ser Thr Ile Ser Ser Phe Phe Pro Pro Gly Tyr Gln
1               5                   10                  15

<210> SEQ ID NO 4
<211> LENGTH: 45
<212> TYPE: PRT
<213> ORGANISM: homo sapiens
<220> FEATURE:
<221> NAME/KEY: misc_feature
<223> OTHER INFORMATION: CD8alpha hinge

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
                35                  40                  45

<210> SEQ ID NO 5
<211> LENGTH: 231
<212> TYPE: PRT
<213> ORGANISM: homo sapiens
<220> FEATURE:
<221> NAME/KEY: misc_feature
<223> OTHER INFORMATION: IgG1 hinge

<400> SEQUENCE: 5

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
                35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Asp Glu Leu Thr Lys
                130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205
```

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 6
<211> LENGTH: 24
<212> TYPE: PRT
<213> ORGANISM: homo sapiens
<220> FEATURE:
<221> NAME/KEY: misc_feature
<223> OTHER INFORMATION: CD8alpha transmembrane domain

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: homo sapiens
<220> FEATURE:
<221> NAME/KEY: misc_feature
<223> OTHER INFORMATION: 41BB transmembrane domain

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 42
<212> TYPE: PRT
<213> ORGANISM: homo sapiens
<220> FEATURE:
<221> NAME/KEY: misc_feature
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 9
<211> LENGTH: 112
<212> TYPE: PRT
<213> ORGANISM: homo sapiens
<220> FEATURE:
<221> NAME/KEY: misc_feature
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys

```
                35                  40                  45
Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110

<210> SEQ ID NO 10
<211> LENGTH: 15
<212> TYPE: PRT
<213> ORGANISM: artificial sequence
<220> FEATURE:
<223> OTHER INFORMATION: G4Sx3 linker sequence

<400> SEQUENCE: 10

Gly Gly Gly Gly Ser Gly Gly Gly Gly Ser Gly Gly Gly Gly Ser
 1               5                  10                  15

<210> SEQ ID NO 11
<211> LENGTH: 117
<212> TYPE: PRT
<213> ORGANISM: artificial sequence
<220> FEATURE:
<223> OTHER INFORMATION: 972- heavy chain

<400> SEQUENCE: 11

Glu Val Gln Leu Val Gln Ser Gly Gly Gly Val Val Arg Pro Gly Gly
 1               5                  10                  15

Ser Leu Arg Leu Pro Cys Ala Ala Ser Gly Phe Thr Phe Asp Asp Tyr
             20                  25                  30

Gly Met Ser Trp Val Arg Gln Ala Pro Gly Lys Gly Leu Glu Trp Val
         35                  40                  45

Ser Gly Ile Asn Trp Asn Gly Gly Ser Thr Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Gly Gly Asp Asp Ala Phe Asp Ile Trp Gly Gln Gly Thr Met
            100                 105                 110

Val Thr Val Ser Ser
        115

<210> SEQ ID NO 12
<211> LENGTH: 108
<212> TYPE: PRT
<213> ORGANISM: artificial sequence
<220> FEATURE:
<223> OTHER INFORMATION: 972- light chain variable region

<400> SEQUENCE: 12

Arg Ile Val Met Thr Gln Ser Pro Gly Thr Leu Ser Val Ser Pro Gly
 1               5                  10                  15

Glu Thr Ala Thr Leu Ser Cys Arg Ala Ser Gln Ser Phe Ser Asn Met
             20                  25                  30

Leu Ala Trp Tyr Gln Gln Lys Ser Gly Gln Pro Pro Arg Leu Leu Ile
         35                  40                  45
```

Tyr Gly Val Ser Thr Arg Ala Ala Gly Val Pro Ala Arg Phe Ser Gly
          50                  55                  60

Ser Gly Ser Gly Thr Glu Phe Thr Leu Thr Ile Ser Asn Leu Gln Ser
65                  70                  75                  80

Glu Asp Phe Ala Val Tyr Tyr Cys Gln Gln Tyr Gly Asp Trp Pro Arg
                85                  90                  95

Tyr Thr Phe Gly Gln Gly Thr Lys Val Glu Arg Lys
            100                 105

<210> SEQ ID NO 13
<211> LENGTH: 124
<212> TYPE: PRT
<213> ORGANISM: artificial sequence
<220> FEATURE:
<223> OTHER INFORMATION: 971- heavy chain

<400> SEQUENCE: 13

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser
        115                 120

<210> SEQ ID NO 14
<211> LENGTH: 107
<212> TYPE: PRT
<213> ORGANISM: artificial sequence
<220> FEATURE:
<223> OTHER INFORMATION: 971- light chain

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys
            100                 105

<210> SEQ ID NO 15
<211> LENGTH: 461
<212> TYPE: PRT
<213> ORGANISM: artificial sequence
<220> FEATURE:
<223> OTHER INFORMATION: 972-v1 polypolypeptide CAR sequence

<400> SEQUENCE: 15

```
Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Ser Gly Trp Ser Glu Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Gly Ile
145                 150                 155                 160

Arg Asn Asn Leu Ala Trp Tyr Gln Gln Lys Pro Gly Lys Ala Pro Lys
                165                 170                 175

Arg Leu Ile Tyr Ala Ala Ser Asn Leu Gln Ser Gly Val Pro Ser Arg
            180                 185                 190

Phe Thr Gly Ser Gly Ser Gly Thr Glu Phe Thr Leu Ile Val Ser Ser
        195                 200                 205

Leu Gln Pro Glu Asp Phe Ala Thr Tyr Tyr Cys Leu Gln His His Ser
    210                 215                 220

Tyr Pro Leu Thr Ser Gly Gly Gly Thr Lys Val Glu Ile Lys Thr Thr
225                 230                 235                 240

Thr Pro Ala Pro Arg Pro Pro Thr Pro Ala Pro Thr Ile Ala Ser Gln
                245                 250                 255

Pro Leu Ser Leu Arg Pro Glu Ala Cys Arg Pro Ala Ala Gly Gly Ala
            260                 265                 270

Val His Thr Arg Gly Leu Asp Phe Ala Cys Asp Ile Tyr Ile Trp Ala
        275                 280                 285

Pro Leu Ala Gly Thr Cys Gly Val Leu Leu Leu Ser Leu Val Ile Thr
    290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
```

```
                 370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
                420                 425                 430

Lys Gly His Asp Gly Leu Tyr Gln Gly Leu Ser Thr Ala Thr Lys Asp
                435                 440                 445

Thr Tyr Asp Ala Leu His Met Gln Ala Leu Pro Pro Arg
            450                 455                 460

<210> SEQ ID NO 16
<211> LENGTH: 647
<212> TYPE: PRT
<213> ORGANISM: artificial sequence
<220> FEATURE:
<223> OTHER INFORMATION: 972-v3 polypolypeptide CAR sequence

<400> SEQUENCE: 16

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Asn Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Ser Gly Trp Ser Glu Tyr Trp Gly Gln Gly Thr Leu Val
                100                 105                 110

Thr Val Ser Ser Gly Gly Gly Gly Ser Gly Gly Gly Gly Ser Gly Gly
                115                 120                 125

Gly Gly Ser Asp Ile Gln Met Thr Gln Ser Pro Ser Ser Leu Ser Ala
                130                 135                 140

Ser Val Gly Asp Arg Val Thr Ile Thr Cys Arg Ala Ser Gln Gly Ile
145                 150                 155                 160

Arg Asn Asn Leu Ala Trp Tyr Gln Gln Lys Pro Gly Lys Ala Pro Lys
                165                 170                 175

Arg Leu Ile Tyr Ala Ala Ser Asn Leu Gln Ser Gly Val Pro Ser Arg
                180                 185                 190

Phe Thr Gly Ser Gly Ser Gly Thr Glu Phe Thr Leu Ile Val Ser Ser
                195                 200                 205

Leu Gln Pro Glu Asp Phe Ala Thr Tyr Tyr Cys Leu Gln His Gln Ser
                210                 215                 220

Tyr Pro Leu Thr Ser Gly Gly Gly Thr Lys Val Glu Ile Lys Glu Pro
225                 230                 235                 240

Lys Ser Pro Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

Leu Met Ile Ala Arg Thr Pro Glu Val Thr Cys Val Val Val Asp Val
```

```
            275                 280                 285
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys Ile Tyr Ile Trp Ala Pro Leu Ala Gly Thr Cys
465                 470                 475                 480

Gly Val Leu Leu Leu Ser Leu Val Ile Thr Leu Tyr Cys Lys Arg Gly
                485                 490                 495

Arg Lys Lys Leu Leu Tyr Ile Phe Lys Gln Pro Phe Met Arg Pro Val
            500                 505                 510

Gln Thr Thr Gln Glu Glu Asp Gly Cys Ser Cys Arg Phe Pro Glu Glu
        515                 520                 525

Glu Glu Gly Gly Cys Glu Leu Arg Val Lys Phe Ser Arg Ser Ala Asp
    530                 535                 540

Ala Pro Ala Tyr Gln Gln Gly Gln Asn Gln Leu Tyr Asn Glu Leu Asn
545                 550                 555                 560

Leu Gly Arg Arg Glu Glu Tyr Asp Val Leu Asp Lys Arg Arg Gly Arg
                565                 570                 575

Asp Pro Glu Met Gly Gly Lys Pro Arg Arg Lys Asn Pro Gln Glu Gly
            580                 585                 590

Leu Tyr Asn Glu Leu Gln Lys Asp Lys Met Ala Glu Ala Tyr Ser Glu
        595                 600                 605

Ile Gly Met Lys Gly Glu Arg Arg Gly Lys Gly His Asp Gly Leu
    610                 615                 620

Tyr Gln Gly Leu Ser Thr Ala Thr Lys Asp Thr Tyr Asp Ala Leu His
625                 630                 635                 640

Met Gln Ala Leu Pro Pro Arg
                645

<210> SEQ ID NO 17
<211> LENGTH: 464
<212> TYPE: PRT
<213> ORGANISM: artificial sequence
<220> FEATURE:
<223> OTHER INFORMATION: 971-v1 polypolypeptide CAR sequence
```

```
<400> SEQUENCE: 17

Gln Val Gln Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Ser Thr Ser Tyr Ala Met Asp Tyr Trp Gly Gln
            100                 105                 110

Gly Thr Thr Val Thr Val Gly Gly Gly Ser Gly Gly Gly Gly Ser
        115                 120                 125

Gly Gly Gly Gly Ser Asp Ile Glu Leu Thr Gln Ser Pro Ala Ser Leu
130                 135                 140

Ser Val Ala Thr Gly Glu Lys Val Thr Ile Arg Cys Met Thr Ser Thr
145                 150                 155                 160

Asp Ile Asp Asp Asp Met Asn Trp Tyr Gln Gln Lys Pro Gly Glu Pro
                165                 170                 175

Pro Lys Phe Leu Ile Ser Glu Gly Asn Thr Leu Arg Pro Gly Val Pro
            180                 185                 190

Ser Arg Phe Ser Ser Ser Gly Thr Gly Thr Asp Phe Val Phe Thr Ile
        195                 200                 205

Glu Asn Thr Leu Ser Glu Asp Val Gly Asp Tyr Tyr Cys Leu Gln Ser
210                 215                 220

Phe Asn Val Pro Leu Thr Phe Gly Asp Gly Thr Lys Leu Glu Lys Ala
225                 230                 235                 240

Leu Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Tyr
        275                 280                 285

Ile Trp Ala Pro Leu Ala Gly Thr Cys Gly Val Leu Leu Leu Ser Leu
290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415
```

```
Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
            435                 440                 445

Thr Lys Asp Thr Tyr Asp Ala Leu His Met Gln Ala Leu Pro Pro Arg
            450                 455                 460

<210> SEQ ID NO 18
<211> LENGTH: 650
<212> TYPE: PRT
<213> ORGANISM: artificial sequence
<220> FEATURE:
<223> OTHER INFORMATION: 971-v3 polypolypeptide CAR sequence

<400> SEQUENCE: 18

Gln Val Gln Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
            35                  40                  45

Ala Ser Ile Ser Thr Gly Gly Tyr Asn Thr Tyr Tyr Ser Asp Asn Val
        50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Ser Thr Ser Tyr Ala Met Asp Tyr Trp Gly Gln
            100                 105                 110

Gly Thr Thr Val Thr Val Gly Gly Gly Ser Gly Gly Gly Ser
            115                 120                 125

Gly Gly Gly Gly Ser Asp Ile Glu Leu Thr Gln Ser Pro Ala Ser Leu
        130                 135                 140

Ser Val Ala Thr Gly Glu Lys Val Thr Ile Arg Cys Met Thr Ser Thr
145                 150                 155                 160

Asp Ile Asp Asp Asp Met Asn Trp Tyr Gln Gln Lys Pro Gly Glu Pro
                165                 170                 175

Pro Lys Phe Leu Ile Ser Glu Gly Asn Thr Leu Arg Pro Gly Val Pro
            180                 185                 190

Ser Arg Phe Ser Ser Ser Gly Thr Gly Thr Asp Phe Val Phe Thr Ile
            195                 200                 205

Glu Asn Thr Leu Ser Glu Asp Val Gly Asp Tyr Tyr Cys Leu Gln Ser
        210                 215                 220

Phe Asn Val Pro Leu Thr Phe Gly Asp Gly Thr Lys Leu Glu Lys Ala
225                 230                 235                 240

Leu Glu Pro Lys Ser Pro Asp Lys Thr His Thr Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ala Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320
```

```
Tyr Asn Ser Thr Tyr Arg Val Ser Val Leu Thr Val Leu His Gln
            325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly Lys Ile Tyr Ile Trp Ala Pro Leu Ala
465                 470                 475                 480

Gly Thr Cys Gly Val Leu Leu Leu Ser Leu Val Ile Thr Leu Tyr Cys
                485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
        515                 520                 525

Pro Glu Glu Glu Glu Gly Gly Cys Glu Leu Arg Val Lys Phe Ser Arg
        530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
            580                 585                 590

Gln Glu Gly Leu Tyr Asn Glu Leu Gln Lys Asp Lys Met Ala Glu Ala
        595                 600                 605

Tyr Ser Glu Ile Gly Met Lys Gly Glu Arg Arg Arg Gly Lys Gly His
        610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 19
<211> LENGTH: 530
<212> TYPE: PRT
<213> ORGANISM: artificial sequence
<220> FEATURE:
<223> OTHER INFORMATION: TAL binding domain  TRAC_T01-L

<400> SEQUENCE: 19

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30
```

```
His Gly Leu Thr Pro Gln Gln Val Ala Ile Ala Ser Asn Asn Gly
        35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
                115                 120                 125

Pro Val Leu Cys Gln Ala His Gly Leu Thr Pro Glu Gln Val Val Ala
                130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
                180                 185                 190

Gln Arg Leu Leu Pro Val Leu Cys Gln Ala His Gly Leu Thr Pro Glu
                195                 200                 205

Gln Val Val Ala Ile Ala Ser Asn Ile Gly Gly Lys Gln Ala Leu Glu
                210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
                260                 265                 270

Leu Thr Pro Glu Gln Val Val Ala Ile Ala Ser Asn Ile Gly Gly Lys
                275                 280                 285

Gln Ala Leu Glu Thr Val Gln Ala Leu Leu Pro Val Leu Cys Gln Ala
                290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
                340                 345                 350

Ile Gly Gly Lys Gln Ala Leu Glu Thr Val Gln Ala Leu Leu Pro Val
                355                 360                 365

Leu Cys Gln Ala His Gly Leu Thr Pro Gln Gln Val Val Ala Ile Ala
                370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
                420                 425                 430

Leu Leu Pro Val Leu Cys Gln Ala His Gly Leu Thr Pro Gln Gln Val
                435                 440                 445
```

-continued

```
Val Ala Ile Ala Ser Asn Gly Gly Lys Gln Ala Leu Glu Thr Val
450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Arg Pro Ala
        515                 520                 525
Leu Glu
    530

<210> SEQ ID NO 20
<211> LENGTH: 530
<212> TYPE: PRT
<213> ORGANISM: artificial sequence
<220> FEATURE:
<223> OTHER INFORMATION: TAL binding domain TRAC_T01-R

<400> SEQUENCE: 20

Leu Thr Pro Glu Gln Val Val Ala Ile Ala Ser His Asp Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Gly Gly
        35                  40                  45
Gly Lys Gln Ala Leu Glu Thr Val Gln Arg Leu Leu Pro Val Leu Cys
    50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
Ser Asn Ile Gly Gly Lys Gln Ala Leu Glu Thr Val Gln Ala Leu Leu
        115                 120                 125
Pro Val Leu Cys Gln Ala His Gly Leu Thr Pro Gln Gln Val Val Ala
    130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Gln
        195                 200                 205
Gln Val Val Ala Ile Ala Ser Asn Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
            260                 265                 270
```

```
Leu Thr Pro Gln Gln Val Val Ala Ile Ala Ser Asn Gly Gly Lys
            275                 280                 285
Gln Ala Leu Glu Thr Val Gln Arg Leu Leu Pro Val Leu Cys Gln Ala
        290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Glu Gln Val Val Ala Ile Ala
    370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530

<210> SEQ ID NO 21
<211> LENGTH: 1464
<212> TYPE: DNA
<213> ORGANISM: artificial
<220> FEATURE:
<223> OTHER INFORMATION: CAR 1

<400> SEQUENCE: 21
atggctctgc cgtcaccgc tctgctgctg ccactggccc tgctgctgca cgcagccaga      60
ccccaggtgc agctgcagca gagcggccct ggcctggtga agccatctca gacactgagc     120
ctgacctgcg ccatctctgg cgacagcgtg agctccaact tgccgcctg gaattggatc      180 agacagtccc catctagggg cctggagtgg ctgggacgca catactatcg gtccacctgg     240
tacaacgact atgccgtgtc cgtgaagtct cgcatcacaa tcaacccga tacctctaag     300 aatcagttca gcctgcagct gaattccgtg acacctgagg acaccgccgt gtactattgc     360
gccagagagg tgagcggcac atccgccttt gatatctggg gccagggcac aatggtgacc     420
gtgtctggag gaggaggaag cggaggagga ggatccggcg gcggcggctc tgacatccag     480
atgacccaga gccttctag cctgagcgcc tccgtgggcg atcgcgtgac aatcacctgt     540
```

| | |
|---|---|
| cgggcctctc agagcatctc ctcttacctg aactggtatc agcagaagcc cggcaaggcc | 600 |
| cctaagctgc tgatctacgc agcaagctcc ctgcagtccg gagtgccatc tcggttctcc | 660 |
| ggctctggca gcggcacaga ctttacactg accatctcta gcctgcagcc tgaggatttc | 720 |
| gccacctact attgccagca gtcctattct acaccactga cctttggcgg cggcaccaag | 780 |
| ctggagatca agaccacaac cccagcaccc agaccccta cacctgcacc aaccatcgca | 840 |
| agccagccac tgtccctgcg ccctgaggca tgtaggccag cagcaggagg agcagtgcac | 900 |
| accaggggcc tggacttcgc ctgcgatatt tacatctggg caccactggc aggaacatgt | 960 |
| ggcgtgctgc tcctgagcct ggtcatcacc ctgtactgca agagaggcag gaagaagctg | 1020 |
| ctgtatatct tcaagcagcc cttcatgcgg cccgtgcaga aacccagga ggaggacggc | 1080 |
| tgctcctgta ggttcccaga agaggaggag ggcggctgtg agctgagagt gaagtttagc | 1140 |
| aggtccgccg atgcaccagc ataccagcag gacagaatc agctgtataa cgagctgaat | 1200 |
| ctgggccgga gagaggagta cgacgtgctg gataagagga ggggaaggga tcctgagatg | 1260 |
| ggaggcaagc cccggagaaa gaaccctcag gagggcctgt acaatgagct gcagaaggac | 1320 |
| aagatggccg aggcctatag cgagatcggc atgaagggag agaggcgccg gggcaaggga | 1380 |
| cacgatggcc tgtaccaggg cctgtccaca gccaccaagg acacctatga tgccctgcat | 1440 |
| atgcaggcac tgcctccaag gtga | 1464 |

<210> SEQ ID NO 22
<211> LENGTH: 1479
<212> TYPE: DNA
<213> ORGANISM: artificial sequence
<220> FEATURE:
<223> OTHER INFORMATION: CAR 2

<400> SEQUENCE: 22

| | |
|---|---|
| atggctctgc ccgtcaccgc tctgctgctg ccactggccc tgctgctgca cgcagccaga | 60 |
| ccccaggtgc agctgcagca gagcggccct ggcctggtga agccatccca gaccctgtct | 120 |
| ctgacatgcg ccatcagcgg cgactccgtg agctccaact ctgccgcctg gaattggatc | 180 |
| agacagtccc catctagggg cctggagtgg ctgggaagga cctactatcg gtccaagtgg | 240 |
| tacaacgact atgccgtgtc tgtgaagagc cgcatcacca tcaaccccga tacatccaag | 300 |
| aatcagttct ctctgcagct gaatagcgtg acccctgagg acacagccgt gtactattgc | 360 |
| gccagagcct ctatgaccgg cggctacagc tatggcgacg ccttttgatat ctggggccag | 420 |
| ggcacactgg tgaccgtgtc cggcggcggc ggctctggag gaggaggaag cggaggagga | 480 |
| ggatccgcca tccgcatgac acagagccct tctagcctga gcgcctccgt gggcgatcgc | 540 |
| gtgacaatca cctgtcgggc ctctcagagc atctcctctt acctgaactg gtatcagcag | 600 |
| aagcccggca aggcccctaa gctgctgatc tacgcagcaa gctccctgca gagcggagtg | 660 |
| ccatcccggt tctccggatc tggaagcgga accgactttt ccctgacaat ctctagcctg | 720 |
| cagcctgagg attccgccac ctactattgc cagcagacat attctacccc actgacattc | 780 |
| ggccagggca caaggtgga gatcaagacc acaaccccag cacccagacc cctacccct | 840 |
| gcaccaacaa tcgcctctca gcccctgagc ctgcgccctg aggcatgtag gccagcagca | 900 |
| ggaggagcag tgcacaccag gggcctggac tttgcctgcg atatttacat ctgggcacca | 960 |
| ctggcaggaa cctgtggcgt gctgctcctg agcctggtca tcaccctgta ctgcaagaga | 1020 |
| ggcaggaaga agctgctgta tatcttcaag cagcccttca tgcggcccgt gcagacaacc | 1080 |
| caggaggagg acggctgctc ctgtaggttc ccagaagagg aggaggcgg ctgtgagctg | 1140 |

```
agagtgaagt tttccaggtc tgccgatgca ccagcatacc agcagggaca gaatcagctg    1200
tataacgagc tgaatctggg ccggagagag gagtacgacg tgctggataa gaggagggga    1260
cgggatcctg agatgggagg caagccccgg agaaagaacc ctcaggaggg cctgtacaat    1320
gagctgcaga aggacaagat ggccgaggcc tatagcgaga tcggcatgaa gggagagagg    1380
cgccggggca agggacacga tggcctgtac cagggcctgt ccacagccac caaggacacc    1440
tatgatgccc tgcatatgca ggcactgcct ccaaggtga                           1479

<210> SEQ ID NO 23
<211> LENGTH: 1467
<212> TYPE: DNA
<213> ORGANISM: artificial sequence
<220> FEATURE:
<223> OTHER INFORMATION: CAR 3

<400> SEQUENCE: 23
atggctctgc ccgtcaccgc tctgctgctg ccactggccc tgctgctgca cgcagccaga     60
ccccaggtgc agctgcagca gagcggccct ggcctggtgg agccaagcca gacactgtcc    120
ctgacctgcg ccatctctgg cgacagcgtg agctccgatt ccgtggcctg gaactggatc    180
aggcagtctc caagccgggg cctggagtgg ctgggcagaa catactatag gtctacctgg    240
tacaatgact atgccggctc cgtgaagtct cgcatcacaa tcaacccga taccagcaag    300 aatcagttct ccctgcagct gacatctgtg acccctgagg acacagccgt gtactattgc    360
accagatcca ggcacaacac atttcgggga atggacgtgt ggggacaggg aaccacagtg    420
accgtgagcg gaggaggagg atccggcgga ggaggctctg gaggaggagg aagcgacatc    480
gtgatgaccc agagcccttc tagcctgtcc gcctctgtgg gcgatagagt gacaatcacc    540
tgtagggcct cccagaccat ctcctcttac ctgaactggt atcagcagaa gcccggcaag    600 gccccaagc tgctgatcta cgacgcaagc tcccctgcag tctggagtgcc aagcagattc    660 agcggctccg gctctggcac cgactttaca ctgaccatca ttccctgca gcctgaggat    720 ttcgccacat actattgcca gcagtcttat accacaccaa tcacatttgg ccagggcacc    780
cgcctggaga tcaagaccac aaccccagca cccagacccc ctacacctgc accaaccatc    840
gcatcccagc cactgtctct gcggcccgag gcatgtaggc cagcagcagg aggagcagtg    900
cacaccaggg gcctggactt cgcctgcgat atttacatct gggcaccact ggcaggaacc    960
tgtggcgtgc tgctcctgag cctggtcatc accctgtact gcaagcgcgg ccggaagaag   1020
ctgctgtata tcttcaagca gccccttcatg cggcccgtgc agacaaccca ggaggaggac   1080
ggctgctcct gtaggttccc agaagaggag gagggaggat gtgagctgag ggtgaagttt   1140
agccggtccg ccgatgcacc agcataccag cagggccaga atcagctgta taacgagctg   1200
aatctgggcc ggagagagga gtacgacgtg ctggataaga ggaggggaag ggatcctgag   1260
atgggaggca gccccggag aaagaaccct caggagggcc tgtacaatga gctgcagaag   1320
gacaagatgg ccgaggccta ttctgagatc ggcatgaagg gagagaggcg ccggggcaag   1380
ggacacgatg gcctgtacca gggcctgagc acagccacca aggacaccta tgatgccctg   1440
catatgcagg cactgcctcc aaggtga                                        1467

<210> SEQ ID NO 24
<211> LENGTH: 1467
<212> TYPE: DNA
<213> ORGANISM: artificial sequence
<220> FEATURE:
```

<223> OTHER INFORMATION: CAR 4

<400> SEQUENCE: 24

```
atggctctgc ccgtcaccgc tctgctgctg ccactggccc tgctgctgca cgcagccaga      60
ccccaggtgc agctgcagca gagcggccct ggcctggtgg agccaagcca gacactgtcc     120
ctgacctgcg ccatctctgg cgacagcgtg agctccaaca cgccgcatg gaattggatc      180
aggcagtccc catctcgggg cctggagtgg ctgggcagaa catactatag gtccacctgg     240
tacaacgact atgccggctc cgtgaagtct cgcatcacaa tcaaccccga taccagcaag     300
aatcagttct ccctgcagct gacatctgtg acccctgagg acacagccgt gtactattgc     360
accagaagca ggcacaatac atttcgggga atggacgtgt ggggacaggg cacactggtg     420
accgtgagcg gaggaggagg atccggcgga ggaggctctg cggcggcgg cagcgacatc      480
cagctgaccc agtccccttc tagcctgagc gcctccgtgg gcgatagagt gacaatcacc     540
tgtagggcct ctcagagcat ctcctcttac ctgaactggt atcagcagaa gcccggcaag     600
gcccctaagc tgctgatcta cgcagcaagc tccctgcagt ctggagtgcc aagcagattc     660
tccggctctg gcagcggcac cgactttaca ctgaccatct ctagcctgca gcctgaggat     720
ttcgccacat actattgcca gcagtcctat tctacaccac tgacctttgg cggcggcacc     780
aaggtggaga tcaagaccac aaccccagca cccagacccc ctacacctgc accaaccatc     840
gcatcccagc cactgtctct gcggcccgag gcatgtaggc cagcagcagg aggagcagtg     900
cacaccaggg gcctggactt cgcctgcgat atctacattt gggcaccact ggcaggaacc     960
tgtggcgtgc tgctcctgag cctggtcatc accctgtact gcaagcgcgg ccggaagaag    1020
ctgctgtata tcttcaagca gcccttcatg cggcccgtgc agacaaccca ggaggaggac    1080
ggctgctccc gtcggttccc agaagaggag gaggaggat gtgagctgag ggtgaagttt    1140
agccggtccg ccgatgcacc agcataccag cagggccaga atcagctgta taacgagctg    1200
aatctgggcc ggagagagga gtacgacgtg ctggataaga ggaggggaag ggatcctgag    1260
atgggaggca agccccggag aaagaaccct caggagggcc tgtacaatga gctgcagaag    1320
gacaagatgg ccgaggccta ttccgagatc ggcatgaagg gagagaggcg ccggggcaag    1380
ggacacgatg gcctgtacca gggcctgtct acagccacca ggacaccta tgatgccctg    1440
catatgcagg cactgcctcc aaggtga                                       1467
```

<210> SEQ ID NO 25
<211> LENGTH: 1455
<212> TYPE: DNA
<213> ORGANISM: artificial sequence
<220> FEATURE:
<223> OTHER INFORMATION: CAR 5 7

<400> SEQUENCE: 25

```
atggctctgc ccgtcaccgc tctgctgctg ccactggccc tgctgctgca cgcagccaga      60
ccccaggtgc agctgcagca gagcggccct ggcctggtgg agccaagcca gaccctgtcc     120
ctgacatgcg ccatctctgg cgacagcgtg agctccgatt ctgtggcctg gaactggatc     180
aggcagagcc caagccgggg cctggagtgg ctgggcagaa cctactatag gtccacatgg     240
tacaatgact atgccggctc cgtgaagtct cggatcacca tcaaccccga tacatccaag     300
aatcagttct ctctgcagct gaacagcgtg acccctgagg acacagccgt gtactattgc     360
gccagagaca ggaatggcat ggacgtgtgg ggccagggaa ccatggtgac agtgtccgga     420
ggaggcggct ctggaggagg aggaagcgga ggaggaggat ccgacatcgt gatgacccag     480
```

```
agcccttcta gcctgtctgc cagcgtgggc gatagagtga caatcacctg tagggcctcc   540
cagtctatct cctcttacct gaactggtat cagcagaagc ccggcaaggc ccctaagctg   600
ctgatctacg atgcctctaa tctggagaca ggcgtgccaa gcagattcag cggctccggc   660
tctggcacag acttcacctt caccatcaca tccctgcagc ctgaggattt cgccacctac   720
tattgccagc agtcttatac cacaccactg acctttggcg gcggcacaaa ggtggagatc   780
aagaccacaa ccccagcacc cagacccoct acccctgcac caacaatcgc ctctcagccc   840
ctgagcctgc ggcccgaggc tgtaggcca gcagcaggag gagcagtgca caccaggggc   900
ctggactttg cctgcgatat ttacatctgg gcaccactgg caggaacctg tggcgtgctg   960
ctcctgagcc tggtcatcac cctgtactgc aagcgcggcc ggaagaagct gctgtatatc  1020
ttcaagcagc ccttcatgcg gcccgtgcag acaacccagg aggaggacgg ctgctcctgt  1080
cggttcccag aagaggagga gggaggatgt gagctgaggg tgaagtttag ccggtccgcc  1140
gatgcaccag cataccagca gggacagaac cagctgtata cgagctgaa tctgggccgg  1200 agagaggagt acgacgtgct ggataagagg aggggacggg accctgagat gggaggcaag  1260
ccccggagaa agaaccctca ggagggcctg tacaatgagc tgcagaagga caagatggcc  1320
gaggcctata gcgagatcgg catgaaggga gagaggcgcc ggggcaaggg acacgatggc  1380
ctgtaccagg gcctgtccac cgccacaaag gacacctatg atgccctgca tatgcaggca  1440
ctgcctccaa ggtga                                                  1455

<210> SEQ ID NO 26
<211> LENGTH: 1464
<212> TYPE: DNA
<213> ORGANISM: artificial sequence
<220> FEATURE:
<223> OTHER INFORMATION: CAR 6-8

<400> SEQUENCE: 26
atggctctgc ccgtcaccgc tctgctgctg ccactggccc tgctgctgca cgcagcccgc    60
cctcaggtgc agctgcagca gtccggccca ggcctggtga agccatccca gacactgtct   120
ctgacctgcg ccatcagcgg cgactccgtg agctcctcta cgccgcctg gaactggatc   180 agacagtctc ctagcagggg cctggagtgg ctgggaagga cctactatcg gtccgcctgg   240
tacaatgact atgccgtgtc tgtgaagagc agaatcacaa tcaaccccga tacctccaag   300
aatcagttct ctctgcagct gaacagcgtg acacctgagg ataccgccgt gtactattgc   360
gccagagaga gcgtgctgct ggacggaatg gacgtgtggg gaaggggaac cacagtgaca   420
gtgtccggag gaggcggctc tggaggagga ggaagcggag gaggaggatc cgccatcagg   480
atgacacagt cccatctac cctgagcgcc tccgtgggcg accgcgtgac aatcacctgt   540
cgggcctctc agagcatctc cacctacctg aattggtatc agcagaaggc cggcaaggcc   600
ccaagactgc tgatcctct gcatcctct ctgcagagcg gagtgccatc aggttctct   660 ggaagcggat ccggcacaga ctttacactg accatcagct ccctgcagcc tgaggatttc   720
gccacctact attgccagca gtcttacagc acaccactga cctttggcgg cggcacaaag   780
gtggagatca gaccacaac cccagcaccc agaccccta cacctgcacc aaccatcgcc   840
tctcagcctc tgagcctgcg cccagaggca tgtaggccag cagcaggagg agcagtgcac   900
accagaggcc tggactttgc ctgcgatatt tatatctggg cacctctggc aggaacatgt   960
ggcgtgctgc tcctgagcct ggtcatcacc ctgtactgca agagaggcag gaagaagctg  1020
```

-continued

```
ctgtatatct tcaagcagcc ctttatgcgc cctgtgcaga caacccagga ggaggacggc    1080
tgcagctgtc ggttcccaga agaggaggag ggcggctgtg agctgagagt gaagttttcc    1140
aggtctgccg atgcaccagc ataccagcag ggacagaacc agctgtataa cgagctgaat    1200
ctgggccgga gagaggagta cgacgtgctg ataagagga ggggaaggga ccccgagatg     1260
ggaggcaagc ctcggagaaa gaacccacag gagggcctgt acaatgagct gcagaaggac    1320
aagatggccg aggcctattc tgagatcggc atgaagggag agaggcgccg ggcaagggga   1380
cacgatggcc tgtaccaggg cctgagcaca gccaccaagg acacctatga tgccctgcat   1440
atgcaggcac tgcctccaag gtga                                          1464
```

<210> SEQ ID NO 27
<211> LENGTH: 1485
<212> TYPE: DNA
<213> ORGANISM: artificial sequence
<220> FEATURE:
<223> OTHER INFORMATION: CAR 7 -9

<400> SEQUENCE: 27

```
atggctctgc ccgtcaccgc tctgctgctg ccactggccc tgctgctgca cgcagccaga    60
cccccaggtg agctgcagca gagcggccct ggcctggtgc agccatccca gacactgtct   120
ctgacctgcg tgatcagcgg cgactccgtg agctccaact ctgccacatg gaattggatc   180
agacagagcc catccagggg cctggagtgg ctggacgca cctactatcg agcaagtgg    240 tacaacgact atgccgtgtc tgtgaagagc agaatcacaa tcaaccccga tacctctaag    300
aatcagttca gcctgcagct gaattccgtg acacctgagg ataccgccgt gtactattgc   360
gccagggacg gcgatggagg aagctactat gactactatt actatggcat ggacgtgtgg   420
ggccagggca ccacagtgac agtgtctgga ggaggaggaa gcggaggagg aggatccggc   480
ggcggcggct ctgacatcca gctgacacag tccccttcta gcctgtctac cagcgtgggc   540
gatcgcgtga caatcacctg tcgggcctcc cagtctatca gcacctacct gaactggtat   600
cagcagaagc ccggcaaggc ccctaagctg ctgatctacg cagcaagcaa tctgcagtcc   660
ggagtgccat ctcgcttctc cggctctggc agcggcacag actttacact gaccatctcc   720
tctctgcagc ctgaggattt cgccacctac ttttgccagc agtcctatac cacaccaatc    780
acattcggcc agggcaccag actggagatc aagaccacaa ccccagcacc caggcccct    840 acacctgcac caaccatcgc aagccagcca ctgtccctgc gccctgaggc atgtaggcca    900
gcagcaggag gagcagtgca caccagaggc ctggactttg cctgcgatat ttacatctgg   960
gcaccactgg caggaacatg tggcgtgctg ctcctgagcc tggtcatcac cctgtactgc   1020
aagagaggca ggaagaagct gctgtatatc ttcaagcagc ccttcatgcg gcccgtgcag   1080
acaacccagg aggaggacgg ctgctcttgt cggttcccag aagaggagga gggcggctgt    1140
gagctgagag tgaagttttc caggtctgcc gatgcaccag cataccagca gggacagaac   1200
cagctgtata cgagctgaa tctgggccgg agagaggagt acgacgtgct ggataagagg    1260
aggggacggg accctgagat gggaggcaag ccccggagaa gaaccctca ggagggcctg    1320 tacaatgagc tgcagaagga caagatggcc gaggcctata gcgagatcgg catgaaggga   1380
gagaggcgcc ggggcaaggg cacgatggcc tgtaccaggg cctgtccac agccaccaag   1440 gacacctatg atgccctgca tatgcaggca ctgcctccaa ggtga                   1485
```

<210> SEQ ID NO 28
<211> LENGTH: 1455

<212> TYPE: DNA
<213> ORGANISM: artificial sequence
<220> FEATURE:
<223> OTHER INFORMATION: CAR 8 12

<400> SEQUENCE: 28

```
atggctctgc cgtcaccgc tctgctgctg ccactggccc tgctgctgca cgcagccaga      60
ccccaggtgc agctgcagca gtccggccct ggcctggtga agccatctca gacactgagc    120
ctgacctgcg ccatctccgg cgactctgtg agctccaact ccgccgcctg gaattggatc    180
agacagagcc atccaggggg cctggagtgg ctgggacgca cctactatcg gagcgcctgg    240
tacaacgact atgccgtgag cgtgaagtcc agaatcacaa tcaaccccga tacctctaag    300
aatcagttca gcctgcagct gtctagcgtg acacctgagg ataccgccgt gtactattgc    360
gccagggacg tggagggctt tgattactgg ggccagggca cactggtgac cgtgtccggc    420
ggcggcggct ctggaggagg aggaagcgga ggaggaggat ccgacatcgt gatgacacag    480
acccttcct ctctgtctgc cagcgtgggc gatcgcgtga caatcacctg tcgggcctcc    540
cagtctatca gctcctacct gaattggtat cagcagaagc ccggcaaggc ccctaagctg    600
ctgatctacg cagcatctag cctgcagtcc ggagtgccat ctcgcttcag cggatccggc    660
tctggcacag actttacact gaccatctcc tctctgcagc ctgaggattt cgccacctac    720
tattgccagc agagctattc cacaccaatc acctttggcc agggcacaag actggagatc    780
aagaccacaa ccccagcacc caggccccct acacctgcac caaccatcgc aagccagcca    840
ctgtccctgc gccctgaggc atgtaggcca gcagcaggag gagcagtgca caccagaggc    900
ctggacttcg cctgcgatat ttacatctgg gcaccactgg caggaacatg tggcgtgctg    960
ctcctgagcc tggtcatcac cctgtactgc aagagaggca ggaagaagct gctgtatatc   1020
ttcaagcagc ccttcatgcg cccgtgcag acaacccagg aggaggacgg ctgcagctgt   1080
cggttcccag aagaggagga gggcggctgt gagctgagag tgaagttttc taggagcgcc   1140
gatgcaccag cataccagca gggacagaac cagctgtata cgagctgaa tctgggccgg   1200
agagaggagt acgacgtgct ggataagagg agggacggg accctgagat gggaggcaag   1260
ccccggagaa agaaccctca ggagggcctg tacaatgagc tgcagaagga caagatggcc   1320
gaggcctatt ctgagatcgg catgaaggga gagaggcgcc ggggcaaggg acacgatggc   1380
ctgtaccagg gcctgagcac agccaccaag gacacctatg atgccctgca tatgcaggca   1440
ctgcctccaa ggtga                                                    1455
```

<210> SEQ ID NO 29
<211> LENGTH: 1470
<212> TYPE: DNA
<213> ORGANISM: artificial sequence
<220> FEATURE:
<223> OTHER INFORMATION: CAR 9 13

<400> SEQUENCE: 29

```
atggctctgc cgtcaccgc tctgctgctg cctctggccc tgctgctgca cgcagcccgc      60
ccacaggtgc agctgcagca gagcggcccc ggcctggtga agcctagcca gacactgtcc    120
ctgacctgcg caatctccgg cgacagcgtg tccggaaaca gggccacatg gaattggatc    180
agacagtctc caagcagggg cctggagtgg ctgggaagga cctactatcg gtccgcctgg    240
tacaacgact atgccgtgtc tgtgaagggc cgcatcacat tcaacccaga taccagcaag    300
aatcagtttt ccctgcagct gaattctgtg acacccgagg ataccgccgt gtactattgc    360
```

```
gccagaggcg agagcggagc agcagcagac gccttcgata tctggggcca gggcaccaca    420
gtgacagtga gcggaggagg aggatccggc ggaggaggct ctggcggcgg cggcagcgac    480
atccagctga cccagagccc accttccctg tctgccagcg tgggcgatcg cgtgacaatc    540
acctgtcggg cctcccagtc tatcagctcc tacctgaact ggtatcagca gaagccaggc    600
aaggccccca agctgctgat ctacgcagca tctagcctgc agtctggagt gccaagcaga    660
ttcagcggat ccggattcgg cacagacttt acactgacca tctcctctct gcagcccgag    720
gatttcgcca cctactattg ccagcagtct tatagcacac ctcagacctt tggccagggc    780
accaaggtgg acatcaagac cacaacccct gcaccaagac caccaacacc agcacctacc    840
atcgcatccc agccactgtc tctgcgcccc gaggcatgta ggcctgcagc aggcggcgcc    900
gtgcacacca ggggcctgga ctttgcctgc gatatttaca tctgggcacc tctggcagga    960
acatgtggcg tgctgctcct gagcctggtc atcaccctgt actgcaagag aggcaggaag   1020
aagctgctgt atatcttcaa gcagcccttc atgcggcccg tgcagacaac ccaggaggag   1080
gacggctgct cctgtaggtt ccctgaagag gaggagggcg gctgtgagct gagagtgaag   1140
ttttccaggt ctgccgatgc accagcatac cagcagggac agaatcagct gtataacgag   1200
ctgaatctgg gccggagaga ggagtacgac gtgctggata agaggagggg acgggatccc   1260
gagatgggag gcaagccacg gagaaagaac ccccaggagg cctgtacaa tgagctgcag   1320
aaggacaaga tggccgaggc ctattctgag atcggcatga aggagagag cgccggggc    1380
aagggacacg atggcctgta ccagggcctg tccacagcca ccaaggacac ctatgatgcc   1440
ctgcatatgc aggcactgcc tccaaggtga                                   1470
```

<210> SEQ ID NO 30
<211> LENGTH: 1470
<212> TYPE: DNA
<213> ORGANISM: artificial sequence
<220> FEATURE:
<223> OTHER INFORMATION: CAR 10 15

<400> SEQUENCE: 30

```
atggctctgc ccgtcaccgc tctgctgctg ccactggccc tgctgctgca cgcagccaga     60
ccccaggtgc agctggtgca gagcggagca gaggtgaaga gcctggcgc cagcgtgaag    120
gtgtcctgca aggcctctgg ctacacattc accagctact atatgcactg ggtgcggcag    180
gcccctggcc agggcctgga gtggatgggc atcatcaacc catccggcgg ctccacctct    240
tacgcccaga gtttcagggg cagagtgaca atgaccaggg acacaagcac ctccacagtg    300
tatatggagc tgagctccct gagatccgag gatacagccg tgtactattg cgccagggag    360
gactctggaa gcggagcctt cgatatctgg ggccagggca ccctggtgac agtgtctgga    420
ggaggaggaa gcggaggagg aggatccggc ggcggcggct ctgagatcgt gctgacccag    480
tctccactga gcctgccagt gacacctggc gagccagccc ccatctcttg tcgctctagc    540
cggtccctgc tgtcttacca cggctacaat tatctggact ggtatctgca gaagccaggc    600
cagagccccc agctgctgat cttcgtggga tccaacaggg ccctggcgt gcctgaccgg    660
ttcagcggat ccggatctgg aaccgacttc accctgaaca tctctagagt ggaggccgag    720
gatgtgggcg tgtactattg catgcagagc ctgcagaccc caagaacatt tggccagggc    780
accaaggtgg agatcaagac cacaacccca gcacccaggc ccctaccccc tgcaccaaca    840
atcgcaagcc agccactgtc cctgcgccct gaggcatgta ggccagcagc aggaggagca    900
gtgcacacca ggggcctgga ctttgcctgc gatatctaca tttgggcacc actggcagga    960
```

```
acctgtggcg tgctgctcct gagcctggtc atcaccctgt actgcaagag aggcaggaag    1020
aagctgctgt atatcttcaa gcagcctttt atgcgcccag tgcagacaac ccaggaggag    1080
gacggctgct cctgtaggtt cccagaagag gaggagggag gatgtgagct gagagtgaag    1140
tttagcaggt ccgccgatgc acctgcatac cagcaggac agaaccagct gtataacgag    1200
ctgaatctgg gccggagaga ggagtacgac gtgctggata gaggaggggg acgggacccc    1260
gagatgggag gcaagccccg gagaaagaac cctcaggagg gcctgtacaa tgagctgcag    1320
aaggacaaga tggccgaggc ctattccgag atcggcatga agggagagag gcgccggggc    1380
aagggacacg atggcctgta ccagggcctg tctaccgcca caaggacac ctatgatgcc    1440 ctgcatatgc aggcactgcc tccaaggtga                                     1470

<210> SEQ ID NO 31
<211> LENGTH: 1473
<212> TYPE: DNA
<213> ORGANISM: artificial sequence
<220> FEATURE:
<223> OTHER INFORMATION: CAR 11 prox 16 m971

<400> SEQUENCE: 31
atggctctgc ccgtcaccgc tctgctgctg ccactggccc tgctgctgca cgcagcaaga      60
ccacaggtgc agctgcagca gagcggccct ggcctggtga agccaagcca gacactgtcc     120
ctgacctgcg ccatcagcgg cgattccgtg agctccaact ccgccgcctg gaattggatc     180
aggcagtccc cttctcgggg cctggagtgg ctgggaagga catactatcg gtctaagtgg     240
tacaacgatt atgccgtgtc tgtgaagagc agaatcacaa tcaaccctga cacctccaag     300
aatcagttct ctctgcagct gaatagcgtg acaccagagg acaccgccgt gtactattgc     360
gccagggagg tgaccggcga cctggaggat gcctttgaca tctggggcca gggcacaatg     420
gtgaccgtgt ctagcggagg aggaggatcc ggaggaggag gatctggcgg cggcggcagc     480
gatatccaga tgacacagtc cccatcctct ctgagcgcct ccgtgggcga cagagtgaca     540
atcacctgta gggcctccca gaccatctgg tcttacctga actggtatca gcagaggccc     600
ggcaaggccc ctaatctgct gatctacgca gcaagctccc tgcagagcgg agtgccatcc     660
agattctctg gcaggggctc cggcacagac ttcaccctga ccatctctag cctgcaggcc     720
gaggacttcg ccacctacta ttgccagcag tcttatagca tcccccagac atttggccag     780
ggcaccaagc tggagatcaa gaccacaacc ccagcaccaa ggccacctac acctgcacca     840
accatcgcct ctcagcccct gagcctgaga cctgaggcat gtaggccagc agcaggagga     900
gcagtccata aaggggtctg gattttgca tgcgacatct acatctgggc acctctggca     960
ggaacatgtg gcgtgctcct gctcagcctg gtcatcaccc tgtactgcaa gagaggcagg    1020
aagaagctgc tgtatatctt caagcagccc ttcatgcgcc ccgtgcagac aacccaggag    1080
gaggatggct gctcctgtag gttcccagaa gaggaggagg aggatgtga gctgcgcgtg    1140 aagttttccc ggtctgccga cgcacctgca taccagcagg ccagaaccca gctgtataac    1200
gagctgaatc tgggccggag agaggagtac gatgtgctgg acaagaggcg cggcagagat    1260
ccagagatgg gcgcaagcc ccggagaaag aaccctcagg agggcctgta caatgagctg    1320
cagaaggata gatggccga ggcctattct gagatcggca tgaagggaga gaggcgccgg    1380
ggcaagggac acgacggact gtaccaggga ctgagcacag ccaccaagga tacctatgac    1440
gccctgcata tgcaggcact gcctccaagg tga                                 1473
```

<210> SEQ ID NO 32
<211> LENGTH: 1704
<212> TYPE: DNA
<213> ORGANISM: artificial sequence
<220> FEATURE:
<223> OTHER INFORMATION: 1 QR3

<400> SEQUENCE: 32

| | | | | | | |
|---|---|---|---|---|---|---|
| atggctctgc | ccgtcaccgc | tctgctgctg | ccactggccc | tgctgctgca | cgccgccaga | 60 |
| cccggcggag | gaggctcttg | ccccctacagc | aaccccagcc | tgtgctctgg | cggcggcggc | 120 |
| agcggaggcg | cgggctccca | ggtgcagctg | cagcagagcg | ccctggcct | ggtgaagcca | 180 |
| tctcagacac | tgagcctgac | ctgcgccatc | tctggcgaca | gcgtgagctc | caactctgcc | 240 |
| gcctggaatt | ggatcagaca | gtccccatct | aggggcctgg | agtggctggg | acgcacatac | 300 |
| tatcggtcca | cctggtacaa | cgactatgcc | gtgtccgtga | agtctcgcat | cacaatcaac | 360 |
| cccgatacct | ctaagaatca | gttcagcctg | cagctgaatt | ccgtgacacc | tgaggacacc | 420 |
| gccgtgtact | attgcgccag | agaggtgagc | ggcacatccg | cctttgatat | ctggggccag | 480 |
| ggcacaatgg | tgaccgtgtc | tggaggagga | ggaagcggag | gaggaggatc | cggcggcggc | 540 |
| ggctctgaca | tccagatgac | ccagagccct | tctagcctga | gcgcctccgt | gggcgatcgc | 600 |
| gtgacaatca | cctgtcgggc | ctctcagagc | atctcctctt | acctgaactg | gtatcagcag | 660 |
| aagcccggca | aggcccctaa | gctgctgatc | tacgcagcaa | gctccctgca | gtccggagtg | 720 |
| ccatctcggt | tctccggctc | tggcagcggc | acagacttta | cactgaccat | ctctagcctg | 780 |
| cagcctgagg | atttcgccac | ctactattgc | cagcagtcct | attctacacc | actgaccttt | 840 |
| ggcggcggca | ccaagctgga | gatcaaggga | agtggaggag | aggaagttg | tccctattca | 900 |
| aacccatccc | tgtgcagcgg | aggaggagga | agcgaactgc | ctactcaggg | aacattcagc | 960 |
| aacgtgtcca | ccaatgtgag | cccagcaaag | cctaccacaa | ccgcatgccc | atactctaac | 1020 |
| cccagcctgt | gcacaaccac | accagcaccc | aggcccccta | ccctgcacc | aacaatcgcc | 1080 |
| tcccagcctc | tgtctctgcg | ccagaggcc | tgcagacccg | ccgccggcgg | agcagtgcac | 1140 |
| acacggggcc | tggactttgc | ctgtgatatc | tatatctggg | ccccactggc | tggaacatgt | 1200 |
| ggcgtgctgc | tgctgtcact | ggtcattacc | ctgtactgta | agcgaggccg | aagaaactg | 1260 |
| ctgtatattt | tcaaacagcc | cttttatgaga | cctgtgcaga | ctaccagga | ggaagacggc | 1320 |
| tgcagctgta | ggttccccga | ggaagaggaa | ggcgggtgtg | agctgagggt | caagtttagc | 1380 |
| cgctccgcag | atgcccctgc | ttaccagcag | gggcagaatc | agctgtataa | cgagctgaat | 1440 |
| ctgggacgga | gagaggaata | cgacgtgctg | gataaaaggc | gcgggagaga | ccccgaaatg | 1500 |
| ggaggcaagc | cacgacggaa | aaaccccag | gagggcctgt | acaatgaact | gcagaaggac | 1560 |
| aaaatggcag | aggcctatag | tgaaatcggg | atgaaggag | agaaggcg | cggcaaggg | 1620 |
| cacgatggcc | tgtaccaggg | gctgtctact | gccaccaagg | acacctatga | tgctctgcat | 1680 |
| atgcaggcac | tgcctccaag | gtga | | | | 1704 |

<210> SEQ ID NO 33
<211> LENGTH: 1719
<212> TYPE: DNA
<213> ORGANISM: artificial sequence
<220> FEATURE:
<223> OTHER INFORMATION: 2QR3

<400> SEQUENCE: 33

| | | | | | | |
|---|---|---|---|---|---|---|
| atggctctgc | ccgtcaccgc | tctgctgctg | ccactggccc | tgctgctgca | cgccgccaga | 60 |

```
cccggcggag gaggctcttg cccctacagc aaccccagcc tgtgctctgg cggcggcggc      120
agcggaggcg gcggctccca ggtgcagctg cagcagagcg ccctggcct  ggtgaagcca      180 tcccagaccc tgtctctgac atgcgccatc agcggcgact ccgtgagctc caactctgcc      240
gcctggaatt ggatcagaca gtccccatct aggggcctgg agtggctggg aaggacctac      300
tatcggtcca gtggtacaa  cgactatgcc gtgtctgtga agagccgcat caccatcaac      360
cccgatacat ccaagaatca gttctctctg cagctgaata gcgtgacccc tgaggacaca      420
gccgtgtact attgcgccag agcctctatg accggcggct acagctatgg cgacgccttt      480
gatatctggg gccagggcac actggtgacc gtgtccggcg gcggcggctc tgaggagga       540 ggaagcggag gaggaggatc cgccatccgc atgacacaga gcccttctag cctgagcgcc      600
tccgtgggcg atcgcgtgac aatcacctgt cgggcctctc agagcatctc ctcttacctg      660
aactggtatc agcagaagcc cggcaaggcc cctaagctgc tgatctacgc agcaagctcc      720
ctgcagagcg gagtgccatc ccggttctcc ggatctggaa gcggaaccga cttttccctg      780
acaatctcta gcctgcagcc tgaggattcc gccacctact attgccagca gacatattct      840
accccactga cattcggcca gggcacaaag gtggagatca agggcagtgg aggaggagga      900
agttgtccct actctaaccc aagcctgtgc agtggaggag gaggaagtga actgcctacc      960
cagggaacat tcagcaacgt gtccaccaat gtgagcccag caaagcctac cacaaccgca     1020
tgcccatact ctaaccccag cctgtgcaca accacaccag cacccaggcc cctaccccct     1080
gcaccaacaa tcgcctccca gcctctgtct ctgcggccag aggcctgcag acccgccgcc     1140
ggcggagcag tgcacacacg gggcctggac tttgcctgtg atatctatat ctgggcacca     1200
ctggccggaa catgtggcgt gctgctgctg tcactggtca ttacactgta ttgtaagcga     1260
ggccggaaga aactgctgta tattttcaaa cagcccttta tgagacctgt gcagactacc     1320
caggaggaag acggctgcag ctgtaggttc cccgaggaag aggaaggcgg tgtgagctg      1380 agggtcaagt ttagccgctc cgcagatgcc cctgcttacc agcagggca  gaatcagctg     1440 tataacgagc tgaatctggg acggagagag gaatacgacg tgctggataa aaggcgcggg     1500
agagaccccg aaatgggagg caagccacga cggaaaaacc cccaggaggg cctgtacaat     1560
gaactgcaga aggacaaaat ggcagaggcc tatagtgaaa tcgggatgaa gggagagaga     1620
aggcgcggca aagggcacga tggcctgtac caggggctgt ctactgccac caaggacacc     1680
tatgatgctc tgcatatgca ggcactgcct ccaaggtga                             1719
```

<210> SEQ ID NO 34
<211> LENGTH: 1707
<212> TYPE: DNA
<213> ORGANISM: artificial sequence
<220> FEATURE:
<223> OTHER INFORMATION: 3QR3

<400> SEQUENCE: 34

```
atggctctgc ccgtcaccgc tctgctgctg ccactggccc tgctgctgca cgccgccaga       60
cccggcggag gaggctcttg cccctacagc aaccccagcc tgtgctctgg cggcggcggc      120
agcggaggcg gcggctccca ggtgcagctg cagcagagcg ccctggcct  ggtggagcca      180 agccagacac tgtccctgac ctgcgccatc tctggcgaca gcgtgagctc cgattccgtg      240
gcctggaact ggatcaggca gtctccaagc cggggcctgg agtggctggg cagaacatac      300
tataggtcta cctggtacaa tgactatgcc ggctccgtga agtctcgcat cacaatcaac      360
```

```
cccgatacca gcaagaatca gttctccctg cagctgacat ctgtgacccc tgaggacaca    420
gccgtgtact attgcaccag atccaggcac aacacatttc ggggaatgga cgtgtgggga    480
cagggaacca cagtgaccgt gagcggagga ggaggatccg gcggaggagg ctctggagga    540
ggaggaagcg acatcgtgat gacccagagc ccttctagcc tgtccgcctc tgtgggcgat    600
agagtgacaa tcacctgtag ggcctcccag accatctcct cttacctgaa ctggtatcag    660
cagaagcccg gcaaggcccc taagctgctg atctacgacg caagctccct gcagtctgga    720
gtgccaagca gattcagcgg ctccggctct ggcaccgact ttacactgac catcaattcc    780
ctgcagcctg aggatttcgc cacatactat tgccagcagt cttataccac accaatcaca    840
tttggccagg gcacccgcct ggagatcaag ggaagcggcg gcggcggctc atgcccttat    900
tcaaacccat ctctgtgctc aggaggagga ggaagcgaac tgcctactca gggaacattc    960
agcaacgtgt ccaccaatgt gagcccagca aagcctacca caaccgcatg cccatactct   1020
aaccccagcc tgtgcacaac cacaccagca cccaggcccc ctaccccctgc accaacaatc   1080 gcctcccagc ctctgtctct gcggccagag gcctgcagac ccgccgccgg cggagcagtg   1140
cacacacggg gcctggactt tgcctgtgat atctatatct gggcaccact ggctggaaca   1200
tgtggcgtgc tgctgctgtc actggtcatt acactgtatt gcaagcgagg ccggaagaaa   1260
ctgctgtata ttttcaaaca gccctttatg agacctgtgc agactaccca ggaggaagac   1320
ggctgcagct gtaggttccc cgaggaagag aaggcgggt gtgagctgag ggtcaagttt   1380
agccgctccg cagatgcccc tgcttaccag caggggcaga atcagctgta taacgagctg   1440
aatctgggac ggagagagga atacgacgtg ctggataaaa ggcgcgggag agaccccgaa   1500
atgggaggca agccacgacg gaaaaacccc caggagggcc tgtacaatga actgcagaag   1560
gacaaaatgg cagaggccta tagtgaaatc gggatgaagg gagagagaag gcgcggcaaa   1620
gggcacgatg gcctgtacca ggggctgtct actgccacca aggacaccta tgatgctctg   1680
catatgcagg cactgcctcc aaggtga                                       1707

<210> SEQ ID NO 35
<211> LENGTH: 1707
<212> TYPE: DNA
<213> ORGANISM: artificial sequence
<220> FEATURE:
<223> OTHER INFORMATION: 4QR3

<400> SEQUENCE: 35
atggctctgc ccgtcaccgc tctgctgctg ccactggccc tgctgctgca cgccgccaga     60
cccggcggag gaggctcttg cccctacagc aaccccagcc tgtgctctgg cggcggcggc    120
agcggaggcg gcggctccca ggtgcagctg cagcagagcg ccctggcct ggtgagcca    180 agccagacac tgtccctgac ctgcgccatc tctggcgaca cgtgagctc aacagcgcc    240 gcatggaatt ggatcaggca gtccccatct cggggcctgg agtggctggg cagaacatac    300
tataggtcca cctggtacaa cgactatgcc ggctccgtga agtctcgcat cacaatcaac    360
cccgatacca gcaagaatca gttctccctg cagctgacat ctgtgacccc tgaggacaca    420
gccgtgtact attgcaccag aagcaggcac aatacatttc ggggaatgga cgtgtgggga    480
cagggcacac tggtgaccgt gagcggagga ggaggatccg gcggaggagg ctctggcggc    540
ggcggcagcg acatccagct gacccagtcc ccttctagcc tgagcgcctc cgtgggcgat    600
agagtgacaa tcacctgtag ggcctctcag agcatctcct cttacctgaa ctggtatcag    660
cagaagcccg gcaaggcccc taagctgctg atctacgcag caagctccct gcagtctgga    720
```

```
gtgccaagca gattctccgg ctctggcagc ggcaccgact ttacactgac catctctagc    780
ctgcagcctg aggatttcgc cacatactat tgccagcagt cctattctac accactgacc    840
tttggcggcg gcaccaaggt ggagatcaag ggaagcggcg gcggcggaag ttgtccatat    900
tcaaacccaa gtctgtgcag cggcggagga ggaagcgaac tgcctactca gggaaccttc    960
agcaacgtgt ccaccaatgt gagcccagca agcctaccaa caaccgcatg cccatactct   1020
aaccccagcc tgtgcacaac cacaccagca cccaggcccc ctaccctgc accaacaatc   1080 gcctcccagc ctctgtctct gcggccagag gcctgcagac cgccgccgg cggagcagtg   1140 cacacacggg gcctggactt tgcctgtgat atctatatct gggcaccact ggccggaaca   1200
tgtggcgtgc tgctgctgtc actggtcatt acactgtact gtaagcgagg ccggaagaaa   1260
ctgctgtata ttttcaaaca gcccttatg agacctgtgc agactaccca ggaggaagac   1320
ggctgcagct gtaggttccc cgaggaagag gaaggcgggt gtgagctgag ggtcaagttt   1380
agccgctccg cagatgcccc tgcttaccag caggggcaga atcagctgta taacgagctg   1440
aatctgggac ggagagagga atacgacgtg ctggataaaa ggcgcgggag agaccccgaa   1500
atgggaggca agccacgacg gaaaaacccc caggagggcc tgtacaatga actgcagaag   1560
gacaaaatgg cagaggccta tagtgaaatc gggatgaagg gagagagaag gcgcggcaaa   1620
gggcacgatg gcctgtacca ggggctgtct actgccacca aggacaccta tgatgctctg   1680
catatgcagg cactgcctcc aaggtga                                       1707

<210> SEQ ID NO 36
<211> LENGTH: 1695
<212> TYPE: DNA
<213> ORGANISM: artificial sequence
<220> FEATURE:
<223> OTHER INFORMATION: 5QR3

<400> SEQUENCE: 36
atggctctgc ccgtcaccgc tctgctgctg ccactggccc tgctgctgca cgccgccaga     60
cccggcggag gaggctcttg cccctacagc aacccccagcc tgtgctctgg cggcggcggc   120
agcggaggcg gcggctccca ggtgcagctg cagcagagcg ccctggcct ggtggagcca    180 agccagaccc tgtccctgac atgcgccatc tctggcgaca gcgtgagctc cgattctgtg    240
gcctggaact ggatcaggca gagcccaagc cggggcctgg agtggctggg cagaacctac    300
tataggtcca catggtacaa tgactatgcc ggctccgtga agtctcggat caccatcaac    360
cccgatacat ccaagaatca gttctctctg cagctgaaca gcgtgacccc tgaggacaca    420
gccgtgtact attgcgccag agacaggaat ggcatggacg tgtgggcca gggaaccatg    480 gtgacagtgt ccgaggaggg cggctctgga ggaggaggaa gcgaggagg aggatccgac    540 atcgtgatga cccagagccc ttctagcctg tctgccagcg tgggcgatag agtgacaatc    600
acctgtaggg cctcccagtc tatctcctct tacctgaact ggtatcagca gaagcccggc    660
aaggccccta agctgctgat ctacgatgcc tctaatctgg agacaggcgt gccaagcaga    720
ttcagcggct ccggctctgg cacagacttc accttcacca tcacatccct gcagcctgag    780
gatttcgcca cctactattg ccagcagtct tataccacac actgaccttt ggcggcggc    840 acaaaggtgg agatcaaggg aagcggagga ggaggaagtt gtccctattc aaatccatca    900
ctgtgcagcg gaggaggagg aagcgaactg cctactcagg gaaccttcag caacgtgtcc    960
accaatgtga gcccagcaaa gcctaccaca accgcatgcc catactctaa ccccagcctg   1020
```

-continued

| | |
|---|---|
| tgcacaacca caccagcacc caggcccect accectgcac aacaategc ctcccagcet | 1080 |
| ctgtctctgc ggccagaggc ctgcagaccg ccgccggcg gagcagtgca cacacggggc | 1140 |
| ctggactttg cctgtgatat ctatatctgg gcaccactgg ctggaacatg cggcgtgctg | 1200 |
| ctgctgtcac tggtcatcac actgtactgt aagcgaggcc ggaagaaact gctgtatatt | 1260 |
| ttcaaacagc cctttatgag acctgtgcag actacccagg aggaagacgg ctgcagctgt | 1320 |
| aggttccccg aggaagagga aggcgggtgt gagctgaggg tcaagtttag ccgctccgca | 1380 |
| gatgcccctg cttaccagca ggggcagaat cagctgtata acgagctgaa tctgggacgg | 1440 |
| agagaggaat acgacgtgct ggataaaagg cgcggggagag acccccgaaat ggggaggcaag | 1500 |
| ccacgacgga aaaaccccca ggagggcctg tacaatgaac tgcagaagga caaaatggca | 1560 |
| gaggcctata gtgaaatcgg gatgaaggga gagagaaggc gcggcaaagg gcacgatggc | 1620 |
| ctgtaccagg ggctgtctac tgccaccaag gacacctatg atgctctgca tatgcaggca | 1680 |
| ctgcctccaa ggtga | 1695 |

<210> SEQ ID NO 37
<211> LENGTH: 1704
<212> TYPE: DNA
<213> ORGANISM: artificial sequence
<220> FEATURE:
<223> OTHER INFORMATION: 6QR3

<400> SEQUENCE: 37

| | |
|---|---|
| atggctctgc ccgtcaccgc tctgctgctg ccactggccc tgctgctgca cgccgccaga | 60 |
| cccggcggag gaggctcttg cccctacagc aaccccagcc tgtgctctgg cggcggcggc | 120 |
| agcggaggcg gcggctccca ggtgcagctg cagcagtccg gcccaggcct ggtgaagcca | 180 |
| tcccagacac tgtctctgac ctgcgccatc agcggcgact ccgtgagctc ctctagcgcc | 240 |
| gcctggaact ggatcagaca gtctcctagc agggggcctgg agtggctggg aaggacctac | 300 |
| tatcggtccg cctggtacaa tgactatgcc gtgtctgtga agagcagaat cacaatcaac | 360 |
| cccgatacct ccaagaatca gttctctctg cagctgaaca gcgtgacacc tgaggatacc | 420 |
| gccgtgtact attgcgccag agagagcgtg ctgctggacg gaatggacgt gtggggaagg | 480 |
| ggaaccacag tgacagtgtc cggaggaggc ggctctggag gaggaggaag cggaggagga | 540 |
| ggatccgcca tcaggatgac acagtcccca tctacccctga cgcctccgt gggcgaccgc | 600 |
| gtgacaatca cctgtcgggc ctctcagagc atctccacct acctgaattg gtatcagcag | 660 |
| aaggccggca aggcccccaag actgctgatc cacgatgcat cctctctgca gagcggagtg | 720 |
| ccatccaggt tctctggaag cggatccggc acagacttta cactgaccat cagctccctg | 780 |
| cagcctgagg atttcgccac ctactattgc cagcagtctt tacagcacac actgaccttt | 840 |
| ggcggcggca caaaggtgga gatcaaggga agcggggag gaggatcttg cccatattca | 900 |
| aacccatcac tgtgctcagg aggaggagga gcgaactgc ctactcaggg aactttcagc | 960 |
| aacgtgtcca ccaatgtgag cccagcaaag cctaccacaa ccgcatgccc atactctaac | 1020 |
| cccagcctgt gcacaaccac accagcaccc aggccccta cccctgcacc aacaatcgcc | 1080 |
| tcccagcctc tgtctctgcg gccagaggcc tgcagacccg ccgccggcgg agcagtgcac | 1140 |
| acacggggcc tggactttgc ctgtgatatc tatatctggg caccactggc cggaacatgt | 1200 |
| ggcgtgctgc tgctgtcact ggtcattaca ctgtactgta agcgaggccg gaagaaactg | 1260 |
| ctgtatattt tcaaacagcc ctttatgaga cctgtgcaga ctacccagga ggaagacggc | 1320 |
| tgcagctgta ggttccccga ggaagaggaa ggcgggtgtg agctgagggt caagtttagc | 1380 |

| | |
|---|---|
| cgctccgcag atgcccctgc ttaccagcag gggcagaatc agctgtataa cgagctgaat | 1440 |
| ctgggacgga gagaggaata cgacgtgctg gataaaaggc gcgggagaga ccccgaaatg | 1500 |
| ggaggcaagc cacgacggaa aaaccccag gagggcctgt acaatgaact gcagaaggac | 1560 |
| aaaatggcag aggcctatag tgaaatcggg atgaagggag agagaaggcg cggcaaaggg | 1620 |
| cacgatggcc tgtaccaggg gctgtctact gccaccaagg acacctatga tgctctgcat | 1680 |
| atgcaggcac tgcctccaag gtga | 1704 |

<210> SEQ ID NO 38
<211> LENGTH: 1725
<212> TYPE: DNA
<213> ORGANISM: artificial sequence
<220> FEATURE:
<223> OTHER INFORMATION: 7QR3

<400> SEQUENCE: 38

| | |
|---|---|
| atggctctgc ccgtcaccgc tctgctgctg ccactggccc tgctgctgca cgccgccaga | 60 |
| cccggcggag gaggctcttg cccctacagc aaccccagcc tgtgctctgg cggcggcggc | 120 |
| agcggaggcg gcggctccca ggtgcagctg cagcagagcg ccctggcct ggtgcagcca | 180 |
| tcccagacac tgtctctgac ctgcgtgatc agcggcgact ccgtgagctc caactctgcc | 240 |
| acatggaatt ggatcagaca gagcccatcc aggggcctgg agtggctggg acgcacctac | 300 |
| tatcggagca agtggtacaa cgactatgcc gtgtctgtga agagcagaat cacaatcaac | 360 |
| cccgatacct ctaagaatca gttcagcctg cagctgaatt ccgtgacacc tgaggatacc | 420 |
| gccgtgtact attgcgccag ggacggcgat ggaggaagct actatgacta ctattactat | 480 |
| ggcatggacg tgtggggcca gggcaccaca gtgacagtgt ctggaggagg aggaagcgga | 540 |
| ggaggaggat ccggcggcgg cggctctgac atccagctga cacagtcccc ttctagcctg | 600 |
| tctaccagcg tgggcgatcg cgtgacaatc acctgtcggg cctcccagtc tatcagcacc | 660 |
| tacctgaact ggtatcagca gaagcccggc aaggccccta gctgctgat ctacgcagca | 720 |
| agcaatctgc agtccggagt gccatctcgc ttctccggct ctggcagcgg cacagacttt | 780 |
| acactgacca tctcctctct gcagcctgag gatttcgcca cctactttg ccagcagtcc | 840 |
| tataccacac caatcacatt cggccagggc accagactgg agatcaaggg aagtggagga | 900 |
| ggaggaagtt gcccttactc taacccaagt ctgtgctcag gaggcggagg aagcgaactg | 960 |
| cctactcagg gaacattcag caacgtgtcc accaatgtga gcccagcaaa gcctaccaca | 1020 |
| accgcatgcc catactctaa ccccagcctg tgcacaacca caccagcacc caggcccct | 1080 |
| accctgcac caacaatcgc ctcccagcct ctgtctctgc ggccagaggc ctgcagaccc | 1140 |
| gccgccggcg gagcagtgca cacacggggc ctggactttg cctgtgatat ctatatctgg | 1200 |
| gcaccactgg ctggaacatg cggagtgctg ctgctgtcac tggtcattac actgtactgt | 1260 |
| aagcgaggcc ggaagaaact gctgtatatt ttcaaacagc cctttatgag acctgtgcag | 1320 |
| actacccagg aggaagacgg ctgcagctgt aggttccccg aggaagagga aggcgggtgt | 1380 |
| gagctgaggg tcaagtttag ccgctccgca gatgcccctg cttaccagca ggggcagaat | 1440 |
| cagctgtata cgagctgaa tctgggacgg agagaggaat acgacgtgct ggataaaagg | 1500 |
| cgcgggagag accccgaaat gggaggcaag ccacgacgga aaaaccccca ggagggcctg | 1560 |
| tacaatgaac tgcagaagga caaaatggca gaggcctata gtgaaatcgg gatgaaggga | 1620 |
| gagagaaggc gcggcaaagg gcacgatggc ctgtaccagg ggctgtctac tgccaccaag | 1680 |

| | |
|---|---|
| gacacctatg atgctctgca tatgcaggca ctgcctccaa ggtga | 1725 |

<210> SEQ ID NO 39
<211> LENGTH: 1695
<212> TYPE: DNA
<213> ORGANISM: artificial sequence
<220> FEATURE:
<223> OTHER INFORMATION: 8QR3

<400> SEQUENCE: 39

| | |
|---|---|
| atggctctgc ccgtcaccgc tctgctgctg ccactggccc tgctgctgca cgccgccaga | 60 |
| cccggcggag gaggctcttg cccctacagc aaccccagcc tgtgctctgg cggcggcggc | 120 |
| agcggaggcg gcggctccca ggtgcagctg cagcagtccg gccctggcct ggtgaagcca | 180 |
| tctcagacac tgagcctgac ctgcgccatc tccggcgact ctgtgagctc caactccgcc | 240 |
| gcctggaatt ggatcagaca gagcccatcc aggggcctgg agtggctggg acgcacctac | 300 |
| tatcggagcg cctggtacaa cgactatgcc gtgagcgtga agtccagaat cacaatcaac | 360 |
| cccgatacct ctaagaatca gttcagcctg cagctgtcta gcgtgacacc tgaggatacc | 420 |
| gccgtgtact attgcgccag ggacgtggag ggctttgatt actggggcca gggcacactg | 480 |
| gtgaccgtgt ccggcggcgg cggctctgga ggaggaggaa gcggaggagg aggatccgac | 540 |
| atcgtgatga cacagacccc ttcctctctg tctgccagcg tgggcgatcg cgtgacaatc | 600 |
| acctgtcggg cctcccagtc tatcagctcc tacctgaatt ggtatcagca gaagcccggc | 660 |
| aaggccccta gctgctgat ctacgcagca tctagcctgc agtccggagt gccatctcgc | 720 |
| ttcagcggat ccggctctgg cacagacttt acactgacca tctcctctct gcagcctgag | 780 |
| gatttcgcca cctactattg ccagcagagc tattccacac caatcacctt tggccagggc | 840 |
| acaagactgg agatcaaggg aagcggggga ggaggatcat gtccatactc taacccatca | 900 |
| ctgtgctctg gaggaggagg aagcgaactg cctactcagg gaaccttcag caacgtgtcc | 960 |
| accaatgtga gcccagcaaa gcctaccaca accgcatgcc catactctaa ccccagcctg | 1020 |
| tgcacaacca caccagcacc caggcccccct acccctgcac caacaatcgc ctcccagcct | 1080 |
| ctgtctctgc ggccagaggc ctgcagaccc gccgccggcg gagcagtgca cacggggc | 1140 |
| ctggactttg cctgtgatat ctatatctgg gcaccactgg ctggaacatg cggcgtgctg | 1200 |
| ctgctgtcac tggtcattac actgtattgt aagcgaggcc ggaagaaact gctgtatatt | 1260 |
| ttcaaacagc cctttatgag acctgtgcag actacccagg aggaagacgg ctgcagctgt | 1320 |
| aggttccccg aggaagagga aggcgggtgt gagctgaggg tcaagtttag ccgctccgca | 1380 |
| gatgcccctg cttaccagca ggggcagaat cagctgtata cgagctgaa tctgggacgg | 1440 |
| agagaggaat acgacgtgct ggataaaagg cgcgggagag accccgaaat gggaggcaag | 1500 |
| ccacgacgga aaaaccccca ggagggcctg tacaatgaac tgcagaagga caaatggca | 1560 |
| gaggcctata gtgaaatcgg gatgaaggga gagagaaggc gcggcaaagg cacgatggc | 1620 |
| ctgtaccagg ggctgtctac tgccaccaag gacacctatg atgctctgca tatgcaggca | 1680 |
| ctgcctccaa ggtga | 1695 |

<210> SEQ ID NO 40
<211> LENGTH: 1710
<212> TYPE: DNA
<213> ORGANISM: artificial sequence
<220> FEATURE:
<223> OTHER INFORMATION: 9QR3

<400> SEQUENCE: 40

| | | | |
|---|---|---|---|
| atggctctgc | ccgtcaccgc | tctgctgctg | ccactggccc  tgctgctgca  cgccgccaga | 60 |
| cccggcggag | gaggctcttg | cccctacagc | aaccccagcc  tgtgctctgg  cggcggcggc | 120 |
| agcggaggcg | cgggctccca | ggtgcagctg | cagcagagcg  ccccggcct  ggtgaagcct | 180 |
| agccagacac | tgtccctgac | ctgcgcaatc | tccggcgaca  cgtgtccgg  aaacagggcc | 240 |
| acatggaatt | ggatcagaca | gtctccaagc | aggggcctgg  agtggctggg  aaggacctac | 300 |
| tatcggtccg | cctggtacaa | cgactatgcc | gtgtctgtga  agggccgcat  acattcaac | 360 |
| ccagatacca | gcaagaatca | gttttccctg | cagctgaatt  ctgtgacacc  cgaggatacc | 420 |
| gccgtgtact | attgcgccag | aggcgagagc | ggagcagcag  cagacgcctt  cgatatctgg | 480 |
| ggccagggca | ccacagtgac | agtgagcgga | ggaggaggat  ccggcggagg  aggctctggc | 540 |
| ggcggcggca | gcgacatcca | gctgacccag | agcccacctt  ccctgtctgc  cagcgtgggc | 600 |
| gatcgcgtga | caatcacctg | tcgggcctcc | cagtctatca  gctcctacct  gaactggtat | 660 |
| cagcagaagc | caggcaaggc | ccccaagctg | ctgatctacg  cagcatctag  cctgcagtct | 720 |
| ggagtgccaa | gcagattcag | cggatccgga | ttcggcacag  actttacact  gaccatctcc | 780 |
| tctctgcagc | ccgaggattt | cgccacctac | tattgccagc  agtcttatag  cacacctcag | 840 |
| acctttggcc | agggcaccaa | ggtggacatc | aagggaagtg  aggaggagg  aagttgtccc | 900 |
| tactcaaacc | catctctgtg | ctcaggagga | ggaggaagtg  aactgcctac  tcagggaaca | 960 |
| ttcagcaacg | tgtccaccaa | tgtgagccca | gcaaagccta  ccacaaccgc  atgcccatac | 1020 |
| tctaacccca | gcctgtgcac | aaccacacca | gcacccaggc  cccctacccc  tgcaccaaca | 1080 |
| atcgcctccc | agcctctgtc | tctgcggcca | gaggcctgca  gacccgccgc  cggcggagca | 1140 |
| gtgcacacac | ggggcctgga | cttttgcctgt | gatatctata  tctgggcacc  actggccgga | 1200 |
| acatgtggcg | tgctgctgct | gtcactggtc | attacactgt  actgtaagcg  aggccggaag | 1260 |
| aaaactgctgt | atattttcaa | acagccctt | atgagacctg  tgcagactac  ccaggaggaa | 1320 |
| gacggctgca | gctgtaggtt | ccccgaggaa | gaggaaggcg  ggtgtgagct  gagggtcaag | 1380 |
| tttagccgct | ccgcagatgc | ccctgcttac | cagcagggc  agaatcagct  gtataacgag | 1440 |
| ctgaatctgg | gacggagaga | ggaatacgac | gtgctggata  aaaggcgcgg  gagagacccc | 1500 |
| gaaatgggag | gcaagccacg | acggaaaaac | ccccaggagg  gcctgtacaa  tgaactgcag | 1560 |
| aaggacaaaa | tggcagaggc | ctatagtgaa | atcgggatga  agggagagag  aaggcgcggc | 1620 |
| aaagggcacg | atggcctgta | ccaggggctg | tctactgcca  ccaaggacac  ctatgatgct | 1680 |
| ctgcatatgc | aggcactgcc | tccaaggtga | | 1710 |

<210> SEQ ID NO 41
<211> LENGTH: 1710
<212> TYPE: DNA
<213> ORGANISM: artificial sequence
<220> FEATURE:
<223> OTHER INFORMATION: 10QR3

<400> SEQUENCE: 41

| | | | |
|---|---|---|---|
| atggctctgc | ccgtcaccgc | tctgctgctg | ccactggccc  tgctgctgca  cgccgccaga | 60 |
| cccggcggag | gaggctcttg | cccctacagc | aaccccagcc  tgtgctctgg  cggcggcggc | 120 |
| agcggaggcg | cgggctccca | ggtgcagctg | gtgcagagcg  agcagaggt  gaagaagcct | 180 |
| ggcgccagct | gaaggtgtc | ctgcaaggcc | tctggctaca  cattcaccag  ctactatatg | 240 |
| cactgggtgc | ggcaggcccc | tggccagggc | ctggagtgga  tgggcatcat  caacccatcc | 300 |

| | |
|---|---|
| ggcggctcca cctcttacgc ccagaagttt cagggcagag tgacaatgac cagggacaca | 360 |
| agcacctcca cagtgtatat ggagctgagc tccctgagat ccgaggatac agccgtgtac | 420 |
| tattgcgcca gggaggactc tggaagcgga gccttcgata tctggggcca gggcaccctg | 480 |
| gtgacagtgt ctggaggagg aggaagcgga ggaggaggat ccggcggcgg cggctctgag | 540 |
| atcgtgctga cccagtctcc actgagcctg ccagtgacac ctggcgagcc agcctccatc | 600 |
| tcttgtcgct ctagccggtc cctgctgtct taccacggct acaattatct ggactggtat | 660 |
| ctgcagaagc caggccagag cccccagctg ctgatcttcg tgggatccaa cagggcccct | 720 |
| ggcgtgcctg accggttcag cggatccgga tctggaaccg acttcaccct gaacatctct | 780 |
| agagtggagg ccgaggatgt gggcgtgtac tattgcatgc agagcctgca gacccccaaga | 840 |
| acatttggcc agggcaccaa ggtggagatc aagggaagcg gcggaggcgg aagttgtccc | 900 |
| tactcaaacc caagtctgtg ctcaggagga ggaggaagcg aactgcctac tcagggaaca | 960 |
| ttcagcaacg tgtccaccaa tgtgagccca gcaaagccta ccacaaccgc atgcccatac | 1020 |
| tctaaccca gcctgtgcac aaccacacca gcacccaggc ccctaccccc tgcaccaaca | 1080 |
| atcgcctccc agcctctgtc tctgcggcca gaggcctgca gacccgccgc cggcggagca | 1140 |
| gtgcacacac ggggcctgga ctttgcctgt gatatctata tctgggcacc actggccgga | 1200 |
| acatgcggag tcctgctgct gtcactggtc attacactgt actgtaagcg aggccggaag | 1260 |
| aaactgctgt atattttcaa acagcccttt atgagacctg tgcagactac ccaggaggaa | 1320 |
| gacggctgca gctgtaggtt ccccgaggaa gaggaaggcg ggtgtgagct gagggtcaag | 1380 |
| tttagccgct ccgcagatgc ccctgcttac cagcaggggc agaatcagct gtataacgag | 1440 |
| ctgaatctgg gacggagaga ggaatacgac gtgctggata aaaggcgcgg gagagacccc | 1500 |
| gaaatgggag gcaagccacg acggaaaaac ccccaggagg gcctgtacaa tgaactgcag | 1560 |
| aaggacaaaa tggcagaggc ctatagtgaa atcgggatga agggagagag aaggcgcggc | 1620 |
| aaagggcacg atggcctgta ccaggggctg tctactgcca ccaaggacac ctatgatgct | 1680 |
| ctgcatatgc aggcactgcc tccaaggtga | 1710 |

<210> SEQ ID NO 42
<211> LENGTH: 1587
<212> TYPE: DNA
<213> ORGANISM: artificial sequence
<220> FEATURE:
<223> OTHER INFORMATION: CAR 4 R2

<400> SEQUENCE: 42

| | |
|---|---|
| atggctctgc ccgtcaccgc tctgctgctg ccctggccc tgctgctgca cgccgcccgg | 60 |
| cctcaggtgc agctgcagca gagcggccct ggcctggtgg agccaagcca gacactgtcc | 120 |
| ctgacctgcg ccatctctgg cgacagcgtg agctccaaca gcgccgcatg gaattggatc | 180 |
| aggcagtccc catctcgggg cctggagtgg ctgggcagaa catactatag gtccaccctgg | 240 |
| tacaacgact atgccggctc cgtgaagtct cgcatcacaa tcaaccccga taccagcaag | 300 |
| aatcagttct ccctgcagct gacatctgtg accctgagg acacagccgt gtactattgc | 360 |
| accagaagca ggcacaatac atttcgggga atggacgtgt ggggacaggg cacactggtg | 420 |
| accgtgagcg gaggaggagg atccggcgga ggaggctctg gcggcggcgg cagcgacatc | 480 |
| cagctgaccc agtcccttc tagcctgagc gcctccgtgg gcgatagagt gacaatcacc | 540 |
| tgtagggcct ctcagagcat ctcctcttac ctgaactggt atcagcagaa gcccggcaag | 600 |
| gcccctaagc tgctgatcta cgcagcaagc tccctgcagt ctggagtgcc aagcagattc | 660 |

```
tccggctctg gcagcggcac cgactttaca ctgaccatct ctagcctgca gcctgaggat      720
ttcgccacat actattgcca gcagtcctat tctacaccac tgacctttgg cggcggcacc      780
aaggtggaga tcaagtctga ccccggaagt ggcggcggcg aagttgccc ttattcaaat       840 ccatccctgt gctctggcgg cggaggaagt tgtcccttata gcaacccag cctgtgctcc      900 ggaggaggag gcagcaccac aaccccagca cccaggcccc ctacacctgc accaaccatc     960
gcctctcagc cactgagcct gcggcctgag gcctgcagac cagccgccgg cggagcagtg    1020
cacacacggg gcctggactt cgcctgtgat atctacatct gggcaccact ggccggaaca    1080
tgtggcgtgt gctgctgtc actggtcatt acactgtact gtaagcgagg ccggaagaaa     1140
ctgctgtata ttttcaaaca gccctttatg agacctgtgc agactaccca ggaggaagac    1200
ggctgcagct gtaggttccc cgaggaagag gaaggcgggt gtgagctgag ggtcaagttt    1260
agccgctccg cagatgcccc tgcttaccag caggggcaga atcagctgta taacgagctg    1320
aatctgggac ggagagagga atacgacgtg ctggataaaa ggcgcgggag agaccccgaa    1380
atgggaggca agccacgacg gaaaaacccc caggagggcc tgtacaatga actgcagaag    1440
gacaaaatgg cagaggccta tagtgaaatc gggatgaagg gagagagaag gcgcggcaaa    1500
gggcacgatg gcctgtacca ggggctgtct actgccacca aggacaccta tgatgctctg    1560
catatgcagg cactgcctcc aaggtga                                        1587
```

<210> SEQ ID NO 43
<211> LENGTH: 1605
<212> TYPE: DNA
<213> ORGANISM: artificial sequence
<220> FEATURE:
<223> OTHER INFORMATION: CAR7_R2

<400> SEQUENCE: 43

```
atggctctgc ccgtcaccgc tctgctgctg cccctggccc tgctgctgca cgccgcccgg       60
cctcaggtgc agctgcagca gagcggccct ggcctggtgc agccatccca gacactgtct      120
ctgacctgcg tgatcagcgg cgactccgtg agctccaact ctgccacatg gaattggatc      180
agacagagcc catccagggg cctggagtgg ctggacgca cctactatcg gagcaagtgg       240
tacaacgact atgccgtgtc tgtgaagagc agaatcacaa tcaacccga tacctctaag       300 aatcagttca gcctgcagct gaattccgtg acacctgagg ataccgccgt gtactattgc      360
gccagggacg gcgatggagg aagctactat gactactatt actatggcat ggacgtgtgg      420
ggccagggca ccacagtgac agtgtctgga ggaggaggaa gcggaggagg aggatccggc      480
ggcggcggct ctgacatcca gctgacacag tcccccttcta gcctgtctac cagcgtgggc     540
gatcgcgtga caatcacctg tcgggcctcc cagtctatca gcacctacct gaactggtat      600
cagcagaagc ccggcaaggc ccctaagctg ctgatctacg cagcaagcaa tctgcagtcc      660
ggagtgccat ctcgcttctc cggctctggc agcggcacag actttacact gaccatctcc      720
tctctgcagc ctgaggattt cgccacctac ttttgccagc agtcctatac cacaccaatc      780
acattcggcc agggcaccag actggagatc aagagcgacc ccggcagtgg aggaggaggc     840
tcttgtccct actctaaccc atctctgtgc agtggcggag gaggctcttg cccttattcc      900
aaccccagcc tgtgctccgg aggaggagc agcaccacaa ccccagcacc caggcccct       960 acacctgcac caaccatcgc ctctcagcca ctgagcctgc ggcctgaggc ctgcagacca    1020
gccgccggcg gagcagtgca cacacggggc ctggacttcg cctgtgatat ctacatctgg    1080
```

-continued

```
gcaccactgg ccggaacatg tggcgtgctg ctgctgtcac tggtcattac actgtactgt    1140
aagcgaggcc ggaagaaact gctgtatatt ttcaaacagc cctttatgag acctgtgcag    1200
actacccagg aggaagacgg ctgcagctgt aggttccccg aggaagagga aggcgggtgt    1260
gagctgaggg tcaagtttag ccgctccgca gatgcccctg cttaccagca ggggcagaat    1320
cagctgtata cgagctgaa tctgggacgg agagaggaat acgacgtgct ggataaaagg    1380
cgcgggagag accccgaaat gggaggcaag ccacgacgga aaaccccca ggagggcctg    1440 tacaatgaac tgcagaagga caaaatggca gaggcctata gtgaaatcgg gatgaaggga    1500
gagagaaggc gcggcaaagg gcacgatggc ctgtaccagg ggctgtctac tgccaccaag    1560
gacacctatg atgctctgca tatgcaggca ctgcctccaa ggtga                    1605
```

<210> SEQ ID NO 44
<211> LENGTH: 1590
<212> TYPE: DNA
<213> ORGANISM: artificial sequence
<220> FEATURE:
<223> OTHER INFORMATION: CAR9 R2

<400> SEQUENCE: 44

```
atggctctgc ccgtcaccgc tctgctgctg cccctggccc tgctgctgca cgccgcccgg      60
cctcaggtgc agctgcagca gagcggcccc ggcctggtga agcctagcca gacactgtcc     120
ctgacctgcg caatctccgg cgacagcgtg tccggaaaca gggccacatg gaattggatc     180
agacagtctc caagcagggg cctggagtgg ctgggaagga cctactatcg gtccgcctgg     240
tacaacgact atgccgtgtc tgtgaagggc cgcatcacat tcaacccaga taccagcaag     300
aatcagtttt ccctgcagct gaattctgtg acacccgagg ataccgccgt gtactattgc     360
gccagaggcg agagcggagc agcagcagac gccttcgata tctggggcca gggcaccaca     420
gtgacagtga gcggaggagg aggatccggc ggaggaggct ctggcggcgg cggcagcgac     480
atccagctga cccagagccc accttccctg tctgccagcg tgggcgatcg cgtgacaatc     540
acctgtcggg cctcccagtc tatcagctcc tacctgaact ggtatcagca gaagccaggc     600
aaggccccca gctgctgat ctacgcagca tctagcctgc agtctggagt gccaagcaga     660
ttcagcggat ccggattcgg cacagacttt acactgacca tctcctctct gcagcccgag     720
gatttcgcca cctactattg ccagcagtct tatagcacac ctcagacctt tggccagggc     780
accaaggtgg acatcaagag cgaccccgga agcggaggag aggaagttg tccctactca     840 aaccctagcc tgtgtagcgg cggcggagga tcttgtccct attctaaccc cagcctgtgc    900
tccggaggag gaggcagcac cacaaccca gcacccaggc ccctacacc tgcaccaacc    960 atcgcctctc agccactgag cctgcggcct gaggcctgca gaccagccgc cggcggagca    1020
gtgcacacac ggggcctgga cttcgcctgt gatatctaca tctgggcacc actggctgga    1080
acatgcggga tgctgctgct gtcactggtc attacactgt actgtaagcg aggccggaag    1140
aaactgctgt atattttcaa acagcccttt atgagacctg tgcagactac ccaggaggaa    1200
gacggctgca gctgtaggtt ccccgaggaa gaggaaggcg ggtgtgagct gagggtcaag    1260
tttagccgct ccgcagatgc ccctgcttac cagcaggggc agaatcagct gtataacgag    1320
ctgaatctgg gacggagaga ggaatacgac gtgctggata aaaggcgcgg gagagacccc    1380
gaaatgggag gcaagccacg acggaaaaac ccccaggagg gcctgtacaa tgaactgcag    1440
aaggacaaaa tggcagaggc ctatagtgaa atcgggatga agggagagag aaggcgcggc    1500
aaagggcacg atggcctgta ccaggggctg tctactgcca ccaaggacac ctatgatgct    1560
```

```
ctgcatatgc aggcactgcc tccaaggtga                                  1590
```

<210> SEQ ID NO 45
<211> LENGTH: 1590
<212> TYPE: DNA
<213> ORGANISM: artificial sequence
<220> FEATURE:
<223> OTHER INFORMATION: CAR10R2

<400> SEQUENCE: 45

```
atggctctgc ccgtcaccgc tctgctgctg cccctggccc tgctgctgca cgccgcccgg    60
cctcaggtgc agctggtgca gagcggagca gaggtgaaga gcctggcgc cagcgtgaag   120
gtgtcctgca aggcctctgg ctacacattc accagctact atatgcactg ggtgcggcag   180
gcccctggcc agggcctgga gtggatgggc atcatcaacc catccggcgg ctccacctct   240
tacgcccaga gtttcagggg cagagtgaca atgaccaggg acacaagcac ctccacagtg   300
tatatggagc tgagctccct gagatccgag gatacagccg tgtactattg cgccagggag   360
gactctggaa gcggagcctt cgatatctgg ggccagggca cctggtgac agtgtctgga   420
ggaggaggaa gcggaggagg aggatccggc ggcggcggct ctgagatcgt gctgacccag   480
tctccactga gcctgccagt gacacctggc gagccagcct ccatctcttg tcgctctagc   540
cggtccctgc tgtcttacca cggctacaat tatctggact ggtatctgca gaagccaggc   600
cagagccccc agctgctgat cttcgtggga tccaacaggg ccctggcgt gcctgaccgg   660
ttcagcggat ccggatctgg aaccgacttc accctgaaca tctctagagt ggaggccgag   720
gatgtgggcg tgtactattg catgcagagc ctgcagaccc aagaacatt tggccagggc   780
accaaggtgg agatcaagag cgaccccgga agcggcggag gaggaagttg tccctattct   840
aacccatctc tgtgcagcgg cggcggagga agttgtcctt attcaaaccc cagcctgtgc   900
tccgaggag gaggcagcac cacaaccccca gcacccaggc cccctacacc tgcaccaacc   960
atcgcctctc agccactgag cctgcggcct gaggcctgca gaccagccgc cggcggagca  1020
gtgcacacac ggggcctgga cttcgcctgt gatatctaca tctgggcacc actggctgga  1080
acatgcggcg tgctgctgct gtcactggtc attacactgt actgtaagcg aggccggaag  1140
aaactgctgt atatttttcaa acagcccttt atgagacctg tgcagactac ccaggaggaa  1200
gacggctgca gctgtaggtt cccccgaggaa gaggaaggcg gtgtgagct gagggtcaag  1260
tttagccgct ccgcagatgc ccctgcttac cagcagggc agaatcagct gtataacgag  1320
ctgaatctgg acggagaga ggaatacgac gtgctggata aaaggcgcgg gagagacccc  1380
gaaatgggag gcaagccacg acggaaaaac ccccaggagg gcctgtacaa tgaactgcag  1440
aaggacaaaa tggcagaggc ctatagtgaa atcgggatga aggagagag aaggcgcggc  1500
aaagggcacg atggcctgta ccagggctg tctactgcca ccaaggacac ctatgatgct  1560
ctgcatatgc aggcactgcc tccaaggtga                                  1590
```

<210> SEQ ID NO 46
<211> LENGTH: 487
<212> TYPE: PRT
<213> ORGANISM: artificial sequence
<220> FEATURE:
<223> OTHER INFORMATION: CAR 1

<400> SEQUENCE: 46

```
Met Ala Leu Pro Val Thr Ala Leu Leu Leu Pro Leu Ala Leu Leu Leu
1               5                   10                  15
```

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
            35                  40                  45

Ser Val Ser Ser Asn Ser Ala Ala Trp Asn Trp Ile Arg Gln Ser Pro
    50                  55                  60

Ser Arg Gly Leu Glu Trp Leu Gly Arg Thr Tyr Tyr Arg Ser Thr Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Glu Val Ser Gly Thr Ser
            115                 120                 125

Ala Phe Asp Ile Trp Gly Gln Gly Thr Met Val Thr Val Ser Gly Gly
130                 135                 140

Gly Gly Ser Gly Gly Gly Gly Ser Gly Gly Gly Ser Asp Ile Gln
145                 150                 155                 160

Met Thr Gln Ser Pro Ser Ser Leu Ser Ala Ser Val Gly Asp Arg Val
            165                 170                 175

Thr Ile Thr Cys Arg Ala Ser Gln Ser Ile Ser Ser Tyr Leu Asn Trp
            180                 185                 190

Tyr Gln Gln Lys Pro Gly Lys Ala Pro Lys Leu Leu Ile Tyr Ala Ala
            195                 200                 205

Ser Ser Leu Gln Ser Gly Val Pro Ser Arg Phe Ser Gly Ser Gly Ser
    210                 215                 220

Gly Thr Asp Phe Thr Leu Thr Ile Ser Ser Leu Gln Pro Glu Asp Phe
225                 230                 235                 240

Ala Thr Tyr Tyr Cys Gln Gln Ser Tyr Ser Thr Pro Leu Thr Phe Gly
                245                 250                 255

Gly Gly Thr Lys Leu Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
            275                 280                 285

Glu Ala Cys Arg Pro Ala Ala Gly Gly Ala Val His Thr Arg Gly Leu
            290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

```
Leu Tyr Asn Glu Leu Gln Lys Asp Lys Met Ala Glu Ala Tyr Ser Glu
            435                 440                 445

Ile Gly Met Lys Gly Glu Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 47
<211> LENGTH: 492
<212> TYPE: PRT
<213> ORGANISM: artificial sequence
<220> FEATURE:
<223> OTHER INFORMATION: CAR 2

<400> SEQUENCE: 47

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
        35                  40                  45

Ser Val Ser Ser Asn Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Ala Ser Met Thr Gly Gly
        115                 120                 125

Tyr Ser Tyr Gly Asp Ala Phe Asp Ile Trp Gly Gln Gly Thr Leu Val
    130                 135                 140

Thr Val Ser Gly Gly Gly Ser Gly Gly Gly Ser Gly Gly Gly
145                 150                 155                 160

Gly Ser Ala Ile Arg Met Thr Gln Ser Pro Ser Ser Leu Ser Ala Ser
                165                 170                 175

Val Gly Asp Arg Val Thr Ile Thr Cys Arg Ala Ser Gln Ser Ile Ser
            180                 185                 190

Ser Tyr Leu Asn Trp Tyr Gln Gln Lys Pro Gly Lys Ala Pro Lys Leu
        195                 200                 205

Leu Ile Tyr Ala Ala Ser Ser Leu Gln Ser Gly Val Pro Ser Arg Phe
    210                 215                 220

Ser Gly Ser Gly Ser Gly Thr Asp Phe Ser Leu Thr Ile Ser Ser Leu
225                 230                 235                 240

Gln Pro Glu Asp Ser Ala Thr Tyr Tyr Cys Gln Gln Thr Tyr Ser Thr
                245                 250                 255

Pro Leu Thr Phe Gly Gln Gly Thr Lys Val Glu Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300
```

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
            325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
            405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
            485                 490

<210> SEQ ID NO 48
<211> LENGTH: 488
<212> TYPE: PRT
<213> ORGANISM: artificial sequence
<220> FEATURE:
<223> OTHER INFORMATION: CAR 3

<400> SEQUENCE: 48

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Glu Pro Ser Gln Thr Leu Ser Leu Thr Cys Ala Ile Ser Gly Asp
            35                  40                  45

Ser Val Ser Ser Asp Ser Val Ala Trp Asn Trp Ile Arg Gln Ser Pro
        50                  55                  60

Ser Arg Gly Leu Glu Trp Leu Gly Arg Thr Tyr Tyr Arg Ser Thr Trp
65                  70                  75                  80

Tyr Asn Asp Tyr Ala Gly Ser Val Lys Ser Arg Ile Thr Ile Asn Pro
            85                  90                  95

Asp Thr Ser Lys Asn Gln Phe Ser Leu Gln Leu Thr Ser Val Thr Pro
            100                 105                 110

Glu Asp Thr Ala Val Tyr Tyr Cys Thr Arg Ser Arg His Asn Thr Phe
            115                 120                 125

Arg Gly Met Asp Val Trp Gly Gln Gly Thr Thr Val Thr Val Ser Gly
            130                 135                 140

Gly Gly Gly Ser Gly Gly Gly Gly Ser Gly Gly Gly Gly Ser Asp Ile
145                 150                 155                 160

Val Met Thr Gln Ser Pro Ser Ser Leu Ser Ala Ser Val Gly Asp Arg
            165                 170                 175

Val Thr Ile Thr Cys Arg Ala Ser Gln Thr Ile Ser Ser Tyr Leu Asn
            180                 185                 190

Trp Tyr Gln Gln Lys Pro Gly Lys Ala Pro Lys Leu Leu Ile Tyr Asp
        195                 200                 205

Ala Ser Ser Leu Gln Ser Gly Val Pro Ser Arg Phe Ser Gly Ser Gly
    210                 215                 220

Ser Gly Thr Asp Phe Thr Leu Thr Ile Asn Ser Leu Gln Pro Glu Asp
225                 230                 235                 240

Phe Ala Thr Tyr Tyr Cys Gln Gln Ser Tyr Thr Thr Pro Ile Thr Phe
                245                 250                 255

Gly Gln Gly Thr Arg Leu Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 49
<211> LENGTH: 488
<212> TYPE: PRT
<213> ORGANISM: artificial sequence
<220> FEATURE:
<223> OTHER INFORMATION: CAR 4

<400> SEQUENCE: 49

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Glu Pro Ser Gln Thr Leu Ser Leu Thr Cys Ala Ile Ser Gly Asp
        35                  40                  45

```
Ser Val Ser Ser Asn Ser Ala Ala Trp Asn Trp Ile Arg Gln Ser Pro
    50              55                  60
Ser Arg Gly Leu Glu Trp Leu Gly Arg Thr Tyr Tyr Arg Ser Thr Trp
65              70                  75                  80
Tyr Asn Asp Tyr Ala Gly Ser Val Lys Ser Arg Ile Thr Ile Asn Pro
                85                  90                  95
Asp Thr Ser Lys Asn Gln Phe Ser Leu Gln Leu Thr Ser Val Thr Pro
                100                 105                 110
Glu Asp Thr Ala Val Tyr Tyr Cys Thr Arg Ser Arg His Asn Thr Phe
            115                 120                 125
Arg Gly Met Asp Val Trp Gly Gln Gly Thr Leu Val Thr Val Ser Gly
    130                 135                 140
Gly Gly Gly Ser Gly Gly Gly Ser Gly Gly Gly Ser Asp Ile
145             150                 155                 160
Gln Leu Thr Gln Ser Pro Ser Ser Leu Ser Ala Ser Val Gly Asp Arg
                165                 170                 175
Val Thr Ile Thr Cys Arg Ala Ser Gln Ser Ile Ser Ser Tyr Leu Asn
            180                 185                 190
Trp Tyr Gln Gln Lys Pro Gly Lys Ala Pro Lys Leu Leu Ile Tyr Ala
    195                 200                 205
Ala Ser Ser Leu Gln Ser Gly Val Pro Ser Arg Phe Ser Gly Ser Gly
210                 215                 220
Ser Gly Thr Asp Phe Thr Leu Thr Ile Ser Ser Leu Gln Pro Glu Asp
225             230                 235                 240
Phe Ala Thr Tyr Tyr Cys Gln Gln Ser Tyr Ser Thr Pro Leu Thr Phe
                245                 250                 255
Gly Gly Gly Thr Lys Val Glu Ile Lys Thr Thr Thr Pro Ala Pro Arg
            260                 265                 270
Pro Pro Thr Pro Ala Pro Thr Ile Ala Ser Gln Pro Leu Ser Leu Arg
    275                 280                 285
Pro Glu Ala Cys Arg Pro Ala Ala Gly Gly Ala Val His Thr Arg Gly
290                 295                 300
Leu Asp Phe Ala Cys Asp Ile Tyr Ile Trp Ala Pro Leu Ala Gly Thr
305             310                 315                 320
Cys Gly Val Leu Leu Leu Ser Leu Val Ile Thr Leu Tyr Cys Lys Arg
                325                 330                 335
Gly Arg Lys Lys Leu Leu Tyr Ile Phe Lys Gln Pro Phe Met Arg Pro
            340                 345                 350
Val Gln Thr Thr Gln Glu Glu Asp Gly Cys Ser Cys Arg Phe Pro Glu
    355                 360                 365
Glu Glu Glu Gly Gly Cys Glu Leu Arg Val Lys Phe Ser Arg Ser Ala
370                 375                 380
Asp Ala Pro Ala Tyr Gln Gln Gly Gln Asn Gln Leu Tyr Asn Glu Leu
385             390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
    435                 440                 445
Glu Ile Gly Met Lys Gly Glu Arg Arg Arg Gly Lys Gly His Asp Gly
450                 455                 460
Leu Tyr Gln Gly Leu Ser Thr Ala Thr Lys Asp Thr Tyr Asp Ala Leu
```

His Met Gln Ala Leu Pro Pro Arg
                485

<210> SEQ ID NO 50
<211> LENGTH: 484
<212> TYPE: PRT
<213> ORGANISM: artificial sequence
<220> FEATURE:
<223> OTHER INFORMATION: CAR 5

<400> SEQUENCE: 50

Met Ala Leu Pro Val Thr Ala Leu Leu Pro Leu Ala Leu Leu Leu
1               5                   10                  15

His Ala Ala Arg Pro Gln Val Gln Leu Gln Gln Ser Gly Pro Gly Leu
                20                  25                  30

Val Glu Pro Ser Gln Thr Leu Ser Leu Thr Cys Ala Ile Ser Gly Asp
            35                  40                  45

Ser Val Ser Ser Asp Ser Val Ala Trp Asn Trp Ile Arg Gln Ser Pro
    50                  55                  60

Ser Arg Gly Leu Glu Trp Leu Gly Arg Thr Tyr Tyr Arg Ser Thr Trp
65                  70                  75                  80

Tyr Asn Asp Tyr Ala Gly Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Asp Arg Asn Gly Met Asp
        115                 120                 125

Val Trp Gly Gln Gly Thr Met Val Thr Val Ser Gly Gly Gly Gly Ser
130                 135                 140

Gly Gly Gly Gly Ser Gly Gly Gly Ser Asp Ile Val Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Asp Ala Ser Asn Leu
        195                 200                 205

Glu Thr Gly Val Pro Ser Arg Phe Ser Gly Ser Gly Ser Gly Thr Asp
    210                 215                 220

Phe Thr Phe Thr Ile Thr Ser Leu Gln Pro Glu Asp Phe Ala Thr Tyr
225                 230                 235                 240

Tyr Cys Gln Gln Ser Tyr Thr Thr Pro Leu Thr Phe Gly Gly Gly Thr
                245                 250                 255

Lys Val Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr

```
            340                 345                 350
Gln Glu Glu Asp Gly Cys Ser Cys Arg Phe Pro Glu Glu Glu Glu Gly
            355                 360                 365

Gly Cys Glu Leu Arg Val Lys Phe Ser Arg Ser Ala Asp Ala Pro Ala
        370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
        450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 51
<211> LENGTH: 487
<212> TYPE: PRT
<213> ORGANISM: artificial sequence
<220> FEATURE:
<223> OTHER INFORMATION: CAR 6-8

<400> SEQUENCE: 51

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
        35                  40                  45

Ser Val Ser Ser Ser Ala Ala Trp Asn Trp Ile Arg Gln Ser Pro
50                  55                  60

Ser Arg Gly Leu Glu Trp Leu Gly Arg Thr Tyr Tyr Arg Ser Ala Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Glu Ser Val Leu Leu Asp
        115                 120                 125

Gly Met Asp Val Trp Gly Arg Gly Thr Thr Val Thr Val Ser Gly Gly
130                 135                 140

Gly Gly Ser Gly Gly Gly Gly Ser Gly Gly Gly Gly Ser Ala Ile Arg
145                 150                 155                 160

Met Thr Gln Ser Pro Ser Thr Leu Ser Ala Ser Val Gly Asp Arg Val
                165                 170                 175

Thr Ile Thr Cys Arg Ala Ser Gln Ser Ile Ser Thr Tyr Leu Asn Trp
            180                 185                 190

Tyr Gln Gln Lys Ala Gly Lys Ala Pro Arg Leu Leu Ile His Asp Ala
        195                 200                 205

Ser Ser Leu Gln Ser Gly Val Pro Ser Arg Phe Ser Gly Ser Gly Ser
210                 215                 220
```

Gly Thr Asp Phe Thr Leu Thr Ile Ser Ser Leu Gln Pro Glu Asp Phe
225                 230                 235                 240

Ala Thr Tyr Tyr Cys Gln Gln Ser Tyr Ser Thr Pro Leu Thr Phe Gly
            245                 250                 255

Gly Gly Thr Lys Val Glu Ile Lys Thr Thr Pro Ala Pro Arg Pro
        260                 265                 270

Pro Thr Pro Ala Pro Thr Ile Ala Ser Gln Pro Leu Ser Leu Arg Pro
    275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
            325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 52
<211> LENGTH: 494
<212> TYPE: PRT
<213> ORGANISM: artificial sequence
<220> FEATURE:
<223> OTHER INFORMATION: CAR 7 9

<400> SEQUENCE: 52

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Gln Pro Ser Gln Thr Leu Ser Leu Thr Cys Val Ile Ser Gly Asp
        35                  40                  45

Ser Val Ser Ser Asn Ser Ala Thr Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Asp Gly Asp Gly Gly Ser
        115                 120                 125

Tyr Tyr Asp Tyr Tyr Tyr Gly Met Asp Val Trp Gly Gln Gly Thr
    130                 135                 140

Thr Val Thr Val Ser Gly Gly Gly Ser Gly Gly Gly Ser Gly
145                 150                 155                 160

Gly Gly Gly Ser Asp Ile Gln Leu Thr Gln Ser Pro Ser Ser Leu Ser
            165                 170                 175

Thr Ser Val Gly Asp Arg Val Thr Ile Thr Cys Arg Ala Ser Gln Ser
        180                 185                 190

Ile Ser Thr Tyr Leu Asn Trp Tyr Gln Gln Lys Pro Gly Lys Ala Pro
    195                 200                 205

Lys Leu Leu Ile Tyr Ala Ala Ser Asn Leu Gln Ser Gly Val Pro Ser
210                 215                 220

Arg Phe Ser Gly Ser Gly Ser Gly Thr Asp Phe Thr Leu Thr Ile Ser
225                 230                 235                 240

Ser Leu Gln Pro Glu Asp Phe Ala Thr Tyr Phe Cys Gln Gln Ser Tyr
            245                 250                 255

Thr Thr Pro Ile Thr Phe Gly Gln Gly Thr Arg Leu Glu Ile Lys Thr
        260                 265                 270

Thr Thr Pro Ala Pro Arg Pro Pro Thr Pro Ala Pro Thr Ile Ala Ser
    275                 280                 285

Gln Pro Leu Ser Leu Arg Pro Glu Ala Cys Arg Pro Ala Ala Gly Gly
290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
            325                 330                 335

Thr Leu Tyr Cys Lys Arg Gly Arg Lys Lys Leu Leu Tyr Ile Phe Lys
        340                 345                 350

Gln Pro Phe Met Arg Pro Val Gln Thr Thr Gln Glu Glu Asp Gly Cys
    355                 360                 365

Ser Cys Arg Phe Pro Glu Glu Glu Gly Gly Cys Glu Leu Arg Val
370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
    435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490

<210> SEQ ID NO 53
<211> LENGTH: 484

```
<212> TYPE: PRT
<213> ORGANISM: artificial sequence
<220> FEATURE:
<223> OTHER INFORMATION: CAR 8 12

<400> SEQUENCE: 53
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |
| His | Ala | Ala | Arg | Pro | Gln | Val | Gln | Leu | Gln | Gln | Ser | Gly | Pro | Gly | Leu |
| | | | 20 | | | | | 25 | | | | | 30 | | |
| Val | Lys | Pro | Ser | Gln | Thr | Leu | Ser | Leu | Thr | Cys | Ala | Ile | Ser | Gly | Asp |
| | | 35 | | | | | 40 | | | | | 45 | | | |
| Ser | Val | Ser | Ser | Asn | Ser | Ala | Ala | Trp | Asn | Trp | Ile | Arg | Gln | Ser | Pro |
| 50 | | | | | 55 | | | | | 60 | | | | | |
| Ser | Arg | Gly | Leu | Glu | Trp | Leu | Gly | Arg | Thr | Tyr | Tyr | Arg | Ser | Ala | Trp |
| 65 | | | | 70 | | | | | 75 | | | | | 80 | |
| Tyr | Asn | Asp | Tyr | Ala | Val | Ser | Val | Lys | Ser | Arg | Ile | Thr | Ile | Asn | Pro |
| | | | | 85 | | | | | 90 | | | | | 95 | |
| Asp | Thr | Ser | Lys | Asn | Gln | Phe | Ser | Leu | Gln | Leu | Ser | Ser | Val | Thr | Pro |
| | | | 100 | | | | | 105 | | | | | 110 | | |
| Glu | Asp | Thr | Ala | Val | Tyr | Tyr | Cys | Ala | Arg | Asp | Val | Glu | Gly | Phe | Asp |
| | 115 | | | | | 120 | | | | | 125 | | | | |
| Tyr | Trp | Gly | Gln | Gly | Thr | Leu | Val | Thr | Val | Ser | Gly | Gly | Gly | Gly | Ser |
| 130 | | | | | 135 | | | | | 140 | | | | | |
| Gly | Gly | Gly | Gly | Ser | Gly | Gly | Gly | Ser | Asp | Ile | Val | Met | Thr | Gln | |
| 145 | | | | | 150 | | | | | 155 | | | | | 160 |
| Thr | Pro | Ser | Ser | Leu | Ser | Ala | Ser | Val | Gly | Asp | Arg | Val | Thr | Ile | Thr |
| | | | | 165 | | | | | 170 | | | | | 175 | |
| Cys | Arg | Ala | Ser | Gln | Ser | Ile | Ser | Ser | Tyr | Leu | Asn | Trp | Tyr | Gln | Gln |
| | | | 180 | | | | | 185 | | | | | 190 | | |
| Lys | Pro | Gly | Lys | Ala | Pro | Lys | Leu | Leu | Ile | Tyr | Ala | Ala | Ser | Ser | Leu |
| | | 195 | | | | | 200 | | | | | 205 | | | |
| Gln | Ser | Gly | Val | Pro | Ser | Arg | Phe | Ser | Gly | Ser | Gly | Ser | Gly | Thr | Asp |
| 210 | | | | | 215 | | | | | 220 | | | | | |
| Phe | Thr | Leu | Thr | Ile | Ser | Ser | Leu | Gln | Pro | Glu | Asp | Phe | Ala | Thr | Tyr |
| 225 | | | | | 230 | | | | | 235 | | | | | 240 |
| Tyr | Cys | Gln | Gln | Ser | Tyr | Ser | Thr | Pro | Ile | Thr | Phe | Gly | Gln | Gly | Thr |
| | | | | 245 | | | | | 250 | | | | | 255 | |
| Arg | Leu | Glu | Ile | Lys | Thr | Thr | Thr | Pro | Ala | Pro | Arg | Pro | Pro | Thr | Pro |
| | | | 260 | | | | | 265 | | | | | 270 | | |
| Ala | Pro | Thr | Ile | Ala | Ser | Gln | Pro | Leu | Ser | Leu | Arg | Pro | Glu | Ala | Cys |
| | | 275 | | | | | 280 | | | | | 285 | | | |
| Arg | Pro | Ala | Ala | Gly | Gly | Ala | Val | His | Thr | Arg | Gly | Leu | Asp | Phe | Ala |
| | 290 | | | | | 295 | | | | | 300 | | | | |
| Cys | Asp | Ile | Tyr | Ile | Trp | Ala | Pro | Leu | Ala | Gly | Thr | Cys | Gly | Val | Leu |
| 305 | | | | | 310 | | | | | 315 | | | | | 320 |
| Leu | Leu | Ser | Leu | Val | Ile | Thr | Leu | Tyr | Cys | Lys | Arg | Gly | Arg | Lys | Lys |
| | | | | 325 | | | | | 330 | | | | | 335 | |
| Leu | Leu | Tyr | Ile | Phe | Lys | Gln | Pro | Phe | Met | Arg | Pro | Val | Gln | Thr | Thr |
| | | | 340 | | | | | 345 | | | | | 350 | | |
| Gln | Glu | Glu | Asp | Gly | Cys | Ser | Cys | Arg | Phe | Pro | Glu | Glu | Glu | Glu | Gly |
| | | 355 | | | | | 360 | | | | | 365 | | | |
| Gly | Cys | Glu | Leu | Arg | Val | Lys | Phe | Ser | Arg | Ser | Ala | Asp | Ala | Pro | Ala |
| | 370 | | | | | 375 | | | | | 380 | | | | |

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
            405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
            450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 54
<211> LENGTH: 489
<212> TYPE: PRT
<213> ORGANISM: artificial sequence
<220> FEATURE:
<223> OTHER INFORMATION: CAR 9 13

<400> SEQUENCE: 54

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
        35                  40                  45

Ser Val Ser Gly Asn Arg Ala Thr Trp Asn Trp Ile Arg Gln Ser Pro
    50                  55                  60

Ser Arg Gly Leu Glu Trp Leu Gly Arg Thr Tyr Tyr Arg Ser Ala Trp
65                  70                  75                  80

Tyr Asn Asp Tyr Ala Val Ser Val Lys Gly Arg Ile Thr Phe Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Gly Glu Ser Gly Ala Ala
        115                 120                 125

Ala Asp Ala Phe Asp Ile Trp Gly Gln Gly Thr Thr Val Thr Val Ser
    130                 135                 140

Gly Gly Gly Gly Ser Gly Gly Gly Ser Gly Gly Gly Gly Ser Asp
145                 150                 155                 160

Ile Gln Leu Thr Gln Ser Pro Pro Ser Leu Ser Ala Ser Val Gly Asp
                165                 170                 175

Arg Val Thr Ile Thr Cys Arg Ala Ser Gln Ser Ile Ser Ser Tyr Leu
            180                 185                 190

Asn Trp Tyr Gln Gln Lys Pro Gly Lys Ala Pro Lys Leu Leu Ile Tyr
        195                 200                 205

Ala Ala Ser Ser Leu Gln Ser Gly Val Pro Ser Arg Phe Ser Gly Ser
    210                 215                 220

Gly Phe Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Ser Thr Pro Gln Thr
                245                 250                 255

Phe Gly Gln Gly Thr Lys Val Asp Ile Lys Thr Thr Thr Pro Ala Pro

```
                    260                 265                 270
Arg Pro Pro Thr Pro Ala Pro Thr Ile Ala Ser Gln Pro Leu Ser Leu
                275                 280                 285
Arg Pro Glu Ala Cys Arg Pro Ala Ala Gly Gly Ala Val His Thr Arg
            290                 295                 300
Gly Leu Asp Phe Ala Cys Asp Ile Tyr Ile Trp Ala Pro Leu Ala Gly
305                 310                 315                 320
Thr Cys Gly Val Leu Leu Leu Ser Leu Val Ile Thr Leu Tyr Cys Lys
                325                 330                 335
Arg Gly Arg Lys Lys Leu Leu Tyr Ile Phe Lys Gln Pro Phe Met Arg
            340                 345                 350
Pro Val Gln Thr Thr Gln Glu Glu Asp Gly Cys Ser Cys Arg Phe Pro
            355                 360                 365
Glu Glu Glu Glu Gly Gly Cys Glu Leu Arg Val Lys Phe Ser Arg Ser
            370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
            420                 425                 430
Glu Gly Leu Tyr Asn Glu Leu Gln Lys Asp Lys Met Ala Glu Ala Tyr
            435                 440                 445
Ser Glu Ile Gly Met Lys Gly Glu Arg Arg Arg Gly Lys Gly His Asp
            450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485

<210> SEQ ID NO 55
<211> LENGTH: 489
<212> TYPE: PRT
<213> ORGANISM: artificial sequence
<220> FEATURE:
<223> OTHER INFORMATION: CAR 10 15

<400> SEQUENCE: 55

Met Ala Leu Pro Val Thr Ala Leu Leu Leu Pro Leu Ala Leu Leu Leu
1               5                   10                  15
His Ala Ala Arg Pro Gln Val Gln Leu Val Gln Ser Gly Ala Glu Val
                20                  25                  30
Lys Lys Pro Gly Ala Ser Val Lys Val Ser Cys Lys Ala Ser Gly Tyr
            35                  40                  45
Thr Phe Thr Ser Tyr Tyr Met His Trp Val Arg Gln Ala Pro Gly Gln
        50                  55                  60
Gly Leu Glu Trp Met Gly Ile Ile Asn Pro Ser Gly Gly Ser Thr Ser
65                  70                  75                  80
Tyr Ala Gln Lys Phe Gln Gly Arg Val Thr Met Thr Arg Asp Thr Ser
                85                  90                  95
Thr Ser Thr Val Tyr Met Glu Leu Ser Ser Leu Arg Ser Glu Asp Thr
            100                 105                 110
Ala Val Tyr Tyr Cys Ala Arg Glu Asp Ser Gly Ser Gly Ala Phe Asp
        115                 120                 125
Ile Trp Gly Gln Gly Thr Leu Val Thr Val Ser Gly Gly Gly Gly Ser
```

```
                130             135             140
Gly Gly Gly Gly Ser Gly Gly Gly Ser Glu Ile Val Leu Thr Gln
145             150             155             160

Ser Pro Leu Ser Leu Pro Val Thr Pro Gly Glu Pro Ala Ser Ile Ser
                165             170             175

Cys Arg Ser Ser Arg Ser Leu Leu Ser Tyr His Gly Tyr Asn Tyr Leu
            180             185             190

Asp Trp Tyr Leu Gln Lys Pro Gly Gln Ser Pro Gln Leu Leu Ile Phe
        195             200             205

Val Gly Ser Asn Arg Ala Pro Gly Val Pro Asp Arg Phe Ser Gly Ser
    210             215             220

Gly Ser Gly Thr Asp Phe Thr Leu Asn Ile Ser Arg Val Glu Ala Glu
225             230             235             240

Asp Val Gly Val Tyr Tyr Cys Met Gln Ser Leu Gln Thr Pro Arg Thr
                245             250             255

Phe Gly Gln Gly Thr Lys Val Glu Ile Lys Thr Thr Thr Pro Ala Pro
            260             265             270

Arg Pro Pro Thr Pro Ala Pro Thr Ile Ala Ser Gln Pro Leu Ser Leu
        275             280             285

Arg Pro Glu Ala Cys Arg Pro Ala Ala Gly Gly Ala Val His Thr Arg
    290             295             300

Gly Leu Asp Phe Ala Cys Asp Ile Tyr Ile Trp Ala Pro Leu Ala Gly
305             310             315             320

Thr Cys Gly Val Leu Leu Leu Ser Leu Val Ile Thr Leu Tyr Cys Lys
                325             330             335

Arg Gly Arg Lys Lys Leu Leu Tyr Ile Phe Lys Gln Pro Phe Met Arg
            340             345             350

Pro Val Gln Thr Thr Gln Glu Asp Gly Cys Ser Cys Arg Phe Pro
        355             360             365

Glu Glu Glu Glu Gly Gly Cys Glu Leu Arg Val Lys Phe Ser Arg Ser
    370             375             380

Ala Asp Ala Pro Ala Tyr Gln Gln Gly Gln Asn Gln Leu Tyr Asn Glu
385             390             395             400

Leu Asn Leu Gly Arg Arg Glu Glu Tyr Asp Val Leu Asp Lys Arg Arg
                405             410             415

Gly Arg Asp Pro Glu Met Gly Gly Lys Pro Arg Arg Lys Asn Pro Gln
            420             425             430

Glu Gly Leu Tyr Asn Glu Leu Gln Lys Asp Lys Met Ala Glu Ala Tyr
        435             440             445

Ser Glu Ile Gly Met Lys Gly Glu Arg Arg Arg Gly Lys Gly His Asp
    450             455             460

Gly Leu Tyr Gln Gly Leu Ser Thr Ala Thr Lys Asp Thr Tyr Asp Ala
465             470             475             480

Leu His Met Gln Ala Leu Pro Pro Arg
                485

<210> SEQ ID NO 56
<211> LENGTH: 567
<212> TYPE: PRT
<213> ORGANISM: artificial sequence
<220> FEATURE:
<223> OTHER INFORMATION: 1RQR3

<400> SEQUENCE: 56

Met Ala Leu Pro Val Thr Ala Leu Leu Leu Pro Leu Ala Leu Leu Leu
```

-continued

```
1               5                   10                  15
His Ala Ala Arg Pro Gly Gly Gly Ser Cys Pro Tyr Ser Asn Pro
            20                  25                  30
Ser Leu Cys Ser Gly Gly Gly Ser Gly Gly Gly Ser Gln Val
            35                  40                  45
Gln Leu Gln Gln Ser Gly Pro Gly Leu Val Lys Pro Ser Gln Thr Leu
 50                      55                  60
Ser Leu Thr Cys Ala Ile Ser Gly Asp Ser Val Ser Ser Asn Ser Ala
 65                      70                  75                  80
Ala Trp Asn Trp Ile Arg Gln Ser Pro Ser Arg Gly Leu Glu Trp Leu
                    85                  90                  95
Gly Arg Thr Tyr Tyr Arg Ser Thr Trp Tyr Asn Asp Tyr Ala Val Ser
                100                 105                 110
Val Lys Ser Arg Ile Thr Ile Asn Pro Asp Thr Ser Lys Asn Gln Phe
            115                 120                 125
Ser Leu Gln Leu Asn Ser Val Thr Pro Glu Asp Thr Ala Val Tyr Tyr
 130                     135                 140
Cys Ala Arg Glu Val Ser Gly Thr Ser Ala Phe Asp Ile Trp Gly Gln
145                     150                 155                 160
Gly Thr Met Val Thr Val Ser Gly Gly Gly Ser Gly Gly Gly Gly
                165                 170                 175
Ser Gly Gly Gly Gly Ser Asp Ile Gln Met Thr Gln Ser Pro Ser Ser
                180                 185                 190
Leu Ser Ala Ser Val Gly Asp Arg Val Thr Ile Thr Cys Arg Ala Ser
            195                 200                 205
Gln Ser Ile Ser Ser Tyr Leu Asn Trp Tyr Gln Gln Lys Pro Gly Lys
 210                     215                 220
Ala Pro Lys Leu Leu Ile Tyr Ala Ala Ser Ser Leu Gln Ser Gly Val
225                     230                 235                 240
Pro Ser Arg Phe Ser Gly Ser Gly Ser Gly Thr Asp Phe Thr Leu Thr
                245                 250                 255
Ile Ser Ser Leu Gln Pro Glu Asp Phe Ala Thr Tyr Tyr Cys Gln Gln
            260                 265                 270
Ser Tyr Ser Thr Pro Leu Thr Phe Gly Gly Gly Thr Lys Leu Glu Ile
 275                     280                 285
Lys Gly Ser Gly Gly Gly Gly Ser Cys Pro Tyr Ser Asn Pro Ser Leu
            290                 295                 300
Cys Ser Gly Gly Gly Gly Ser Glu Leu Pro Thr Gln Gly Thr Phe Ser
305                     310                 315                 320
Asn Val Ser Thr Asn Val Ser Pro Ala Lys Pro Thr Thr Thr Ala Cys
                325                 330                 335
Pro Tyr Ser Asn Pro Ser Leu Cys Thr Thr Pro Ala Pro Arg Pro
            340                 345                 350
Pro Thr Pro Ala Pro Thr Ile Ala Ser Gln Pro Leu Ser Leu Arg Pro
            355                 360                 365
Glu Ala Cys Arg Pro Ala Ala Gly Gly Ala Val His Thr Arg Gly Leu
 370                     375                 380
Asp Phe Ala Cys Asp Ile Tyr Ile Trp Ala Pro Leu Ala Gly Thr Cys
385                     390                 395                 400
Gly Val Leu Leu Leu Ser Leu Val Ile Thr Leu Tyr Cys Lys Arg Gly
                405                 410                 415
Arg Lys Lys Leu Leu Tyr Ile Phe Lys Gln Pro Phe Met Arg Pro Val
            420                 425                 430
```

-continued

Gln Thr Thr Gln Glu Glu Asp Gly Cys Ser Cys Arg Phe Pro Glu Glu
            435                 440                 445

Glu Glu Gly Gly Cys Glu Leu Arg Val Lys Phe Ser Arg Ser Ala Asp
450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
                485                 490                 495

Asp Pro Glu Met Gly Gly Lys Pro Arg Arg Lys Asn Pro Gln Glu Gly
            500                 505                 510

Leu Tyr Asn Glu Leu Gln Lys Asp Lys Met Ala Glu Ala Tyr Ser Glu
            515                 520                 525

Ile Gly Met Lys Gly Glu Arg Arg Arg Gly Lys Gly His Asp Gly Leu
            530                 535                 540

Tyr Gln Gly Leu Ser Thr Ala Thr Lys Asp Thr Tyr Asp Ala Leu His
545                 550                 555                 560

Met Gln Ala Leu Pro Pro Arg
            565

<210> SEQ ID NO 57
<211> LENGTH: 572
<212> TYPE: PRT
<213> ORGANISM: artificial sequence
<220> FEATURE:
<223> OTHER INFORMATION: 2RQR3

<400> SEQUENCE: 57

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
            20                  25                  30

Ser Leu Cys Ser Gly Gly Gly Gly Ser Gly Gly Gly Gly Ser Gln Val
            35                  40                  45

Gln Leu Gln Gln Ser Gly Pro Gly Leu Val Lys Pro Ser Gln Thr Leu
50                  55                  60

Ser Leu Thr Cys Ala Ile Ser Gly Asp Ser Val Ser Ser Asn Ser Ala
65                  70                  75                  80

Ala Trp Asn Trp Ile Arg Gln Ser Pro Ser Arg Gly Leu Glu Trp Leu
                85                  90                  95

Gly Arg Thr Tyr Tyr Arg Ser Lys Trp Tyr Asn Asp Tyr Ala Val Ser
            100                 105                 110

Val Lys Ser Arg Ile Thr Ile Asn Pro Asp Thr Ser Lys Asn Gln Phe
            115                 120                 125

Ser Leu Gln Leu Asn Ser Val Thr Pro Glu Asp Thr Ala Val Tyr Tyr
130                 135                 140

Cys Ala Arg Ala Ser Met Thr Gly Gly Tyr Ser Tyr Gly Asp Ala Phe
145                 150                 155                 160

Asp Ile Trp Gly Gln Gly Thr Leu Val Thr Val Ser Gly Gly Gly Gly
                165                 170                 175

Ser Gly Gly Gly Gly Ser Gly Gly Gly Gly Ser Ala Ile Arg Met Thr
            180                 185                 190

Gln Ser Pro Ser Ser Leu Ser Ala Ser Val Gly Asp Arg Val Thr Ile
            195                 200                 205

Thr Cys Arg Ala Ser Gln Ser Ile Ser Ser Tyr Leu Asn Trp Tyr Gln
210                 215                 220

Gln Lys Pro Gly Lys Ala Pro Lys Leu Leu Ile Tyr Ala Ala Ser Ser
225                 230                 235                 240

Leu Gln Ser Gly Val Pro Ser Arg Phe Ser Gly Ser Gly Ser Gly Thr
            245                 250                 255

Asp Phe Ser Leu Thr Ile Ser Ser Leu Gln Pro Glu Asp Ser Ala Thr
        260                 265                 270

Tyr Tyr Cys Gln Gln Thr Tyr Ser Thr Pro Leu Thr Phe Gly Gln Gly
    275                 280                 285

Thr Lys Val Glu Ile Lys Gly Ser Gly Gly Gly Ser Cys Pro Tyr
290                 295                 300

Ser Asn Pro Ser Leu Cys Ser Gly Gly Gly Ser Glu Leu Pro Thr
305                 310                 315                 320

Gln Gly Thr Phe Ser Asn Val Ser Thr Asn Val Ser Pro Ala Lys Pro
            325                 330                 335

Thr Thr Thr Ala Cys Pro Tyr Ser Asn Pro Ser Leu Cys Thr Thr Thr
        340                 345                 350

Pro Ala Pro Arg Pro Pro Thr Pro Ala Pro Thr Ile Ala Ser Gln Pro
    355                 360                 365

Leu Ser Leu Arg Pro Glu Ala Cys Arg Pro Ala Ala Gly Gly Ala Val
370                 375                 380

His Thr Arg Gly Leu Asp Phe Ala Cys Asp Ile Tyr Ile Trp Ala Pro
385                 390                 395                 400

Leu Ala Gly Thr Cys Gly Val Leu Leu Leu Ser Leu Val Ile Thr Leu
            405                 410                 415

Tyr Cys Lys Arg Gly Arg Lys Lys Leu Leu Tyr Ile Phe Lys Gln Pro
        420                 425                 430

Phe Met Arg Pro Val Gln Thr Thr Gln Glu Glu Asp Gly Cys Ser Cys
    435                 440                 445

Arg Phe Pro Glu Glu Glu Glu Gly Gly Cys Glu Leu Arg Val Lys Phe
450                 455                 460

Ser Arg Ser Ala Asp Ala Pro Ala Tyr Gln Gln Gly Gln Asn Gln Leu
465                 470                 475                 480

Tyr Asn Glu Leu Asn Leu Gly Arg Arg Glu Glu Tyr Asp Val Leu Asp
            485                 490                 495

Lys Arg Arg Gly Arg Asp Pro Glu Met Gly Gly Lys Pro Arg Arg Lys
        500                 505                 510

Asn Pro Gln Glu Gly Leu Tyr Asn Glu Leu Gln Lys Asp Lys Met Ala
    515                 520                 525

Glu Ala Tyr Ser Glu Ile Gly Met Lys Gly Glu Arg Arg Arg Gly Lys
530                 535                 540

Gly His Asp Gly Leu Tyr Gln Gly Leu Ser Thr Ala Thr Lys Asp Thr
545                 550                 555                 560

Tyr Asp Ala Leu His Met Gln Ala Leu Pro Pro Arg
            565                 570

<210> SEQ ID NO 58
<211> LENGTH: 568
<212> TYPE: PRT
<213> ORGANISM: artificial sequence
<220> FEATURE:
<223> OTHER INFORMATION: 3RQR3

<400> SEQUENCE: 58

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Ser Gly Gly Gly Ser Gly Gly Gly Ser Gln Val
        35                  40                  45

Gln Leu Gln Gln Ser Gly Pro Gly Leu Val Glu Pro Ser Gln Thr Leu
50                  55                  60

Ser Leu Thr Cys Ala Ile Ser Gly Asp Ser Val Ser Ser Asp Ser Val
65                  70                  75                  80

Ala Trp Asn Trp Ile Arg Gln Ser Pro Ser Arg Gly Leu Glu Trp Leu
                85                  90                  95

Gly Arg Thr Tyr Tyr Arg Ser Thr Trp Tyr Asn Asp Tyr Ala Gly Ser
            100                 105                 110

Val Lys Ser Arg Ile Thr Ile Asn Pro Asp Thr Ser Lys Asn Gln Phe
        115                 120                 125

Ser Leu Gln Leu Thr Ser Val Thr Pro Glu Asp Thr Ala Val Tyr Tyr
130                 135                 140

Cys Thr Arg Ser Arg His Asn Thr Phe Arg Gly Met Asp Val Trp Gly
145                 150                 155                 160

Gln Gly Thr Thr Val Thr Val Ser Gly Gly Gly Ser Gly Gly Gly
            165                 170                 175

Gly Ser Gly Gly Gly Gly Ser Asp Ile Val Met Thr Gln Ser Pro Ser
            180                 185                 190

Ser Leu Ser Ala Ser Val Gly Asp Arg Val Thr Ile Thr Cys Arg Ala
        195                 200                 205

Ser Gln Thr Ile Ser Ser Tyr Leu Asn Trp Tyr Gln Gln Lys Pro Gly
        210                 215                 220

Lys Ala Pro Lys Leu Leu Ile Tyr Asp Ala Ser Ser Leu Gln Ser Gly
225                 230                 235                 240

Val Pro Ser Arg Phe Ser Gly Ser Gly Ser Gly Thr Asp Phe Thr Leu
            245                 250                 255

Thr Ile Asn Ser Leu Gln Pro Glu Asp Phe Ala Thr Tyr Tyr Cys Gln
            260                 265                 270

Gln Ser Tyr Thr Thr Pro Ile Thr Phe Gly Gln Gly Thr Arg Leu Glu
        275                 280                 285

Ile Lys Gly Ser Gly Gly Gly Gly Ser Cys Pro Tyr Ser Asn Pro Ser
        290                 295                 300

Leu Cys Ser Gly Gly Gly Gly Ser Glu Leu Pro Thr Gln Gly Thr Phe
305                 310                 315                 320

Ser Asn Val Ser Thr Asn Val Ser Pro Ala Lys Pro Thr Thr Thr Ala
            325                 330                 335

Cys Pro Tyr Ser Asn Pro Ser Leu Cys Thr Thr Thr Pro Ala Pro Arg
            340                 345                 350

Pro Pro Thr Pro Ala Pro Thr Ile Ala Ser Gln Pro Leu Ser Leu Arg
        355                 360                 365

Pro Glu Ala Cys Arg Pro Ala Ala Gly Gly Ala Val His Thr Arg Gly
        370                 375                 380

Leu Asp Phe Ala Cys Asp Ile Tyr Ile Trp Ala Pro Leu Ala Gly Thr
385                 390                 395                 400

Cys Gly Val Leu Leu Leu Ser Leu Val Ile Thr Leu Tyr Cys Lys Arg
            405                 410                 415

Gly Arg Lys Lys Leu Leu Tyr Ile Phe Lys Gln Pro Phe Met Arg Pro
            420                 425                 430

Val Gln Thr Thr Gln Glu Glu Asp Gly Cys Ser Cys Arg Phe Pro Glu
            435                 440                 445

Glu Glu Glu Gly Gly Cys Glu Leu Arg Val Lys Phe Ser Arg Ser Ala
    450                 455                 460

Asp Ala Pro Ala Tyr Gln Gln Gly Gln Asn Gln Leu Tyr Asn Glu Leu
465                 470                 475                 480

Asn Leu Gly Arg Arg Glu Glu Tyr Asp Val Leu Asp Lys Arg Arg Gly
                485                 490                 495

Arg Asp Pro Glu Met Gly Gly Lys Pro Arg Arg Lys Asn Pro Gln Glu
                500                 505                 510

Gly Leu Tyr Asn Glu Leu Gln Lys Asp Lys Met Ala Glu Ala Tyr Ser
            515                 520                 525

Glu Ile Gly Met Lys Gly Glu Arg Arg Arg Gly Lys Gly His Asp Gly
530                 535                 540

Leu Tyr Gln Gly Leu Ser Thr Ala Thr Lys Asp Thr Tyr Asp Ala Leu
545                 550                 555                 560

His Met Gln Ala Leu Pro Pro Arg
                565

<210> SEQ ID NO 59
<211> LENGTH: 568
<212> TYPE: PRT
<213> ORGANISM: artificial sequence
<220> FEATURE:
<223> OTHER INFORMATION: 4RQR3

<400> SEQUENCE: 59

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Ser Gly Gly Gly Gly Ser Gly Gly Gly Gly Ser Gln Val
            35                  40                  45

Gln Leu Gln Gln Ser Gly Pro Gly Leu Val Glu Pro Ser Gln Thr Leu
    50                  55                  60

Ser Leu Thr Cys Ala Ile Ser Gly Asp Ser Val Ser Ser Asn Ser Ala
65                  70                  75                  80

Ala Trp Asn Trp Ile Arg Gln Ser Pro Ser Arg Gly Leu Glu Trp Leu
                85                  90                  95

Gly Arg Thr Tyr Tyr Arg Ser Thr Trp Tyr Asn Asp Tyr Ala Gly Ser
                100                 105                 110

Val Lys Ser Arg Ile Thr Ile Asn Pro Asp Thr Ser Lys Asn Gln Phe
            115                 120                 125

Ser Leu Gln Leu Thr Ser Val Thr Pro Glu Asp Thr Ala Val Tyr Tyr
    130                 135                 140

Cys Thr Arg Ser Arg His Asn Thr Phe Arg Gly Met Asp Val Trp Gly
145                 150                 155                 160

Gln Gly Thr Leu Val Thr Val Ser Gly Gly Gly Gly Ser Gly Gly Gly
                165                 170                 175

Gly Ser Gly Gly Gly Gly Ser Asp Ile Gln Leu Thr Gln Ser Pro Ser
            180                 185                 190

Ser Leu Ser Ala Ser Val Gly Asp Arg Val Thr Ile Thr Cys Arg Ala
                195                 200                 205

Ser Gln Ser Ile Ser Ser Tyr Leu Asn Trp Tyr Gln Gln Lys Pro Gly
    210                 215                 220

```
Lys Ala Pro Lys Leu Leu Ile Tyr Ala Ala Ser Ser Leu Gln Ser Gly
225                 230                 235                 240

Val Pro Ser Arg Phe Ser Gly Ser Gly Ser Gly Thr Asp Phe Thr Leu
                245                 250                 255

Thr Ile Ser Ser Leu Gln Pro Glu Asp Phe Ala Thr Tyr Tyr Cys Gln
            260                 265                 270

Gln Ser Tyr Ser Thr Pro Leu Thr Phe Gly Gly Gly Thr Lys Val Glu
        275                 280                 285

Ile Lys Gly Ser Gly Gly Gly Ser Cys Pro Tyr Ser Asn Pro Ser
290                 295                 300

Leu Cys Ser Gly Gly Gly Ser Glu Leu Pro Thr Gln Gly Thr Phe
305                 310                 315                 320

Ser Asn Val Ser Thr Asn Val Ser Pro Ala Lys Pro Thr Thr Thr Ala
                325                 330                 335

Cys Pro Tyr Ser Asn Pro Ser Leu Cys Thr Thr Pro Ala Pro Arg
                340                 345                 350

Pro Pro Thr Pro Ala Pro Thr Ile Ala Ser Gln Pro Leu Ser Leu Arg
            355                 360                 365

Pro Glu Ala Cys Arg Pro Ala Ala Gly Gly Ala Val His Thr Arg Gly
        370                 375                 380

Leu Asp Phe Ala Cys Asp Ile Tyr Ile Trp Ala Pro Leu Ala Gly Thr
385                 390                 395                 400

Cys Gly Val Leu Leu Leu Ser Leu Val Ile Thr Leu Tyr Cys Lys Arg
                405                 410                 415

Gly Arg Lys Lys Leu Leu Tyr Ile Phe Lys Gln Pro Phe Met Arg Pro
            420                 425                 430

Val Gln Thr Thr Gln Glu Glu Asp Gly Cys Ser Cys Arg Phe Pro Glu
        435                 440                 445

Glu Glu Glu Gly Gly Cys Glu Leu Arg Val Lys Phe Ser Arg Ser Ala
    450                 455                 460

Asp Ala Pro Ala Tyr Gln Gln Gly Gln Asn Gln Leu Tyr Asn Glu Leu
465                 470                 475                 480

Asn Leu Gly Arg Arg Glu Glu Tyr Asp Val Leu Asp Lys Arg Arg Gly
                485                 490                 495

Arg Asp Pro Glu Met Gly Gly Lys Pro Arg Arg Lys Asn Pro Gln Glu
            500                 505                 510

Gly Leu Tyr Asn Glu Leu Gln Lys Asp Lys Met Ala Glu Ala Tyr Ser
        515                 520                 525

Glu Ile Gly Met Lys Gly Glu Arg Arg Arg Gly Lys Gly His Asp Gly
    530                 535                 540

Leu Tyr Gln Gly Leu Ser Thr Ala Thr Lys Asp Thr Tyr Asp Ala Leu
545                 550                 555                 560

His Met Gln Ala Leu Pro Pro Arg
                565

<210> SEQ ID NO 60
<211> LENGTH: 564
<212> TYPE: PRT
<213> ORGANISM: artificial sequence
<220> FEATURE:
<223> OTHER INFORMATION: 5RQR3

<400> SEQUENCE: 60

Met Ala Leu Pro Val Thr Ala Leu Leu Leu Pro Leu Ala Leu Leu Leu
1               5                   10                  15
```

-continued

His Ala Ala Arg Pro Gly Gly Gly Ser Cys Pro Tyr Ser Asn Pro
            20                  25                  30

Ser Leu Cys Ser Gly Gly Gly Ser Gly Gly Gly Ser Gln Val
            35              40              45

Gln Leu Gln Gln Ser Gly Pro Gly Leu Val Glu Pro Ser Gln Thr Leu
50                      55                  60

Ser Leu Thr Cys Ala Ile Ser Gly Asp Ser Val Ser Ser Asp Ser Val
65                  70                  75                  80

Ala Trp Asn Trp Ile Arg Gln Ser Pro Ser Arg Gly Leu Glu Trp Leu
                85                  90                  95

Gly Arg Thr Tyr Tyr Arg Ser Thr Trp Tyr Asn Asp Tyr Ala Gly Ser
            100                 105                 110

Val Lys Ser Arg Ile Thr Ile Asn Pro Asp Thr Ser Lys Asn Gln Phe
        115                 120                 125

Ser Leu Gln Leu Asn Ser Val Thr Pro Glu Asp Thr Ala Val Tyr Tyr
    130                 135                 140

Cys Ala Arg Asp Arg Asn Gly Met Asp Val Trp Gly Gln Gly Thr Met
145                 150                 155                 160

Val Thr Val Ser Gly Gly Gly Ser Gly Gly Gly Gly Ser Gly Gly
                165                 170                 175

Gly Gly Ser Asp Ile Val Met Thr Gln Ser Pro Ser Ser Leu Ser Ala
            180                 185                 190

Ser Val Gly Asp Arg Val Thr Ile Thr Cys Arg Ala Ser Gln Ser Ile
        195                 200                 205

Ser Ser Tyr Leu Asn Trp Tyr Gln Gln Lys Pro Gly Lys Ala Pro Lys
    210                 215                 220

Leu Leu Ile Tyr Asp Ala Ser Asn Leu Glu Thr Gly Val Pro Ser Arg
225                 230                 235                 240

Phe Ser Gly Ser Gly Ser Gly Thr Asp Phe Thr Phe Thr Ile Thr Ser
                245                 250                 255

Leu Gln Pro Glu Asp Phe Ala Thr Tyr Tyr Cys Gln Gln Ser Tyr Thr
            260                 265                 270

Thr Pro Leu Thr Phe Gly Gly Gly Thr Lys Val Glu Ile Lys Gly Ser
        275                 280                 285

Gly Gly Gly Gly Ser Cys Pro Tyr Ser Asn Pro Ser Leu Cys Ser Gly
    290                 295                 300

Gly Gly Gly Ser Glu Leu Pro Thr Gln Gly Thr Phe Ser Asn Val Ser
305                 310                 315                 320

Thr Asn Val Ser Pro Ala Lys Pro Thr Thr Thr Ala Cys Pro Tyr Ser
                325                 330                 335

Asn Pro Ser Leu Cys Thr Thr Thr Pro Ala Pro Arg Pro Pro Thr Pro
            340                 345                 350

Ala Pro Thr Ile Ala Ser Gln Pro Leu Ser Leu Arg Pro Glu Ala Cys
        355                 360                 365

Arg Pro Ala Ala Gly Gly Ala Val His Thr Arg Gly Leu Asp Phe Ala
    370                 375                 380

Cys Asp Ile Tyr Ile Trp Ala Pro Leu Ala Gly Thr Cys Gly Val Leu
385                 390                 395                 400

Leu Leu Ser Leu Val Ile Thr Leu Tyr Cys Lys Arg Gly Arg Lys Lys
                405                 410                 415

Leu Leu Tyr Ile Phe Lys Gln Pro Phe Met Arg Pro Val Gln Thr Thr
            420                 425                 430

Gln Glu Glu Asp Gly Cys Ser Cys Arg Phe Pro Glu Glu Glu Glu Gly

```
                435                 440                 445
Gly Cys Glu Leu Arg Val Lys Phe Ser Arg Ser Ala Asp Ala Pro Ala
450                 455                 460

Tyr Gln Gln Gly Gln Asn Gln Leu Tyr Asn Glu Leu Asn Leu Gly Arg
465                 470                 475                 480

Arg Glu Glu Tyr Asp Val Leu Asp Lys Arg Gly Arg Asp Pro Glu
                485                 490                 495

Met Gly Gly Lys Pro Arg Arg Lys Asn Pro Gln Glu Gly Leu Tyr Asn
                500                 505                 510

Glu Leu Gln Lys Asp Lys Met Ala Glu Ala Tyr Ser Glu Ile Gly Met
                515                 520                 525

Lys Gly Glu Arg Arg Arg Gly Lys Gly His Asp Gly Leu Tyr Gln Gly
                530                 535                 540

Leu Ser Thr Ala Thr Lys Asp Thr Tyr Asp Ala Leu His Met Gln Ala
545                 550                 555                 560

Leu Pro Pro Arg

<210> SEQ ID NO 61
<211> LENGTH: 567
<212> TYPE: PRT
<213> ORGANISM: artificial sequence
<220> FEATURE:
<223> OTHER INFORMATION: 6RQR3

<400> SEQUENCE: 61

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Ser Gly Gly Gly Ser Gly Gly Gly Ser Gln Val
                35                  40                  45

Gln Leu Gln Gln Ser Gly Pro Gly Leu Val Lys Pro Ser Gln Thr Leu
50                  55                  60

Ser Leu Thr Cys Ala Ile Ser Gly Asp Ser Val Ser Ser Ser Ser Ala
65                  70                  75                  80

Ala Trp Asn Trp Ile Arg Gln Ser Pro Ser Arg Gly Leu Glu Trp Leu
                85                  90                  95

Gly Arg Thr Tyr Tyr Arg Ser Ala Trp Tyr Asn Asp Tyr Ala Val Ser
                100                 105                 110

Val Lys Ser Arg Ile Thr Ile Asn Pro Asp Thr Ser Lys Asn Gln Phe
                115                 120                 125

Ser Leu Gln Leu Asn Ser Val Thr Pro Glu Asp Thr Ala Val Tyr Tyr
                130                 135                 140

Cys Ala Arg Glu Ser Val Leu Leu Asp Gly Met Asp Val Trp Gly Arg
145                 150                 155                 160

Gly Thr Thr Val Thr Val Ser Gly Gly Gly Ser Gly Gly Gly Gly
                165                 170                 175

Ser Gly Gly Gly Gly Ser Ala Ile Arg Met Thr Gln Ser Pro Ser Thr
                180                 185                 190

Leu Ser Ala Ser Val Gly Asp Arg Val Thr Ile Thr Cys Arg Ala Ser
                195                 200                 205

Gln Ser Ile Ser Thr Tyr Leu Asn Trp Tyr Gln Gln Lys Ala Gly Lys
                210                 215                 220

Ala Pro Arg Leu Leu Ile His Asp Ala Ser Ser Leu Gln Ser Gly Val
225                 230                 235                 240
```

-continued

```
Pro Ser Arg Phe Ser Gly Ser Gly Ser Gly Thr Asp Phe Thr Leu Thr
            245                 250                 255

Ile Ser Ser Leu Gln Pro Glu Asp Phe Ala Thr Tyr Tyr Cys Gln Gln
        260                 265                 270

Ser Tyr Ser Thr Pro Leu Thr Phe Gly Gly Gly Thr Lys Val Glu Ile
    275                 280                 285

Lys Gly Ser Gly Gly Gly Gly Ser Cys Pro Tyr Ser Asn Pro Ser Leu
290                 295                 300

Cys Ser Gly Gly Gly Gly Ser Glu Leu Pro Thr Gln Gly Thr Phe Ser
305                 310                 315                 320

Asn Val Ser Thr Asn Val Ser Pro Ala Lys Pro Thr Thr Thr Ala Cys
                325                 330                 335

Pro Tyr Ser Asn Pro Ser Leu Cys Thr Thr Thr Pro Ala Pro Arg Pro
            340                 345                 350

Pro Thr Pro Ala Pro Thr Ile Ala Ser Gln Pro Leu Ser Leu Arg Pro
        355                 360                 365

Glu Ala Cys Arg Pro Ala Ala Gly Gly Ala Val His Thr Arg Gly Leu
    370                 375                 380

Asp Phe Ala Cys Asp Ile Tyr Ile Trp Ala Pro Leu Ala Gly Thr Cys
385                 390                 395                 400

Gly Val Leu Leu Leu Ser Leu Val Ile Thr Leu Tyr Cys Lys Arg Gly
                405                 410                 415

Arg Lys Lys Leu Leu Tyr Ile Phe Lys Gln Pro Phe Met Arg Pro Val
            420                 425                 430

Gln Thr Thr Gln Glu Glu Asp Gly Cys Ser Cys Arg Phe Pro Glu Glu
        435                 440                 445

Glu Glu Gly Gly Cys Glu Leu Arg Val Lys Phe Ser Arg Ser Ala Asp
    450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
                485                 490                 495

Asp Pro Glu Met Gly Gly Lys Pro Arg Arg Lys Asn Pro Gln Glu Gly
            500                 505                 510

Leu Tyr Asn Glu Leu Gln Lys Asp Lys Met Ala Glu Ala Tyr Ser Glu
        515                 520                 525

Ile Gly Met Lys Gly Glu Arg Arg Arg Gly Lys Gly His Asp Gly Leu
    530                 535                 540

Tyr Gln Gly Leu Ser Thr Ala Thr Lys Asp Thr Tyr Asp Ala Leu His
545                 550                 555                 560

Met Gln Ala Leu Pro Pro Arg
                565

<210> SEQ ID NO 62
<211> LENGTH: 574
<212> TYPE: PRT
<213> ORGANISM: artificial sequence
<220> FEATURE:
<223> OTHER INFORMATION: 7RQR3

<400> SEQUENCE: 62

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30
```

```
Ser Leu Cys Ser Gly Gly Gly Ser Gly Gly Gly Ser Gln Val
        35                  40                  45

Gln Leu Gln Gln Ser Gly Pro Gly Leu Val Gln Pro Ser Gln Thr Leu
    50                  55                  60

Ser Leu Thr Cys Val Ile Ser Gly Asp Ser Val Ser Ser Asn Ser Ala
65                  70                  75                  80

Thr Trp Asn Trp Ile Arg Gln Ser Pro Ser Arg Gly Leu Glu Trp Leu
                85                  90                  95

Gly Arg Thr Tyr Tyr Arg Ser Lys Trp Tyr Asn Asp Tyr Ala Val Ser
            100                 105                 110

Val Lys Ser Arg Ile Thr Ile Asn Pro Asp Thr Ser Lys Asn Gln Phe
    115                 120                 125

Ser Leu Gln Leu Asn Ser Val Thr Pro Glu Asp Thr Ala Val Tyr Tyr
    130                 135                 140

Cys Ala Arg Asp Gly Asp Gly Ser Tyr Tyr Asp Tyr Tyr Tyr
145                 150                 155                 160

Gly Met Asp Val Trp Gly Gln Gly Thr Thr Val Thr Val Ser Gly Gly
                165                 170                 175

Gly Gly Ser Gly Gly Gly Gly Ser Gly Gly Gly Gly Ser Asp Ile Gln
            180                 185                 190

Leu Thr Gln Ser Pro Ser Ser Leu Ser Thr Ser Val Gly Asp Arg Val
        195                 200                 205

Thr Ile Thr Cys Arg Ala Ser Gln Ser Ile Ser Thr Tyr Leu Asn Trp
    210                 215                 220

Tyr Gln Gln Lys Pro Gly Lys Ala Pro Lys Leu Leu Ile Tyr Ala Ala
225                 230                 235                 240

Ser Asn Leu Gln Ser Gly Val Pro Ser Arg Phe Ser Gly Ser Gly Ser
                245                 250                 255

Gly Thr Asp Phe Thr Leu Thr Ile Ser Ser Leu Gln Pro Glu Asp Phe
            260                 265                 270

Ala Thr Tyr Phe Cys Gln Gln Ser Tyr Thr Thr Pro Ile Thr Phe Gly
        275                 280                 285

Gln Gly Thr Arg Leu Glu Ile Lys Gly Ser Gly Gly Gly Gly Ser Cys
    290                 295                 300

Pro Tyr Ser Asn Pro Ser Leu Cys Ser Gly Gly Gly Ser Glu Leu
305                 310                 315                 320

Pro Thr Gln Gly Thr Phe Ser Asn Val Ser Thr Asn Val Ser Pro Ala
                325                 330                 335

Lys Pro Thr Thr Thr Ala Cys Pro Tyr Ser Asn Pro Ser Leu Cys Thr
            340                 345                 350

Thr Thr Pro Ala Pro Arg Pro Pro Thr Pro Ala Pro Thr Ile Ala Ser
        355                 360                 365

Gln Pro Leu Ser Leu Arg Pro Glu Ala Cys Arg Pro Ala Ala Gly Gly
    370                 375                 380

Ala Val His Thr Arg Gly Leu Asp Phe Ala Cys Asp Ile Tyr Ile Trp
385                 390                 395                 400

Ala Pro Leu Ala Gly Thr Cys Gly Val Leu Leu Leu Ser Leu Val Ile
                405                 410                 415

Thr Leu Tyr Cys Lys Arg Gly Arg Lys Lys Leu Leu Tyr Ile Phe Lys
            420                 425                 430

Gln Pro Phe Met Arg Pro Val Gln Thr Thr Gln Glu Glu Asp Gly Cys
        435                 440                 445
```

```
Ser Cys Arg Phe Pro Glu Glu Glu Gly Cys Glu Leu Arg Val
    450                 455                 460

Lys Phe Ser Arg Ser Ala Asp Ala Pro Ala Tyr Gln Gln Gly Gln Asn
465                 470                 475                 480

Gln Leu Tyr Asn Glu Leu Asn Leu Gly Arg Arg Glu Glu Tyr Asp Val
                485                 490                 495

Leu Asp Lys Arg Arg Gly Arg Asp Pro Glu Met Gly Gly Lys Pro Arg
            500                 505                 510

Arg Lys Asn Pro Gln Glu Gly Leu Tyr Asn Glu Leu Gln Lys Asp Lys
                515                 520                 525

Met Ala Glu Ala Tyr Ser Glu Ile Gly Met Lys Gly Glu Arg Arg Arg
530                 535                 540

Gly Lys Gly His Asp Gly Leu Tyr Gln Gly Leu Ser Thr Ala Thr Lys
545                 550                 555                 560

Asp Thr Tyr Asp Ala Leu His Met Gln Ala Leu Pro Pro Arg
                565                 570

<210> SEQ ID NO 63
<211> LENGTH: 564
<212> TYPE: PRT
<213> ORGANISM: artificial sequence
<220> FEATURE:
<223> OTHER INFORMATION: 8RQR3

<400> SEQUENCE: 63

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Ser Gly Gly Gly Gly Ser Gly Gly Gly Gly Ser Gln Val
            35                  40                  45

Gln Leu Gln Gln Ser Gly Pro Gly Leu Val Lys Pro Ser Gln Thr Leu
        50                  55                  60

Ser Leu Thr Cys Ala Ile Ser Gly Asp Ser Val Ser Ser Asn Ser Ala
65                  70                  75                  80

Ala Trp Asn Trp Ile Arg Gln Ser Pro Ser Arg Gly Leu Glu Trp Leu
                85                  90                  95

Gly Arg Thr Tyr Tyr Arg Ser Ala Trp Tyr Asn Asp Tyr Ala Val Ser
                100                 105                 110

Val Lys Ser Arg Ile Thr Ile Asn Pro Asp Thr Ser Lys Asn Gln Phe
            115                 120                 125

Ser Leu Gln Leu Ser Ser Val Thr Pro Glu Asp Thr Ala Val Tyr Tyr
        130                 135                 140

Cys Ala Arg Asp Val Glu Gly Phe Asp Tyr Trp Gly Gln Gly Thr Leu
145                 150                 155                 160

Val Thr Val Ser Gly Gly Gly Gly Ser Gly Gly Gly Gly Ser Gly Gly
                165                 170                 175

Gly Gly Ser Asp Ile Val Met Thr Gln Thr Pro Ser Ser Leu Ser Ala
            180                 185                 190

Ser Val Gly Asp Arg Val Thr Ile Thr Cys Arg Ala Ser Gln Ser Ile
        195                 200                 205

Ser Ser Tyr Leu Asn Trp Tyr Gln Gln Lys Pro Gly Lys Ala Pro Lys
210                 215                 220

Leu Leu Ile Tyr Ala Ala Ser Ser Leu Gln Ser Gly Val Pro Ser Arg
225                 230                 235                 240
```

```
Phe Ser Gly Ser Gly Ser Gly Thr Asp Phe Thr Leu Thr Ile Ser Ser
                245                 250                 255

Leu Gln Pro Glu Asp Phe Ala Thr Tyr Tyr Cys Gln Gln Ser Tyr Ser
            260                 265                 270

Thr Pro Ile Thr Phe Gly Gln Gly Thr Arg Leu Glu Ile Lys Gly Ser
        275                 280                 285

Gly Gly Gly Gly Ser Cys Pro Tyr Ser Asn Pro Ser Leu Cys Ser Gly
    290                 295                 300

Gly Gly Gly Ser Glu Leu Pro Thr Gln Gly Thr Phe Ser Asn Val Ser
305                 310                 315                 320

Thr Asn Val Ser Pro Ala Lys Pro Thr Thr Thr Ala Cys Pro Tyr Ser
                325                 330                 335

Asn Pro Ser Leu Cys Thr Thr Thr Pro Ala Pro Arg Pro Pro Thr Pro
            340                 345                 350

Ala Pro Thr Ile Ala Ser Gln Pro Leu Ser Leu Arg Pro Glu Ala Cys
        355                 360                 365

Arg Pro Ala Ala Gly Gly Ala Val His Thr Arg Gly Leu Asp Phe Ala
    370                 375                 380

Cys Asp Ile Tyr Ile Trp Ala Pro Leu Ala Gly Thr Cys Gly Val Leu
385                 390                 395                 400

Leu Leu Ser Leu Val Ile Thr Leu Tyr Cys Lys Arg Gly Arg Lys Lys
                405                 410                 415

Leu Leu Tyr Ile Phe Lys Gln Pro Phe Met Arg Pro Val Gln Thr Thr
            420                 425                 430

Gln Glu Glu Asp Gly Cys Ser Cys Arg Phe Pro Glu Glu Glu Glu Gly
        435                 440                 445

Gly Cys Glu Leu Arg Val Lys Phe Ser Arg Ser Ala Asp Ala Pro Ala
    450                 455                 460

Tyr Gln Gln Gly Gln Asn Gln Leu Tyr Asn Glu Leu Asn Leu Gly Arg
465                 470                 475                 480

Arg Glu Glu Tyr Asp Val Leu Asp Lys Arg Arg Gly Arg Asp Pro Glu
                485                 490                 495

Met Gly Gly Lys Pro Arg Arg Lys Asn Pro Gln Glu Gly Leu Tyr Asn
            500                 505                 510

Glu Leu Gln Lys Asp Lys Met Ala Glu Ala Tyr Ser Glu Ile Gly Met
        515                 520                 525

Lys Gly Glu Arg Arg Arg Gly Lys Gly His Asp Gly Leu Tyr Gln Gly
    530                 535                 540

Leu Ser Thr Ala Thr Lys Asp Thr Tyr Asp Ala Leu His Met Gln Ala
545                 550                 555                 560

Leu Pro Pro Arg

<210> SEQ ID NO 64
<211> LENGTH: 569
<212> TYPE: PRT
<213> ORGANISM: artificial sequence
<220> FEATURE:
<223> OTHER INFORMATION: 9RQR3

<400> SEQUENCE: 64

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
            20                  25                  30

Ser Leu Cys Ser Gly Gly Gly Gly Ser Gly Gly Gly Gly Ser Gln Val
```

```
            35                  40                  45
Gln Leu Gln Gln Ser Gly Pro Gly Leu Val Lys Pro Ser Gln Thr Leu
 50                  55                  60

Ser Leu Thr Cys Ala Ile Ser Gly Asp Ser Val Ser Gly Asn Arg Ala
 65                  70                  75                  80

Thr Trp Asn Trp Ile Arg Gln Ser Pro Ser Arg Gly Leu Glu Trp Leu
                     85                  90                  95

Gly Arg Thr Tyr Tyr Arg Ser Ala Trp Tyr Asn Asp Tyr Ala Val Ser
                100                 105                 110

Val Lys Gly Arg Ile Thr Phe Asn Pro Asp Thr Ser Lys Asn Gln Phe
                115                 120                 125

Ser Leu Gln Leu Asn Ser Val Thr Pro Glu Asp Thr Ala Val Tyr Tyr
130                 135                 140

Cys Ala Arg Gly Glu Ser Gly Ala Ala Ala Asp Ala Phe Asp Ile Trp
145                 150                 155                 160

Gly Gln Gly Thr Thr Val Thr Val Ser Gly Gly Gly Ser Gly Gly
                165                 170                 175

Gly Gly Ser Gly Gly Gly Ser Asp Ile Gln Leu Thr Gln Ser Pro
                180                 185                 190

Pro Ser Leu Ser Ala Ser Val Gly Asp Arg Val Thr Ile Thr Cys Arg
                195                 200                 205

Ala Ser Gln Ser Ile Ser Ser Tyr Leu Asn Trp Tyr Gln Gln Lys Pro
210                 215                 220

Gly Lys Ala Pro Lys Leu Leu Ile Tyr Ala Ala Ser Ser Leu Gln Ser
225                 230                 235                 240

Gly Val Pro Ser Arg Phe Ser Gly Ser Gly Phe Gly Thr Asp Phe Thr
                245                 250                 255

Leu Thr Ile Ser Ser Leu Gln Pro Glu Asp Phe Ala Thr Tyr Tyr Cys
                260                 265                 270

Gln Gln Ser Tyr Ser Thr Pro Gln Thr Phe Gly Gln Gly Thr Lys Val
                275                 280                 285

Asp Ile Lys Gly Ser Gly Gly Gly Ser Cys Pro Tyr Ser Asn Pro
290                 295                 300

Ser Leu Cys Ser Gly Gly Gly Gly Ser Glu Leu Pro Thr Gln Gly Thr
305                 310                 315                 320

Phe Ser Asn Val Ser Thr Asn Val Ser Pro Ala Lys Pro Thr Thr Thr
                325                 330                 335

Ala Cys Pro Tyr Ser Asn Pro Ser Leu Cys Thr Thr Thr Pro Ala Pro
                340                 345                 350

Arg Pro Pro Thr Pro Ala Pro Thr Ile Ala Ser Gln Pro Leu Ser Leu
                355                 360                 365

Arg Pro Glu Ala Cys Arg Pro Ala Ala Gly Gly Ala Val His Thr Arg
                370                 375                 380

Gly Leu Asp Phe Ala Cys Asp Ile Tyr Ile Trp Ala Pro Leu Ala Gly
385                 390                 395                 400

Thr Cys Gly Val Leu Leu Leu Ser Leu Val Ile Thr Leu Tyr Cys Lys
                405                 410                 415

Arg Gly Arg Lys Lys Leu Leu Tyr Ile Phe Lys Gln Pro Phe Met Arg
                420                 425                 430

Pro Val Gln Thr Thr Gln Glu Glu Asp Gly Cys Ser Cys Arg Phe Pro
                435                 440                 445

Glu Glu Glu Glu Gly Gly Cys Glu Leu Arg Val Lys Phe Ser Arg Ser
                450                 455                 460
```

Ala Asp Ala Pro Ala Tyr Gln Gln Gly Gln Asn Gln Leu Tyr Asn Glu
465                 470                 475                 480

Leu Asn Leu Gly Arg Arg Glu Tyr Asp Val Leu Asp Lys Arg Arg
            485                 490                 495

Gly Arg Asp Pro Glu Met Gly Gly Lys Pro Arg Arg Lys Asn Pro Gln
            500                 505                 510

Glu Gly Leu Tyr Asn Glu Leu Gln Lys Asp Lys Met Ala Glu Ala Tyr
            515                 520                 525

Ser Glu Ile Gly Met Lys Gly Glu Arg Arg Arg Gly Lys Gly His Asp
530                 535                 540

Gly Leu Tyr Gln Gly Leu Ser Thr Ala Thr Lys Asp Thr Tyr Asp Ala
545                 550                 555                 560

Leu His Met Gln Ala Leu Pro Pro Arg
                565

<210> SEQ ID NO 65
<211> LENGTH: 569
<212> TYPE: PRT
<213> ORGANISM: artificial sequence
<220> FEATURE:
<223> OTHER INFORMATION: 10RQR3

<400> SEQUENCE: 65

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Ser Gly Gly Gly Ser Gly Gly Gly Ser Gln Val
            35                  40                  45

Gln Leu Val Gln Ser Gly Ala Glu Val Lys Lys Pro Gly Ala Ser Val
    50                  55                  60

Lys Val Ser Cys Lys Ala Ser Gly Tyr Thr Phe Thr Ser Tyr Tyr Met
65                  70                  75                  80

His Trp Val Arg Gln Ala Pro Gly Gln Gly Leu Glu Trp Met Gly Ile
                85                  90                  95

Ile Asn Pro Ser Gly Gly Ser Thr Ser Tyr Ala Gln Lys Phe Gln Gly
                100                 105                 110

Arg Val Thr Met Thr Arg Asp Thr Ser Thr Ser Thr Val Tyr Met Glu
            115                 120                 125

Leu Ser Ser Leu Arg Ser Glu Asp Thr Ala Val Tyr Tyr Cys Ala Arg
130                 135                 140

Glu Asp Ser Gly Ser Gly Ala Phe Asp Ile Trp Gly Gln Gly Thr Leu
145                 150                 155                 160

Val Thr Val Ser Gly Gly Gly Gly Ser Gly Gly Gly Gly Ser Gly Gly
                165                 170                 175

Gly Gly Ser Glu Ile Val Leu Thr Gln Ser Pro Leu Ser Leu Pro Val
            180                 185                 190

Thr Pro Gly Glu Pro Ala Ser Ile Ser Cys Arg Ser Ser Arg Ser Leu
            195                 200                 205

Leu Ser Tyr His Gly Tyr Asn Tyr Leu Asp Trp Tyr Leu Gln Lys Pro
210                 215                 220

Gly Gln Ser Pro Gln Leu Leu Ile Phe Val Gly Ser Asn Arg Ala Pro
225                 230                 235                 240

Gly Val Pro Asp Arg Phe Ser Gly Ser Gly Ser Gly Thr Asp Phe Thr
                245                 250                 255

```
Leu Asn Ile Ser Arg Val Glu Ala Glu Asp Val Gly Val Tyr Tyr Cys
            260                 265                 270

Met Gln Ser Leu Gln Thr Pro Arg Thr Phe Gly Gln Gly Thr Lys Val
        275                 280                 285

Glu Ile Lys Gly Ser Gly Gly Gly Gly Ser Cys Pro Tyr Ser Asn Pro
    290                 295                 300

Ser Leu Cys Ser Gly Gly Gly Gly Ser Glu Leu Pro Thr Gln Gly Thr
305                 310                 315                 320

Phe Ser Asn Val Ser Thr Asn Val Ser Pro Ala Lys Pro Thr Thr Thr
                325                 330                 335

Ala Cys Pro Tyr Ser Asn Pro Ser Leu Cys Thr Thr Thr Pro Ala Pro
            340                 345                 350

Arg Pro Pro Thr Pro Ala Pro Thr Ile Ala Ser Gln Pro Leu Ser Leu
        355                 360                 365

Arg Pro Glu Ala Cys Arg Pro Ala Ala Gly Gly Ala Val His Thr Arg
    370                 375                 380

Gly Leu Asp Phe Ala Cys Asp Ile Tyr Ile Trp Ala Pro Leu Ala Gly
385                 390                 395                 400

Thr Cys Gly Val Leu Leu Leu Ser Leu Val Ile Thr Leu Tyr Cys Lys
                405                 410                 415

Arg Gly Arg Lys Lys Leu Leu Tyr Ile Phe Lys Gln Pro Phe Met Arg
            420                 425                 430

Pro Val Gln Thr Thr Gln Glu Glu Asp Gly Cys Ser Cys Arg Phe Pro
        435                 440                 445

Glu Glu Glu Glu Gly Gly Cys Glu Leu Arg Val Lys Phe Ser Arg Ser
    450                 455                 460

Ala Asp Ala Pro Ala Tyr Gln Gln Gly Gln Asn Gln Leu Tyr Asn Glu
465                 470                 475                 480

Leu Asn Leu Gly Arg Arg Glu Glu Tyr Asp Val Leu Asp Lys Arg Arg
                485                 490                 495

Gly Arg Asp Pro Glu Met Gly Gly Lys Pro Arg Arg Lys Asn Pro Gln
            500                 505                 510

Glu Gly Leu Tyr Asn Glu Leu Gln Lys Asp Lys Met Ala Glu Ala Tyr
        515                 520                 525

Ser Glu Ile Gly Met Lys Gly Glu Arg Arg Arg Gly Lys Gly His Asp
    530                 535                 540

Gly Leu Tyr Gln Gly Leu Ser Thr Ala Thr Lys Asp Thr Tyr Asp Ala
545                 550                 555                 560

Leu His Met Gln Ala Leu Pro Pro Arg
                565

<210> SEQ ID NO 66
<211> LENGTH: 528
<212> TYPE: PRT
<213> ORGANISM: artificial sequence
<220> FEATURE:
<223> OTHER INFORMATION: CAR4 R2

<400> SEQUENCE: 66

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Glu Pro Ser Gln Thr Leu Ser Leu Thr Cys Ala Ile Ser Gly Asp
        35                  40                  45
```

```
Ser Val Ser Ser Asn Ser Ala Ala Trp Asn Trp Ile Arg Gln Ser Pro
    50                  55                  60

Ser Arg Gly Leu Glu Trp Leu Gly Arg Thr Tyr Tyr Arg Ser Thr Trp
65                  70                  75                  80

Tyr Asn Asp Tyr Ala Gly Ser Val Lys Ser Arg Ile Thr Ile Asn Pro
                85                  90                  95

Asp Thr Ser Lys Asn Gln Phe Ser Leu Gln Leu Thr Ser Val Thr Pro
            100                 105                 110

Glu Asp Thr Ala Val Tyr Tyr Cys Thr Arg Ser Arg His Asn Thr Phe
        115                 120                 125

Arg Gly Met Asp Val Trp Gly Gln Gly Thr Leu Val Thr Val Ser Gly
    130                 135                 140

Gly Gly Gly Ser Gly Gly Gly Ser Gly Gly Gly Ser Asp Ile
145                 150                 155                 160

Gln Leu Thr Gln Ser Pro Ser Ser Leu Ser Ala Ser Val Gly Asp Arg
                165                 170                 175

Val Thr Ile Thr Cys Arg Ala Ser Gln Ser Ile Ser Ser Tyr Leu Asn
            180                 185                 190

Trp Tyr Gln Gln Lys Pro Gly Lys Ala Pro Lys Leu Leu Ile Tyr Ala
        195                 200                 205

Ala Ser Ser Leu Gln Ser Gly Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Ser Tyr Ser Thr Pro Leu Thr Phe
                245                 250                 255

Gly Gly Gly Thr Lys Val Glu Ile Lys Ser Asp Pro Gly Ser Gly Gly
            260                 265                 270

Gly Gly Ser Cys Pro Tyr Ser Asn Pro Ser Leu Cys Ser Gly Gly Gly
        275                 280                 285

Gly Ser Cys Pro Tyr Ser Asn Pro Ser Leu Cys Ser Gly Gly Gly Gly
    290                 295                 300

Ser Thr Thr Thr Pro Ala Pro Arg Pro Pro Thr Pro Ala Pro Thr Ile
305                 310                 315                 320

Ala Ser Gln Pro Leu Ser Leu Arg Pro Glu Ala Cys Arg Pro Ala Ala
                325                 330                 335

Gly Gly Ala Val His Thr Arg Gly Leu Asp Phe Ala Cys Asp Ile Tyr
            340                 345                 350

Ile Trp Ala Pro Leu Ala Gly Thr Cys Gly Val Leu Leu Leu Ser Leu
        355                 360                 365

Val Ile Thr Leu Tyr Cys Lys Arg Gly Arg Lys Lys Leu Leu Tyr Ile
    370                 375                 380

Phe Lys Gln Pro Phe Met Arg Pro Val Gln Thr Thr Gln Glu Glu Asp
385                 390                 395                 400

Gly Cys Ser Cys Arg Phe Pro Glu Glu Glu Glu Gly Gly Cys Glu Leu
                405                 410                 415

Arg Val Lys Phe Ser Arg Ser Ala Asp Ala Pro Ala Tyr Gln Gln Gly
            420                 425                 430

Gln Asn Gln Leu Tyr Asn Glu Leu Asn Leu Gly Arg Arg Glu Glu Tyr
        435                 440                 445

Asp Val Leu Asp Lys Arg Arg Gly Arg Asp Pro Glu Met Gly Gly Lys
450                 455                 460
```

```
Pro Arg Arg Lys Asn Pro Gln Glu Gly Leu Tyr Asn Glu Leu Gln Lys
465                 470                 475                 480

Asp Lys Met Ala Glu Ala Tyr Ser Glu Ile Gly Met Lys Gly Glu Arg
            485                 490                 495

Arg Arg Gly Lys Gly His Asp Gly Leu Tyr Gln Gly Leu Ser Thr Ala
            500                 505                 510

Thr Lys Asp Thr Tyr Asp Ala Leu His Met Gln Ala Leu Pro Pro Arg
            515                 520                 525

<210> SEQ ID NO 67
<211> LENGTH: 534
<212> TYPE: PRT
<213> ORGANISM: artificial sequence
<220> FEATURE:
<223> OTHER INFORMATION: CAR7R2

<400> SEQUENCE: 67

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
                20                  25                  30

Val Gln Pro Ser Gln Thr Leu Ser Leu Thr Cys Val Ile Ser Gly Asp
            35                  40                  45

Ser Val Ser Ser Asn Ser Ala Thr Trp Asn Trp Ile Arg Gln Ser Pro
50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Asp Gly Asp Gly Gly Ser
            115                 120                 125

Tyr Tyr Asp Tyr Tyr Tyr Gly Met Asp Val Trp Gly Gln Gly Thr
130                 135                 140

Thr Val Thr Val Ser Gly Gly Gly Gly Ser Gly Gly Gly Gly Ser Gly
145                 150                 155                 160

Gly Gly Gly Ser Asp Ile Gln Leu Thr Gln Ser Pro Ser Ser Leu Ser
                165                 170                 175

Thr Ser Val Gly Asp Arg Val Thr Ile Thr Cys Arg Ala Ser Gln Ser
            180                 185                 190

Ile Ser Thr Tyr Leu Asn Trp Tyr Gln Gln Lys Pro Gly Lys Ala Pro
            195                 200                 205

Lys Leu Leu Ile Tyr Ala Ala Ser Asn Leu Gln Ser Gly Val Pro Ser
210                 215                 220

Arg Phe Ser Gly Ser Gly Ser Gly Thr Asp Phe Thr Leu Thr Ile Ser
225                 230                 235                 240

Ser Leu Gln Pro Glu Asp Phe Ala Thr Tyr Phe Cys Gln Gln Ser Tyr
                245                 250                 255

Thr Thr Pro Ile Thr Phe Gly Gln Gly Thr Arg Leu Glu Ile Lys Ser
            260                 265                 270

Asp Pro Gly Ser Gly Gly Gly Ser Cys Pro Tyr Ser Asn Pro Ser
            275                 280                 285

Leu Cys Ser Gly Gly Gly Gly Ser Cys Pro Tyr Ser Asn Pro Ser Leu
290                 295                 300
```

```
Cys Ser Gly Gly Gly Ser Thr Thr Thr Pro Ala Pro Arg Pro Pro
305                 310                 315                 320

Thr Pro Ala Pro Thr Ile Ala Ser Gln Pro Leu Ser Leu Arg Pro Glu
            325                 330                 335

Ala Cys Arg Pro Ala Ala Gly Gly Ala Val His Thr Arg Gly Leu Asp
            340                 345                 350

Phe Ala Cys Asp Ile Tyr Ile Trp Ala Pro Leu Ala Gly Thr Cys Gly
            355                 360                 365

Val Leu Leu Leu Ser Leu Val Ile Thr Leu Tyr Cys Lys Arg Gly Arg
370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
            405                 410                 415

Glu Gly Gly Cys Glu Leu Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
            435                 440                 445

Gly Arg Arg Glu Glu Tyr Asp Val Leu Asp Lys Arg Arg Gly Arg Asp
450                 455                 460

Pro Glu Met Gly Gly Lys Pro Arg Arg Lys Asn Pro Gln Glu Gly Leu
465                 470                 475                 480

Tyr Asn Glu Leu Gln Lys Asp Lys Met Ala Glu Ala Tyr Ser Glu Ile
            485                 490                 495

Gly Met Lys Gly Glu Arg Arg Arg Gly Lys Gly His Asp Gly Leu Tyr
            500                 505                 510

Gln Gly Leu Ser Thr Ala Thr Lys Asp Thr Tyr Asp Ala Leu His Met
            515                 520                 525

Gln Ala Leu Pro Pro Arg
            530

<210> SEQ ID NO 68
<211> LENGTH: 529
<212> TYPE: PRT
<213> ORGANISM: artificial sequence
<220> FEATURE:
<223> OTHER INFORMATION: CAR9R2

<400> SEQUENCE: 68

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
        35                  40                  45

Ser Val Ser Gly Asn Arg Ala Thr Trp Asn Trp Ile Arg Gln Ser Pro
    50                  55                  60

Ser Arg Gly Leu Glu Trp Leu Gly Arg Thr Tyr Tyr Arg Ser Ala Trp
65                  70                  75                  80

Tyr Asn Asp Tyr Ala Val Ser Val Lys Gly Arg Ile Thr Phe Asn Pro
            85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Gly Glu Ser Gly Ala Ala
            115                 120                 125
```

Ala Asp Ala Phe Asp Ile Trp Gly Gln Gly Thr Thr Val Thr Val Ser
130                 135                 140

Gly Gly Gly Gly Ser Gly Gly Gly Ser Gly Gly Gly Gly Ser Asp
145                 150                 155                 160

Ile Gln Leu Thr Gln Ser Pro Pro Ser Leu Ser Ala Ser Val Gly Asp
            165                 170                 175

Arg Val Thr Ile Thr Cys Arg Ala Ser Gln Ser Ile Ser Ser Tyr Leu
            180                 185                 190

Asn Trp Tyr Gln Gln Lys Pro Gly Lys Ala Pro Lys Leu Leu Ile Tyr
        195                 200                 205

Ala Ala Ser Ser Leu Gln Ser Gly Val Pro Ser Arg Phe Ser Gly Ser
210                 215                 220

Gly Phe Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Ser Thr Pro Gln Thr
                245                 250                 255

Phe Gly Gln Gly Thr Lys Val Asp Ile Lys Ser Asp Pro Gly Ser Gly
            260                 265                 270

Gly Gly Gly Ser Cys Pro Tyr Ser Asn Pro Ser Leu Cys Ser Gly Gly
        275                 280                 285

Gly Gly Ser Cys Pro Tyr Ser Asn Pro Ser Leu Cys Ser Gly Gly Gly
    290                 295                 300

Gly Ser Thr Thr Thr Pro Ala Pro Arg Pro Pro Thr Pro Ala Pro Thr
305                 310                 315                 320

Ile Ala Ser Gln Pro Leu Ser Leu Arg Pro Glu Ala Cys Arg Pro Ala
                325                 330                 335

Ala Gly Gly Ala Val His Thr Arg Gly Leu Asp Phe Ala Cys Asp Ile
            340                 345                 350

Tyr Ile Trp Ala Pro Leu Ala Gly Thr Cys Gly Val Leu Leu Leu Ser
            355                 360                 365

Leu Val Ile Thr Leu Tyr Cys Lys Arg Gly Arg Lys Lys Leu Leu Tyr
370                 375                 380

Ile Phe Lys Gln Pro Phe Met Arg Pro Val Gln Thr Thr Gln Glu Glu
385                 390                 395                 400

Asp Gly Cys Ser Cys Arg Phe Pro Glu Glu Glu Glu Gly Gly Cys Glu
                405                 410                 415

Leu Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Arg Gly Arg Asp Pro Glu Met Gly Gly
450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
            515                 520                 525

Arg

<210> SEQ ID NO 69

<211> LENGTH: 529
<212> TYPE: PRT
<213> ORGANISM: artificial sequence
<220> FEATURE:
<223> OTHER INFORMATION: CAR10R2

<400> SEQUENCE: 69

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Glu Asp Ser Gly Ser Gly Ala Phe Asp
        115                 120                 125

Ile Trp Gly Gln Gly Thr Leu Val Thr Val Ser Gly Gly Gly Gly Ser
    130                 135                 140

Gly Gly Gly Gly Ser Gly Gly Gly Ser Glu Ile Val Leu Thr Gln
145                 150                 155                 160

Ser Pro Leu Ser Leu Pro Val Thr Pro Gly Glu Pro Ala Ser Ile Ser
                165                 170                 175

Cys Arg Ser Ser Arg Ser Leu Leu Ser Tyr His Gly Tyr Asn Tyr Leu
            180                 185                 190

Asp Trp Tyr Leu Gln Lys Pro Gly Gln Ser Pro Gln Leu Leu Ile Phe
        195                 200                 205

Val Gly Ser Asn Arg Ala Pro Gly Val Pro Asp Arg Phe Ser Gly Ser
    210                 215                 220

Gly Ser Gly Thr Asp Phe Thr Leu Asn Ile Ser Arg Val Glu Ala Glu
225                 230                 235                 240

Asp Val Gly Val Tyr Tyr Cys Met Gln Ser Leu Gln Thr Pro Arg Thr
                245                 250                 255

Phe Gly Gln Gly Thr Lys Val Glu Ile Lys Ser Asp Pro Gly Ser Gly
            260                 265                 270

Gly Gly Gly Ser Cys Pro Tyr Ser Asn Pro Ser Leu Cys Ser Gly Gly
        275                 280                 285

Gly Gly Ser Cys Pro Tyr Ser Asn Pro Ser Leu Cys Ser Gly Gly Gly
    290                 295                 300

Gly Ser Thr Thr Thr Pro Ala Pro Arg Pro Pro Thr Pro Ala Pro Thr
305                 310                 315                 320

Ile Ala Ser Gln Pro Leu Ser Leu Arg Pro Glu Ala Cys Arg Pro Ala
                325                 330                 335

Ala Gly Gly Ala Val His Thr Arg Gly Leu Asp Phe Ala Cys Asp Ile
            340                 345                 350

Tyr Ile Trp Ala Pro Leu Ala Gly Thr Cys Gly Val Leu Leu Leu Ser
        355                 360                 365

Leu Val Ile Thr Leu Tyr Cys Lys Arg Gly Arg Lys Lys Leu Leu Tyr
    370                 375                 380
```

```
Ile Phe Lys Gln Pro Phe Met Arg Pro Val Gln Thr Thr Gln Glu Glu
385                 390                 395                 400

Asp Gly Cys Ser Cys Arg Phe Pro Glu Glu Glu Gly Gly Cys Glu
            405                 410                 415

Leu Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
            435                 440                 445

Tyr Asp Val Leu Asp Lys Arg Arg Gly Arg Asp Pro Glu Met Gly Gly
        450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
            485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg
```

<210> SEQ ID NO 70
<211> LENGTH: 59
<212> TYPE: DNA
<213> ORGANISM: artificial sequence
<220> FEATURE:
<223> OTHER INFORMATION: TARGET TALEN(R)
<220> FEATURE:
<221> NAME/KEY: misc_feature
<222> LOCATION: (44)..(44)
<223> OTHER INFORMATION: r is a or g

<400> SEQUENCE: 70
rgatcctctt gtcccacaga tatccagaac cctgaccctg ccgrgtacca gctgagaga        59

<210> SEQ ID NO 71
<211> LENGTH: 121
<212> TYPE: PRT
<213> ORGANISM: artificial sequence
<220> FEATURE:
<223> OTHER INFORMATION: VH CAR1

<400> SEQUENCE: 71

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Thr Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Glu Val Ser Gly Thr Ser Ala Phe Asp Ile Trp
            100                 105                 110

Gly Gln Gly Thr Met Val Thr Val Ser
        115                 120
```

<210> SEQ ID NO 72
<211> LENGTH: 107
<212> TYPE: PRT
<213> ORGANISM: artificial sequence
<220> FEATURE:
<223> OTHER INFORMATION: VL CAR1

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys
            100                 105

<210> SEQ ID NO 73
<211> LENGTH: 126
<212> TYPE: PRT
<213> ORGANISM: artificial sequence
<220> FEATURE:
<223> OTHER INFORMATION: VH CAR2

<400> SEQUENCE: 73

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ala Ser Met Thr Gly Gly Tyr Ser Tyr Gly Asp
            100                 105                 110

Ala Phe Asp Ile Trp Gly Gln Gly Thr Leu Val Thr Val Ser
        115                 120                 125

<210> SEQ ID NO 74
<211> LENGTH: 107
<212> TYPE: PRT
<213> ORGANISM: artificial sequence
<220> FEATURE:
<223> OTHER INFORMATION: VL CAR2

<400> SEQUENCE: 74

Ala Ile Arg Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Ser Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105
```

<210> SEQ ID NO 75
<211> LENGTH: 122
<212> TYPE: PRT
<213> ORGANISM: artificial sequence
<220> FEATURE:
<223> OTHER INFORMATION: VH CAR3

<400> SEQUENCE: 75

```
Gln Val Gln Leu Gln Gln Ser Gly Pro Gly Leu Val Glu Pro Ser Gln
1               5                   10                  15

Thr Leu Ser Leu Thr Cys Ala Ile Ser Gly Asp Ser Val Ser Ser Asp
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Thr Trp Tyr Asn Asp Tyr Ala
    50                  55                  60

Gly Ser Val Lys Ser Arg Ile Thr Ile Asn Pro Asp Thr Ser Lys Asn
65                  70                  75                  80

Gln Phe Ser Leu Gln Leu Thr Ser Val Thr Pro Glu Asp Thr Ala Val
                85                  90                  95

Tyr Tyr Cys Thr Arg Ser Arg His Asn Thr Phe Arg Gly Met Asp Val
            100                 105                 110

Trp Gly Gln Gly Thr Thr Val Thr Val Ser
            115                 120
```

<210> SEQ ID NO 76
<211> LENGTH: 107
<212> TYPE: PRT
<213> ORGANISM: artificial sequence
<220> FEATURE:
<223> OTHER INFORMATION: VL CAR3

<400> SEQUENCE: 76

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Thr Thr Pro Ile
                85                  90                  95
```

```
Thr Phe Gly Gln Gly Thr Arg Leu Glu Ile Lys
            100                 105

<210> SEQ ID NO 77
<211> LENGTH: 122
<212> TYPE: PRT
<213> ORGANISM: artificial sequence
<220> FEATURE:
<223> OTHER INFORMATION: VH CAR4

<400> SEQUENCE: 77

Gln Val Gln Leu Gln Gln Ser Gly Pro Gly Leu Val Glu Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Thr Trp Tyr Asn Asp Tyr Ala
    50                  55                  60

Gly Ser Val Lys Ser Arg Ile Thr Ile Asn Pro Asp Thr Ser Lys Asn
65                  70                  75                  80

Gln Phe Ser Leu Gln Leu Thr Ser Val Thr Pro Glu Asp Thr Ala Val
                85                  90                  95

Tyr Tyr Cys Thr Arg Ser Arg His Asn Thr Phe Arg Gly Met Asp Val
            100                 105                 110

Trp Gly Gln Gly Thr Leu Val Thr Val Ser
        115                 120

<210> SEQ ID NO 78
<211> LENGTH: 107
<212> TYPE: PRT
<213> ORGANISM: artificial sequence
<220> FEATURE:
<223> OTHER INFORMATION: VL CAR4

<400> SEQUENCE: 78

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 79
<211> LENGTH: 118
<212> TYPE: PRT
<213> ORGANISM: artificial sequence
<220> FEATURE:
<223> OTHER INFORMATION: VH CAR5

<400> SEQUENCE: 79
```

```
Gln Val Gln Leu Gln Gln Ser Gly Pro Gly Leu Val Glu Pro Ser Gln
1               5                   10                  15

Thr Leu Ser Leu Thr Cys Ala Ile Ser Gly Asp Ser Val Ser Ser Asp
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Thr Trp Tyr Asn Asp Tyr Ala
50                  55                  60

Gly Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Asp Arg Asn Gly Met Asp Val Trp Gly Gln Gly
            100                 105                 110

Thr Met Val Thr Val Ser
            115

<210> SEQ ID NO 80
<211> LENGTH: 107
<212> TYPE: PRT
<213> ORGANISM: artificial sequence
<220> FEATURE:
<223> OTHER INFORMATION: VL CAR5

<400> SEQUENCE: 80

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Thr Ser Leu Gln Pro
65                  70                  75                  80

Glu Asp Phe Ala Thr Tyr Tyr Cys Gln Gln Ser Tyr Thr Thr Pro Leu
            85                  90                  95

Thr Phe Gly Gly Gly Thr Lys Val Glu Ile Lys
            100                 105

<210> SEQ ID NO 81
<211> LENGTH: 121
<212> TYPE: PRT
<213> ORGANISM: artificial sequence
<220> FEATURE:
<223> OTHER INFORMATION: VH CAR6

<400> SEQUENCE: 81

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Ala Trp Tyr Asn Asp Tyr Ala
50                  55                  60

Val Ser Val Lys Ser Arg Ile Thr Ile Asn Pro Asp Thr Ser Lys Asn
65                  70                  75                  80
```

```
Gln Phe Ser Leu Gln Leu Asn Ser Val Thr Pro Glu Asp Thr Ala Val
                85                  90                  95

Tyr Tyr Cys Ala Arg Glu Ser Val Leu Leu Asp Gly Met Asp Val Trp
            100                 105                 110

Gly Arg Gly Thr Thr Val Thr Val Ser
        115                 120

<210> SEQ ID NO 82
<211> LENGTH: 107
<212> TYPE: PRT
<213> ORGANISM: artificial sequence
<220> FEATURE:
<223> OTHER INFORMATION: VL CAR6

<400> SEQUENCE: 82

Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Ala Gly Lys Ala Pro Arg Leu Leu Ile
        35                  40                  45

His Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 83
<211> LENGTH: 128
<212> TYPE: PRT
<213> ORGANISM: artificial sequence
<220> FEATURE:
<223> OTHER INFORMATION: VH CAR7

<400> SEQUENCE: 83

Gln Val Gln Leu Gln Gln Ser Gly Pro Gly Leu Val Gln Pro Ser Gln
1               5                   10                  15

Thr Leu Ser Leu Thr Cys Val Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Asp Gly Gly Ser Tyr Tyr Asp Tyr Tyr
            100                 105                 110

Tyr Tyr Gly Met Asp Val Trp Gly Gln Gly Thr Thr Val Thr Val Ser
        115                 120                 125

<210> SEQ ID NO 84
<211> LENGTH: 107
<212> TYPE: PRT
```

```
<213> ORGANISM: artificial sequence
<220> FEATURE:
<223> OTHER INFORMATION: VL CAR7

<400> SEQUENCE: 84

Asp Ile Gln Leu Thr Gln Ser Pro Ser Leu Ser Thr Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Thr Thr Pro Ile
                85                  90                  95

Thr Phe Gly Gln Gly Thr Arg Leu Glu Ile Lys
            100                 105

<210> SEQ ID NO 85
<211> LENGTH: 118
<212> TYPE: PRT
<213> ORGANISM: artificial sequence
<220> FEATURE:
<223> OTHER INFORMATION: VH CAR8

<400> SEQUENCE: 85

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Ala Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Val Glu Gly Phe Asp Tyr Trp Gly Gln Gly
            100                 105                 110

Thr Leu Val Thr Val Ser
        115

<210> SEQ ID NO 86
<211> LENGTH: 107
<212> TYPE: PRT
<213> ORGANISM: artificial sequence
<220> FEATURE:
<223> OTHER INFORMATION: VL CAR8

<400> SEQUENCE: 86

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 87
<211> LENGTH: 123
<212> TYPE: PRT
<213> ORGANISM: artificial sequence
<220> FEATURE:
<223> OTHER INFORMATION: VH CAR9

<400> SEQUENCE: 87

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Gly Asn
            20                  25                  30

Arg Ala Thr Trp Asn Trp Ile Arg Gln Ser Pro Ser Arg Gly Leu Glu
        35                  40                  45

Trp Leu Gly Arg Thr Tyr Tyr Arg Ser Ala Trp Tyr Asn Asp Tyr Ala
    50                  55                  60

Val Ser Val Lys Gly Arg Ile Thr Phe Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Glu Ser Gly Ala Ala Ala Asp Ala Phe Asp
            100                 105                 110

Ile Trp Gly Gln Gly Thr Thr Val Thr Val Ser
        115                 120

<210> SEQ ID NO 88
<211> LENGTH: 107
<212> TYPE: PRT
<213> ORGANISM: artificial sequence
<220> FEATURE:
<223> OTHER INFORMATION: VL CAR9

<400> SEQUENCE: 88

Asp Ile Gln Leu Thr Gln Ser Pro Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys
            100                 105
```

```
<210> SEQ ID NO 89
<211> LENGTH: 118
<212> TYPE: PRT
<213> ORGANISM: artificial sequence
<220> FEATURE:
<223> OTHER INFORMATION: VH CAR10

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Asp Ser Gly Ser Gly Ala Phe Asp Ile Trp Gly Gln Gly
            100                 105                 110

Thr Leu Val Thr Val Ser
        115

<210> SEQ ID NO 90
<211> LENGTH: 112
<212> TYPE: PRT
<213> ORGANISM: artificial sequence
<220> FEATURE:
<223> OTHER INFORMATION: VL CAR10

<400> SEQUENCE: 90

Glu Ile Val Leu Thr Gln Ser Pro Leu Ser Leu Pro Val Thr Pro Gly
1               5                   10                  15

Glu Pro Ala Ser Ile Ser Cys Arg Ser Ser Arg Ser Leu Leu Ser Tyr
                20                  25                  30

His Gly Tyr Asn Tyr Leu Asp Trp Tyr Leu Gln Lys Pro Gly Gln Ser
            35                  40                  45

Pro Gln Leu Leu Ile Phe Val Gly Ser Asn Arg Ala Pro Gly Val Pro
        50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly Val Tyr Tyr Cys Met Gln Ser
                85                  90                  95

Leu Gln Thr Pro Arg Thr Phe Gly Gln Gly Thr Lys Val Glu Ile Lys
            100                 105                 110

<210> SEQ ID NO 91
<211> LENGTH: 9
<212> TYPE: PRT
<213> ORGANISM: artificial sequence
<220> FEATURE:
<223> OTHER INFORMATION: R

<400> SEQUENCE: 91

Cys Pro Tyr Ser Asn Pro Ser Leu Cys
1               5

<210> SEQ ID NO 92
```

```
<211> LENGTH: 24
<212> TYPE: PRT
<213> ORGANISM: artificial sequence
<220> FEATURE:
<223> OTHER INFORMATION: Q

<400> SEQUENCE: 92

Glu Leu Pro Thr Gln Gly Thr Phe Ser Asn Val Ser Thr Asn Val Ser
1               5                   10                  15

Pro Ala Lys Pro Thr Thr Thr Ala
            20

<210> SEQ ID NO 93
<211> LENGTH: 489
<212> TYPE: PRT
<213> ORGANISM: artificial sequence
<220> FEATURE:
<223> OTHER INFORMATION: CAR distal CD22

<400> SEQUENCE: 93

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Lys Leu Ser Cys Ala Ala Ser Gly Phe
        35                  40                  45

Ala Phe Ser Ile Tyr Asp Met Ser Trp Val Arg Gln Thr Pro Glu Lys
    50                  55                  60

Arg Leu Glu Trp Val Ala Tyr Ile Ser Ser Gly Gly Gly Thr Tyr Tyr
65                  70                  75                  80

Pro Asp Thr Val Lys Gly Arg Phe Thr Ile Ser Arg Asp Asn Ala Lys
                85                  90                  95

Asn Thr Leu Tyr Leu Gln Met Ser Ser Leu Lys Ser Glu Asp Thr Ala
            100                 105                 110

Met Tyr Tyr Cys Ala Arg His Ser Gly Tyr Gly Thr His Trp Gly Val
        115                 120                 125

Leu Phe Ala Tyr Trp Gly Gln Gly Thr Leu Val Thr Val Ser Ala Gly
    130                 135                 140

Gly Gly Gly Ser Gly Gly Gly Gly Ser Gly Gly Gly Gly Ser Asp Ile
145                 150                 155                 160

Gln Met Thr Gln Thr Thr Ser Ser Leu Ser Ala Ser Leu Gly Asp Arg
                165                 170                 175

Val Thr Ile Ser Cys Arg Ala Ser Gln Asp Ile Ser Asn Tyr Leu Asn
            180                 185                 190

Trp Tyr Gln Gln Lys Pro Asp Gly Thr Val Lys Leu Leu Ile Tyr Tyr
        195                 200                 205

Thr Ser Ile Leu His Ser Gly Val Pro Ser Arg Phe Ser Gly Ser Gly
    210                 215                 220

Ser Gly Thr Asp Tyr Ser Leu Thr Ile Ser Asn Leu Glu Gln Glu Asp
225                 230                 235                 240

Phe Ala Thr Tyr Phe Cys Gln Gln Gly Asn Thr Leu Pro Trp Thr Phe
                245                 250                 255

Gly Gly Gly Thr Lys Leu Glu Ile Lys Ala Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
```

|     |     |     |     |     |     |     |     |     |     |
| --- | --- | --- | --- | --- | --- | --- | --- | --- | --- |
|     |     | 290 |     |     | 295 |     |     | 300 |     |

Gly Leu Asp Phe Ala Cys Asp Ile Tyr Ile Trp Ala Pro Leu Ala Gly
305                     310                     315                     320

Thr Cys Gly Val Leu Leu Ser Leu Val Ile Thr Leu Tyr Cys Lys
                    325                     330                     335

Arg Gly Arg Lys Lys Leu Leu Tyr Ile Phe Lys Gln Pro Phe Met Arg
                340                     345                     350

Pro Val Gln Thr Thr Gln Glu Glu Asp Gly Cys Ser Cys Arg Phe Pro
            355                     360                     365

Glu Glu Glu Glu Gly Gly Cys Glu Leu Arg Val Lys Phe Ser Arg Ser
    370                     375                     380

Ala Asp Ala Pro Ala Tyr Gln Gln Gly Gln Asn Gln Leu Tyr Asn Glu
385                     390                     395                     400

Leu Asn Leu Gly Arg Arg Glu Glu Tyr Asp Val Leu Asp Lys Arg Arg
                405                     410                     415

Gly Arg Asp Pro Glu Met Gly Gly Lys Pro Arg Arg Lys Asn Pro Gln
            420                     425                     430

Glu Gly Leu Tyr Asn Glu Leu Gln Lys Asp Lys Met Ala Glu Ala Tyr
        435                     440                     445

Ser Glu Ile Gly Met Lys Gly Glu Arg Arg Arg Gly Lys Gly His Asp
    450                     455                     460

Gly Leu Tyr Gln Gly Leu Ser Thr Ala Thr Lys Asp Thr Tyr Asp Ala
465                     470                     475                     480

Leu His Met Gln Ala Leu Pro Pro Arg
                485

<210> SEQ ID NO 94
<211> LENGTH: 1470
<212> TYPE: DNA
<213> ORGANISM: artificial sequence
<220> FEATURE:
<223> OTHER INFORMATION: CAR distal CD22

<400> SEQUENCE: 94

| | | | | | |
|---|---|---|---|---|---|
| atggctctgc | ccgtcaccgc | tctgctgctg | ccactggccc | tgctgctgca | cgcagcaagg | 60 |
| cctgaggtgc | agctggtgga | atccggagga | ggcctggtga | agcctggcgg | ctctctgaag | 120 |
| ctgagctgtg | ccgcctccgg | cttcgccttt | tccatctacg | acatgtcttg | ggtgaggcag | 180 |
| accccagaga | agcgcctgga | gtgggtggcc | tatatcagct | ccggcggcgg | cacctactat | 240 |
| cccgacacag | tgaagggccg | gttcaccatc | tctagagata | cgccaagaa | tacactgtac | 300 |
| ctgcagatgt | ctagcctgaa | gagcgaggat | accgccatgt | actattgcgc | aaggcactcc | 360 |
| ggatacggaa | cacactgggg | cgtgctgttt | gcctattggg | gccagggcac | cctggtgaca | 420 |
| gtgagcgccg | gaggaggagg | aagcggcgga | ggaggctccg | gcggcggcgg | ctctgacatc | 480 |
| cagatgaccc | agaccacatc | cctctctagc | gcctccctgg | gcgacagggt | gacaatctct | 540 |
| tgtagagcca | gccaggatat | ctccaactac | ctgaattggt | atcagcagaa | gcctgatggc | 600 |
| accgtgaagc | tgctgatcta | ctatacatct | atcctgcaca | gcggagtgcc | atcccggttc | 660 |
| tctggaagcg | gatccggaac | cgactactct | ctgacaatca | gcaacctgga | gcaggaggat | 720 |
| ttcgccacct | atttttgcca | gcagggcaat | accctgcctt | ggacatttgg | cggcggcaca | 780 |
| aagctggaga | tcaaggccac | cacaaccct | gcaccaaggc | caccaacacc | agcacctacc | 840 |
| atcgcatctc | agcctctgag | cctgagacca | gaggcatgta | ggccagcagc | aggaggagca | 900 |
| gtgcacacaa | ggggactgga | ttttgcctgt | gatatctaca | tctgggcacc | tctggcagga | 960 |

-continued

```
acatgtggcg tgctcctgct cagcctggtc atcaccctgt actgcaagag aggcaggaag    1020
aagctgctgt atatcttcaa gcagcccttc atgagacccg tgcagacaac ccaggaggag    1080
gacggctgct cctgtaggtt cccagaagag gaggagggag gatgtgagct gcgcgtgaag    1140 tttttcccggt ctgccgatgc acctgcatac cagcagggac agaatcagct gtataacgag    1200
ctgaatctgg gccggagaga ggagtacgac gtgctggata agaggagggg aagggaccca    1260
gagatgggag gcaagcctcg gagaaagaac ccacaggagg gcctgtacaa tgagctgcag    1320
aaggacaaga tggccgaggc ctattctgag atcggcatga agggagagag gcgccggggc    1380
aagggacacg atggcctgta ccagggcctg tccacagcca ccaaggacac ctatgatgcc    1440
ctgcatatgc aggcactgcc tccaaggtga                                      1470
```

<210> SEQ ID NO 95
<211> LENGTH: 495
<212> TYPE: PRT
<213> ORGANISM: artificial sequence
<220> FEATURE:
<223> OTHER INFORMATION: description of artificial sequence: synthetic polypeptide
<220> FEATURE:
<221> NAME/KEY: misc_feature
<223> OTHER INFORMATION: 4G7-CAR version 1

<400> SEQUENCE: 95

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Ile Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Gly Ser Arg Val
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
    210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
```

```
                    245                 250                 255
Pro Phe Thr Phe Gly Ala Gly Thr Lys Leu Glu Leu Lys Arg Ala Asp
                260                 265                 270

Thr Thr Thr Pro Ala Pro Arg Pro Pro Thr Pro Ala Pro Thr Ile Ala
            275                 280                 285

Ser Gln Pro Leu Ser Leu Arg Pro Glu Ala Cys Arg Pro Ala Ala Gly
        290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 96
<211> LENGTH: 495
<212> TYPE: PRT
<213> ORGANISM: artificial sequence
<220> FEATURE:
<223> OTHER INFORMATION: description of artificial sequence: synthetic
      polypeptide
<220> FEATURE:
<221> NAME/KEY: misc_feature
<223> OTHER INFORMATION: 4G7-CAR version 2

<400> SEQUENCE: 96

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
        35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95
```

Ser Thr Ala Tyr Met Glu Leu Ser Ser Leu Thr Ser Glu Asp Ser Ala
                100                 105                 110

Val Tyr Tyr Cys Ala Arg Gly Thr Tyr Tyr Gly Ser Arg Val Phe
        115                 120                 125

Asp Tyr Trp Gly Gln Gly Thr Thr Leu Thr Val Ser Ser Gly Gly Gly
        130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
        195                 200                 205

Ile Tyr Arg Met Ser Asn Leu Ala Ser Gly Val Pro Asp Arg Phe Ser
        210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
        290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
        450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 97
<211> LENGTH: 5
<212> TYPE: PRT

```
<213> ORGANISM: Artificial Sequence
<220> FEATURE:
<223> OTHER INFORMATION: pentapeptide linker

<400> SEQUENCE: 97

Gly Gly Gly Gly Ser
1               5

<210> SEQ ID NO 98
<211> LENGTH: 18
<212> TYPE: PRT
<213> ORGANISM: Artificial Sequence
<220> FEATURE:
<223> OTHER INFORMATION: 18-mer linker

<400> SEQUENCE: 98

Gly Gly Ser Ser Arg Ser Ser Ser Ser Gly Gly Gly Gly Ser Gly Gly
1               5                   10                  15

Gly Gly

<210> SEQ ID NO 99
<211> LENGTH: 15
<212> TYPE: PRT
<213> ORGANISM: Artificial Sequence
<220> FEATURE:
<223> OTHER INFORMATION: 15-mer linker

<400> SEQUENCE: 99

Arg Gly Arg Gly Arg Gly Arg Gly Arg Ser Arg Gly Gly Gly Ser
1               5                   10                  15

<210> SEQ ID NO 100
<211> LENGTH: 4
<212> TYPE: PRT
<213> ORGANISM: Artificial Sequence
<220> FEATURE:
<223> OTHER INFORMATION: Linker

<400> SEQUENCE: 100

Gly Gly Gly Ser
1

<210> SEQ ID NO 101
<211> LENGTH: 4
<212> TYPE: PRT
<213> ORGANISM: Artificial Sequence
<220> FEATURE:
<223> OTHER INFORMATION: Linker

<400> SEQUENCE: 101

Ser Gly Gly Ser
1

<210> SEQ ID NO 102
<211> LENGTH: 5
<212> TYPE: PRT
<213> ORGANISM: Artificial Sequence
<220> FEATURE:
<223> OTHER INFORMATION: Linker

<400> SEQUENCE: 102

Ser Ser Gly Gly Ser
1               5

<210> SEQ ID NO 103
<211> LENGTH: 4
```

```
<212> TYPE: PRT
<213> ORGANISM: Artificial Sequence
<220> FEATURE:
<223> OTHER INFORMATION: Linker

<400> SEQUENCE: 103

Gly Gly Gly Gly
1

<210> SEQ ID NO 104
<211> LENGTH: 5
<212> TYPE: PRT
<213> ORGANISM: Artificial Sequence
<220> FEATURE:
<223> OTHER INFORMATION: Linker

<400> SEQUENCE: 104

Ser Gly Gly Gly Gly
1               5

<210> SEQ ID NO 105
<211> LENGTH: 6
<212> TYPE: PRT
<213> ORGANISM: Artificial Sequence
<220> FEATURE:
<223> OTHER INFORMATION: Linker

<400> SEQUENCE: 105

Ser Gly Gly Gly Gly Ser
1               5

<210> SEQ ID NO 106
<211> LENGTH: 6
<212> TYPE: PRT
<213> ORGANISM: Artificial Sequence
<220> FEATURE:
<223> OTHER INFORMATION: Linker

<400> SEQUENCE: 106

Gly Gly Gly Gly Gly Ser
1               5

<210> SEQ ID NO 107
<211> LENGTH: 7
<212> TYPE: PRT
<213> ORGANISM: Artificial Sequence
<220> FEATURE:
<223> OTHER INFORMATION: Linker

<400> SEQUENCE: 107

Ser Gly Gly Gly Gly Gly Ser
1               5

<210> SEQ ID NO 108
<211> LENGTH: 6
<212> TYPE: PRT
<213> ORGANISM: Artificial Sequence
<220> FEATURE:
<223> OTHER INFORMATION: Linker

<400> SEQUENCE: 108

Ser Gly Gly Gly Gly Gly
1               5

<210> SEQ ID NO 109
<211> LENGTH: 7
<212> TYPE: PRT
```

```
<213> ORGANISM: Artificial Sequence
<220> FEATURE:
<223> OTHER INFORMATION: Linker

<400> SEQUENCE: 109

Gly Ser Gly Gly Gly Gly Ser
1               5

<210> SEQ ID NO 110
<211> LENGTH: 8
<212> TYPE: PRT
<213> ORGANISM: Artificial Sequence
<220> FEATURE:
<223> OTHER INFORMATION: Linker

<400> SEQUENCE: 110

Gly Gly Gly Gly Gly Gly Gly Ser
1               5

<210> SEQ ID NO 111
<211> LENGTH: 8
<212> TYPE: PRT
<213> ORGANISM: Artificial Sequence
<220> FEATURE:
<223> OTHER INFORMATION: Linker

<400> SEQUENCE: 111

Ser Gly Gly Gly Gly Gly Gly Gly
1               5

<210> SEQ ID NO 112
<211> LENGTH: 9
<212> TYPE: PRT
<213> ORGANISM: Artificial Sequence
<220> FEATURE:
<223> OTHER INFORMATION: Linker

<400> SEQUENCE: 112

Ser Gly Gly Gly Gly Gly Gly Gly Ser
1               5

<210> SEQ ID NO 113
<211> LENGTH: 11
<212> TYPE: PRT
<213> ORGANISM: Artificial Sequence
<220> FEATURE:
<223> OTHER INFORMATION: Linker

<400> SEQUENCE: 113

Ser Gly Gly Gly Gly Ser Gly Gly Gly Gly Ser
1               5                   10

<210> SEQ ID NO 114
<211> LENGTH: 24
<212> TYPE: PRT
<213> ORGANISM: Artificial Sequence
<220> FEATURE:
<223> OTHER INFORMATION: mAb-specific epitope

<400> SEQUENCE: 114

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 115
```

```
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 115

Cys Gln Phe Asp Leu Ser Thr Arg Arg Leu Lys Cys
1               5                   10

<210> SEQ ID NO 116
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 116

Cys Gln Tyr Asn Leu Ser Ser Arg Ala Leu Lys Cys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 117

Cys Val Trp Gln Arg Trp Gln Lys Ser Tyr Val Cys
1               5                   10

<210> SEQ ID NO 118
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 118

Cys Met Trp Asp Arg Phe Ser Arg Trp Tyr Lys Cys
1               5                   10

<210> SEQ ID NO 119
<211> LENGTH: 25
<212> TYPE: PRT
<213> ORGANISM: Artificial Sequence
<220> FEATURE:
<223> OTHER INFORMATION: mAb-specific epitope

<400> SEQUENCE: 119

Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25

<210> SEQ ID NO 120
<211> LENGTH: 19
<212> TYPE: PRT
<213> ORGANISM: Artificial Sequence
<220> FEATURE:
<223> OTHER INFORMATION: mAb-specific epitope

<400> SEQUENCE: 120

Ser Gly Thr Tyr Leu Cys Gly Ala Ile Ser Leu Ala Pro Lys Ala Gln
1               5                   10                  15
```

Ile Lys Glu

<210> SEQ ID NO 121
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 121

Gly Gln Asn Asp Thr Ser Gln Thr Ser Ser Pro Ser
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Linker

<400> SEQUENCE: 122

Gly Gly Gly Gly Ser Gly Gly Gly Gly Ser Gly Gly Gly Gly Ser
1               5                   10                  15

<210> SEQ ID NO 123
<211> LENGTH: 16
<212> TYPE: DNA
<213> ORGANISM: Artificial Sequence
<220> FEATURE:
<223> OTHER INFORMATION: TRAC target sequence

<400> SEQUENCE: 123
ttgtcccaca gatatc                                                   16

<210> SEQ ID NO 124
<211> LENGTH: 19
<212> TYPE: DNA
<213> ORGANISM: Artificial Sequence
<220> FEATURE:
<223> OTHER INFORMATION: TRAC target sequence

<400> SEQUENCE: 124
ttgtcccaca gatatccag                                                19

<210> SEQ ID NO 125
<211> LENGTH: 15
<212> TYPE: DNA
<213> ORGANISM: Artificial Sequence
<220> FEATURE:
<223> OTHER INFORMATION: Sequence cleaved by TALEN

<400> SEQUENCE: 125
agaaccctga ccctg                                                    15

<210> SEQ ID NO 126
<211> LENGTH: 49
<212> TYPE: DNA
<213> ORGANISM: Artificial Sequence
<220> FEATURE:
<223> OTHER INFORMATION: Target sequence

<400> SEQUENCE: 126
ttgtcccaca gatatccaga accctgaccc tgccgtgtac cagctgaga              49

<210> SEQ ID NO 127
<211> LENGTH: 454

```
<212> TYPE: PRT
<213> ORGANISM: Artificial sequence
<220> FEATURE:
<223> OTHER INFORMATION: Synthetic

<400> SEQUENCE: 127
```

| | | | | | | | | | | | | | | |
|---|---|---|---|---|---|---|---|---|---|---|---|---|---|---|
| Met | Ala | Leu | Pro | Val | Thr | Ala | Leu | Leu | Pro | Leu | Ala | Leu | Leu | His |
| 1 | | | | 5 | | | | | 10 | | | | | 15 |
| Ala | Ala | Arg | Pro | Glu | Val | Gln | Leu | Val | Gln | Ser | Gly | Gly | Gly | Val |
| | | | 20 | | | | | 25 | | | | | 30 | |
| Arg | Pro | Gly | Gly | Ser | Leu | Arg | Leu | Pro | Cys | Ala | Ala | Ser | Gly | Phe | Thr |
| | | 35 | | | | | 40 | | | | | 45 | | | |
| Phe | Asp | Asp | Tyr | Gly | Met | Ser | Trp | Val | Arg | Gln | Ala | Pro | Gly | Lys | Gly |
| 50 | | | | | 55 | | | | | 60 | | | | | |
| Leu | Glu | Trp | Val | Ser | Gly | Ile | Asn | Trp | Asn | Gly | Ser | Thr | Gly | Tyr |
| 65 | | | | 70 | | | | | 75 | | | | | 80 |
| Ala | Asp | Ser | Val | Lys | Gly | Arg | Phe | Thr | Ile | Ser | Arg | Asp | Asn | Ala | Lys |
| | | | | 85 | | | | | 90 | | | | | 95 | |
| Asn | Ser | Leu | Tyr | Leu | Gln | Met | Asn | Ser | Leu | Arg | Ala | Glu | Asp | Thr | Ala |
| | | | 100 | | | | | 105 | | | | | 110 | | |
| Leu | Tyr | His | Cys | Ala | Arg | Gly | Gly | Asp | Ala | Phe | Asp | Ile | Trp | Gly |
| | | 115 | | | | | 120 | | | | | 125 | | |
| Gln | Gly | Thr | Met | Val | Thr | Val | Ser | Ser | Gly | Gly | Gly | Ser | Gly | Gly |
| | 130 | | | | | 135 | | | | | 140 | | | |
| Gly | Gly | Ser | Gly | Gly | Gly | Ser | Arg | Ile | Val | Met | Thr | Gln | Ser | Pro |
| 145 | | | | | 150 | | | | | 155 | | | | | 160 |
| Gly | Thr | Leu | Ser | Val | Ser | Pro | Gly | Glu | Thr | Ala | Thr | Leu | Ser | Cys | Arg |
| | | | | 165 | | | | | 170 | | | | | 175 | |
| Ala | Ser | Gln | Ser | Phe | Ser | Asn | Met | Leu | Ala | Trp | Tyr | Gln | Gln | Lys | Ser |
| | | | 180 | | | | | 185 | | | | | 190 | | |
| Gly | Gln | Pro | Pro | Arg | Leu | Leu | Ile | Tyr | Gly | Val | Ser | Thr | Arg | Ala | Ala |
| | 195 | | | | | 200 | | | | | 205 | | | | |
| Gly | Val | Pro | Ala | Arg | Phe | Ser | Gly | Ser | Gly | Ser | Gly | Thr | Glu | Phe | Thr |
| 210 | | | | | 215 | | | | | 220 | | | | | |
| Leu | Thr | Ile | Ser | Asn | Leu | Gln | Ser | Glu | Asp | Phe | Ala | Val | Tyr | Tyr | Cys |
| 225 | | | | | 230 | | | | | 235 | | | | | 240 |
| Gln | Gln | Tyr | Gly | Asp | Trp | Pro | Arg | Tyr | Thr | Phe | Gly | Gln | Gly | Thr | Lys |
| | | | | 245 | | | | | 250 | | | | | 255 | |
| Val | Glu | Arg | Lys | Gly | Leu | Ala | Val | Ser | Thr | Ile | Ser | Ser | Phe | Phe | Pro |
| | | | 260 | | | | | 265 | | | | | 270 | | |
| Pro | Gly | Tyr | Gln | Ile | Tyr | Ile | Trp | Ala | Pro | Leu | Ala | Gly | Thr | Cys | Gly |
| | 275 | | | | | 280 | | | | | 285 | | | | |
| Val | Leu | Leu | Leu | Ser | Leu | Val | Ile | Thr | Leu | Tyr | Cys | Lys | Arg | Gly | Arg |
| | 290 | | | | | 295 | | | | | 300 | | | | |
| Lys | Lys | Leu | Leu | Tyr | Ile | Phe | Lys | Gln | Pro | Phe | Met | Arg | Pro | Val | Gln |
| 305 | | | | | 310 | | | | | 315 | | | | | 320 |
| Thr | Thr | Gln | Glu | Glu | Asp | Gly | Cys | Ser | Cys | Arg | Phe | Pro | Glu | Glu | Glu |
| | | | | 325 | | | | | 330 | | | | | 335 | |
| Glu | Gly | Gly | Cys | Glu | Leu | Arg | Val | Lys | Phe | Ser | Arg | Ser | Ala | Asp | Ala |
| | | | 340 | | | | | 345 | | | | | 350 | | |
| Pro | Ala | Tyr | Gln | Gln | Gly | Gln | Asn | Gln | Leu | Tyr | Asn | Glu | Leu | Asn | Leu |
| | | 355 | | | | | 360 | | | | | 365 | | | |
| Gly | Arg | Arg | Glu | Glu | Tyr | Asp | Val | Leu | Asp | Lys | Arg | Arg | Gly | Arg | Asp |
| | 370 | | | | | 375 | | | | | 380 | | | | |

```
Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
            405                 410                 415

Gly Met Lys Gly Glu Arg Arg Arg Gly Lys Gly His Asp Gly Leu Tyr
        420                 425                 430

Gln Gly Leu Ser Thr Ala Thr Lys Asp Thr Tyr Asp Ala Leu His Met
        435                 440                 445

Gln Ala Leu Pro Pro Arg
        450

<210> SEQ ID NO 128
<211> LENGTH: 483
<212> TYPE: PRT
<213> ORGANISM: Artificial sequence
<220> FEATURE:
<223> OTHER INFORMATION: Synthetic

<400> SEQUENCE: 128

Met Ala Leu Pro Val Thr Ala Leu Leu Pro Leu Ala Leu Leu Leu His
1               5                   10                  15

Ala Ala Arg Pro Glu Val Gln Leu Val Gln Ser Gly Gly Gly Val Val
            20                  25                  30

Arg Pro Gly Gly Ser Leu Arg Leu Pro Cys Ala Ala Ser Gly Phe Thr
        35                  40                  45

Phe Asp Asp Tyr Gly Met Ser Trp Val Arg Gln Ala Pro Gly Lys Gly
    50                  55                  60

Leu Glu Trp Val Ser Gly Ile Asn Trp Asn Gly Ser Thr Gly Tyr
65              70                  75                  80

Ala Asp Ser Val Lys Gly Arg Phe Thr Ile Ser Arg Asp Asn Ala Lys
            85                  90                  95

Asn Ser Leu Tyr Leu Gln Met Asn Ser Leu Arg Ala Glu Asp Thr Ala
        100                 105                 110

Leu Tyr His Cys Ala Arg Gly Gly Asp Ala Phe Asp Ile Trp Gly
    115                 120                 125

Gln Gly Thr Met Val Thr Val Ser Ser Gly Gly Gly Ser Gly Gly
        130                 135                 140

Gly Gly Ser Gly Gly Gly Gly Ser Arg Ile Val Met Thr Gln Ser Pro
145                 150                 155                 160

Gly Thr Leu Ser Val Ser Pro Gly Glu Thr Ala Thr Leu Ser Cys Arg
            165                 170                 175

Ala Ser Gln Ser Phe Ser Asn Met Leu Ala Trp Tyr Gln Gln Lys Ser
        180                 185                 190

Gly Gln Pro Pro Arg Leu Leu Ile Tyr Gly Val Ser Thr Arg Ala Ala
    195                 200                 205

Gly Val Pro Ala Arg Phe Ser Gly Ser Gly Ser Gly Thr Glu Phe Thr
210                 215                 220

Leu Thr Ile Ser Asn Leu Gln Ser Glu Asp Phe Ala Val Tyr Tyr Cys
225                 230                 235                 240

Gln Gln Tyr Gly Asp Trp Pro Arg Tyr Thr Phe Gly Gln Gly Thr Lys
            245                 250                 255

Val Glu Arg Lys Thr Thr Thr Pro Ala Pro Arg Pro Pro Thr Pro Ala
        260                 265                 270

Pro Thr Ile Ala Ser Gln Pro Leu Ser Leu Arg Pro Glu Ala Cys Arg
    275                 280                 285
```

```
Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
                340                 345                 350

Glu Glu Asp Gly Cys Ser Cys Arg Phe Pro Glu Glu Glu Glu Gly Gly
                355                 360                 365

Cys Glu Leu Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
                435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 129
<211> LENGTH: 460
<212> TYPE: PRT
<213> ORGANISM: Artificial sequence
<220> FEATURE:
<223> OTHER INFORMATION: Synthetic

<400> SEQUENCE: 129

Met Ala Leu Pro Val Thr Ala Leu Leu Leu Pro Leu Ala Leu Leu Leu His
1               5                   10                  15

Ala Ala Arg Pro Gln Val Gln Leu Gln Gln Ser Gly Pro Gly Leu Val
                20                  25                  30

Lys Pro Ser Gln Thr Leu Ser Leu Thr Cys Ala Ile Ser Gly Asp Ser
            35                  40                  45

Val Ser Ser Asn Ser Ala Ala Trp Asn Trp Ile Arg Gln Ser Pro Ser
50                  55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Glu Val Thr Gly Asp Leu Glu
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Leu Ser Ala Ser Val Gly Asp
```

```
                    165                 170                 175

Arg Val Thr Ile Thr Cys Arg Ala Ser Gln Thr Ile Trp Ser Tyr Leu
                180                 185                 190

Asn Trp Tyr Gln Gln Arg Pro Gly Lys Ala Pro Asn Leu Leu Ile Tyr
            195                 200                 205

Ala Ala Ser Ser Leu Gln Ser Gly Val Pro Ser Arg Phe Ser Gly Arg
        210                 215                 220

Gly Ser Gly Thr Asp Phe Thr Leu Thr Ile Ser Ser Leu Gln Ala Glu
225                 230                 235                 240

Asp Phe Ala Thr Tyr Tyr Cys Gln Gln Ser Tyr Ser Ile Pro Gln Thr
                245                 250                 255

Phe Gly Gln Gly Thr Lys Leu Glu Ile Lys Gly Leu Ala Val Ser Thr
            260                 265                 270

Ile Ser Ser Phe Phe Pro Pro Gly Tyr Gln Ile Tyr Ile Trp Ala Pro
        275                 280                 285

Leu Ala Gly Thr Cys Gly Val Leu Leu Leu Ser Leu Val Ile Thr Leu
290                 295                 300

Tyr Cys Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg
450                 455                 460

<210> SEQ ID NO 130
<211> LENGTH: 489
<212> TYPE: PRT
<213> ORGANISM: Artificial sequence
<220> FEATURE:
<223> OTHER INFORMATION: Synthetic

<400> SEQUENCE: 130

Met Ala Leu Pro Val Thr Ala Leu Leu Pro Leu Ala Leu Leu Leu His
1               5                   10                  15

Ala Ala Arg Pro Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Tyr
```

-continued

```
             65                  70                  75                  80
Asn Asp Tyr Ala Val Ser Val Lys Ser Arg Ile Thr Ile Asn Pro Asp
                     85                  90                  95
Thr Ser Lys Asn Gln Phe Ser Leu Gln Leu Asn Ser Val Thr Pro Glu
                     100                 105                 110
Asp Thr Ala Val Tyr Tyr Cys Ala Arg Glu Val Thr Gly Asp Leu Glu
                     115                 120                 125
Asp Ala Phe Asp Ile Trp Gly Gln Gly Thr Met Val Thr Val Ser Ser
                     130                 135                 140
Gly Gly Gly Gly Ser Gly Gly Gly Ser Gly Gly Gly Gly Ser Asp
145                  150                 155                 160
Ile Gln Met Thr Gln Ser Pro Ser Ser Leu Ser Ala Ser Val Gly Asp
                     165                 170                 175
Arg Val Thr Ile Thr Cys Arg Ala Ser Gln Thr Ile Trp Ser Tyr Leu
                     180                 185                 190
Asn Trp Tyr Gln Gln Arg Pro Gly Lys Ala Pro Asn Leu Leu Ile Tyr
                     195                 200                 205
Ala Ala Ser Ser Leu Gln Ser Gly Val Pro Ser Arg Phe Ser Gly Arg
                     210                 215                 220
Gly Ser Gly Thr Asp Phe Thr Leu Thr Ile Ser Ser Leu Gln Ala Glu
225                  230                 235                 240
Asp Phe Ala Thr Tyr Tyr Cys Gln Gln Ser Tyr Ser Ile Pro Gln Thr
                     245                 250                 255
Phe Gly Gln Gly Thr Lys Leu Glu Ile Lys Thr Thr Thr Pro Ala Pro
                     260                 265                 270
Arg Pro Pro Thr Pro Ala Pro Thr Ile Ala Ser Gln Pro Leu Ser Leu
                     275                 280                 285
Arg Pro Glu Ala Cys Arg Pro Ala Ala Gly Gly Ala Val His Thr Arg
                     290                 295                 300
Gly Leu Asp Phe Ala Cys Asp Ile Tyr Ile Trp Ala Pro Leu Ala Gly
305                  310                 315                 320
Thr Cys Gly Val Leu Leu Leu Ser Leu Val Ile Thr Leu Tyr Cys Lys
                     325                 330                 335
Arg Gly Arg Lys Lys Leu Leu Tyr Ile Phe Lys Gln Pro Phe Met Arg
                     340                 345                 350
Pro Val Gln Thr Thr Gln Glu Glu Asp Gly Cys Ser Cys Arg Phe Pro
                     355                 360                 365
Glu Glu Glu Glu Gly Gly Cys Glu Leu Arg Val Lys Phe Ser Arg Ser
370                  375                 380
Ala Asp Ala Pro Ala Tyr Gln Gln Gly Gln Asn Gln Leu Tyr Asn Glu
385                  390                 395                 400
Leu Asn Leu Gly Arg Arg Glu Glu Tyr Asp Val Leu Asp Lys Arg Arg
                     405                 410                 415
Gly Arg Asp Pro Glu Met Gly Gly Lys Pro Arg Arg Lys Asn Pro Gln
                     420                 425                 430
Glu Gly Leu Tyr Asn Glu Leu Gln Lys Asp Lys Met Ala Glu Ala Tyr
                     435                 440                 445
Ser Glu Ile Gly Met Lys Gly Glu Arg Arg Arg Gly Lys Gly His Asp
                     450                 455                 460
Gly Leu Tyr Gln Gly Leu Ser Thr Ala Thr Lys Asp Thr Tyr Asp Ala
465                  470                 475                 480
Leu His Met Gln Ala Leu Pro Pro Arg
                     485
```

```
<210> SEQ ID NO 131
<211> LENGTH: 6
<212> TYPE: PRT
<213> ORGANISM: Artificial sequence
<220> FEATURE:
<223> OTHER INFORMATION: Synthetic

<400> SEQUENCE: 131

Gln Ser Ile Ser Ser Tyr
1               5

<210> SEQ ID NO 132
<211> LENGTH: 10
<212> TYPE: PRT
<213> ORGANISM: Artificial sequence
<220> FEATURE:
<223> OTHER INFORMATION: Synthetic

<400> SEQUENCE: 132

Gln Gln Ser Tyr Ser Ser Thr Pro Gln Thr
1               5                   10

<210> SEQ ID NO 133
<211> LENGTH: 11
<212> TYPE: PRT
<213> ORGANISM: Artificial sequence
<220> FEATURE:
<223> OTHER INFORMATION: Synthetic

<400> SEQUENCE: 133

Gly Asp Ser Val Ser Ser Gly Asn Arg Ala Thr
1               5                   10

<210> SEQ ID NO 134
<211> LENGTH: 10
<212> TYPE: PRT
<213> ORGANISM: Artificial sequence
<220> FEATURE:
<223> OTHER INFORMATION: Synthetic

<400> SEQUENCE: 134

Thr Tyr Tyr Arg Ser Ala Trp Tyr Asn Asp
1               5                   10

<210> SEQ ID NO 135
<211> LENGTH: 14
<212> TYPE: PRT
<213> ORGANISM: Artificial sequence
<220> FEATURE:
<223> OTHER INFORMATION: Synthetic

<400> SEQUENCE: 135

Ala Arg Gly Glu Ser Gly Ala Ala Ala Asp Ala Phe Asp Ile
1               5                   10

<210> SEQ ID NO 136
<211> LENGTH: 454
<212> TYPE: PRT
<213> ORGANISM: Artificial sequence
<220> FEATURE:
<223> OTHER INFORMATION: Synthetic

<400> SEQUENCE: 136

Met Glu Thr Asp Thr Leu Leu Leu Trp Val Leu Leu Leu Trp Val Pro
1               5                   10                  15
```

-continued

```
Gly Ser Thr Gly Glu Val Gln Leu Val Gln Ser Gly Gly Val Val
            20                  25                  30

Arg Pro Gly Gly Ser Leu Arg Leu Pro Cys Ala Ala Ser Gly Phe Thr
        35                  40                  45

Phe Asp Asp Tyr Gly Met Ser Trp Val Arg Gln Ala Pro Gly Lys Gly
50                  55                  60

Leu Glu Trp Val Ser Gly Ile Asn Trp Asn Gly Ser Thr Gly Tyr
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Leu Tyr His Cys Ala Arg Gly Gly Asp Asp Ala Phe Asp Ile Trp Gly
        115                 120                 125

Gln Gly Thr Met Val Thr Val Ser Ser Gly Gly Gly Ser Gly Gly
130                 135                 140

Gly Gly Ser Gly Gly Gly Ser Arg Ile Val Met Thr Gln Ser Pro
145                 150                 155                 160

Gly Thr Leu Ser Val Ser Pro Gly Glu Thr Ala Thr Leu Ser Cys Arg
        165                 170                 175

Ala Ser Gln Ser Phe Ser Asn Met Leu Ala Trp Tyr Gln Gln Lys Ser
            180                 185                 190

Gly Gln Pro Pro Arg Leu Leu Ile Tyr Gly Val Ser Thr Arg Ala Ala
        195                 200                 205

Gly Val Pro Ala Arg Phe Ser Gly Ser Gly Ser Gly Thr Glu Phe Thr
210                 215                 220

Leu Thr Ile Ser Asn Leu Gln Ser Glu Asp Phe Ala Val Tyr Tyr Cys
225                 230                 235                 240

Gln Gln Tyr Gly Asp Trp Pro Arg Tyr Thr Phe Gly Gln Gly Thr Lys
            245                 250                 255

Val Glu Arg Lys Gly Leu Ala Val Ser Thr Ile Ser Ser Phe Phe Pro
        260                 265                 270

Pro Gly Tyr Gln Ile Tyr Ile Trp Ala Pro Leu Ala Gly Thr Cys Gly
        275                 280                 285

Val Leu Leu Leu Ser Leu Val Ile Thr Leu Tyr Cys Lys Arg Gly Arg
290                 295                 300

Lys Lys Leu Leu Tyr Ile Phe Lys Gln Pro Phe Met Arg Pro Val Gln
305                 310                 315                 320

Thr Thr Gln Glu Glu Asp Gly Cys Ser Cys Arg Phe Pro Glu Glu Glu
            325                 330                 335

Glu Gly Gly Cys Glu Leu Arg Val Lys Phe Ser Arg Ser Ala Asp Ala
        340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
            405                 410                 415

Gly Met Lys Gly Glu Arg Arg Arg Gly Lys Gly His Asp Gly Leu Tyr
        420                 425                 430

Gln Gly Leu Ser Thr Ala Thr Lys Asp Thr Tyr Asp Ala Leu His Met
```

<210> SEQ ID NO 137
<211> LENGTH: 483
<212> TYPE: PRT
<213> ORGANISM: Artificial sequence
<220> FEATURE:
<223> OTHER INFORMATION: Synthetic

<400> SEQUENCE: 137

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Gly Gly Val Val
            20                  25                  30

Arg Pro Gly Gly Ser Leu Arg Leu Pro Cys Ala Ala Ser Gly Phe Thr
        35                  40                  45

Phe Asp Asp Tyr Gly Met Ser Trp Val Arg Gln Ala Pro Gly Lys Gly
    50                  55                  60

Leu Glu Trp Val Ser Gly Ile Asn Trp Asn Gly Gly Ser Thr Gly Tyr
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Leu Tyr His Cys Ala Arg Gly Gly Asp Asp Ala Phe Asp Ile Trp Gly
        115                 120                 125

Gln Gly Thr Met Val Thr Val Ser Ser Gly Gly Gly Ser Gly Gly
    130                 135                 140

Gly Gly Ser Gly Gly Gly Ser Arg Ile Val Met Thr Gln Ser Pro
145                 150                 155                 160

Gly Thr Leu Ser Val Ser Pro Gly Glu Thr Ala Thr Leu Ser Cys Arg
                165                 170                 175

Ala Ser Gln Ser Phe Ser Asn Met Leu Ala Trp Tyr Gln Gln Lys Ser
            180                 185                 190

Gly Gln Pro Pro Arg Leu Leu Ile Tyr Gly Val Ser Thr Arg Ala Ala
        195                 200                 205

Gly Val Pro Ala Arg Phe Ser Gly Ser Gly Ser Gly Thr Glu Phe Thr
    210                 215                 220

Leu Thr Ile Ser Asn Leu Gln Ser Glu Asp Phe Ala Val Tyr Tyr Cys
225                 230                 235                 240

Gln Gln Tyr Gly Asp Trp Pro Arg Tyr Thr Phe Gly Gln Gly Thr Lys
                245                 250                 255

Val Glu Arg Lys Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln

```
                340                 345                 350
Glu Glu Asp Gly Cys Ser Cys Arg Phe Pro Glu Glu Glu Gly Gly
            355                 360                 365
Cys Glu Leu Arg Val Lys Phe Ser Arg Ser Ala Asp Ala Pro Ala Tyr
    370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Gly Arg Asp Pro Glu Met
                405                 410                 415
Gly Gly Lys Pro Arg Arg Lys Asn Pro Gln Glu Gly Leu Tyr Asn Glu
            420                 425                 430
Leu Gln Lys Asp Lys Met Ala Glu Ala Tyr Ser Glu Ile Gly Met Lys
        435                 440                 445
Gly Glu Arg Arg Arg Gly Lys Gly His Asp Gly Leu Tyr Gln Gly Leu
            450                 455                 460
Ser Thr Ala Thr Lys Asp Thr Tyr Asp Ala Leu His Met Gln Ala Leu
465                 470                 475                 480
Pro Pro Arg

<210> SEQ ID NO 138
<211> LENGTH: 460
<212> TYPE: PRT
<213> ORGANISM: Artificial sequence
<220> FEATURE:
<223> OTHER INFORMATION: Synthetic

<400> SEQUENCE: 138

Met Glu Thr Asp Thr Leu Leu Leu Trp Val Leu Leu Leu Trp Val Pro
1               5                   10                  15
Gly Ser Thr Gly Gln Val Gln Leu Gln Gln Ser Gly Pro Gly Leu Val
            20                  25                  30
Lys Pro Ser Gln Thr Leu Ser Leu Thr Cys Ala Ile Ser Gly Asp Ser
        35                  40                  45
Val Ser Ser Asn Ser Ala Ala Trp Asn Trp Ile Arg Gln Ser Pro Ser
    50                  55                  60
Arg Gly Leu Glu Trp Leu Gly Arg Thr Tyr Tyr Arg Ser Lys Trp Tyr
65                  70                  75                  80
Asn Asp Tyr Ala Val Ser Val Lys Ser Arg Ile Thr Ile Asn Pro Asp
                85                  90                  95
Thr Ser Lys Asn Gln Phe Ser Leu Gln Leu Asn Ser Val Thr Pro Glu
            100                 105                 110
Asp Thr Ala Val Tyr Tyr Cys Ala Arg Glu Val Thr Gly Asp Leu Glu
        115                 120                 125
Asp Ala Phe Asp Ile Trp Gly Gln Gly Thr Met Val Thr Val Ser Ser
    130                 135                 140
Gly Gly Gly Gly Ser Gly Gly Gly Ser Gly Gly Gly Gly Ser Asp
145                 150                 155                 160
Ile Gln Met Thr Gln Ser Pro Ser Ser Leu Ser Ala Ser Val Gly Asp
                165                 170                 175
Arg Val Thr Ile Thr Cys Arg Ala Ser Gln Thr Ile Trp Ser Tyr Leu
            180                 185                 190
Asn Trp Tyr Gln Gln Arg Pro Gly Lys Ala Pro Asn Leu Leu Ile Tyr
        195                 200                 205
Ala Ala Ser Ser Leu Gln Ser Gly Val Pro Ser Arg Phe Ser Gly Arg
    210                 215                 220
```

Gly Ser Gly Thr Asp Phe Thr Leu Thr Ile Ser Ser Leu Gln Ala Glu
225                 230                 235                 240

Asp Phe Ala Thr Tyr Tyr Cys Gln Gln Ser Tyr Ser Ile Pro Gln Thr
            245                 250                 255

Phe Gly Gln Gly Thr Lys Leu Glu Ile Lys Gly Leu Ala Val Ser Thr
        260                 265                 270

Ile Ser Ser Phe Phe Pro Pro Gly Tyr Gln Ile Tyr Ile Trp Ala Pro
    275                 280                 285

Leu Ala Gly Thr Cys Gly Val Leu Leu Leu Ser Leu Val Ile Thr Leu
290                 295                 300

Tyr Cys Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
            325                 330                 335

Arg Phe Pro Glu Glu Glu Glu Gly Gly Cys Glu Leu Arg Val Lys Phe
        340                 345                 350

Ser Arg Ser Ala Asp Ala Pro Ala Tyr Gln Gln Gly Gln Asn Gln Leu
    355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
            405                 410                 415

Glu Ala Tyr Ser Glu Ile Gly Met Lys Gly Glu Arg Arg Arg Gly Lys
        420                 425                 430

Gly His Asp Gly Leu Tyr Gln Gly Leu Ser Thr Ala Thr Lys Asp Thr
    435                 440                 445

Tyr Asp Ala Leu His Met Gln Ala Leu Pro Pro Arg
    450                 455                 460

<210> SEQ ID NO 139
<211> LENGTH: 489
<212> TYPE: PRT
<213> ORGANISM: Artificial sequence
<220> FEATURE:
<223> OTHER INFORMATION: Synthetic

<400> SEQUENCE: 139

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Ile Asn Pro Asp
            85                  90                  95

Thr Ser Lys Asn Gln Phe Ser Leu Gln Leu Asn Ser Val Thr Pro Glu
        100                 105                 110

Asp Thr Ala Val Tyr Tyr Cys Ala Arg Glu Val Thr Gly Asp Leu Glu
    115                 120                 125

-continued

```
Asp Ala Phe Asp Ile Trp Gly Gln Gly Thr Met Val Thr Val Ser Ser
            130                 135                 140
Gly Gly Gly Gly Ser Gly Gly Gly Ser Gly Gly Gly Ser Asp
145                 150                 155                 160
Ile Gln Met Thr Gln Ser Pro Ser Ser Leu Ser Ala Ser Val Gly Asp
                165                 170                 175
Arg Val Thr Ile Thr Cys Arg Ala Ser Gln Thr Ile Trp Ser Tyr Leu
            180                 185                 190
Asn Trp Tyr Gln Gln Arg Pro Gly Lys Ala Pro Asn Leu Leu Ile Tyr
        195                 200                 205
Ala Ala Ser Ser Leu Gln Ser Gly Val Pro Ser Arg Phe Ser Gly Arg
210                 215                 220
Gly Ser Gly Thr Asp Phe Thr Leu Thr Ile Ser Ser Leu Gln Ala Glu
225                 230                 235                 240
Asp Phe Ala Thr Tyr Tyr Cys Gln Gln Ser Tyr Ser Ile Pro Gln Thr
                245                 250                 255
Phe Gly Gln Gly Thr Lys Leu Glu Ile Lys Thr Thr Thr Pro Ala Pro
            260                 265                 270
Arg Pro Pro Thr Pro Ala Pro Thr Ile Ala Ser Gln Pro Leu Ser Leu
        275                 280                 285
Arg Pro Glu Ala Cys Arg Pro Ala Ala Gly Gly Ala Val His Thr Arg
290                 295                 300
Gly Leu Asp Phe Ala Cys Asp Ile Tyr Ile Trp Ala Pro Leu Ala Gly
305                 310                 315                 320
Thr Cys Gly Val Leu Leu Leu Ser Leu Val Ile Thr Leu Tyr Cys Lys
                325                 330                 335
Arg Gly Arg Lys Lys Leu Leu Tyr Ile Phe Lys Gln Pro Phe Met Arg
            340                 345                 350
Pro Val Gln Thr Thr Gln Glu Glu Asp Gly Cys Ser Cys Arg Phe Pro
        355                 360                 365
Glu Glu Glu Glu Gly Gly Cys Glu Leu Arg Val Lys Phe Ser Arg Ser
370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
            420                 425                 430
Glu Gly Leu Tyr Asn Glu Leu Gln Lys Asp Lys Met Ala Glu Ala Tyr
        435                 440                 445
Ser Glu Ile Gly Met Lys Gly Glu Arg Arg Arg Gly Lys Gly His Asp
450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485

<210> SEQ ID NO 140
<211> LENGTH: 469
<212> TYPE: PRT
<213> ORGANISM: Artificial sequence
<220> FEATURE:
<223> OTHER INFORMATION: Synthetic

<400> SEQUENCE: 140
```

-continued

```
Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Ser Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Glu Val Thr Gly Asp Leu Glu Asp Ala Phe Asp
            100                 105                 110
Ile Trp Gly Gln Gly Thr Met Val Thr Val Ser Ser Gly Gly Gly Gly
            115                 120                 125
Ser Gly Gly Gly Gly Ser Gly Gly Gly Ser Asp Ile Gln Met Thr
    130                 135                 140
Gln Ser Pro Ser Ser Leu Ser Ala Ser Val Gly Asp Arg Val Thr Ile
145                 150                 155                 160
Thr Cys Arg Ala Ser Gln Thr Ile Trp Ser Tyr Leu Asn Trp Tyr Gln
            165                 170                 175
Gln Arg Pro Gly Lys Ala Pro Asn Leu Leu Ile Tyr Ala Ala Ser Ser
            180                 185                 190
Leu Gln Ser Gly Val Pro Ser Arg Phe Ser Gly Arg Gly Ser Gly Thr
    195                 200                 205
Asp Phe Thr Leu Thr Ile Ser Ser Leu Gln Ala Glu Asp Phe Ala Thr
    210                 215                 220
Tyr Tyr Cys Gln Gln Ser Tyr Ser Ile Pro Gln Thr Phe Gly Gln Gly
225                 230                 235                 240
Thr Lys Leu Glu Ile Lys Thr Thr Thr Pro Ala Pro Arg Pro Pro Thr
            245                 250                 255
Pro Ala Pro Thr Ile Ala Ser Gln Pro Leu Ser Leu Arg Pro Glu Ala
            260                 265                 270
Cys Arg Pro Ala Ala Gly Gly Ala Val His Thr Arg Gly Leu Asp Phe
    275                 280                 285
Ala Cys Asp Ile Tyr Ile Trp Ala Pro Leu Ala Gly Thr Cys Gly Val
    290                 295                 300
Leu Leu Leu Ser Leu Val Ile Thr Leu Tyr Cys Lys Arg Gly Arg Lys
305                 310                 315                 320
Lys Leu Leu Tyr Ile Phe Lys Gln Pro Phe Met Arg Pro Val Gln Thr
            325                 330                 335
Thr Gln Glu Glu Asp Gly Cys Ser Cys Arg Phe Pro Glu Glu Glu Glu
            340                 345                 350
Gly Gly Cys Glu Leu Arg Val Lys Phe Ser Arg Ser Ala Asp Ala Pro
    355                 360                 365
Ala Tyr Gln Gln Gly Gln Asn Gln Leu Tyr Asn Glu Leu Asn Leu Gly
    370                 375                 380
Arg Arg Glu Glu Tyr Asp Val Leu Asp Lys Arg Arg Gly Arg Asp Pro
385                 390                 395                 400
Glu Met Gly Gly Lys Pro Arg Arg Lys Asn Pro Gln Glu Gly Leu Tyr
            405                 410                 415
```

```
Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
        450                 455                 460

Ala Leu Pro Pro Arg
465

<210> SEQ ID NO 141
<211> LENGTH: 16
<212> TYPE: DNA
<213> ORGANISM: Artificial sequence
<220> FEATURE:
<223> OTHER INFORMATION: Synthetic

<400> SEQUENCE: 141
ttgtcccaca gatatc                                                    16

<210> SEQ ID NO 142
<211> LENGTH: 19
<212> TYPE: DNA
<213> ORGANISM: Artificial sequence
<220> FEATURE:
<223> OTHER INFORMATION: Synthetic

<400> SEQUENCE: 142
ttgtcccaca gatatccag                                                 19

<210> SEQ ID NO 143
<211> LENGTH: 15
<212> TYPE: DNA
<213> ORGANISM: Artificial sequence
<220> FEATURE:
<223> OTHER INFORMATION: Synthetic

<400> SEQUENCE: 143
agaaccctga ccctg                                                     15

<210> SEQ ID NO 144
<211> LENGTH: 9
<212> TYPE: PRT
<213> ORGANISM: Artificial sequence
<220> FEATURE:
<223> OTHER INFORMATION: Synthetic

<400> SEQUENCE: 144

Gln Gln Ser Tyr Ser Ile Pro Gln Thr
1               5
```

UNIVERSAL CHIMERIC ANTIGEN RECEPTOR T CELLS SPECIFIC FOR CD22

CROSS REFERENCE TO RELATED APPLICATIONS

This application is a national phase application under 35 U.S.C. § 371 of PCT International Application No. PCT/EP2018/058368, filed Mar. 30, 2018, which claims priority to PCT International Application No. PCT/EP2017/076800, filed Oct. 19, 2017, Danish Application No. PA201770542, filed Jun. 30, 2017, Danish Application No. PA201770240, filed Mar. 31, 2017, and Danish Application No. PA201770239, filed Mar. 31, 2017, each of which are hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 287,206 Byte ASCII (.txt) file named "38038-251_SEQUENCE LISTING_ST25," created on Jan. 11, 2023.

FIELD OF THE INVENTION

The present invention generally relates to the field of immunotherapy, and more specifically to Universal chimeric antigen receptor T cells specific for CD22 (UCART22) that are engineered human primary immune cells comprising at least one edited gene, preferably a gene coding a TCR subunit and/or a CD52 gene, and a Chimeric Antigen Receptors (CAR) specific for the cluster of differentiation 22 (CD22), (CAR CD22), and to methods for engineering said cells. The invention further relates to UCART 22 for their use in patients who may or may not be the initial donor of cells ("allogenic" or "autologous" CD22 CAR engineered primary human immune cells) as a treatment for relapse refractory hematological cancers. The cells expressing a CD22 according to the invention are particularly efficient and safe for immunotherapy in particular against aggressive or relapsed cancer.

BACKGROUND OF THE INVENTION

More than 45,000 deaths were expected from hematological cancer (non-Hodgkin's lymphoma, leukemia) in the United States in 2000 (Greenlee et al., CA Cancer J. Clin., 50:7-33 (2000)). The numbers published in 2014 were similar and despite advances in treatments such as chemotherapy, the prognosis for such cancers remains basically unchanged. (E K Mai, U Bertsch, J Dürig, C Kunz, M Haenel, I W Blau, M Munder, A Jauch, B Schurich, T Hielscher, M Merz, B Huegle-Doerr, A Seckinger, D Hose, J Hillengass, M S Raab, K Neben, H-W Lindemann, M Zeis, C Gerecke, I G H Schmidt-Wolf, K Weisel, C Scheid, H Salwender and H Goldschmidt. Phase III trial of bortezomib, cyclophosphamide and dexamethasone (VCD) versus bortezomib, doxorubicin and dexamethasone (PAd) in newly diagnosed myeloma. Leukemia (19 Mar. 2015) I doi: 10.1038/leu.2015.80.

Unique among the new investigational treatments for these hematologic cancers is the genetic modification of cells with cytolytic capacity such as T cells through the gene-transfer of a chimeric antigen receptor (CAR) (Jena, Dotti et al. 2010). CARs are synthetic receptors consisting of a targeting moiety that is associated with one or more signaling intracellular domains in a single molecule or in multiple transmembrane domains forming a multimer. In some cases, the binding moiety of a CAR consists of an antigen-binding domain from a single-chain antibody (scFv), comprising the variable fragments of a monoclonal antibody joined by a linker. Binding moieties based on receptor or ligand domains have also been used successfully to prepare a CAR. Signaling domains from co-stimulatory molecules of the T cell receptor (TCR), as well as particular transmembrane and hinge domains have been added to form CARs of second and third generations, leading to successful therapeutic trials in humans. In these studies, T-cells from a patient suffering a hematological ("liquid") cancer were redirected against malignant cells expressing for example CD19 or CD22 (June et al., 2011, Haso et al., 2013) and reinjected into the same patient. (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B-cell precursor acute lymphoblastic leukemia. Blood. 2013 Feb. 14; 121(7):1165-74. doi: 10.1182/blood-2012-06-438002. Epub 2012 Dec. 14). Methods allowing immune cells from one individual to be engineered before reinjection to the same individual—usually suffering from a cancer- are not well adapted in particular for aggressive forms of cancers that may be a race against time. Moreover, such method may be problematic or uncertain in patient whose immune system is altered.

To palliate this problem, immunotherapy using CAR-expressing so called "allogeneic" T cells (also called universal or "off the shelf" T cells) was recently implemented and the two first patients treated with such cells are still in remission about two years after treatment.

Nevertheless, there are still aspects of such therapy that may be improved, such as efficiency in the presence of anti-T cell drugs, efficiency against escaping cancer cells, persistence, means of control, etc. Indeed, it seems that cancer cells—by downregulating the expression of surface antigen recognized by CARs, may escape the treatment and subsist, despite the persistence of redirected immune in treated patients. Further, one the primary adverse, and sometimes lethal, effect observed in patients treated either with autologous or allogeneic T cells, is the cytokine release syndrome.

Thus, there is still a need for developing efficient and safe treatments for these pathologies, in particular for their aggressive or refractory/relapsed forms of hematological cancers.

BRIEF SUMMARY OF THE INVENTION

Here, the inventors have developed new efficient chimeric antigen receptor (CAR) specific for and targeting CD22 (anti-CD22 CAR or CAR CD22), Universal ANTI-CD22 CAR T cells "UCART22" comprising engineered primary human T cells with at least an inactivated TRAC gene, wherein the CAR targeting CD22 comprises, optionally a safety marker allowing the number (and activity) of said UCART22 cells to be controlled.

"Universal" means that said cells are "off the shelve" engineered cells (UCART) wherein at least the TCR was inactivated, preferably by deletion of the TRAC gene using the TALEN® technology. Inactivated means preferentially that a genomic sequence is deleted, inserted or mutated, more preferentially deleted or inserted. Consequently, cells may be administered to a patient and induce no or very reduced Graft versus host disease (GVHD) (intensity grade 0 to 2) as compared to a GVHD measured in a immunohistoincompatible individual after "allogeneic" transplantation or transfer of immune cells with no alteration of the genomic DNA encoding a sub unit of the TCR. In the new efficient "UCART22" of the invention, at least one additional gene modification that is, an inactivation in a CD52, a dCK, and/or a beta2microglobulinare gene, or an insertion of a HIF-1alpha gene conferring resistance to hypoxia, is contemplated.

These new UCART22 are particularly efficient for adoptive transfer in a patient suffering a CD22-mediated pathology, whether or not said patient is the initial donor of immune cells and whether or not said patient is already under a therapy that affects T immunity.

UCART 22 cells of the invention can be used in patients treated with at least one chemical or antibody drug usually used to treat CD22-mediated pathology, such as Campath and/or Purine nucleotide analogs (PNAs). In vitro, UCART 22 cells of the invention can survive and be active in the presence of said drug used at least at a dose that kills more than 50% of the cells.

Significant and unexpected clinical advantages of the new engineered isolated primary immune cells UCART 22 are observed, including low cytokine release, no or very mild graft versus host disease and still a significant activity against the refractory relapsed forms of hematological cancer cells. evidence that affinity driven antibody may be more stringent.

The CD22 CART cell (UCART22), optionally combined to a protein kinase C inhibitor such as bryostatin 1 as a pharmaceutical composition of the invention, is particularly useful in for the treatment of CLL, ALL, Multiple myeloma, (MM), Blastic plasmacytoid dendritic cell neoplasm (BPDCN), especially refractory/relapse ALL, refractory/relapse CLL and or aggressive forms of these diseases, more preferably refractory or relapse B-ALL.

The engineered immune cells of the present invention not only display high level of in vivo activity toward malignant cells, less cytokine release but also their number and activity is controlled conferring safety and efficiency for immunotherapy.

Preferably, a UCART22 of the invention is used for treating a patient with relapse or refractory B ALL.

The present invention provides:
1. A Chimeric Antigen Receptor (CAR) specific for CD22 (ANTI-CD22 CAR) comprising:
   i) at least one extracellular domain comprising:
      an antigen binding domain specific for CD22, optionally a leader sequence,
      a hinge domain selected from FcRIIIα, CD8alpha, IgG1, IgG4, and PD1, preferably from CD8 alpha,
   ii) a transmembrane domain, and
   iii) an intracellular signaling domain
wherein said antigen binding domain specific for CD22 comprises a single chain variable fragment (scfv) specific for CD22, said scfv comprising a heavy chain variable (VH) and light chain variable (VL), comprising one of the following combination of sequences:
(SEQ ID NO: 71 and SEQ ID NO: 72), (SEQ ID NO: 73, SEQ ID NO: 74) (SEQ ID NO: 75, SEQ ID NO: 76) (SEQ ID NO: 77, SEQ ID NO: 78) (SEQ ID NO: 79, SEQ ID NO: 80) (SEQ ID NO: 81, SEQ ID NO: 82) (SEQ ID NO: 83, SEQ ID NO: 84) (SEQ ID NO: 85, SEQ ID NO: 86) (SEQ ID NO: 87, SEQ ID NO: 88) or (SEQ ID NO: 89, SEQ ID NO: 90), more preferably a combination of sequences selected from (SEQ ID NO: 77, SEQ ID NO: 78), (SEQ ID NO: 83, SEQ ID NO: 84), (SEQ ID NO: 87, SEQ ID NO: 88), and (SEQ ID NO: 89, SEQ ID NO:90) even more preferably the combination of sequence (SEQ ID NO: 87, SEQ ID NO: 88).

2. The ANTI-CD22 CAR according to 1 wherein said scfv specific for CD22 comprises a VH and a VL linked to each other by a linker $L_1$.

3. The ANTI-CD22 CAR according to any one of 1 to 2 wherein said scfv specific for CD22 is linked to a transmembrane domain by a hinge selected from a hinge from FcRIIIα, CD8alpha, IgG1, preferably from CD8 alpha.

4. The ANTI-CD22 CAR according to any one of 1 to 3 wherein the intracellular domain comprises a CD3zeta signaling domain and a 4-1BB signaling domain.

5. The anti-CD22 CAR according to any one of 1 to 4 comprising a sequence selected from any one of the following sequences SEQ ID NO: 46 to SEQ ID NO: 55.

6. The ANTI-CD22 CAR according to any one of 1 to 5 comprising at least one, preferably two, more preferably three, even more preferably four monoclonal antibody (mAb)-specific epitopes, preferably inserted into the linker L of the scfv specific for CD22 and/or into the hinge.

7. The ANTI-CD22 CAR according to any one of 1 to 6, wherein the mAb-specific epitope is a polypeptide selected from: CPYSNPSLC (SEQ ID NO: 91), NSELLSLINDMPITNDQKKLMSNN (SEQ ID NO: 114), CQFDLSTRRLKC (SEQ ID NO: 115), CQYNLSSRALKC (SEQ ID NO: 116), CVWQRWQKSYVC (SEQ ID NO: 117), SFVLNWYRMSPSNQTDKLAAFPEDR (SEQ ID NO: 119), SGTYLCGAISLAPKAQIKE (SEQ ID NO: 120), ELPTQGTFSNVSTNVSPAKPTTTA (SEQ ID NO: 92), GQNDTSQTSSPS (SEQ ID NO: 121), preferably ELPTQGTFSNVSTNVSPAKPTTTA (SEQ ID NO: 92) and/or CPYSNPSLC (SEQ ID NO:91).

8. The anti-CD22 CAR according to any one of 1 to 7 comprising a sequence selected from any one of the following sequences SEQ ID NO: 56 to SEQ ID NO: 69, preferably an anti-CD22 CAR of SEQ ID NO: 54, more preferably an anti-CD22 CAR of SEQ ID NO: 64.

The present invention provides,
An anti-CD22 CAR of SEQ ID NO: 46,
An anti-CD22 CAR of SEQ ID NO: 47
An anti-CD22 CAR of SEQ ID NO: 48
An anti-CD22 CAR of SEQ ID NO: 49
An anti-CD22 CAR of SEQ ID NO: 50
An anti-CD22 CAR of SEQ ID NO: 51
An anti-CD22 CAR of SEQ ID NO: 52
An anti-CD22 CAR of SEQ ID NO: 53
An anti-CD22 CAR of SEQ ID NO: 54
An anti-CD22 CAR of SEQ ID NO: 55
An anti-CD22 CAR of SEQ ID NO: 56
An anti-CD22 CAR of SEQ ID NO: 57
An anti-CD22 CAR of SEQ ID NO: 58
An anti-CD22 CAR of SEQ ID NO: 59
An anti-CD22 CAR of SEQ ID NO: 60
An anti-CD22 CAR of SEQ ID NO: 61
An anti-CD22 CAR of SEQ ID NO: 62
An anti-CD22 CAR of SEQ ID NO: 63
An anti-CD22 CAR of SEQ ID NO: 64
An anti-CD22 CAR of SEQ ID NO: 65
An anti-CD22 CAR of SEQ ID NO: 66
An anti-CD22 CAR of SEQ ID NO: 67
An anti-CD22 CAR of SEQ ID NO: 68
An anti-CD22 CAR of SEQ ID NO: 69

The present invention provides a UCART22 comprising one of the following sequences SEQ ID NO: 56 to SEQ ID NO: 69, preferably an anti-CD22 CAR of SEQ ID NO: 54, more preferably an anti-CD22 CAR of SEQ ID NO: 64.

UCART22 means a human primary immune cell endowed with a CD22 CAR of the invention and at least one edited gene, preferably one edited gene selected from TRAC, dCK, CD52, GR, HIF-1alpha. Edited means that said gene is modified for example inactivated or overexpressed using tools of gene editing, in particular TALEN.

The present invention provides UCART22 comprising one of the following sequences SEQ ID NO: 56 to SEQ ID NO: 69, preferably an anti-CD22 CAR of SEQ ID NO: 54, more preferably an anti-CD22 CAR of SEQ ID NO: 64 and the corresponding encoding sequence (SEQ ID NO: 21 to SEQ ID NO: 30, SEQ ID NO: 32 to SEQ ID NO: 45).

The present invention also provides a UCART22 comprising a SEQ ID NO: 31 and SEQ ID NO: 18.

The present invention provides a pharmaceutical composition comprising UCART22 comprising one of the following sequences SEQ ID NO: 56 to SEQ ID NO: 69, preferably an anti-CD22 CAR of SEQ ID NO: 54, more preferably an anti-CD22 CAR of SEQ ID NO: 64.

9. The ANTI-CD22 CAR according to any one of 1 to 8 comprising 3 mAb-specific epitopes having an amino acid sequence of CPYSNPSLC (SEQ ID NO: 91) and one mAb-specific epitope having an amino acid sequence of ELPTQGTFSNVSTNVSPAKPTTTA (SEQ ID NO: 92).
10. The anti-CD22 CAR according to 9 comprising a sequence selected from any one of the following sequences SEQ ID NO: 56 to SEQ ID NO: 65.
11. The ANTI-CD22 CAR according to any one of 1 to 10, wherein the CD22 CAR is a single-chain CAR or a multi-chain CAR, preferably a single-chain CAR comprising an additional scfv specific for one of the following tumor-associated surface antigens selected from CD19, CD20, CD30, a major histocompatibility complex (MHC) molecule, an Immunoglobulin (Ig), CD3, CDS, CD34, CD79, preferably CD79b, CD138, B7-1 (CD80), BCMA (CD269, TNFRSF 17), FLT-3, or PAX5.
12. A polynucleotide encoding an ANTI-CD22 CAR according to any one of 1 to 11.
13. A vector comprising a polynucleotide according to 12.
14. An immune cell endowed with the ANTI-CD22 CAR according to any one of 1 to 11, preferably further comprising the polynucleotide or the vector according to 12 or 13.
15. The immune cell according to 14 comprising at least one edited gene, preferably an inactivated gene coding for one of the T Cell Receptor domain, more preferably a TRAC Knock out gene (UCART 22).
16. A population of cells comprising the UCART 22 according to 15.
17. A pharmaceutical composition comprising the UCART 22 according to 15 or a population of cells comprising said UCART 22 according to 16 and a pharmaceutically acceptable excipient.
18. The pharmaceutical composition according to 17 further comprising a bryostatin, preferably bryostatin-1.
19. The pharmaceutical composition according to 17 or 18 for its use as a medication for preventing or treating a patient suffering a CD22-mediated cancer or a CD22-mediated inflammatory disease.
20. The pharmaceutical composition for its use according to 19, wherein treating a patient comprises a step of administering the pharmaceutical composition twice (re dosing) to avoid a relapse/refractory development of the cancer.
21. The pharmaceutical composition for its use according to any one 19 to 20, wherein treating a patient comprises administering at least one mAb, preferably QBEND-10 and or rituximab, in a patient, at a dose allowing contacting said UCART22 with at least one specific mAb.
22. The pharmaceutical composition for its use according to any one of 19 to 21 for the treatment of a CD22-mediated hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22 expressing hematological cancer selected from (lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD22-expressing hematological cancer, even more preferably an aggressive form of said CD22-related hematological cancer.
23. The pharmaceutical composition for its use according to any one of 19 to 22 for the treatment of a relapse or refractory CD22-expressing B ALL, preferably as a pediatric indication.

The present invention provides a Chimeric Antigen Receptor (CAR) specific for CD22 (a CD22 CAR) wherein said CD22 CAR comprises:
i) at least one extracellular domain comprising:
an antigen binding domain specific for CD22, optionally a leader sequence,
a hinge domain selected from FcRIIIα, CD8alpha, IgG1, IgG4, and PD1, preferably from CD8 alpha,
ii) a transmembrane domain, and
iii) an intracellular signaling domain
wherein said antigen binding domain specific for CD22 comprises a scfv specific for CD22 comprising at least a combination of a VH chain, and of a VL chain,
said VH comprising a CDR1 with one of the following successive amino acid sequences: G, D or Y, S or T, V or F, S or T, S or G, N, S or D, S or R, A, T or Y, and A, T or Y,
a CDR2 with one of the successive amino acid sequences: T or I, Y or I, Y or N, R or P, S, K, A, G or T, W or G, Y or S, and N or T,
a CDR3 with one of the successive amino acid sequences: A or T, R, E, D, S, A or G, V, G, S, D, R or E, T, D, V, S, H or M, G, L, N or T, D or G, L, Y, T or A, E, Y, L, S, F, T, G or A, D, Y, G, R, S, N or E, A or G, F or V, D, and I, V or Y, wherein X is an amino acid,
said VL comprising a CDR1 with one of the successive amino acid sequences: Q or R, T or S, preferably S, I or L, W or S, preferably S, S or T and Y.
a CDR2 with one of the successive amino acid sequences: A, D or V, A, D or V and S.
a CDR3 with one of the successive amino acid sequences: Q, M, Q, S, T, Y, L, S, T, Q, T, preferably T, P, Q, I, L, R, T.

The present invention provides an anti-CD22 CAR comprising a scfv specific for CD22 comprising:
a VL with the following sequences QSISSY (SEQ ID NO: 131), AAS and QQSYSSTPQT (SEQ ID NO: 132) corresponding to the CDR1, CDR2 and CDR3, respectively and a VH with the following sequences GDSVSSGNRAT (SEQ ID NO: 133), TYYRSAWYND (SEQ ID NO: 134) and ARGESGAAADAFDI (SEQ ID NO: 135), corresponding to the CDR1, CDR2 and CDR3, respectively.

In one embodiment, the present invention provides an anti-CD22 CAR according to any one of the above wherein said scfv specific for CD22 comprises:
a VH comprising one of following successive amino acid sequences:

(SEQ ID NO: 71)
QVQLQQSGPGLVKPSQTLSLTCAISGDSVSSNSAAWNWIRQSPSRGLEWL
GRTYYRSTWYNDYAVSVKSRITINPDTSKNQFSLQLNSVTPEDTAVYYCA
REVSGTSAFDIWGQGTMVTVS, (SEQ ID NO: 73)
QVQLQQSGPGLVKPSQTLSLTCAISGDSVSSNSAAWNWIRQSPSRGLEWL
GRTYYRSKWYNDYAVSVKSRITINPDTSKNQFSLQLNSVTPEDTAVYYCA
RASMTGGYSYGDAFDIWGQGTLVTVS, (SEQ ID NO: 75)
QVQLQQSGPGLVEPSQTLSLTCAISGDSVSSDSVAWNWIRQSPSRGLEWL
GRTYYRSTWYNDYAGSVKSRITINPDTSKNQFSLQLTSVTPEDTAVYYCT
RSRHNTFRGMDVWGQGTTVTVS, (SEQ ID NO: 77)
QVQLQQSGPGLVEPSQTLSLTCAISGDSVSSNSAAWNWIRQSPSRGLEWL
GRTYYRSTWYNDYAGSVKSRITINPDTSKNQFSLQLTSVTPEDTAVYYCT
RSRHNTFRGMDVWGQGTLVTVS, (SEQ ID NO: 79)
QVQLQQSGPGLVEPSQTLSLTCAISGDSVSSDSVAWNWIRQSPSRGLEWL
GRTYYRSTWYNDYAGSVKSRITINPDTSKNQFSLQLNSVTPEDTAVYYCA
RDRNGMDVWGQGTMVTVS, (SEQ ID NO: 81)
QVQLQQSGPGLVKPSQTLSLTCAISGDSVSSSAAWNWIRQSPSRGLEWL
GRTYYRSAWYNDYAVSVKSRITINPDTSKNQFSLQLNSVTPEDTAVYYCA
RESVLLDGMDVWGRGTTVTVS, (SEQ ID NO: 83)
QVQLQQSGPGLVQPSQTLSLTCVISGDSVSSNSATWNWIRQSPSRGLEWL
GRTYYRSKWYNDYAVSVKSRITINPDTSKNQFSLQLNSVTPEDTAVYYCA
RDGDGGSYYDYYYYGMDVWGQGTTVTVS, (SEQ ID NO: 85)
QVQLQQSGPGLVKPSQTLSLTCAISGDSVSSNSAAWNWIRQSPSRGLEWL
GRTYYRSAWYNDYAVSVKSRITINPDTSKNQFSLQLSSVTPEDTAVYYCA
RDVEGFDYWGQGTLVTVS, (SEQ ID NO: 87)
QVQLQQSGPGLVKPSQTLSLTCAISGDSVSGNRATWNWIRQSPSRGLEWL
GRTYYRSAWYNDYAVSVKGRITFNPDTSKNQFSLQLNSVTPEDTAVYYCA
RGESGAAADAFDIWGQGTTVTVS, (SEQ ID NO: 89)
QVQLVQSGAEVKKPGASVKVSCKASGYTFTSYYMHWVRQAPGQGLEWMGI
INPSGGSTSYAQKFQGRVTMTRDTSTSTVYMELSSLRSEDTAVYYCARED
SGSGAFDIWGQGTLVTVS, and a VL comprising one of the following successive amino acid sequences:

(SEQ ID NO: 72)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPLTFGG
GTKLEIK, (SEQ ID NO: 74)
AIRMTQSPSSLSASVGDRVTITCRASQSISSYLNWYQQKPGKAPKLLIYA
ASSLQSGVPSRFSGSGSGTDFSLTISSLQPEDSATYYCQQTYSTPLTFGQ
GTKVEIK, (SEQ ID NO: 76)
DIVMTQSPSSLSASVGDRVTITCRASQTISSYLNWYQQKPGKAPKLLIYD
ASSLQSGVPSRFSGSGSGTDFTLTINSLQPEDFATYYCQQSYTTPITFGQ
GTRLEIK, (SEQ ID NO: 78)
DIQLTQSPSSLSASVGDRVTITCRASQSISSYLNWYQQKPGKAPKLLIYA
ASSLQSGVPSRFSGSGSGTDFTLTISSLQPEDFATYYCQQSYSTPLTFGG
GTKVEIK, (SEQ ID NO: 80)
DIVMTQSPSSLSASVGDRVTITCRASQSISSYLNWYQQKPGKAPKLLIYD
ASNLETGVPSRFSGSGSGTDFTFTITSLQPEDFATYYCQQSYTTPLTFGG
GTKVEIK, (SEQ ID NO: 82)
AIRMTQSPSTLSASVGDRVTITCRASQSISTYLNWYQQKAGKAPRLLIHD
ASSLQSGVPSRFSGSGSGTDFTLTISSLQPEDFATYYCQQSYSTPLTFGG
GTKVEIK, (SEQ ID NO: 84)
DIQLTQSPSSLSTSVGDRVTITCRASQSISTYLNWYQQKPGKAPKLLIYA
ASNLQSGVPSRFSGSGSGTDFTLTISSLQPEDFATYFCQQSYTTPITFGQ
GTRLEIK, (SEQ ID NO: 86)
DIVMTQTPSSLSASVGDRVTITCRASQSISSYLNWYQQKPGKAPKLLIYA
ASSLQSGVPSRFSGSGSGTDFTLTISSLQPEDFATYYCQQSYSTPITFGQ
GTRLEIK, (SEQ ID NO: 88)
DIQLTQSPPSLSASVGDRVTITCRASQSISSYLNWYQQKPGKAPKLLIYA
ASSLQSGVPSRFSGSGFGTDFTLTISSLQPEDFATYYCQQSYSTPQTFGQ
GTKVDIK, (SEQ ID NO: 90)
EIVLTQSPLSLPVTPGEPASISCRSSRSLLSYHGYNYLDWYLQKPGQSPQ
LLIFVGSNRAPGVPDRFSGSGSGTDFTLNISRVEAEDVGVYYCMQSLQTP
RTFGQGTKVEIK, preferably said scfv comprises the following successive amino acid sequences (SEQ ID NO: 87)
QVQLQQSGPGLVKPSQTLSLTCAISGDSVSGNRATWNWIRQSPSRGLEWL
GRTYYRSAWYNDYAVSVKGRITFNPDTSKNQFSLQLNSVTPEDTAVYYCA
RGESGAAADAFDIWGQGTTVTVS
and (SEQ ID NO: 88)
DIQLTQSPPSLSASVGDRVTITCRASQSISSYLNWYQQKPGKAPKLLIYA
ASSLQSGVPSRFSGSGFGTDFTLTISSLQPEDFATYYCQQSYSTPQTFGQ
GTKVDIK.

In one embodiment, the present invention provides an anti-CD22 CAR according to any one of the above wherein said scfv specific for CD22 comprises a sequence selected from SEQ ID NO: 71 to SEQ ID NO: 90, preferably one of the following combination of sequences (SEQ ID NO: 71 and SEQ ID NO: 72), (SEQ ID NO: 73, SEQ ID NO: 74), (SEQ ID NO: 75, SEQ ID NO: 76), (SEQ ID NO: 77, SEQ ID NO: 78), (SEQ ID NO: 79, SEQ ID NO: 80), (SEQ ID NO: 81, SEQ ID NO: 82), (SEQ ID NO: 83, SEQ ID NO: 84), (SEQ ID NO: 85, SEQ ID NO: 86), (SEQ ID NO: 87, SEQ ID NO: 88), or (SEQ ID NO: 89, SEQ ID NO: 90), more preferably a combination of sequences (SEQ ID NO: 87, SEQ ID NO: 88),
more preferably a sequence selected from (SEQ ID NO: 77, SEQ ID NO: 78), (SEQ ID NO: 87, SEQ ID NO: 88) and (SEQ ID NO: 89, SEQ ID NO: 90), even more preferably the combination of sequences (SEQ ID NO: 87, SEQ ID NO: 88).

In one embodiment, the present invention provides the anti-CD22 CAR according to any one of the above wherein said scfv specific for CD22 comprises a VH and a VL linked to each other by a linker L1.

In one embodiment, the present invention provides the anti-CD22 CAR according to any one of the above wherein said scfv specific for CD22 is linked to a transmembrane domain by a hinge selected from a hinge from FcRIIIα, CD8alpha, IgG1, preferably a hinge from CD8 alpha.

In one embodiment, the present invention provides the anti-CD22 CAR according to any one of the above comprising at least one, preferably two, more preferably three, even more preferably four monoclonal antibody (mAb)-specific epitopes, preferably inserted into the linker L1 of the scfv specific for CD22 and/or into the hinge.

In one embodiment, the present invention provides the anti-CD22 CAR according to any one of the above wherein said molecular antibody (mAb)-specific epitope, is a mAb-specific epitope specifically recognized by an monoclonal antibody selected from ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably from rituximab (R) and/or from QBEND-10 (Q).

In one embodiment, the present invention provides the anti-CD22 CAR according to any one of the above wherein a mAb-specific epitope is an epitope to be bound by an epitope-specific mAb for in vitro cell sorting and/or in vivo cell depletion of T cells expressing a CAR comprising such epitope.

In one embodiment, the present invention provides the anti-CD22 CAR according to any one of the above wherein the extracellular binding domain comprises one of the following sequences:
$V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-;
$(L)_x$-Epitope1-$(L)_x$-Epitope2-$(L)_x$-$V_1$-$L_1$-$V_2$-$(L)_x$-Epitope3-$(L)_x$-;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$-;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;
wherein,
V1 is VL and V2 is VH or V1 is VH and V2 is VL;
L1 is a linker suitable to link the VH chain to the VL chain;
L1 is a linker comprising glycine and serine residues, and each occurrence of L in the extracellular binding domain can be identical or different to other occurrence of L in the same extracellular binding domain, and,
x is 0 or 1 and each occurrence of x is selected independently from the others; and,
Epitope 1, Epitope 2 and Epitope 3 are mAb-specific epitopes and can be identical or different.

In one embodiment, the present invention provides the anti-CD22 CAR according to any one of the above embodiments wherein the extracellular binding domain comprises one of the following sequences:
$V_1$-$L_1$-$V_2$-L-Epitope1; $V_1$-$L_1$-$V_2$-L-Epitope1-L; $V_1$-$L_1$-$V_2$-L-Epitope1-L-Epitope2; $V_1$-$L_1$-$V_2$-L-Epitope1-L-Epitope2-L; $V_1$-$L_1$-$V_2$-L-Epitope1-L-Epitope2-L-Epitope3; $V_1$-$L_1$-$V_2$-L-Epitope1-L-Epitope2-L-Epitope3-L; $V_1$-$L_1$-$V_2$-Epitope1; $V_1$-$L_1$-$V_2$-Epitope1-L; $V_1$-$L_1$-$V_2$-Epitope1-L-Epitope2; $V_1$-$L_1$-$V_2$-Epitope1-L-Epitope2-L; $V_1$-$L_1$-$V_2$-Epitope1-L-Epitope2-L-Epitope3; $V_1$-$L_1$-$V_2$-Epitope1-L-Epitope2-L-Epitope3-L; Epitope1-$V_1$-$L_1$-$V_2$; Epitope1-L-$V_1$-$L_1$-$V_2$; L-Epitope1-$V_1$-$L_1$-$V_2$; L-Epitope1-L-$V_1$-$L_1$-$V_2$; Epitope1-L-Epitope2-$V_1$-$L_1$-$V_2$; Epitope1-L-Epitope2-L-$V_1$-$L_1$-$V_2$; L-Epitope1-L-Epitope2-$V_1$-$L_1$-$V_2$; L-Epitope1-L-Epitope2-L-$V_1$-$L_1$-$V_2$; Epitope1-L-Epitope2-L-Epitope3-$V_1$-$L_1$-$V_2$; Epitope1-L-Epitope2-L-Epitope3-L-$V_1$-$L_1$-$V_2$; L-Epitope1-L-Epitope2-L-Epitope3-$V_1$-$L_1$-$V_2$; L-Epitope1-L-Epitope2-L-Epitope3-L-$V_1$-$L_1$-$V_2$; $V_1$-L-Epitope1-L-$V_2$; L-Epitope1-L-$V_1$-L-Epitope2-L-$V_2$; $V_1$-L-Epitope1-L-$V_2$-L-Epitope2-L; $V_1$-L-Epitope1-L-$V_2$-L-Epitope2-L-Epitope3; $V_1$-L-Epitope1-L-$V_2$-L-Epitope2-Epitope3; $V_1$-L-Epitope1-L-$V_2$-L-Epitope2-L-Epitope3-Epitope4; L-Epitope1-L-$V_1$-L-Epitope2-L-$V_2$-L-Epitope3-L; Epitope1-L-$V_1$-L-Epitope2-L-$V_2$-L-Epitope3-L; L-Epitope1-L-$V_1$-L-Epitope2-L-$V_2$-L-Epitope3; L-Epitope1-L-$V_1$-$L_1$-$V_2$-L-Epitope2-L; L-Epitope1-L-$V_1$-$L_1$-$V_2$-L-Epitope2-L-Epitope3; L-Epitope1-L-$V_1$-$L_1$-$V_2$-L-Epitope2-Epitope3, or Epitope1-L-$V_1$-$L_1$-$V_2$-L-Epitope2-L-Epitope3-Epitope4 wherein
$V_1$ is $V_L$ and $V_2$ is $V_H$ or $V_1$ is $V_H$ and $V_2$ is $V_L$;
$L_1$ is any linker suitable to link the $V_H$ chain to the $V_L$ chain;
L is a linker comprising glycine and serine residues, and each occurrence of L in the extracellular binding domain can be identical or different to other occurrences of L in the same extracellular binding domain, and, Epitope 1, Epitope 2 and Epitope 3 are mAb-specific epitopes and can be identical or different.

In one embodiment, the present invention provides:
the anti-CD22 CAR according to any one of the above, wherein $L_1$ is a linker comprising Glycine and/or Serine.

Linker L1

The anti-CD22 CAR according to any one of the above wherein $L_1$ is a linker comprising the amino acid sequence (Gly-Gly-Gly-Ser)$_n$ (SEQ ID NO: 100)$_n$ or (Gly-Gly-Gly-Gly-Ser)$_n$ (SEQ ID NO: 97)$_n$, where n is 1, 2, 3, 4 or 5 or a linker comprising the amino acid sequence (Gly$_4$Ser)$_4$ (SEQ ID NO: 97)$_4$ or (Gly$_4$Ser)$_3$ (SEQ ID NO: 97)$_3$.

The anti-CD22 CAR according to any one of the above wherein L is a linker having an amino acid sequence selected from SGG, GGS, SGGS (SEQ ID NO: 101), SSGGS (SEQ ID NO: 102), GGGG (SEQ ID NO: 103), SGGGG (SEQ ID NO: 104), GGGGS (SEQ ID NO: 97), SGGGGS (SEQ ID NO: 105), GGGGGS (SEQ ID NO: 106), SGGGGGS (SEQ ID NO: 107), SGGGGG (SEQ ID NO: 108), GSGGGGS (SEQ ID NO: 109), GGGGGGGS (SEQ ID NO: 110), SGGGGGGG (SEQ ID NO: 111), SGGGGGGGS (SEQ ID NO: 112), and SGGGGSGGGGS (SEQ ID NO: 113), preferably L is a linker comprising the amino acid sequence SGGGG (SEQ ID NO: 104), GGGGS (SEQ ID NO: 97) or SGGGGS (SEQ ID NO: 105).

The anti-CD22 CAR according to any one of the above, wherein Epitope 1, Epitope 2, Epitope 3 and Epitope 4 are independently selected from a mAb-specific epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably Epitope 1, Epitope 2, Epitope 3 and Epitope 4 are recognized by rituximab or QBEND-10.

These mAb may be as in Table 1 below.

TABLE 1

| Antibody | Indication | Drug bank accession n° (or other n° if stated) | Target/Antigen |
| --- | --- | --- | --- |
| Ibritumomab tiuxetan | Non-Hodgkin lymphoma (with yttrium-90 or indium-111) | DB00078 | CD20 |
| Muromonab-CD3 | Transplant rejection | DB00075 | T cell CD3 Receptor |
| Tositumomab | Non-Hodgkin lymphoma | DB00081 | CD20 |
| Abciximab | Cardiovascular disease | DB00054 | inhibition of glycoprotein IIb/IIIa |
| Basiliximab | Transplant rejection | DB00074 | IL-2Rα receptor (CD25) |
| Brentuximab vedotin | Anaplastic large cell lymphoma | DB08870 | CD30 |
| Cetuximab | Colorectal cancer, Head and neck cancer | DB00002 | epidermal growth factor receptor |
| Infliximab | Several autoimmune disorders | DB00065 | inhibition of TNF-α signaling |
| Rituximab | Non-Hodgkin lymphoma | DB00073 | CD20 |
| Alemtuzumab | Chronic lymphocytic leukemia | DB00087 | CD52 |
| Bevacizumab | Colorectal cancer, Age related macular degeneration (off-label) | DB00112 | Vascular endothelial growth factor (VEGF) |
| Certolizumab pegol | Crohn's disease | DB08904 | inhibition of TNF-α signaling |
| Daclizumab | Transplant rejection | DB00111 | IL-2Ra receptor (CD25) |
| Eculizumab | Paroxysmal nocturnal hemoglobinuria | DB01257 | Complement system protein |
| Efalizumab | Psoriasis | DB00095 | CD11a |
| Gemtuzumab | Acute myelogenous leukemia (with calicheamicin) | DB00056 | CD33 |
| Natalizumab | Multiple sclerosis and Crohn's disease | DB00108 | alpha-4 (α4) integrin |
| Omalizumab | mainly allergy-related asthma | DB00043 | immunoglobulin E (IgE) |
| Palivizumab | Respiratory Syncytial Virus | DB00110 | an epitope of the RSV F protein |
| Ranibizumab | Macular degeneration | DB01270 | Vascular endothelial growth factor A (VEGF-A) |
| Tocilizumab (or Atlizumab) | Rheumatoid arthritis | DB06273 | Anti- IL-6R |
| Trastuzumab | Breast cancer | DB00072 | ErbB2 |
| Vedolizumab | Crohn's disease, ulcerative colitis | CAS n°943609-66-3 | integrin $α_4β_7$ |
| Adalimumab | Several auto-immune disorders | DB00051 | inhibition of TNF-α signaling |

TABLE 1-continued

| Antibody | Indication | Drug bank accession n° (or other n° if stated) | Target/ Antigen |
| --- | --- | --- | --- |
| Belimumab | Systemic lupus erythematosus | DB08879 | inihibition of B-cell activating factor |
| Canakinumab | Cryopyrin-associated periodic syndrome (CAPS) | DB06168 | IL-1β |
| Denosumab | Postmenopausal osteoporosis, Solid tumor's bony metastases | DB06643 | RANK Ligand inhibitor |
| Golimumab | Rheumatoid arthritis, Psoriatic arthritis, and Ankylosing spondylitis | DB06674 | TNF-alpha inihibitor |
| Ipilimumab (MDX-101) | Melanoma | DB06186 | blocks CTLA-4 |
| Ofatumumab | Chronic lymphocytic leukemia | CAS n° 679818-59-8 | CD20 |
| Panitumumab | Colorectal cancer | DB01269 | epidermal growth factor receptor |
| Ustekinumab | Psoriatic Arthritis, Plaque Psoriasis | DB05679 | IL-12, IL-23 |
| Nivolumab | renal cell carcinoma, lung cancer, melanoma, and advanced or metastatic solid tumors | CAS n°946414-94-4 | PD-1 |

In one embodiment, the present invention provides the anti-CD22 CAR according to any one of the above, wherein the mAb-specific epitope is a polypeptide selected from:

CPYSNPSLC, (SEQ ID NO: 91)

NSELLSLINDMPITNDQKKLMSNN, (SEQ ID NO: 114)

CQFDLSTRRLKC, (SEQ ID NO: 115)

CQYNLSSRALKC, (SEQ ID NO: 116)

CVWQRWQKSYVC, (SEQ ID NO: 117)

SFVLNWYRMSPSNQTDKLAAFPEDR, (SEQ ID NO: 119)

SGTYLCGAISLAPKAQIKE, (SEQ ID NO: 120)

ELPTQGTFSNVSTNVSPAKPTTTA, (SEQ ID NO: 92)

GQNDTSQTSSPS. (SEQ ID NO: 121)

In one embodiment, the present invention provides the anti-CD22 CAR according to any one of the above, wherein the mAb-specific epitope has the following amino acid sequence:

ELPTQGTFSNVSTNVSPAKPTTTA (SEQ ID NO: 92)
and/or

CPYSNPSLC. (SEQ ID NO: 91)

The anti-CD22 CAR according to the above comprising 3 mAb-specific epitopes having an amino acid sequence of CPYSNPSLC (SEQ ID NO: 91) and one having an amino acid sequence of ELPTQGTFSNVSTNVSPAKPTTTA (SEQ ID NO: 92).

In one embodiment, the present invention provides the anti-CD22 CAR according to any one of the above, wherein VH and VL are one of the following combinations selected from:
a VH of SEQ ID NO: 71 and a VL of SEQ ID NO: 72; a VH of SEQ ID NO: 73 and a VL of SEQ ID NO: 74; a VH of SEQ ID NO: 75 and a VL of SEQ ID NO: 76; a VH of SEQ ID NO: 77 and a VL of SEQ ID NO: 78; a VH of SEQ ID NO: 79 and a VL of SEQ ID NO: 80; a VH of SEQ ID NO: 81 and a VL of SEQ ID NO: 82; a VH of SEQ ID NO: 83 and a VL of SEQ ID NO: 84; a VH of SEQ ID NO: 85 and a VL of SEQ ID NO: 86; a VH of SEQ ID NO: 87 and a VL of SEQ ID NO: 88; a VH of SEQ ID NO: 89 and a VL of SEQ ID NO: 90, preferably a VH of SEQ ID NO: 87 and a VL of SEQ ID NO: 88.

In one embodiment, the present invention provides the anti-CD22 CAR according to any one of the above, wherein said VH chain has a sequence of more than 80% identity, preferably more than 90%, and more preferably more than 95% identity with any one of the following sequences: SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, and SEQ ID NO: 89 and said VL chain has a sequence of over 80% identity, preferably over 90%, and more preferably over 95% identity with any one of the following sequences SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88 or SEQ ID NO: 90.

The anti-CD22 CAR according to the above, wherein said VH chain has a sequence of over 80% identity, preferably over 90%, and more preferably over 95% identity with SEQ ID NO: 71, and said VL chain has a sequence of over 80% identity, preferably over 90%, and more preferably over 95% identity with SEQ ID NO 72.

The anti-CD22 CAR according to the above, wherein said VH chain has a sequence of over 80% identity, preferably over 90%, and more preferably over 95% identity with SEQ ID NO: 73, and said VL chain has a sequence of over 80% identity, preferably over 90%, and more preferably over 95% identity with SEQ ID NO: 74.

The anti-CD22 CAR according to the above, wherein said VH chain has a sequence of over 80% identity, preferably over 90%, and more preferably over 95% identity with SEQ ID NO: 75, and said VL chain has a sequence of over 80% identity, preferably over 90%, and more preferably over 95% identity with SEQ ID NO: 76.

The anti-CD22 CAR according to the above, wherein said VH chain has a sequence of over 80% identity, preferably over 90%, and more preferably over 95% identity with SEQ ID NO: 77, and said VL chain has a sequence of over 80% identity, preferably over 90%, and more preferably over 95% identity with SEQ ID NO: 78.

The anti-CD22 CAR according to the above, wherein said VH chain has a sequence of over 80% identity, preferably over 90%, and more preferably over 95% identity with SEQ ID NO: 79, and said VL chain has a sequence of over 80% identity, preferably over 90%, and more preferably over 95% identity with SEQ ID NO: 80.

The anti-CD22 CAR according to the above, wherein said VH chain has a sequence of over 80% identity, preferably over 90%, and more preferably over 95% identity with SEQ ID NO: 81, and said VL chain has a sequence of over 80% identity, preferably over 90%, and more preferably over 95% identity with SEQ ID NO: 82, The anti-CD22 CAR according to the above, wherein said VH chain has a sequence of over 80% identity, preferably over 90%, and more preferably over identity 95% with SEQ ID NO: 83, and said VL chain has a sequence of over 80% identity, preferably over 90%, and more preferably over 95% identity with SEQ ID NO: 84.

The anti-CD22 CAR according to the above, wherein said VH chain has a sequence of over 80% identity, preferably over 90%, and more preferably over 95% identity with SEQ ID NO: 85, and said VL chain has a sequence of over 80% identity, preferably over 90%, and more preferably over 95% identity with SEQ ID NO: 86., The anti-CD22 CAR according to the above, wherein said VH chain has a sequence of over 80% identity, preferably over 90%, and more preferably over 95% identity with SEQ ID NO: 87, and said VL chain has a sequence of over 80% identity, preferably over 90%, and more preferably over 95% identity with SEQ ID NO: 88, The anti-CD22 CAR according to the above, wherein said VH chain has a sequence of over 80% identity, preferably over 90%, and more preferably over 95% identity with SEQ ID NO: 89, and said VL chain has a sequence of over 80% identity, preferably over 90%, and more preferably over 95% identity with SEQ ID NO: 90.

The anti-CD22 CAR according to any one of the above wherein the transmembrane domain comprises the transmembrane region(s) of the alpha, beta or zeta chain of the T-cell receptor, PD-1, 4-1BB, OX40, ICOS, CTLA-4, LAG3, 2B4, BTLA4, TIM-3, TIGIT, SIRPA, CD28, CD3 epsilon, CD45, CD4, CD5, CD8, CD9, CD16, CD22, CD33, CD37, CD64, CD80, CD86, CD134, CD137 or CD154.

The anti-CD22 CAR according to any one of the above wherein the transmembrane domain comprises a transmembrane region(s) of PD-1 or CD8 alpha.

The anti-CD22 CAR according to any one of the above wherein the transmembrane domain comprises a transmembrane region(s) of CD8 alpha.

The anti-CD22 CAR according to any one of the above wherein the intracellular domain comprises a CD3zeta signaling domain.

The anti-CD22 CAR according to any one of the above wherein the intracellular domain comprises a 4-1BB domain.

The anti-CD22 CAR according to any one of the above wherein the intracellular domain comprises a CD3zeta signaling domain and a 4-1BB domain.

The anti-CD22 CAR according to any one of the above, wherein the CD22 CAR is a single-chain CAR, preferably a single-chain anti-CD22 CAR comprising an additional scfv specific for one of the following tumor-associated surface antigen selected from CD19, CD20, CD30, a major histocompatibility complex (MHC) molecule, an Immunoglobulin (Ig), CD3, CD34, CD79, preferably CD79b, CD138, B7-1 (CD80), BCMA (CD269, TNFRSF 17) or FLT-3, PAX 5.

The anti-CD22 CAR according to any one of the above, wherein the CD22 CAR is a single-chain CAR, preferably a single-chain anti-CD22 CAR comprising an additional scfv specific for CD19. The anti-CD22 CAR according to any one of the above, wherein the said CD22 CAR is a polypeptide comprising over 80% identity, over 90%, over 95% identity with or is identical to SEQ ID NO: 46 to SEQ ID NO: 69, preferably SEQ ID NO: 56 to SEQ ID NO: 65, more preferably with SEQ ID N° 64.

The anti-CD22 CAR according to any one of the above wherein the CD22 CAR is a multi-chain CAR, preferably a multi chain CAR comprising an additional scfv specific for one of the following tumor-associated surface antigen selected from CD19, CD20, CD30, a major histocompatibility complex (MHC) molecule, an Immunoglobulin (Ig), CD3, CD34, CD79, preferably CD79b, CD138, B7-1 (CD80), BCMA (CD269, TNFRSF 17) or FLT-3, PAX5.

The anti-CD22 CAR according to any one of the above comprising at least one additional antigen binding domain.

The present invention provides a polynucleotide encoding an anti-CD22 CAR as described in any of the above embodiments.

The present invention provides a vector encoding an anti-CD22 CAR as described in any of the above embodiments.

Cell

The present invention provides an immune cell endowed with an anti-CD22 CAR as any of the above and with a vector encoding said anti-CD22 CAR, preferably a human immune cell, more preferably a human immune T cell.

The present invention provides a population of cells comprising an immune cell endowed with an anti-CD22 CAR as any of the above and with a vector encoding said anti-CD22 CAR, preferably a human immune cell, more preferably a human immune T cell.

The present invention provides an engineered human Cell, preferably an engineered human T Cell comprising an anti-CD22 CAR as any of the above and a vector encoding said anti-CD22 CAR and at least one edited gene.

The at least one edited gene may be a gene which is edited for rendering the cell resistant to a drug, or resistant to hypoxia, preferably this gene may be a dCK gene, a CD56 gene, a glucocorticoid receptor (GR) gene.

The TCR of these cells may be intact, of said cells may express a TCR participating to the efficiency of said cell as a treatment.

Resistant means that the cell will survive and be active (have for example a CTL activity) under condition (at a concentration) that can be measured in the blood of a patient treated with said drug, or in the environment created by a tumor. For example hypoxia means 1 to 5% 02.

The present invention also provides an engineered human T Cell Receptor Knock Out (TCR KO) cell endowed with a Chimeric Antigen Receptor (CAR) specific for CD22 (UCART22)

UCART means a universal CAR-expressing TCR KO (inactivated) T cell

"Universal" means that said cells has been modified, edited to be suitable for immunotherapy in any host, in need thereof, comprises at least a deficient TCR and/or no cell surface expression of TCRalpha/beta.

UCART 22 means a universal anti-CD22 CAR-expressing TCR KO (inactivated) T cell

The present invention provides therefore a UCART 22 comprising as any one of the anti-CD22 CAR (or CD22 CAR) described above.

In these UCART22 cells at least one gene encoding a TCR subunit, preferably the TRAC gene, is inactivated resulting in an inactivation of the TCR.

In another embodiment the present invention provides said UCART22 cell comprising at least one other edited gene, preferably HIF-1alpha, GR, CD56, dCK.

The present invention provides UCART 22 comprises:
i) at least one extracellular domain comprising:
  an antigen binding domain specific for CD22, optionally a leader sequence,
  a hinge domain selected from FcRIIIα, CD8alpha, IgG1, IgG4, and PD1, preferably from CD8 alpha,
ii) a transmembrane domain, and
iii) an intracellular signaling domain, and
at least one additional edited gene, preferably a deleted CD52 gene.

In one embodiment, the present invention provides the UCART CD22 according to the above: wherein said CD22 CAR comprises a scfv specific for CD22 comprising at least a combination of a VH chain, and of a VL chain, said VH comprising a CDR1 with one of the following successive amino acid sequences: G, D or Y, S or T, V or F, S or T, S or G, N, S or D, S or R, A, T or Y, and A, T or Y,
a CDR2 with one of the successive amino acid sequences: T or I, Y or I, Y or N, R or P, S, K, A, G or T, W or G, Y or S, and N or T,
a CDR3 with one of the successive amino acid sequences: A or T, R, E, D, S, A or G, V, G, S, D, R or E, T, D, V, S, H or M, G, L, N or T, D or G, xxxxx, L, Y, T or A, E, Y, L, S, F, T, G or A, D, Y, G, R, S, N or E, A or G, F or V, D, and I, V or Y, wherein X is an amino acid,
said VL comprising a CDR1 with one of the successive amino acid sequences: Q or R, T or S, preferably S, I or L, W or S, preferably S, S or T and Y.
a CDR2 with one of the successive amino acid sequences: A, D or V, A, D or V and S.
a CDR3 with one of the successive amino acid sequences Q, M, Q, S, T, Y, L, S, T, Q, I or T, preferably T, P, Q, I, L, R, T.

In one embodiment, the present invention provides the UCART CD22 according to any one of the above wherein said anti-CD22 CAR comprises a scfv specific for CD22 comprising at least a combination of a VH chain, and of a VL chain,
said VH comprising a CDR1 with one of the following successive amino acid sequences: G, D or Y, S or T, V or F, S or T, S or G, N, S or D, S or R, A, T or Y, and A, T or Y,
a CDR2 with one of the successive amino acid sequences: T or I, Y or I, Y or N, R or P, S, K, A, G or T, W or G, Y or S, and N or T,
a CDR3 with one of the successive amino acid sequences: A or T, R, E, D, S, A or G, V, G, S, D, R or E, T, D, V, S, H or M, G, L, N or T, D or G, xxxxx, L, Y, T or A, E, Y, L, S, F, T, G or A, D, Y, G, R, S, N or E, A or G, F or V, D, and I, V or Y, wherein X is an amino acid,
said VL comprising a CDR1 with one of the successive amino acid sequences: Q or R, T or S, preferably S, I or L, W or S, preferably S, S or T and Y.
a CDR2 with one of the successive amino acid sequences: A, D or V, A, D or V and S.
a CDR3 with one of the successive amino acid sequences Q, M, Q, S, T, Y, L, S, T, Q, T, preferably T, P, Q, I, L, R, T.

The UCART 22 according to any one of the above wherein said anti-CD22 CAR comprises a scfv specific for CD22 comprising: a VL with the following sequences QSISSY (SEQ ID NO: 131), AAS and QQSYSSTPQT (SEQ ID NO: 132) corresponding to the CDR1, CDR2 and CDR3, a VH with the following sequences GDSVSSGN-RAT (SEQ ID NO: 133), TYYRSAWYND (SEQ ID NO: 134) and ARGESGAAADAFDI (SEQ ID NO: 135).

The UCART 22 according to any one of the above wherein said CD22 CAR comprises a scfv specific for CD22 comprising:
a VH comprising one of following successive amino acid sequences:

```
                                        (SEQ ID NO: 13)
QVQLQQSGPGLVKPSQTLSLTCAISGDSVSSNSAAWNWIRQSPSRGLEWL

GRTYYRSKWYNDYAVSVKSRITINPDTSKNQFSLQLNSVTPEDTAVYYCA

REVTGDLEDAFDIWGQGTMVTVSS, (SEQ ID NO: 71)
QVQLQQSGPGLVKPSQTLSLTCAISGDSVSSNSAAWNWIRQSPSRGLEWL

GRTYYRSTWYNDYAVSVKSRITINPDTSKNQFSLQLNSVTPEDTAVYYCA

REVSGTSAFDIWGQGTMVTVS, (SEQ ID NO: 73)
QVQLQQSGPGLVKPSQTLSLTCAISGDSVSSNSAAWNWIRQSPSRGLEWL

GRTYYRSKWYNDYAVSVKSRITINPDTSKNQFSLQLNSVTPEDTAVYYCA

RASMTGGYSYGDAFDIWGQGTLVTVS, (SEQ ID NO: 75)
QVQLQQSGPGLVEPSQTLSLTCAISGDSVSSDSVAWNWIRQSPSRGLEWL

GRTYYRSTWYNDYAGSVKSRITINPDTSKNQFSLQLTSVTPEDTAVYYCT

RSRHNTFRGMDVWGQGTTVTVS, (SEQ ID NO: 77)
QVQLQQSGPGLVEPSQTLSLTCAISGDSVSSNSAAWNWIRQSPSRGLEWL

GRTYYRSTWYNDYAGSVKSRITINPDTSKNQFSLQLTSVTPEDTAVYYCT

RSRHNTFRGMDVWGQGTLVTVS, (SEQ ID NO: 79)
QVQLQQSGPGLVEPSQTLSLTCAISGDSVSSDSVAWNWIRQSPSRGLEWL

GRTYYRSTWYNDYAGSVKSRITINPDTSKNQFSLQLNSVTPEDTAVYYCA

RDRNGMDVWGQGTMVTVS, (SEQ ID NO: 81)
QVQLQQSGPGLVKPSQTLSLTCAISGDSVSSSSAAWNWIRQSPSRGLEWL

GRTYYRSAWYNDYAVSVKSRITINPDTSKNQFSLQLNSVTPEDTAVYYCA

RESVLLDGMDVWGRGTTVTVS,
```

-continued (SEQ ID NO: 83)
QVQLQQSGPGLVQPSQTLSLTCVISGDSVSSNSATWNWIRQSPSRGLEWL

GRTYYRSKWYNDYAVSVKSRITINPDTSKNQFSLQLNSVTPEDTAVYYCA

RDGDGGSYYDYYYYGMDVWGQGTTVTVS, (SEQ ID NO: 85)
QVQLQQSGPGLVKPSQTLSLTCAISGDSVSSNSAAWNWIRQSPSRGLEWL

GRTYYRSAWYNDYAVSVKSRITINPDTSKNQFSLQLSSVTPEDTAVYYCA

RDVEGFDYWGQGTLVTVS, (SEQ ID NO: 87)
QVQLQQSGPGLVKPSQTLSLTCAISGDSVSGNRATWNWIRQSPSRGLEWL

GRTYYRSAWYNDYAVSVKGRITFNPDTSKNQFSLQLNSVTPEDTAVYYCA

RGESGAAADAFDIWGQGTTVTVS, (SEQ ID NO: 89)
QVQLVQSGAEVKKPGASVKVSCKASGYTFTSYYMHWVRQAPGQGLEWMGI

INPSGGSTSYAQKFQGRVTMTRDTSTSTVYMELSSLRSEDTAVYYCARED

SGSGAFDIWGQGTLVTVS, and a VL comprising one of the following successive amino acid sequences:

(SEQ ID NO: 14)
DIQMTQSPSSLSASVGDRVTITCRASQTIWSYLNWYQQRPGKAPNLLIYA

ASSLQSGVPSRFSGRGSGTDFTLTISSLQAEDFATYYCQQSYSIPQTFGQ

GTKLEIK, (SEQ ID NO: 72)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPLTFGG

GTKLEIK, (SEQ ID NO: 74)
AIRMTQSPSSLSASVGDRVTITCRASQSISSYLNWYQQKPGKAPKLLIYA

ASSLQSGVPSRFSGSGSGTDFSLTISSLQPEDSATYYCQQTYSTPLTFGQ

GTKVEIK, (SEQ ID NO: 76)
DIVMTQSPSSLSASVGDRVTITCRASQTISSYLNWYQQKPGKAPKLLIYD

ASSLQSGVPSRFSGSGSGTDFTLTINSLQPEDFATYYCQQSYTTPITFGQ

GTRLEIK, (SEQ ID NO: 78)
DIQLTQSPSSLSASVGDRVTITCRASQSISSYLNWYQQKPGKAPKLLIYA

ASSLQSGVPSRFSGSGSGTDFTLTISSLQPEDFATYYCQQSYSTPLTFGG

GTKVEIK, (SEQ ID NO: 80)
DIVMTQSPSSLSASVGDRVTITCRASQSISSYLNWYQQKPGKAPKLLIYD

ASNLETGVPSRFSGSGSGTDFTFTITSLQPEDFATYYCQQSYTTPLTFGQ

GTKVEIK, (SEQ ID NO: 82)
AIRMTQSPSTLSASVGDRVTITCRASQSISTYLNWYQQKAGKAPRLLIHD

ASSLQSGVPSRFSGSGSGTDFTLTISSLQPEDFATYYCQQSYSTPLTFGG

GTKVEIK, (SEQ ID NO: 84)
DIQLTQSPSSLSTSVGDRVTITCRASQSISTYLNWYQQKPGKAPKLLIYA

ASNLQSGVPSRFSGSGSGTDFTLTISSLQPEDFATYFCQQSYTTPITFGQ

GTRLEIK, (SEQ ID NO: 86)
DIVMTQTPSSLSASVGDRVTITCRASQSISSYLNWYQQKPGKAPKLLIYA

ASSLQSGVPSRFSGSGSGTDFTLTISSLQPEDFATYYCQQSYSTPITFGQ

GTRLEIK, (SEQ ID NO: 88)
DIQLTQSPPSLSASVGDRVTITCRASQSISSYLNWYQQKPGKAPKLLIYA

ASSLQSGVPSRFSGSGFGTDFTLTISSLQPEDFATYYCQQSYSTPQTFGQ

GTKVDIK, (SEQ ID NO: 90)
EIVLTQSPLSLPVTPGEPASISCRSSRSLLSYHGYNYLDWYLQKPGQSPQ

LLIFVGSNRAPGVPDRFSGSGSGTDFTLNISRVEAEDVGVYYCMQSLQTP

RTFGQGTKVEIK, preferably said scfv comprises the following successive amino acid sequences (SEQ ID NO: 87)
QVQLQQSGPGLVKPSQTLSLTCAISGDSVSGNRATWNWIRQSPSRGLEWL

GRTYYRSAWYNDYAVSVKGRITFNPDTSKNQFSLQLNSVTPEDTAVYYCA

RGESGAAADAFDIWGQGTTVTVS
and (SEQ ID NO: 88)
DIQLTQSPPSLSASVGDRVTITCRASQSISSYLNWYQQKPGKAPKLLIYA

ASSLQSGVPSRFSGSGFGTDFTLTISSLQPEDFATYYCQQSYSTPQTFGQ

GTKVDIK.

The UCART 22 according to any one of the above wherein said scfv specific for CD22 comprises a sequence selected from SEQ ID NO: 13, SEQ ID NO:14, SEQ ID NO: 71 to SEQ ID NO: 90, preferably one of the following combination of sequences (SEQ ID NO 13, SEQ ID NO:14), (SEQ ID NO: 71 and SEQ ID NO: 72), (SEQ ID NO: 73, SEQ ID NO: 74), (SEQ ID NO: 75, SEQ ID NO: 76), (SEQ ID NO: 77, SEQ ID NO: 78), (SEQ ID NO: 79, SEQ ID NO: 80), (SEQ ID NO: 81, SEQ ID NO: 82), (SEQ ID NO: 83, SEQ ID NO: 84), (SEQ ID NO: 85, SEQ ID NO: 86), (SEQ ID NO: 87, SEQ ID NO: 88), or (SEQ ID NO: 89, SEQ ID NO: 90), more preferably a combination of sequences (SEQ ID NO: 87, SEQ ID NO: 88), more preferably a sequence selected from SEQ ID NO: 71 to SEQ ID NO: 90, preferably one of the following combination of sequences (SEQ ID NO: 71 and SEQ ID NO: 72), (SEQ ID NO: 73, SEQ ID NO: 74) (SEQ ID NO: 75, SEQ ID NO: 76), (SEQ ID NO: 77, SEQ ID NO: 78), (SEQ ID NO: 79, SEQ ID NO: 80), (SEQ ID NO: 81, SEQ ID NO: 82), (SEQ ID NO: 83, SEQ ID NO: 84), (SEQ ID NO: 85, SEQ ID NO: 86), (SEQ ID NO: 87, SEQ ID NO: 88), or (SEQ ID NO: 89, SEQ ID NO: 90), even more preferably a combination of sequences (SEQ ID NO: 87, SEQ ID NO: 88).

The UCART 22 according to any one of the above wherein said scfv specific for CD22 comprises a VH and a VL linked to each other by a linker L1.

The UCART 22 according to any one of the above wherein said scfv specific for CD22 is linked to a transmembrane domain by a hinge selected from a hinge from FcRIIIα, CD8alpha, IgG1, preferably from CD8 alpha.

The UCART 22 according to any one of the above may comprise at least one, preferably two, more preferably three, even more preferably four monoclonal antibody (mAb)-specific epitopes, preferably inserted into the linker L of the scfv specific for CD22 and/or into the hinge.

The invention provides a UCART 22 according to any one of the above wherein said molecular antibody (mAb)-specific epitope, is a mAb-specific epitope specifically recognized by an monoclonal antibody selected from ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably from rituximab (R) and/or from QBEND-10 (Q).

The UCART 22 according to any one of the above wherein a mAb-specific epitope is an epitope to be bound by a specific mAb for in vitro cell sorting and/or in vivo cell depletion of T cells expressing a CAR comprising such epitope.

The UCART 22 according to any one of the above wherein the extracellular binding domain comprises one of the following sequences:

$V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(1-)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(1-)_x$-;
$(L)_x$-Epitope1-$(L)_x$-Epitope2-$(L)_x$-$V_1$-$L_1$-$V_2$-$(L)_x$-Epitope3-$(1-)_x$-;
$(L)_x$-Epitope1-$(L)_x$-Epitope2-$(L)_x$-$V_1$-$L_1$-$V_2$-$(L)_x$-Epitope3-$(L)_x$-Epitope4-$(1-)_x$-;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(1-)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;
wherein,
$V_1$ is VL and $V_2$ is VH or $V_1$ is VH and $V_2$ is VL;
$L_1$ is a linker suitable to link the VH chain to the VL chain;
L is a linker comprising glycine and serine residues, and each occurrence of L in the extracellular binding domain can be identical or different to other occurrence of L in the same extracellular binding domain, and,
x is 0 or 1 and each occurrence of x is selected independently from the others; and,
Epitope 1, Epitope 2 and Epitope 3 are mAb-specific epitopes and can be identical or different.

The invention provides a UCART 22 according to any one of the above embodiments wherein the extracellular binding domain comprises one of the following sequences:

$V_1$-$L_1$-$V_2$-L-Epitope1; $V_1$-$L_1$-$V_2$-L-Epitope1-L; $V_1$-$L_1$-$V_2$-L-Epitope1-L-Epitope2; $V_1$-$L_1$-$V_2$-L-Epitope1-L-Epitope2-L; $V_1$-$L_1$-$V_2$-L-Epitope1-L-Epitope2-L-Epitope3; $V_1$-$L_1$-$V_2$-Epitope1-L-Epitope2-L-Epitope3-L; $V_1$-$L_1$-$V_2$-Epitope1; $V_1$-$L_1$-$V_2$-Epitope1-L; $V_1$-$L_1$-$V_2$-Epitope1-L-Epitope2; $V_1$-$L_1$-$V_2$-Epitope1-L-Epitope2-L; $V_1$-$L_1$-$V_2$-Epitope1-L-Epitope2-L-Epitope3; $V_1$-$L_1$-$V_2$-Epitope1-L-Epitope2-L-Epitope3-L; Epitope1-$V_1$-$L_1$-$V_2$; Epitope1-L-$V_1$-$L_1$-$V_2$; L-Epitope1-$V_1$-$L_1$-$V_2$; L-Epitope1-L-$V_1$-$L_1$-$V_2$; Epitope1-L-Epitope2-$V_1$-$L_1$-$V_2$; Epitope1-L-Epitope2-L-$V_1$-$L_1$-$V_2$; L-Epitope1-L-Epitope2-$V_1$-$L_1$-$V_2$; L-Epitope1-L-Epitope2-L-$V_1$-$L_1$-$V_2$; Epitope1-L-Epitope2-L-Epitope3-$V_1$-$L_1$-$V_2$; Epitope1-L-Epitope2-L-Epitope3-L-$V_1$-1_1-$V_2$; L-Epitope1-L-Epitope2-L-Epitope3-$V_1$-$L_1$-$V_2$; L-Epitope1-L-Epitope2-L-Epitope3-L-$V_1$-$L_1$-$V_2$; $V_1$-L-Epitope1-L-$V_2$; L-Epitope1-L-$V_1$-L-Epitope2-L-$V_2$; $V_1$-L-Epitope1-L-$V_2$-L-Epitope2-L; $V_1$-L-Epitope1-L-$V_2$-L-Epitope2-L-Epitope3; $V_1$-L-Epitope1-L-$V_2$-L-Epitope2-Epitope3; $V_1$-L-Epitope1-L-$V_2$-L-Epitope2-L-Epitope3-Epitope4; L-Epitope1-L-$V_1$-L-Epitope2-L-$V_2$-L-Epitope3-L; Epitope1-L-$V_1$-L-Epitope2-L-$V_2$-L-Epitope3-L; L-Epitope1-L-$V_1$-L-Epitope2-L-$V_2$-L-Epitope3; L-Epitope1-L-$V_1$-$L_1$-$V_2$-L-Epitope2-L; L-Epitope1-L-$V_1$-$L_1$-$V_2$-L-Epitope2-L-Epitope3; L-Epitope1-L-$V_1$-$L_1$-$V_2$-L-Epitope2-Epitope3, or Epitope1-L-$V_1$-$L_1$-$V_2$-L-Epitope2-L-Epitope3-Epitope4 wherein
$V_1$ is $V_L$ and $V_2$ is $V_H$ or $V_1$ is $V_H$ and $V_2$ is VL;
$L_1$ is any linker suitable to link the $V_H$ chain to the $V_L$ chain;
L is a linker comprising glycine and serine residues, and each occurrence of L in the extracellular binding domain can be identical or different to other occurrences of L in the same extracellular binding domain, and,
Epitope 1, Epitope 2 and Epitope 3 are mAb-specific epitopes and can be identical or different.

In the UCART 22 according to any one of the above $L_1$ may be a linker comprising Glycine and/or Serine. The invention provides a UCART 22 according to any one of the above wherein $L_1$ is a linker comprising the amino acid sequence (Gly-Gly-Gly-Ser)$_n$ or (Gly-Gly-Gly-Gly-Ser)$_n$, where n is 1, 2, 3, 4 or 5 or a linker comprising the amino acid sequence (Gly$_4$Ser)$_4$ or (Gly$_4$Ser)$_3$.

The invention provides a UCART 22 according to any one of the above wherein L is a linker comprising Glycine and/or Serine.

The UCART 22 according to any one of the above wherein L is a linker having an amino acid sequence selected from SGG, GGS, SGGS (SEQ ID NO: 101), SSGGS (SEQ ID NO: 102), GGGG (SEQ ID NO: 103), SGGGG (SEQ ID NO: 104), GGGGS (SEQ ID NO: 97), SGGGGS (SEQ ID NO: 105), GGGGGS (SEQ ID NO: 106), SGGGGGS (SEQ ID NO: 107), SGGGGG (SEQ ID NO: 108), GSGGGGS (SEQ ID NO: 109), GGGGGGS (SEQ ID NO: 110), SGGGGGGG (SEQ ID NO: 111), SGGGGGGGS (SEQ ID NO: 112), and SGGGGSGGGGS (SEQ ID NO: 113), preferably L is a linker having the amino acid sequence SGGGG (SEQ ID NO: 104), GGGGS (SEQ ID NO: 97) or SGGGGS (SEQ ID NO: 105).

The invention provides a UCART 22 according to any one of the above, wherein Epitope 1, Epitope 2, Epitope 3 and Epitope 4 are independently selected from mAb-specific epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably Epitope 1, Epitope 2, Epitope 3 and Epitope 4 are recognized by rituximab or QBEND-10. The UCART 22 according to any one of the above, wherein the mAb-specific epitope is a polypeptide selected from: CPYSNPSLC (SEQ ID NO: 91), NSELLSLINDMPITNDQKKLMSNN (SEQ ID NO: 114), CQFDLSTRRLKC (SEQ ID NO: 115), CQYNLSSRALKC (SEQ ID NO: 116), CVWQRWQKSYVC (SEQ ID NO: 117), SFVLNWYRMSPSNQTDKLAAFPEDR (SEQ ID NO: 119), SGTYLCGAISLAPKAQIKE (SEQ ID NO: 120), ELPTQGTFSNVSTNVSPAKPTTTA (SEQ ID NO: 92), GQNDTSQTSSPS (SEQ ID NO: 121).

The UCART 22 according to any one of the above, wherein the mAb-specific epitope has the following amino acid sequence of ELPTQGTFSNVSTNVSPAKPTTTA (SEQ ID NO: 92) and/or CPYSNPSLC (SEQ ID NO: 91).

The UCART 22 according to the above comprising 3 mAb-specific epitopes having an amino acid sequence of CPYSNPSLC (SEQ ID NO: 91) and one having an amino acid sequence of ELPTQGTFSNVSTNVSPAKPTTTA (SEQ ID NO: 92).

The UCART 22 according to any one of the above, wherein the VH and VL of the anti-CD22 CAR are selected from:
a VH of SEQ ID NO: 71 and a VL of SEQ ID NO: 72; a VH of SEQ ID NO: 73 and a VL of SEQ ID NO: 74; a VH of SEQ ID NO: 75 and a VL of SEQ ID NO: 76; a VH of SEQ ID NO: 77 and a VL of SEQ ID NO: 78; a VH of SEQ ID NO: 79 and a VL of SEQ ID NO: 80; a VH of SEQ ID NO: 81 and a VL of SEQ ID NO: 82; a VH of SEQ ID NO: 83 and a VL of SEQ ID NO: 84; a VH of SEQ ID NO: 85 and a VL of SEQ ID NO: 86; a VH of SEQ ID NO: 87 and a VL of SEQ ID NO: 88; a VH of SEQ ID NO: 89 and a VL of SEQ ID NO: 90, preferably a VH of SEQ ID NO: 87 and a VL of SEQ ID NO: 88.

The UCART 22 according to any one of the above, wherein said VH chain has a sequence of more than 80% identity, preferably more than 90%, and more preferably more than 95% identity with any one of the following sequences: SEQ ID NO: 71, 73, 75, 77, 79, 81, 83, 85, 87, and 89 and said VL chain has a sequence of over 80% identity, preferably over 90%, and more preferably over 95% identity with any one of the following sequences SEQ ID NO: 72, 74, 76, 78, 80, 82, 84, 86, 88 or 90.

The UCART 22 according to the above, wherein said VH chain has a sequence of over 80% identity, preferably over 90%, and more preferably over 95% identity with SEQ ID NO: 71, and said VL chain has a sequence of over 80% identity, preferably over 90%, and more preferably over 95% identity with SEQ ID NO: 72, The UCART 22 according to the above, wherein said VH chain has a sequence of over 80% identity, preferably over 90%, and more preferably over 95% identity with SEQ ID NO: 73, and said VL chain has a sequence of over 80% identity, preferably over 90%, and more preferably over 95% identity with SEQ ID NO: 74, The UCART 22 according to the above, wherein said VH chain has a sequence of over 80% identity, preferably over 90%, and more preferably over 95% identity with SEQ ID NO: 75, and said VL chain has a sequence of over 80% identity, preferably over 90%, and more preferably over 95% identity with SEQ ID NO: 76, The UCART 22 according to the above, wherein said VH chain has a sequence of over 80% identity, preferably over 90%, and more preferably over 95% identity with SEQ ID NO: 77, and said VL chain has a sequence of over 80% identity, preferably over 90%, and more preferably over 95% identity with SEQ ID NO: 78, The UCART 22 according to the above, wherein said VH chain has a sequence of over 80% identity, preferably over 90%, and more preferably over 95% identity with SEQ ID NO: 79, and said VL chain has a sequence of over 80% identity, preferably over 90%, and more preferably over 95% identity with SEQ ID NO: 80, The UCART 22 according to the above, wherein said VH chain has a sequence of over 80% identity, preferably over 90%, and more preferably over identity 95% with SEQ ID NO: 81, and said VL chain has a sequence of over 80% identity, preferably over 90%, and more preferably over 95% identity with SEQ ID NO: 82, The UCART 22 according to the above, wherein said VH chain has a sequence of over 80% identity, preferably over 90%, and more preferably over 95% with SEQ ID NO: 83, and said VL chain has a sequence of over 80% identity, preferably over 90%, and more preferably over 95% with SEQ ID NO: 84, The UCART 22 according to the above, wherein said VH chain has a sequence of over 80% identity, preferably over 90%, and more preferably over 95% with SEQ ID NO: 85, and said VL chain has a sequence of over 80% identity, preferably over 90%, and more preferably over 95% identity with SEQ ID NO: 86, The UCART 22 according to the above, wherein said VH chain has a sequence of over 80% identity, preferably over 90%, and more preferably over 95% with SEQ ID NO: 87, and said VL chain has a sequence of over 80% identity, preferably over 90%, and more preferably over 95% identity with SEQ ID NO: 88, The UCART 22 according to the above, wherein said VH chain has a sequence of over 80% identity, preferably over 90%, and more preferably over identity 95% with SEQ ID NO: 89, and said VL chain has a sequence of over 80% identity, preferably over 90%, and more preferably over 95% identity with SEQ ID NO: 90, The invention provides a UCART 22 according to any one of the above wherein the transmembrane domain comprises the transmembrane region(s) of the alpha, beta or zeta chain of the T-cell receptor, PD-1, 4-1BB, OX40, ICOS, CTLA-4, LAG3, 2B4, BTLA4, TIM-3, TIGIT, SIRPA, CD28, CD3 epsilon, CD45, CD4, CD5, CD8, CD9, CD16, CD22, CD33, CD37, CD64, CD80, CD86, CD134, CD137 or CD154.

The UCART 22 according to any one of the above wherein the transmembrane domain comprises a transmembrane region of PD-1 or CD8 alpha.

The UCART 22 according to any one of the above wherein the transmembrane domain comprises a transmembrane region of CD8 alpha.

The UCART 22 according to any one of the above wherein the intracellular domain comprises a CD3zeta signaling domain.

The UCART 22 according to any one of the above wherein the intracellular domain comprises a 4-1BB domain.

The UCART 22 according to any one of the above wherein the intracellular domain comprises CD3zeta signaling domain and a 4-1BB domain.

The present invention provides a UCART 22 according to any one of the above, wherein the CD22 CAR is a single-chain CAR, preferably a single-chain CAR comprising an additional scfv specific for one of the following tumor-associated surface antigen selected from CD19, CD20, CD30, a major histocompatibility complex (MHC) molecule, an Immunoglobulin (Ig), CD3, CD34, CD79, preferably CD79b, CD138, B7-1 (CD80), BCMA (CD269, TNFRSF 17) or FLT-3, PAX5.

As other second extracellular binding domain in a scCAR or in a mcCAR may be any extracellular binding domain binding specific to an antigen associated (coexpressed—even temporarily) to CD22 on pathological cells, such as CD34, CD10, CD79a, CD20, IgD, CDS, CD23, CD19, STATS, CD3, CD30, BCMA, PAX5.

As other second extracellular binding domain in a scCAR or in a mcCAR may be any extracellular binding domain binding specific to an antigen associated (coexpressed—even temporarily) to CD22 on pathological cells, CD19, CD20, CD30, glycosphingolipids, a major histocompatibility complex (MHC) molecule, an Ig, CD3, CD34, CD79, preferably CD79a, CD138, B7-1 (CD80), B7-2 (CD86), a major histocompatibility complex (MHC) molecule, BCMA (CD269, TNFRSF 17) or FLT-3, Pax5.

The present invention provides a UCART 22 according to any one of the above, wherein the said CD22 CAR shares over 80% identity, over 90%, over 95% identity with or is identical to SEQ ID NO: 46 to SEQ ID NO: 69, preferably SEQ ID NO: 56 to SEQ ID NO: 65, more preferably with SEQ ID NO: 64.

The present invention provides a UCART 22 according to any one of the above wherein the CD22 CAR is a multi-chain CAR, preferably a multichain CAR comprising an additional scfv specific for one of the following tumor-associated surface antigen selected from CD19, CD20, CD30, a major histocompatibility complex (MHC) molecule, an Immunoglobulin (Ig), CD3, CD34, CD79, preferably CD79b, CD138, B7-1 (CD80), BCMA (CD269, TNFRSF 17) or FLT-3, PAX5.

As other second extracellular binding domain on a multichain CAR may be any extracellular binding domain binding specific to an antigen associated (coexpressed—even temporarily) to CD22 on pathological cells, The UCART 22 according to any one of the above comprising an expression vector encoding a CD22 CAR of the invention.

In one embodiment, the present invention provides the UCART 22 according to any one of the above, wherein said cell is derived or is an inflammatory T-lymphocytes, cytotoxic T-lymphocytes, regulatory T-lymphocytes or helper T-lymphocytes, a Natural Killer T cells.

In one embodiment, the present invention provides a pharmaceutical composition comprising a pharmaceutically acceptable excipient and an anti-CD22 CAR as described above, or the UCART 22 according to any one of the above, preferably an additional compound which is a compound of the bryostatin family and the UCART 22 according to any one of the above, more preferably bryostatine-1 and the UCART 22 according to any one of the above.

The present invention provides a UCART 22 according to the above or the pharmaceutical composition according to the above for use as a medicament.

In Summary the Present Invention Provides the Following Objects:

1. A Chimeric Antigen Receptor (CAR) specific for CD22 (ANTI-CD22 CAR) comprising:
i) at least one extracellular domain comprising:
an antigen binding domain specific for CD22, optionally a leader sequence,
a hinge domain selected from FcRIIIα, CD8alpha, IgG1, IgG4, and PD1, preferably from CD8 alpha,
ii) a transmembrane domain, and
iii) an intracellular signaling domain.

wherein said antigen binding domain specific for CD22 comprises a single chain variable fragment (scfv) specific for CD22, said scfv comprising a heavy chain variable (VH) and light chain variable (VL), comprising one of the following combination of sequences:
(SEQ ID NO: 71 and SEQ ID NO: 72), (SEQ ID NO: 73, SEQ ID NO: 74), (SEQ ID NO: 75, SEQ ID NO: 76), (SEQ ID NO: 77, SEQ ID NO: 78), (SEQ ID NO: 79, SEQ ID NO: 80), (SEQ ID NO: 81, SEQ ID NO: 82), (SEQ ID NO: 83, SEQ ID NO: 84), (SEQ ID NO: 85, SEQ ID NO: 86), (SEQ ID NO: 87, SEQ ID NO: 88), or (SEQ ID NO: 89, SEQ ID NO: 90), more preferably a combination of sequences selected from (SEQ ID NO: 77, SEQ ID NO: 78), (SEQ ID NO: 83, SEQ ID NO: 84), (SEQ ID NO: 87, SEQ ID NO: 88), and (SEQ ID NO: 89, SEQ ID NO: 90) even more preferably the combination of sequences (SEQ ID NO: 87, SEQ ID NO: 88).

2. The ANTI-CD22 CAR according to embodiment 1 wherein said scfv specific for CD22 comprises a VH and a VL linked to each other by a linker L1, preferably L1 is GGGGS (SEQ ID NO: 97).

3. The ANTI-CD22 CAR according to any one of embodiment 1 to 2 wherein said scfv specific for CD22 is linked to a transmembrane domain by a hinge selected from a hinge from FcRIIIα, CD8alpha, IgG1, preferably from CD8 alpha.

4. The ANTI-CD22 CAR according to any one of embodiment 1 to 3 wherein the intracellular domain comprises a CD3zeta signaling domain and a 4-1BB signaling domain.

5. The anti-CD22 CAR according to any one of embodiment 1 to 4 comprising a sequence selected from any one of the following sequences SEQ ID NO: 46 to SEQ ID NO: 55.

6. The ANTI-CD22 CAR according to any one of embodiment 1 to 5 comprising at least one, preferably two, more preferably three, even more preferably four monoclonal antibody (mAb)-specific epitopes, preferably inserted into the linker L1 of the scfv specific for CD22 and/or into the hinge.

7. The ANTI-CD22 CAR according to any one of embodiment 1 to 6, wherein the mAb-specific epitope is a polypeptide selected from: CPYSNPSLC (SEQ ID NO: 91), NSELLSLINDMPITNDQKKLMSNN (SEQ ID NO: 114), CQFDLSTRRLKC (SEQ ID NO: 115), CQYNLSSRALKC (SEQ ID NO: 116), CVWQRWQKSYVC (SEQ ID NO: 117), SFVLNWYRMSPSNQTDKLAAFPEDR (SEQ ID NO: 119), SGTYLCGAISLAPKAQIKE (SEQ ID NO: 120), ELPTQGTFSNVSTNVSPAKPTTTA (SEQ ID NO: 92), GQNDTSQTSSPS (SEQ ID NO: 121), preferably ELPTQGTFSNVSTNVSPAKPTTTA (SEQ ID NO: 92) and/or CPYSNPSLC (SEQ ID NO: 91).

8. The anti-CD22 CAR according to any one of embodiment 1 to 7 comprising a sequence selected from any one of the following sequences SEQ ID N: 56 to SEQ ID N: 69.

9. The ANTI-CD22 CAR according to any one of embodiment 1 to 8 comprising 2 mAb-specific epitopes having an amino acid sequence of CPYSNPSLC (SEQ ID NO: 91) or 3 mAb-specific epitopes having an amino acid sequence of CPYSNPSLC (SEQ ID NO: 91) and one mAb-specific epitope having an amino acid sequence of ELPTQGTFSNVSTNVSPAKPTTTA (SEQ ID NO: 92).

10. The anti-CD22 CAR according to embodiment 9 comprising a sequence selected from any one of the following sequences SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65.

11. The ANTI-CD22 CAR according to any one of embodiment 1 to 10, wherein the ANTI-CD22 CAR is a single-chain CAR or a multi-chain CAR, comprising an additional scfv specific for one of the following tumor-associated surface antigens selected from CD19, CD20, CD30, a major histocompatibility complex (MHC) molecule, an Immunoglobulin (Ig), CD3, CD5, CD34, CD79, preferably CD79b, CD138, B7-1 (CD80), BCMA (CD269, TNFRSF 17), FLT-3, or PAX5.

12. A polynucleotide encoding an ANTI-CD22 CAR according to any one of embodiment 1 to 11.

13. A vector comprising a polynucleotide according to embodiment 12.

14. An immune cell endowed with the ANTI-CD22 CAR according to any one of embodiments 1 to 11, preferably further comprising the polynucleotide or the vector according to embodiment 12 or embodiment 13.

15. The immune cell according to embodiment 14 comprising at least one edited gene, preferably an inactivated gene coding for one of the T Cell Receptor domain, more preferably a TRAC Knock out gene (UCART22).

16. The immune cell according to embodiment 14 or 15 wherein the immune cell is a human immune cell, preferably a human immune T cell, more preferably an engineered human immune T Cell comprising an inactivated TRAC gene and undetectable level of TCR at the cell surface by flow cytometry.

17. The engineered human immune T Cell Receptor Knock Out (TCR KO) T cell according to embodiment 16 endowed with an ANTI-CD22 according to any one of embodiment 1 to 11 (UCART22), preferably expressed at the cell surface, wherein and at least one additional gene is edited or engineered, said gene is selected from a gene encoding a $\beta_2$ Microglobulin (B2M), an Aryl hydrocarbon receptor (AHR), a Transforming growth factor $\beta$ receptor) (TGF $\beta$ receptor), an Interleukin 10 receptor (IL-10 R), a Programmed cell death protein 1, a combination thereof.

18. The UCART22 of embodiment 17 wherein said at least one additional gene comprises a mutation, a deletion or an insertion, inactivating its activity and/or expression.

19. The UCART22 according to embodiment 17 wherein a gene encoding $\beta_2$ Microglobulin (B2M), is inactivated.

20. The UCART22 according to embodiment 17 wherein a gene encoding Aryl hydrocarbon receptor (AHR), is inactivated.

21 The UCART22 according to embodiment 17 wherein a gene encoding Transforming growth factor 3 receptor) (TGF $\beta$ receptor), is inactivated.

22. The UCART22 according to embodiment 17 wherein a gene encoding Interleukin 10 receptor (IL-10 R), is inactivated.

23. The UCART22 according to embodiment 17 wherein a gene encoding Programmed cell death protein 1 (PD1), is inactivated.

24. The UCART22 comprising an ANTI-CD22 CAR according to any one of the embodiments 1 to 11 and a polynucleotide coding said ANTI-CD22 CAR, inserted into the CD25 gene.

25. The UCART22 according to any one of embodiment 14 to 24 wherein the ANTI-CD22 CAR is a single-chain CAR or a multi-chain CAR.

26. The UCART22 according to embodiment 25 wherein the ANTI-CD22 CAR is a multi-chain CAR.

27. The UCART22 according to embodiment 26 of the above wherein the ANTI-CD22 CAR is a multi-chain CAR comprising an additional scfv specific for CD19.

28. A population of cells comprising the UCART22 according to any one of embodiment to 14 to 27.

29. The population of cells comprising the UCART22 according to embodiment 28 and a UCART19, preferably a UCART19 expressing an anti-CD19 CAR comprising a sequence of SEQ ID NO:95 or SEQ ID NO:96 at the cell surface.

30. The population of cells comprising the UCART22 according to embodiment 28 and wherein cells expressing said anti-CD22 CAR also express an anti-CD19 CAR, preferably said anti-CD19 CAR comprises a sequence of SEQ ID NO:95 or SEQ ID NO:96 at the cell surface.

31. A pharmaceutical composition comprising the UCART22 according to any one embodiment 14 to 27 or a population of cells according to embodiment 28 to 30 and a pharmaceutically acceptable excipient.

32. The pharmaceutical composition of embodiment 31 further comprising a Bryostatin, preferably Bryostatin-1.

33. The pharmaceutical composition of embodiment 31 further comprising an antibody used to prepare the CD22 CAR scfv.

34 The pharmaceutical composition of embodiment 31 further comprising an antibody used to prepare the CD19 CAR scfv.

35. A kit comprising a UCART22 according to any one of embodiment 14 to 27 and a UCART19 for a successive (at least once) or a concomitant or a successive (at least once) and then concomitant administration in a patient in need thereof.

36 The kit according to embodiment 35 wherein the UCART 19 is used first at least once, twice or several times, and then the UCART 22 is used alone or with the UCART19 at least once, twice or several times.

37. The kit according to embodiment 35 wherein the UCART 22 is used first at least once, twice or several times, and then the UCART 19 is used alone or with the UCART22 at least once, twice or several times.

38. The kit as any one of embodiment 35 to 37 further comprising a lymphodepleting treatment, administered before the UCART.

39. The kit according to embodiment 38 wherein lymphodepletion is achieved using fludarabine and cyclophosphamide, preferably fludarabine 25 mg/m$^2$ i.v. x 5 doses on days −6 to −2 and cyclophosphamide 60 mg/kg i.v. for 1 dose on day −5.

40. The kit according to any one of embodiment 35 to 39 comprising at least one other UCART cell directed against a cancer antigen selected from CD79a, CD79b, CD20, CD30, CD52, CD40, CD80, CD86, CD74, VEGF.

41. The pharmaceutical composition according to embodiment 31 to 34 or the kit according to embodiment 35 to 40 for use as a medication for preventing or treating a patient suffering a CD19-mediated cancer or a CD19-mediated inflammatory disease.

42. The pharmaceutical composition according to embodiment 31 to 34 or the kit according to embodiment 35 to 40 for use as a medication for preventing or treating a patient suffering a CD22-mediated cancer or a CD22-mediated inflammatory disease.

43. The pharmaceutical composition according to embodiment 31 to 34 or the kit according to embodiment 35 to 40 for its use for treating a patient comprising a step of administering the pharmaceutical composition or part of the kit at least twice (re dosing) to avoid a relapse/refractory development of the cancer.

45. The pharmaceutical composition according to embodiment 31 to 34 or the kit according to embodiment 35 to 40 for its use for treating a patient comprising administering at least one monoclonal antibody (mAb), preferably QBEND-10 and or rituximab, in a patient, at a dose allowing contacting said UCART22 with at least one specific mAb.

46. The pharmaceutical composition according to embodiment 31 to 34 or the kit according to embodiment 35 to 40 for its use for the treatment of a CD22-mediated hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22 expressing hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD22-expressing hematological cancer, even more preferably an aggressive form of said CD22-related hematological cancer.

47. The pharmaceutical composition according to embodiment 31 to 34 or the kit according to embodiment 35 to 40 for its use for the treatment of a CD19-mediated hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD19 (?) expressing hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD19-expressing hematological cancer, even more preferably an aggressive form of said CD19-related hematological cancer.

48 The pharmaceutical composition according to embodiment 31 to 34 or the kit according to embodiment 35 to 40 for its use for the treatment of a relapse or refractory CD22-expressing B ALL, preferably as a pediatric indication.

49. The pharmaceutical composition according to embodiment 31 to 34 or the kit according to embodiment 35 to 40 for its use for the treatment of a relapse or refractory CD19-expressing B ALL, preferably as a pediatric indication.

A Chimeric Antigen Receptor specific for CD22 (CD22 CAR)
comprising
i) at least one extracellular domain comprising:
a hinge
an antigen binding domain comprising a scfv specific for CD22, optionally a leader sequence,
ii) a transmembrane domain from CD8alpha, and
iii) an intracellular signaling domain,
wherein said scfv specific for CD22 comprises at least a combination of a VH chain, a linker, and a VL chain,
said VH comprising a CDR1 with one of the successive amino acid sequences: G, D or Y, S or T, V or F, S or T, S or G, N S or D, S or R, AT or Y, and AT or Y,
a CDR2 with one of the successive amino acid sequences: T or I, Y or I, Y or N, R or P, S, KAG or T, W or G, Y or S, and N or T,
a CDR3 with one of the successive amino acid sequences: A or T, R, EDSA or G, VGSDR or E, TDVSH or M, GLN or T, D or G, xxxxx, LYT or A, EYLSFTG or A, DYGRSN or E, A or G, F or V, D, and I, V or Y, wherein X is an amino acid,
said VL comprising a CDR1 with one of the successive amino acid sequences: Q or R, T or S, preferably S, I or L, W or S, preferably S, S or T and Y.
a CDR2 with one of the successive amino acid sequences: AD or V, AD or V and S.
a CDR3 with one of the successive amino acid sequences QM, Q, ST, YL, STQ, I or T, preferably T, PQILR, T.

The CD22 CAR as above
wherein said CD22 CAR comprises a scfv specific for CD22 comprises
a VL with the following sequences: QSISSY (SEQ ID NO: 131), AAS and QQSYSSTPQT ((SEQ ID NO: 132) corresponding to the CDR1, CDR2 and CDR3, a VH with the following sequences GDSVSSGNRAT (SEQ ID NO: 133), TYYRSAWYND (SEQ ID NO: 134) and ARGESGAAADAFDI (SEQ ID NO: 135).

The anti-CD22 CAR according to the above comprising a hinge domain selected from FcRIIIα, CD8alpha, IgG1, IgG4, and PD1, preferably from CD8 alpha.

The CD22 CAR according to the above wherein said antigen binding domain specific for CD22 comprises a single chain variable fragment (scfv) specific for CD22, said scfv comprising a heavy chain variable (VH) and light chain variable (VL), comprising one of the following combination of sequences: (SEQ ID NO: 71 and SEQ ID NO: 72), (SEQ ID NO: 73, SEQ ID NO: 74), (SEQ ID NO: 75, SEQ ID NO: 76), (SEQ ID NO: 77, SEQ ID NO: 78), (SEQ ID NO: 79, SEQ ID NO: 80), (SEQ ID NO: 81, SEQ ID NO: 82), (SEQ ID NO: 83, SEQ ID NO: 84), (SEQ ID NO: 85, SEQ ID NO: 86), (SEQ ID NO: 87, SEQ ID NO: 88), or (SEQ ID NO: 89, SEQ ID NO: 90), more preferably a combination of sequences selected from (SEQ ID NO: 77, SEQ ID NO: 78), (SEQ ID NO: 83, SEQ ID NO: 84), (SEQ ID NO: 87, SEQ ID NO: 88), and (SEQ ID NO: 89, SEQ ID NO: 90) even more preferably the combination of sequences (SEQ ID NO: 87, SEQ ID NO: 88).

A Chimeric Antigen Receptor (CAR) specific for CD22 (ANTI-CD22 CAR) comprising a heavy chain variable (VH) of SEQ ID NO: 71 and light chain variable (VL) of SEQ ID NO:72, or having at least 80%, preferably at least 90%, even more preferably 98% identity with said sequence.

An anti-CD22 CAR comprising a VH of SEQ ID NO: 73 and a VL of SEQ ID NO: 74 or having at least 80%, preferably at least 90%, even more preferably 98% identity with said sequence.

An anti-CD22 CAR comprising a VH of SEQ ID NO: 75 and a VL of SEQ ID NO: 76 or a having at least 80%, preferably at least 90%, even more preferably 98% identity with said sequence.

An anti-CD22 CAR comprising a VH of SEQ ID NO: 77, and a VL of SEQ ID NO: 78 or having at least 80%, preferably at least 90%, even more preferably 98% identity with said sequence.

An anti-CD22 CAR comprising a VH of SEQ ID NO: 79 and a VL of SEQ ID NO: 80 or having at least 80%, preferably at least 90%, even more preferably 98% identity with said sequence.

An anti-CD22 CAR comprising a VH of SEQ ID NO: 81 or a VL of SEQ ID NO: 82 or having at least 80%, preferably at least 90%, even more preferably 98% identity with said sequence.

An anti-CD22 CAR comprising a VH of SEQ ID NO: 83 or a VL of SEQ ID NO: 84 or having at least 80%, preferably at least 90%, even more preferably 98% identity with said sequence.

An anti-CD22 CAR comprising a VH of SEQ ID NO: 85 and a VL of SEQ ID NO: 86 or having at least 80%, preferably at least 90%, even more preferably 98% identity with said sequence.

An anti-CD22 CAR comprising a VH of SEQ ID NO: 87 and a VL of SEQ ID NO: 88 or having at least 80%, preferably at least 90%, even more preferably 98% identity with said sequence.

An anti-CD22 CAR comprising a VH of SEQ ID NO: 89 and a VL of SEQ ID NO: 90, or having at least 80%, preferably at least 90%, even more preferably 98% identity with said sequence.

The ANTI-CD22 CAR according to any one of the above wherein a scfv specific for CD22 comprising a VH and a VL linked to each other by a linker L1, preferably a linker comprising 1 to 3 "GGGGS" motif (SEQ ID NO: 97), more preferably one GGGGS motif (SEQ ID NO: 97).

The ANTI-CD22 CAR according to any one of the above wherein said scfv specific for CD22 is linked to a transmembrane domain by a hinge selected from a hinge from FcRIIIα, CD8alpha, IgG1, preferably from CD8 alpha.

The ANTI-CD22 CAR according to any one of the above comprising an intracellular domain, said an intracellular domain comprising a CD3zeta signaling domain and a 4-1BB signaling domain.

The anti-CD22 CAR as any one of the above comprising one of the following sequences: SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 54, SEQ ID NO: 55, or a sequence having at least 80%, preferably at least 90%, even more preferably 98% identity with said sequence.

The anti-CD22 CAR as any one of the above wherein the anti-CD22 CAR comprises at least one, preferably two, three or four monoclonal antibody (mAb)-specific epitopes, preferably two inserted into the linker L of the scfv specific for CD22 and/or into the hinge.

The anti-CD22 CAR as any one of the above, wherein the mAb-specific epitope is a polypeptide selected from: CPYSNPSLC (SEQ ID NO: 91), NSELLSLINDMPITNDQKKLMSNN (SEQ ID NO: 114), CQFDLSTRRLKC (SEQ ID NO: 115), CQYNLSSRALKC (SEQ ID NO: 116), CVWQRWQKSYVC (SEQ ID NO: 117), SFVLNWYRMSPSNQTDKLAAFPEDR (SEQ ID NO: 119), SGTYLCGAISLAPKAQIKE (SEQ ID NO: 120), ELPTQGTFSNVSTNVSPAKPTTTA (SEQ ID NO: 92), GQNDTSQTSSPS (SEQ ID NO: 121), preferably ELPTQGTFSNVSTNVSPAKPTTTA (SEQ ID NO: 92) and/or CPYSNPSLC (SEQ ID NO: 92 and SEQ ID NO: 91).

The anti-CD22 CAR as any one of the above comprising a sequence selected from any one of the following sequences SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or having at least 80%, preferably at least 90%, even more preferably 98% identity with said sequence. A polynucleotide encoding an ANTI-CD22 CAR according to any one of the above or a polynucleotide having at least 80% identity with SEQ ID NO:21, or SEQ ID NO:22, SEQ ID NO: 23, SEQ ID NO: 24, SEQ ID NO: 25, SEQ ID NO: 26, SEQ ID NO:28, SEQ ID NO: 29, SEQ ID NO: 30.

A vector comprising a polynucleotide according to any one of the polynucleotides selected from SEQ ID NO:21, or SEQ ID NO:22, SEQ ID NO: 23, SEQ ID NO: 24, SEQ ID NO: 25, SEQ ID NO: 26, SEQ ID NO: 27, SEQ ID NO:28, SEQ ID NO: 29, SEQ ID NO: 30 or a polynucleotide having at least 80% identity with SEQ ID NO:21, or SEQ ID NO:22, SEQ ID NO: 23, SEQ ID NO: 24, SEQ ID NO: 25, SEQ ID NO: 26, SEQ ID NO: 27, SEQ ID NO:28, SEQ ID NO: 29, SEQ ID NO: 30.

An engineered human T Cell Receptor Knock Out (TCR KO) T cell expressing at the cell surface a CD22 CAR (UCART22) said UCART22 comprising an exogenous polynucleotide encoding said CD22 CAR inserted into the TRAC gene.

A UCART22 comprising an exogenous polynucleotide encoding said CD22 CAR inserted into the TRAC gene, said exogenous polynucleotide comprising a sequence having at least 80% identity with SEQ ID NO:21, or SEQ ID NO:22, SEQ ID NO: 23, SEQ ID NO: 24, SEQ ID NO: 25, SEQ ID NO: 26, SEQ ID NO: 27, SEQ ID NO:28, SEQ ID NO: 29, SEQ ID NO: 30 and expressing at the cell surface the corresponding CD22 CAR.

The UCART22 as above wherein and at least one additional gene is edited or engineered, said gene is selected from a gene encoding β2 Microglobulin (B2M), Aryl hydrocarbon receptor (AHR), Transforming growth factor βreceptor) (TGF βreceptor), Interleukin 10 receptor (IL-10 R), Programmed cell death protein 1, a combination thereof.

The UCART22 as above wherein and at least one additional gene comprises a mutation, a deletion or an insertion inactivating its activity and/or expression said gene selected from a gene encoding $β_2$ Microglobulin (B2M), Aryl hydrocarbon receptor (AHR), Transforming growth factor β receptor) (TGF β receptor), Interleukin 10 receptor (IL-10 R), Programmed cell death protein 1, a combination thereof.

The UCART22 as above wherein a gene encoding β2 Microglobulin (B2M), is inactivated.

The UCART22 as above wherein a gene encoding Aryl hydrocarbon receptor (AHR), is inactivated.

The UCART22 as above wherein a gene encoding Transforming growth factor βreceptor) (TGF βreceptor), is inactivated.

The UCART22 as above wherein a gene encoding Interleukin 10 receptor (IL-10 R), is inactivated.

The UCART22 as above wherein a gene encoding Programmed cell death protein 1 (PD1), is inactivated.

The UCART22 as above comprising an anti-CD22 CAR according to any one of claims 1 to 16 and a polynucleotide coding said anti-CD22 CAR (UCART22) inserted into the genome, preferably into the TRAC gene.

The UCART22 as above comprising an anti-CD22 CAR according to any one of the above and a polynucleotide coding said anti-CD22 CAR (UCART22) inserted into the genome, into the CD25 gene.

The UCART22 according to any one of the above wherein the anti-CD22 CAR is a single-chain CAR or a multi-chain CAR.

The UCART22 according to any one of the above wherein the anti-CD22 CAR is a single-chain CAR comprising an additional scfv specific for any one of the following tumor-associated surface antigens selected from CD19, CD20, CD30, a major histocompatibility complex (MHC) molecule, an Immunoglobulin (Ig), CD3, CD5, CD34, CD79, preferably CD79b, CD138, B7-1 (CD80), BCMA (CD269, TNFRSF 17), FLT-3, or PAX5, preferably CD19.

The UCART22 according to any one of the above wherein the anti-CD22 CAR is a single-chain CAR comprising an additional scfv specific for CD19.

The UCART22 according to any one of the above expressing an anti-CD22 CAR and an anti-CD19CAR, preferably of SEQ ID NO:94 or of SEQ ID NO:95.

The UCART22 according to any one of the above wherein the anti-CD22 CAR is a single-chain CAR comprising an additional scfv specific for CD20.

The UCART22 according to any one of the above wherein the anti-CD22 CAR is a single-chain CAR comprising an additional scfv specific for CD30.

The UCART22 according to any one of the above wherein the anti-CD22 CAR is a single-chain CAR comprising an additional scfv specific for a major histocompatibility complex (MHC) molecule.

The UCART22 according to any one of the above wherein the anti-CD22 CAR is a single-chain CAR comprising an additional scfv specific for an Immunoglobulin (Ig).

The UCART22 according to any one of the above wherein the anti-CD22 CAR is a single-chain CAR comprising an additional scfv specific for CD3.

The UCART22 according to any one of the above wherein the anti-CD22 CAR is a single-chain CAR comprising an additional scfv specific for CDS.

The UCART22 according to any one of the above wherein the anti-CD22 CAR is a single-chain CAR comprising an additional scfv specific for CD34.

The UCART22 according to any one of the above wherein the anti-CD22 CAR is a single-chain CAR comprising an additional scfv specific for CD79, preferably CD79b.

The UCART22 according to any one of the above wherein the anti-CD22 CAR is a single-chain CAR comprising an additional scfv specific for CD138.

The UCART22 according to any one of the above wherein the anti-CD22 CAR is a single-chain CAR comprising an additional scfv specific for CD80.

The UCART22 according to any one of the above wherein the anti-CD22 CAR is a single-chain CAR comprising an additional scfv specific for BCMA (CD269).

The UCART22 according to any one of the above wherein the anti-CD22 CAR is a single-chain CAR comprising an additional scfv specific for TNFRSF 17, The UCART22 according to any one of the above wherein the anti-CD22 CAR is a single-chain CAR comprising an additional scfv specific for FLT-3.

The UCART22 according to any one of the above wherein the anti-CD22 CAR is a multi-chain CAR.

The UCART22 according to any one of the above wherein the anti-CD22 CAR is a multi-chain CAR comprising an additional scfv specific for CD19.

The UCART22 according to any one of the above wherein the anti-CD22 CAR is a multi-chain CAR, comprising an additional scfv specific for CD79 a or CD79b.

A population of cells comprising the UCART 22 according to any one of the above.

A population of cells comprising the UCART 22 according to any one of the above and a UCART 19, preferably a UCART19 expressing an anti-CD19 CAR comprising a sequence of SEQ ID NO:95 or SEQ ID NO:96 at the cell surface.

A population of cells comprising the UCART 22 according to any one of the above and wherein cells expressing said anti-CD22 CAR also express an anti-CD19 CAR, preferably said anti-CD19 CAR comprises a sequence of SEQ ID NO:95 or SEQ ID NO:96 at the cell surface.

A kit comprising a UCART 22 and a UCART19 for a successive (at least once) or a concomitant or a successive (at least once) and then concomitant administration in a patient in need thereof.

The kit as above wherein the UCART 19 is used first at least once, twice or several times, and then the UCART 22, alone or with the UCART19.

The kit as above wherein the UCART 22 is used first at least once, twice or several times, and then the UCART 19, alone or with the UCART22.

The kit as above further comprising a lymphodepleting treatment, administered before the UCART.

The kit as above wherein lymphodepletion is achieved using fludarabine and cyclophosphamide, preferably fludarabine 25 mg/m$^2$ i.v. x 5 doses on days −6 to −2 and cyclophosphamide 60 mg/kg i.v. for 1 dose on day −5.

The kit as above comprising at least one other UCART cell directed against a cancer antigen selected from CD79a, CD79b, CD20, CD30, CD52, CD40, CD80, CD86, 74 VEGF.

A pharmaceutical composition comprising the UCART 22 according to a above or a population of cells comprising said UCART 22 according a above and a pharmaceutically acceptable excipient.

The pharmaceutical composition a above further comprising a Bryostatin, preferably Bryostatin-1.

The pharmaceutical composition or the kit as above for its use as a medication for preventing or treating a patient suffering a CD22-mediated cancer or a CD22-mediated inflammatory disease.

The pharmaceutical composition or the kit as above for its use according the above, wherein treating a patient comprises a step of administering the pharmaceutical composition at least twice (re dosing) to avoid a relapse/refractory development of the cancer.

The pharmaceutical composition or the kit as above for its use according to any one of the above, wherein treating a patient comprises administering at least one monoclonal antibody (mAb), preferably QBEND-10 and or rituximab, in a patient, at a dose allowing contacting said UCART22 with at least one specific mAb.

The pharmaceutical composition or the kit as above for its use according to any one of the above for the treatment of a CD22-mediated hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22 expressing hematological cancer selected from (lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD22-expressing hematological cancer, even more preferably an aggressive form of said CD22-related hematological cancer.

The pharmaceutical composition or the kit as above for its use according to any one of the above for the treatment of a CD19-mediated hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22 expressing hematological cancer selected from (lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD19-expressing hematological cancer, even more preferably an aggressive form of said CD19-related hematological cancer.

The pharmaceutical composition or the kit as above for its use as above for the treatment of a relapse or refractory CD22-expressing B ALL, preferably as a pediatric indication.

The pharmaceutical composition or the kit as above for its use as above for the treatment of a relapse or refractory CD19-expressing B ALL, preferably as a pediatric indication.

Methods

A Method for preparing any one of anti-CD22 CAR of SEQ ID NOs: 46 to 69 of the invention, and corresponding UCART22 of the invention is an object of the present invention.

In one embodiment, the present invention provides a method for engineering a cell of the invention, comprising:
(a) Introducing into an immune cell at least one polynucleotide encoding a chimeric antigen receptor specific for CD22 (CAR CD22) [as in any one of the above], preferably of SEQ ID NO: 21 to SEQ ID NO: 45, more preferably from SEQ ID NO: 32 to SEQ ID NO: 45, even more preferably of SEQ ID NO:29 or SEQ ID NO: 40, and even more preferably SEQ ID NO: 40.
(b) optionally purifying the CD22 CAR expressing cells, preferably using for example rituximab and/or QBEND-10
(c) editing at least one gene, by deleting, mutating, inserting a sequence into, or chemically modifying, said gene, preferably editing a gene conferring resistance to a drug or deleting a gene encoding a TCR subunit, more preferably deleting the TRAC gene using TALEN®
(d) purifying the CD22 CAR TCR negative expressing cells.

In a particular embodiment, the invention provides a method for engineering a cell, comprising:
(a) editing at least one gene, by inactivating said gene by inserting into said gene at least one polynucleotide encoding a chimeric antigen receptor specific for CD22 (CAR CD22) [as in any one of the above], preferably of SEQ ID NO: 21 to SEQ ID NO: 45, more preferably from SEQ ID NO: 32 to SEQ ID NO: 45, even more preferably of SEQ ID NO: 29 or SEQ ID NO: 40, and even more preferably SEQ ID NO: 40, preferably said gene is a TRAC gene, a CD52 gene, a dCK gene, a GR gene, or a combination.

In a preferred embodiment, the invention provides a method for engineering a UCART22 cell, comprising:
(a) editing at least one gene coding for a subunit of the TCR, preferably a TRAC gene, by inactivating said gene by inserting into said gene at least one polynucleotide encoding a chimeric antigen receptor specific for CD22 (CAR CD22) [as in any one of the above], preferably of SEQ ID NO: 21 to SEQ ID NO: 45, more preferably from SEQ ID NO: 32 to SEQ ID NO: 45, even more preferably of SEQ ID NO:29 or SEQ ID NO:40, and even more preferably SEQ ID NO:40, preferably said gene is a TRAC gene, a CD52 gene, a dCK gene, a GR gene, or a combination.

Preferably inactivating the TRAC gene is accomplished by using TALEN®- and even more preferably by targeted insertion of said at least one polynucleotide encoding the chimeric antigen receptor CAR (or another gene) using TALEN® into the TRAC gene and AAV vector.

This is referring to patent application Number PA 2016 70840 filed on 27 Oct. 2016, incorporated herein by reference in its entirety.

For AAV6 reagents the following documents described such reagents U.S. Pat. No. 8,846,387 B2 (Eyquem et al., 2017, MacLeod, 2017)

The invention provides a method for engineering a UCART 22, as above wherein step (c) followed by step (d) of gene editing is before step (a) of CAR transduction and expression.

The invention provides a method for engineering a UCART 22 according to the above, wherein the step of gene editing comprises introducing a genetic material, preferably an mRNA encoding an enzyme for editing a polynucleotide into said cells.

The invention provides a method for engineering a UCART 22 according to the above, wherein said enzyme is a rare endonuclease such as a TALEN, a Crispr a MegaTAL or an enzyme of DNA post-translational modification such as a methyl transferase, into said cells.

The invention provides a method for engineering a UCART 22 according to anyone of the above wherein the step of transducing an anti-CD22 CAR construct is concomitant to the step of introducing the genetic material for gene editing, preferably an anti-CD22 CAR Construct comprises any one of the SEQ ID NO: 21 to 45.

The invention provides a method for engineering a UCART 22 according to anyone of the above comprising a step of editing a second gene, preferably a CD52 gene, more preferably deleting said CD52 gene.

In one embodiment the method comprises one step of gene editing wherein the anti-CD22 CAR construct is introduced with a genetic material, preferably an mRNA encoding an enzyme for editing at least two genes into said cells.

In a preferred embodiment the CD22 CAR of the invention is introduced into the cell using retroviral particles (rLV) in combination with Retronectin®.

The method for engineering a UCART 22 according to anyone of the above wherein 2 genes are edited at the same step of gene editing, preferably TRAC and CD52, TRAC and HIF-1alpha.

The method for engineering a UCART 22 according to anyone of the above wherein at least 2 genes are edited at different and successive steps of gene editing is also provided The method for engineering a UCART 22 according to anyone of the above comprising:
(a) Providing an immune cell;
(b) Introducing into said cell at least a polynucleotide encoding a chimeric antigen receptor specific for CD22 [as in any one of the above].
(c) Expressing at least temporally said polynucleotide into said cell optionally for cell sorting
(d) editing at least one gene, by deleting, mutating, introducing a sequence or chemically modifying said gene, preferably deleting a gene encoding a TCR subunit, more preferably deleting the TRAC gene using TALEN®- and even more preferably deleting the TRAC gene by targeted insertion of said at least one polynucleotide encoding the chimeric antigen receptor using TALEN® into the TRAC gene.
(2) editing a second and/or a third gene, preferably CD52 and/or IL-10R genes, CD52 and/or TGFbeta R genes, CD52 and/or AHR, CD52 and/or PD1, The method for engineering a UCART 22 according to the above, wherein a gene is edited to confer resistance to hypoxia.

The method for engineering an immune cell as above, wherein said immune cell is a T-cell, preferably a human T cell.

In one embodiment, the present invention provides a method for cell sorting engineered immune cell expressing at its cell surface an anti-CD22 CAR comprising at least one mAb-specific epitope said method comprising—contacting a population of immune cells comprising said engineered immune cells with a monoclonal antibody specific for the mAb-specific epitope;

The method according to the above wherein the monoclonal antibody specific for the mAb-specific epitope is conjugated to a fluorophore and the step of selecting the cells that bind to the monoclonal antibody is done by Fluorescence Activated Cell Sorting (FACS).

The method according to the above wherein the monoclonal antibody specific for the mAb-specific epitope is conjugated to a magnetic particle and the step of selecting the cells that bind to the monoclonal antibody is done by Magnetic Activated Cell Sorting (MACS).

The method according to any one of the above wherein the anti-CD22 CAR comprises a mAb-specific epitope having an amino acid sequence of SEQ ID NO: 91 and the monoclonal antibody used to contact the population of immune cells is rituximab.

The method according to any one of the above wherein the CD22CAR comprises an mAb-specific epitope having an amino acid sequence of SEQ ID NO: 92 and the antibody used to contact the population of immune cells is QBEND-10.

The method according to any one of the above wherein the CD22CAR comprises an mAb-specific epitope having an amino acid sequence of SEQ ID NO: 91 and SEQ ID NO: 92 and the antibodies used to contact the population of immune cells are QBEND-10 and rituximab.

The method according to any one of the above wherein the CD22 CAR comprises two mAb-specific epitopes and two monoclonal antibodies are used to contact the population of immune cells, preferably said monoclonal antibodies are QBEND-10 and rituximab.

The method according to any one of the above for enriching in engineered immune cell to at least 70%, 75%, 80%, 85%, 90%, 95%, preferably at least 99% of anti-CD22 CAR-expressing immune cells.

The UCART 22 according to any one the above for use in a method for in vivo depleting said UCART22 cell comprising administering at least one mAb-specific epitope in a patient, at a dose allowing contacting said UCART22 with at least one epitope-specific mAb. In a preferred embodiment sais mAb is rituximab.

The method according to any one of the above wherein the epitope-specific mAb is conjugated with a molecule able to activate the complement system.

The method according to any one of the above wherein, wherein a cytotoxic drug is coupled to the epitope-specific mAb.

In one embodiment, the present invention provides a method for in vivo depleting an engineered immune cell expressing at its cell surface an anti-CD22 CAR comprising at least one mAb-specific epitope in a patient, comprising contacting said engineered immune cell with bi-specific mAb (BsAb) able to bind both the mAb-specific epitope borne on said cells and to an surface antigen borne on an effector (and cytotoxic) cell.

In one embodiment, the present invention provides a method according to any one of the above, wherein said immune cell is a T-cell, preferably an inflammatory T-lymphocytes, cytotoxic T-lymphocytes, regulatory T-lymphocytes or helper T-lymphocytes, a Natural Killer T cells.

The invention provides a CD22CAR+ cell, a UCART 22 according to the above or the pharmaceutical composition comprising said CD22CAR+ cell, a UCART 22 according to the above for use as a medicament for the treatment of cancer.

The invention provides a UCART 22 according to the above or the pharmaceutical composition according to the above, preferably a therapeutically effective amount of UCART 22 according to any one of the above or of the pharmaceutical composition according to the above, for use as a medicament for the treatment of a CD22-mediated pathology, preferably a CD22-expressing cancer, preferably a CD22 expressing hematological cancer.

The invention provides therapeutically effective amount of UCART 22 or of the pharmaceutical composition according to the above for use as a medication in the treatment of a hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22 expressing hematological cancer selected from (lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD22-expressing hematological cancer, even more preferably an aggressive form of said CD22-related hematological cancer.

The invention provides a therapeutically effective amount of UCART 22 or of the pharmaceutical composition according to the above for use as a medication in the treatment of a refractory hematological cancer selected from refractory (lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a refractory CD22 expressing hematological cancer selected from refractory CD22 expressing (lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapsed CD22-expressing hematological cancer, even more preferably an aggressive form of said CD22-related hematological cancer.

The invention provides a therapeutically effective amount of UCART 22 or of the pharmaceutical composition according to the above for use as a medication in the treatment of a refractory CD22 positive B-ALL.

The invention provides a therapeutically effective amount of UCART 22 or of the pharmaceutical composition according to the above for use as a medication in the treatment of a relapsed CD22 positive B-ALL.

The invention provides a therapeutically effective amount of UCART 22 or of the pharmaceutical composition according to the above for use as a medication for treating a patient wherein said patient suffers from a cancer selected from alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, cancer of the gallbladder, cancer of the pleura, cancer of the nose, cancer of the nasal cavity, cancer of the middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), hypopharynx cancer, kidney cancer, larynx cancer, liver cancer, lung cancer (e.g., non-small cell lung carcinoma), malignant mesothelioma, mastocytoma, melanoma, nasopharynx cancer, ovarian cancer, pancreatic cancer, peritoneum cancer, omentum cancer, mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer.

BRIEF DESCRIPTION OF THE FIGURES

FIG. 2 illustrates examples of CD22 CAR according to the invention, comprising a scfv specific for CD22, optionally comprising a safety switch, a hinge and a transmembrane domain from CD8 alpha, an intracellular domains from 4-1BB and CD3 zeta, optionally a domain conferring resistance to hypoxia.

At least a rituximab (R) mAb-specific epitopes (black box), preferably 3 rituximab mAb-specific epitopes and more preferably 3 rituximab mAb-specific epitopes and a QBEND-10 (Q) mAb-specific epitopes (grey box) are inserted into the CD22 CAR R may be inserted into the scfv, between a VH and a VL domain (or a VL and a VH domain) and/or into the hinge

DETAILED DESCRIPTION OF THE INVENTION

Figure 1:
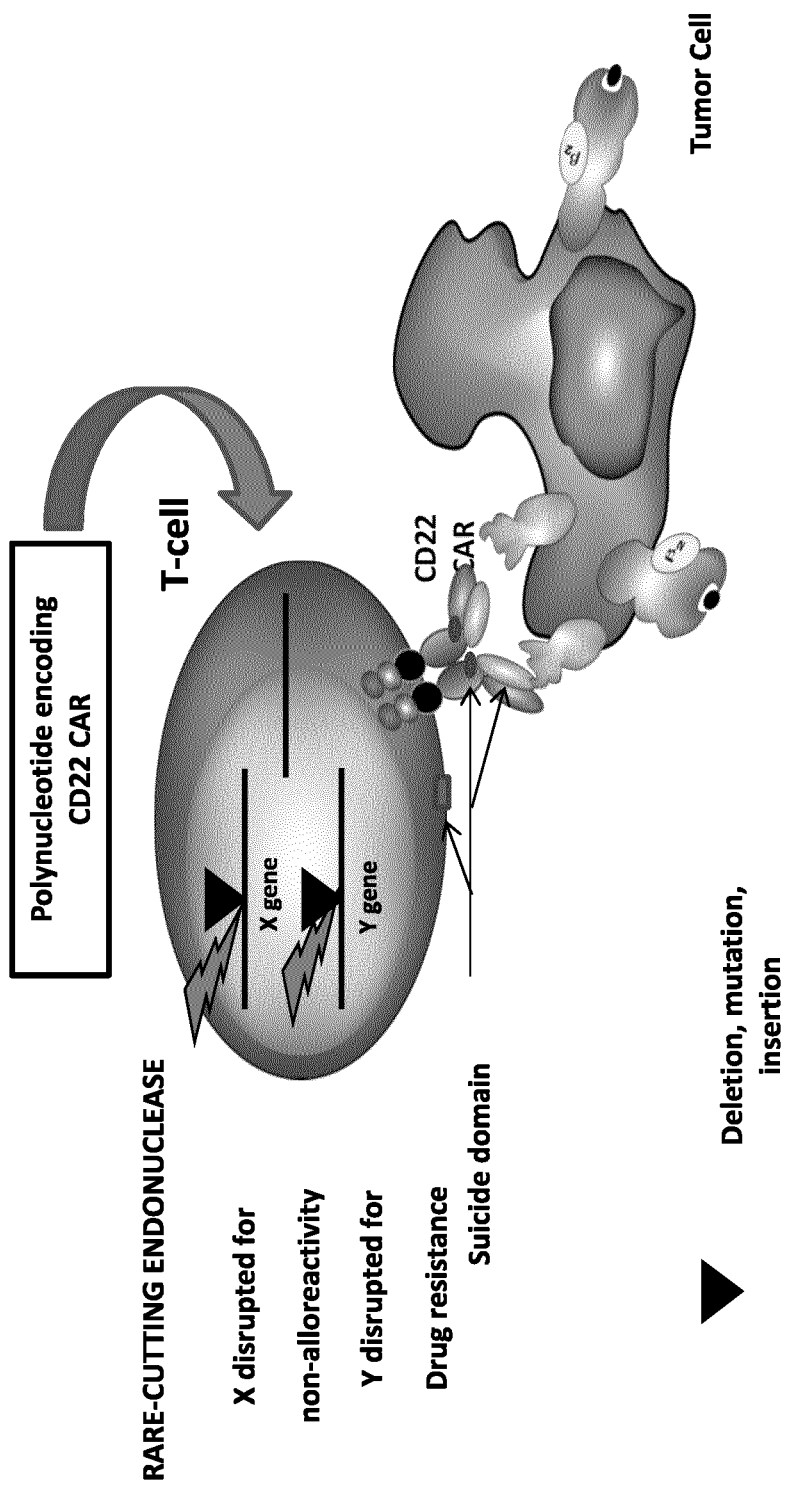
FIG. 1: Schematic representation of an engineered immune cell according to the invention The engineered immune cell presented in FIG. 1 may be a T-cell endowed with a polynucleotide encoding a CAR of the invention. This T-cell is further engineered to allow a better and safer engraftment into the patient. X, or Y is an edited gene that may be mutated, deleted and/or having an insertion. For instance a gene expressing a component of the T cell receptor (TCR) for example the TCRalpha or TCRbeta may be deleted or may comprise an insertion, Y may be a gene involved into the sensitivity of T-cells to immune-suppressive drugs like dCK (with respect to resistance to purine nucleotide analogues) or CD52 (with respect to Campath) or HPRT (with respect to 6-Thioguanine).

Unless specifically defined herein, all technical and scientific terms used have the same meaning as commonly understood by a skilled artisan in the fields of gene therapy, biochemistry, genetics, immunology and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

CD22 specific Chimeric Antigen Receptors

The present invention relates to new designs of anti-CD22 chimeric antigen receptor (CAR or CD22 CAR or anti-CD22 CAR or CAR CD22) which are chimeric antigen receptor capable of binding to CD22 in particular to the proximal domain of CD22 and to induce degranulation, eventually lysis of a target cells, preferably even under hypoxia or in a patient treated with PNA or/and CAMPATH.

The CD22 specific Chimeric Antigen Receptors of the invention comprises an extracellular domain comprising an extracellular ligand-binding domain and a hinge, optionally a suicide domain, a transmembrane domain and an intracellular domain comprising a signaling transducing domain.

Expressed at a cell surface, an anti-CD22 CAR according to the present invention comprises an extracellular domain that comprises an extracellular ligand-binding domain.

The term "extracellular ligand-binding domain" as used herein is defined as an oligo- or polypeptide that is capable of binding at least one epitope of CD22. Preferably, the extracellular ligand-binding domain will be capable of interacting at least partially with a cell surface molecule interacting with CD22 and with another cell surface antigen or another membrane bound antigen, or of interacting directly with CD22, or of interacting with human CD22, more precisely of interacting directly with the proximal region of human CD22 (from amino acid 243 to amino acid 687).

In one embodiment, a CD22 CAR according to the present invention comprises an extracellular domain that comprises an extracellular ligand-binding domain capable of interacting with the proximal region of CD22 (from amino acid 243 to amino acid 687) and with the distal part of CD22 (from aa 20 to aa 425).

In the present invention, the full length extracellular domain of CD22 is from amino acid (aa) 20-to aa 687, the membrane proximal domain of CD22 is from aa 243 to aa 687, the membrane distal domain of CD22 is from aa 20 to aa 425.

In one embodiment, the extracellular ligand-binding domain may be chosen to recognize a particular form (glycosylated) CD22 that acts as a cell surface marker on target cells associated with a particular disease state.

In a preferred embodiment, said extracellular ligand-binding domain comprises at least one single chain antibody fragment (scFv) comprising the light ($V_L$) and the heavy ($V_H$) variable fragment of a target antigen specific monoclonal anti CD22 antibody joined by a linker, in particular a flexible linker. Said $V_L$ and $V_H$ are preferably from the antibody m971 as mentioned in Tables 3 to 4 below. They are preferably linked together by a flexible linker comprising for instance the sequence SEQ ID NO.10.

For the purpose of the present invention, specific parts of the fully human anti-CD22 antibody, m971 antibody (m971) previously identified using phage display methodology and characterized. (Xiao X, Ho M, Zhu Z, Pastan I, Dimitrov D S. Identification and characterization of fully human anti-CD22 monoclonal antibodies. mAbs. 2009; 1(3):297-303) were combined to specific sequences to produce new CD22 CARs, according to the invention. See also WO 2014065961 which is incorporated by reference.

A preferred embodiment of the invention provides CARs comprising an antigen-binding domain comprising, consisting of, or consisting essentially of, a single chain variable fragment (scFv) of the antigen binding domain of m971 with the following moieties as in Table 2.

TABLE 2

| Sequence of different domains in CD22 CAR | | |
|---|---|---|
| Functional domains | SEQ ID # | Raw amino acid sequence |
| CD8α signal peptide (or sequence leader) | SEQ ID NO: 1 | MALPVTALLLPLALLLHAARP |
| Alternative signal peptide | SEQ ID NO: 2 | METDTLLLWVLLLWVPGSTG |
| FcγRIIIα hinge | SEQ ID NO: 3 | GLAVSTISSFFPPGYQ |
| CD8α hinge | SEQ ID NO: 4 | TTTPAPRPPTPAPTIASQPLSLRP EACRPAAGGAVHTRGLDFACD |
| IgG1 hinge | SEQ ID NO: 5 | EPKSPDKTHTCPPCPAPPVAGPS VFLFPPKPKDTLMIARTPEVTCV VVDVSHEDPEVKFNWYVDGVE VHNAKTKPREEQYNSTYRVVSV LTVLHQDWLNGKEYKCKVSNKA LPAPIEKTISKAKGQPREPQVYTL PPSRDELTKNQVSLTCLVKGFYP SDIAVEWESNGQPENNYKTTPP VLDSDGSFFLYSKLTVDKSRWQ QGNVFSCSVMHEALHNHYTQK SLSLSPGK |
| CD8α transmembrane domain | SEQ ID NO: 6 | IYIWAPLAGTCGVLLLSLVITLYC |
| 41BB transmembrane domain | SEQ ID NO: 7 | IISFFLALTSTALLFLLFFLTLRFSV V |
| 41BB intracellular domain | SEQ ID NO: 8 | KRGRKKLLYIFKQPFMRPVQTT QEEDGCSCRFPEEEEGGCEL |
| CD3ζ intracellular domain | SEQ ID NO: 9 | RVKFSRSADAPAYQQGQNQLY NELNLGRREEYDVLDKRRGRDP EMGGKPRRKNPQEGLYNELQK DKMAEAYSEIGMKGERRRGKG HDGLYQGLSTATKDTYDALHM QALPPR |
| Linker | SEQ ID NO: 10 | GGGGSGGGGSGGGGS |

TABLE 3

CD22 CAR of structure V-1

| CAR Designation V-1 | CAR Structure | | | | | | |
|---|---|---|---|---|---|---|---|
| | signal peptide | VH | VL | FcγRIIIα hinge | CD8α TM | 41BB-IC | CD3ζ CD |
| m971 (SEQ ID NO. 17) | SEQ ID NO: 1 | One among SEQ ID NO: 71, 73, 75 77, 79, 81, 83, 85, 87 or 89 | One among SEQ ID NO: 72, 74, 76, 78, 80, 82, 84, 86, 88, 90 | SEQ ID NO: 3 | SEQ ID NO: 6 | SEQ ID NO: 8 | SEQ ID NO: 9 |

TABLE 4

CAR of structure V-3

| CAR Designation V-3 | CAR Structure | | | | | | |
|---|---|---|---|---|---|---|---|
| | signal peptide | VH | VL | CD8αhinge | CD8α - TM | 41BB - IC | CD3ζ CD |
| m971(SEQ ID NO: 18) | SEQ ID NO: 1 | One among SEQ ID NO: 71, 73, 75 77, 79, 81, 83, 85, 87 or 89 | One among SEQ ID NO: 72, 74, 76, 78, 80, 82, 84, 86, 88, 90 | SEQ ID NO: 4 | SEQ ID NO: 6 | SEQ ID NO: 8 | SEQ ID NO: 9 |

SCFV

In the present invention, a scfv is a fusion protein of the variable region of the heavy ($V_{H\ domain}$) and light chain ($V_{L\ domain}$) of an immunoglobulin or a part of an immunoglobulin specific for CD22, connected with a short linker peptide of 10 to 25 amino acids, preferably of SEQ ID NO. 10.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 71.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 72.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 71. and a polypeptide sequence displaying at least 90%, 91%, 92% 93% 94%, 95%, 96%, 97%, 98%, 99% or 100% identity with an amino acid sequence selected from the group consisting of SEQ ID NO: 72.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 73.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 74.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 73. and a polypeptide sequence displaying at least 90%, 91%, 92% 93% 94%, 95%, 96%, 97%, 98%, 99% or 100% identity with an amino acid sequence selected from the group consisting of SEQ ID NO: 74.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 75.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 76.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 75. and a polypeptide sequence displaying at least 90%, 91%, 92% 93% 94%, 95%, 96%, 97%, 98%, 99% or 100% identity with an amino acid sequence selected from the group consisting of SEQ ID NO: 76.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 77.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 78.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 78. and a polypeptide sequence displaying at least 90%, 91%, 92% 93% 94%, 95%, 96%, 97%, 98%, 99% or 100% identity with an amino acid sequence selected from the group consisting of SEQ ID NO: 78.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 79.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 80.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 79. and a polypeptide sequence displaying at least 90%, 91%, 92% 93% 94%, 95%, 96%, 97%, 98%, 99% or 100% identity with an amino acid sequence selected from the group consisting of SEQ ID NO: 80.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 81.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 82.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 81. and a polypeptide sequence displaying at least 90%, 91%, 92% 93% 94%, 95%, 96%, 97%, 98%, 99% or 100% identity with an amino acid sequence selected from the group consisting of SEQ ID NO: 82.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 83.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 84.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 83. and a polypeptide sequence displaying at least 90%, 91%, 92% 93% 94%, 95%, 96%, 97%, 98%, 99% or 100% identity with an amino acid sequence selected from the group consisting of SEQ ID NO: 84.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 85.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 86.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 85. and a polypeptide sequence displaying at least 90%, 91%, 92% 93% 94%, 95%, 96%, 97%, 98%, 99% or 100% identity with an amino acid sequence selected from the group consisting of SEQ ID NO: 86.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 87.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 88.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 87. and a polypeptide sequence displaying at least 90%, 91%, 92% 93% 94%, 95%, 96%, 97%, 98%, 99% or 100% identity with an amino acid sequence selected from the group consisting of SEQ ID NO: 88.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 89.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 90.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 89. and a polypeptide sequence displaying at least 90%, 91%, 92% 93% 94%, 95%, 96%, 97%, 98%, 99% or 100% identity with an amino acid sequence selected from the group consisting of SEQ ID NO: 90.

In a more preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 87. and a polypeptide sequence displaying at least 90%, 91%, 92% 93% 94%, 95%, 96%, 97%, 98%, 99% or 100% identity with an amino acid sequence selected from the group consisting of SEQ ID NO: 88.

Hinge

The extracellular domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region is used to provide more flexibility and accessibility for the extracellular ligand-binding domain. A hinge region may comprise up to 300 amino acids, preferably 10 to 100 amino acids and most preferably 10 to 50 amino acids. Hinge region may be derived from all or part of naturally occurring molecules, such as from all or part of the extracellular region of CD8, or CD4, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of a human CD8 alpha chain, FcRIIIα receptor or IgG1, respectively referred to in this specification as SEQ ID NO. 4, SEQ ID NO. 5 and SEQ ID NO.6, or in a more preferred embodiment, a hinge polypeptide which display at least 80%, preferably at least 90%, 95% 97% 99% or 100% sequence identity with SEQ ID NO:4, even more preferably 100% sequence identity with SEQ ID NO:4.

A Hinge from IgG4 or from PD1 is part of the present invention and disclosed in WO2016120216 and may be used in the construction of a CD22 CAR according to the invention.

An anti-CD22 CAR according to the present invention is anchored into the membrane of the cell. Thus, such CD22 CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, or δ, polypeptide constituting CD3 complex, IL2 receptor p55 (α chain), p75 (β chain) or chain, subunit chain of Fc receptors, in particular Fc receptor III or CD proteins. Alternatively the transmembrane domain can be synthetic and can comprise predominantly hydrophobic residues such as leucine and valine.

In a preferred embodiment said transmembrane domain is derived from the human CD8 alpha chain (e.g. NP_001139345.1).

An anti-CD22 CAR according to the invention generally further comprises a transmembrane domain (TM) more particularly from CD8α, showing identity with the polypeptides of SEQ ID NO. 6 or 7. Preferably, a CAR according to the invention comprises a TM showing at least 70%, preferably at least 80%, more preferably at least 90%, 91%, 92%, 93%, 94%, 95%, 96%, 97%, 98%, 99% or 100% sequence identity with the polypeptides of SEQ ID NO. 6.

An anti-CD22 CAR according to the invention generally further comprises a transmembrane domain (TM) from CD8α showing identity with the polypeptides of SEQ ID NO. 6. Preferably, a CAR according to the invention comprises a TM showing at least 70%, preferably at least 80%, more preferably at least 90%, 91%, 92%, 93%, 94%, 95%, 96%, 97%, 98%, 99% or 100% sequence identity with the polypeptides of SEQ ID NO. 6.

Intracellular Domain

An anti-CD22 CAR according to the present invention comprises an intracellular domain that comprises a signal transducing domain or intracellular signaling domain.

The signal transducing domain or intracellular signaling domain of an anti-CD22 CAR according to the present invention is responsible for intracellular signaling following the binding of extracellular ligand binding domain to the target resulting in the activation of the immune cell and immune response (cytolytic activity against the target cell). In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain in an anti-CD22 CAR of the invention can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% 99% or 100% sequence identity with amino acid sequence selected from the group consisting of (SEQ ID NO: 9). Optionally said CD3zeta signaling domain is comprising a polypeptide sequence displaying at least 90%, 91%, 92% 93% 94%, 95%, 96%, 97%, 98%, 99% or 100% identity with SEQ ID NO: 9.

In a more preferred embodiment, the signaling transducing domain of the CD22 CAR consists in a CD3zeta signaling domain of SEQ ID NO: 9 and excludes any sequence from human CD28 signaling domain. In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the an anti-CD22 CAR of the present invention comprises a part of co-stimulatory signal molecule consisting of fragment of 4-1BB (GenBank: AAA53133.) In particular the signal transduction domain of the CAR of the present invention comprises amino acid sequence which comprises at least 70%, preferably at least 80%, more preferably at least 90%, 95% 97% 99% or 100% sequence identity with amino acid sequence selected from the group consisting of SEQ ID NO: 8.

In a more preferred embodiment, the signal transduction domain of the an anti-CD22 CAR of the present invention comprises no sequence from CD28 (NP_006130.1).

In an even more preferred embodiment, all the embodiments of the present invention comprise no sequence from CD28 (NP_006130.1).

In an even more preferred embodiment the signal transduction domain of an anti-CD22 CAR of the present invention comprises a part of co-stimulatory signal molecule 4-1BB (GenBank: AAA53133) and no sequence from CD28 (NP_006130.1).

Anti-CD22 CAR or CD22 CAR

The present invention provides a CD22 specific chimeric antigen receptor (CD22 CAR, or CAR CD22 an anti-CD22 CAR) comprising:
An extracellular domain comprising:
a binding domain specific for CD22, preferably a binding domain specific for human CD22, more preferably said binding domain specific for human CD22 is a single-chain variable fragment (scFv).
a hinge, preferably from CD8 alpha
a transmembrane domain, preferably from CD8 alpha
an intracellular domain comprising:
a co-stimulatory signal molecule from human 4-113B, and
an intracellular signaling domain comprising a human CD3zeta signaling domain.

The present invention provides an anti-CD22 CAR comprising:
An extracellular domain comprising:
a binding domain specific for CD22, preferably a binding domain specific for human CD22, more preferably said binding domain specific for human CD22 is a single-chain variable fragment (scFv) comprising a combination of VH and LV as described above, preferably one of the following combinations SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, more preferably SEQ ID NO: 87 and SEQ ID NO: 89,
a hinge, from CD8 alpha
a transmembrane domain from CD8 alpha,
an intracellular domain comprising:
a co-stimulatory signal molecule from human 4-113B, and
an intracellular signaling domain comprising a human CD3zeta signaling domain.

In a preferred embodiment the anti-CD22 CAR of the invention has no sequence from CD28.

In a preferred embodiment, the anti-CD22 CAR of the invention does not contain any sequence from CD28 and comprises a sequence leader, a TM domain and a hinge from CD8 cc, preferably no sequence from CD28 and comprises a sequence leader of SEQ ID NO. 1, a TM domain of SEQ ID NO. 6 of and a hinge of SEQ ID NO. 4 from CD8 cc.

In one embodiment, the anti-CD22 CAR of the invention comprises a leader sequence from human CD8α (SEQ ID NO.1.) or a leader sequence having at least 95% identity with SEQ ID NO.1.

In another embodiment, the anti-CD22 CAR of the invention comprises a leader sequence of SEQ ID NO.2 or a leader sequence having at least 95% identity with SEQ ID NO.2.

In one embodiment the present invention provides an anti-CD22 CAR (or CD22 CAR) comprising:
a binding domain specific for CD22, preferably a binding domain specific for human CD22, more preferably said domain specific for human CD22 comprises a single-chain variable fragment (scFv), preferably comprising one of the following combinations SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, more preferably SEQ ID NO: 87 and SEQ ID NO: 88,
a hinge from human CD8 alpha (from CD8α)
a transmembrane domain from human CD8alpha(α)
a co-stimulatory signal molecule from human 4-1BB
an intracellular signaling domain comprising a human CD3zeta signaling domain.

In one embodiment the present invention provides a CD22 specific chimeric antigen receptor (CD22 CAR) comprising:
a binding domain specific for CD22, preferably a binding domain specific for human CD22, more preferably said domain specific for human CD22 is a single-chain variable fragment (scFv), comprising preferably one of the following combinations SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, more preferably SEQ ID NO: 87 and SEQ ID NO: 88,
a hinge from human FcRIIIα
a transmembrane domain from human CD8alpha(α)
a co-stimulatory signal molecule from human 4-1BB
an intracellular signaling domain comprising a human CD3zeta signaling domain.

The present invention also provides a CD22 specific chimeric antigen receptor (CD22 CAR) comprising:
a binding domain specific for CD22, preferably a binding domain specific for human CD22, more preferably said domain specific for human CD22 is a single-chain variable fragment (scFv), comprising one of the following combinations: SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, more preferably SEQ ID NO: 87 and SEQ ID NO: 88, a hinge from human IgG1
a transmembrane domain from human CD8alpha(α)
a co-stimulatory signal molecule from human 4-1BB
an intracellular signaling domain comprising a human CD3zeta signaling domain.

These three last embodiments encompass a CD22 CAR with a signal peptide of SEQ ID NO: 1 or of SEQ ID NO: 2, preferably of SEQ ID NO: 1.

More preferably, said CD22 CAR has no sequence from CD28.

The scfv of the invention is derived from an antibody specific for CD22, it comprises a VH domain separated to a VL domain by a linker, said VH and/or VL domains contributing to the binding to CD22.

In a preferred embodiment a scfv of the invention comprises from one of the following combinations: SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, more preferably SEQ ID NO: 87 and SEQ ID NO: 88.

In the present invention, a scfv may be a fusion protein of the variable regions of the heavy ($V_{H\ domain}$) of SEQ ID NO.12: and light chains ($V_{L\ domain}$) of SEQ ID NO.13: of an immunoglobulin specific for CD22, m971, connected with a linker peptide of SEQ ID NO: 10.

In one embodiment said scfv of the invention further comprises a leader sequence (or signal peptide), preferably said leader sequence is linked to the VH domain.

An embodiment wherein said leader sequence is linked to the VL domain is part of the present invention.

In one embodiment, a VH domain is linked to a hinge, in another embodiment a VL domain is linked to said hinge.

The present invention provides a scfv linked to a hinge having different length preferably a hinge from CD8α, IgG1 or FcRIIIα (See FIG. 2), more preferably from CD8α, Preferably, the present invention provides a CD22 CAR comprising:
  a signal peptide, for example a signal peptide of SEQ ID NO. 2 or from CD8alpha of SEQ ID NO. 1.
  a (scFv) comprising a VH domain separated from a VL domain by a linker, said VH and VL and linker contributing to the binding to CD22, preferably from one of the following combinations: SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, more preferably SEQ ID NO: 87 and SEQ ID NO: 88,
  a hinge from human CD8 alpha chain or a Hinge from human IgG1 or a hinge from FcRIIIα, preferably from CD8 alpha.
  a transmembrane domain (TM) from CD8alpha(α)
  a co-stimulatory signal molecule from human 4-1BB
  an intracellular signaling domain comprising the CD3zeta signaling domain.

One of the CD22 CAR of the invention consists in:
  a leader sequence (for example a CD8 a, leader sequence or a CD8α, signal peptide) (SEQ ID NO:1)
  an anti-CD22 scfv comprising a VH, a linker, and a VL, or a VL, a linker, and a VH, said VH and VL are derived from one of the following combinations: SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, preferably from SEQ ID NO: 87 and SEQ ID NO: 88,
  a CD8 a, hinge (SEQ ID NO:4)
  a CD8 a, TM (SEQ ID NO:6)
  a co-stimulatory signal molecule from 4-1BB (SEQ ID NO:8)
  an intracellular CD3zeta signaling domain (SEQ ID NO:9).

Linker-SCFV

A linker according to the invention may be for example, a multimer of the pentapeptide (GGGGS)n or (G4S)n or (Gly4Ser)n with n=1 to 4, preferably n=3, the 18-mer GGSSRSSSSGGGGSGGGG (SEQ ID NO: 98) (Andris-Widhopf et al., 2011) and the 20-mer (G4S)4 (Schaefer et al., 2010). A linker according to the invention may include sequences with added functionalities, e.g. an epitope tag (Sblattero & Bradbury, 2000 Nature Biotechnology 18, 75-80), at least on sequence of SEQ ID NO: 91, preferably 2, separated by a linker, sequences improving scFv properties of the present invention, often in the context of particular antibody sequences.

Amongst other linkers suitable within the present invention is the 15-mer peptide linker (RGRGRGRGRSRGGGS) (SEQ ID NO: 99) (Zhihong Shen, Heping Yan, Ying Zhang, Raymond L. Mernaugh, and Xiangqun Zeng (2008), Anal Chem. 80(6): 1910-1917).

In a preferred embodiment, a linker linking the VH to the VL sequence (or the VL to the VH sequence) is a linker of formula (G4S)n wherein n is 1 to 3; preferably n=3 of sequence (G4S)3 (SEQ ID NO: 10).

In a more preferred embodiment L1 is G45 (n=1).

In one embodiment the present invention provides:
A CD22 CAR comprising:
  a human CD8α leader sequence (CD8α leader or CD8α signal peptide) of SEQ ID NO: 1
  an anti-CD22 scfv comprising one of the following combinations: SEQ ID NO: 77 and SEQ ID NO: 78, SEQ ID NO:83 and SEQ ID NO:84, SEQ ID NO: 87 and SEQ ID NO: 88, SEQ ID NO: 89 and SEQ ID NO: 90, preferably SEQ ID NO: 87 and SEQ ID NO: 88,
a human CD8α hinge of SEQ ID NO: 4,
a human CD8α TM of SEQ ID NO: 6
a co-stimulatory signal molecule from 4-1BB of SEQ ID NO: 8
an intracellular CD3zeta signaling domain of SEQ ID NO: 9.

In one embodiment the present invention also provides:
A CD22 CAR comprising:
  a human CD8α leader sequence (CD8α leader or CD8α signal peptide) of SEQ ID NO. 1
  an anti-CD22 scfv comprising one of the following combinations: SEQ ID NO: 77 and SEQ ID NO: 78, SEQ ID NO: 83 and SEQ ID NO: 84, SEQ ID NO: 87 and SEQ ID NO: 88, SEQ ID NO: 89 and SEQ ID NO: 90, preferably SEQ ID NO: 87 and SEQ ID NO: 88,
a human FcγRIIIα hinge of SEQ ID NO.3,
a human CD8α TM of SEQ ID NO.6
a co-stimulatory signal molecule from 4-1BB of SEQ ID NO.8
an intracellular CD3zeta signaling domain of SEQ ID NO. 9.

In one embodiment, the present invention provides:
A CD22 CAR comprising:
  a human CD8α leader sequence (CD8α leader or CD8α signal peptide) of SEQ ID NO. 1, an anti-CD22 scfv comprising one of the following combinations: SEQ ID NO: 77 and SEQ ID NO: 78, a SEQ ID NO: 83 and SEQ ID NO: 84, SEQ ID NO: 87 and SEQ ID NO: 88, SEQ ID NO: 89 and SEQ ID NO: 90, more preferably SEQ ID NO: 87 and SEQ ID NO: 88,
a human FcγRIIIα hinge of SEQ ID NO.3,
a human CD8α TM of SEQ ID NO.6
a co-stimulatory signal molecule from 4-1BB of SEQ ID NO.8
an intracellular CD3zeta signaling domain of SEQ ID NO. 9.

In one embodiment, the present invention provides a CD22 specific chimeric antigen receptor (CD22 CAR) comprising:
  a signal peptide having an amino acid sequence with at least 80%, more preferably at least 90%, 95% 97%, 99% or 100% sequence identity with the polypeptide of SEQ ID NO. 1 or 2; preferably the signal peptide has an amino acid sequence with at least 80%, more preferably at least 90%, 95% 97%, 99% or 100% sequence identity with the polypeptide of SEQ ID NO: 1.
  a VH domain separated to a VL domain by a linker, said VH and VL contributing to the binding to CD22; said linker having at least 90%, 95% 97%, 99% or 100% sequence identity with the polypeptide of SEQ ID NO: 10,
Said VH domain having at least 90%, 95% 97%, 99% or 100% sequence identity with the polypeptide of SEQ ID NO: 87,
Said VL domain having at least 90%, 95% 97%, 99% or 100% sequence identity with the polypeptide of SEQ ID NO: 88,
  a hinge derived from human CD8 alpha chain having an amino acid sequence with at least 80%, more preferably at least 80%, 90%, 95% 97%, 99% or 100% sequence identity with the polypeptide of SEQ ID NO: 4;
  a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO: 6;
  a co-stimulatory signal molecule derived from human 4-1BB (or 4-1BB intracellular domain) having an amino acid sequence with at least 70%, preferably at least 80%, more preferably at least 90%, 95% 97%, 99% or 100% sequence identity with amino acid sequence selected from the group consisting of SEQ ID NO: 8;
  an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO:

In a preferred embodiment, the CD22 specific chimeric antigen receptor (CD22 CAR) of the present invention does not comprise any sequence from human CD28, in particular from human CD28 intra signaling domain. In a more preferred embodiment, the CD22 specific chimeric antigen receptor (CD22 CAR) of the present invention does not comprise any sequence from human CD28, in particular from human CD28 intra signaling domain and further contains a signal peptide from CD8α, preferably fused to the VH domain of a scfv specific for CD22.

In one embodiment, the present invention provides a CD22 CAR of SEQ ID NO. 64.

In one embodiment, the present invention provides a CD22 CAR having an amino acid sequence with at least 90%, 91%, 92%, 93%, 94%, 95%, 96%, 97%, 98%, 99% or 100% identity with the polypeptide of SEQ ID NO:64.

In one embodiment the present invention provides a CD22 CAR having a sequence with at least 90%, 91%, 92%, 93%, 94%, 95%, 96%, 97%, 98%, 99% or 100% identity with the polynucleotide of SEQ ID NO:40.

The UCART 22 of the invention may comprise one of the following sequences:

```
v1-m971 (FcγRIIIα-CD8αTM-41BB.IC-CD3ζ.IC)
                                      (SEQ ID NO: 129)
MALPVTALLPLALLLHAARPQVQLQQSGPGLVKPSQTLSLTCAISGDSVS

SNSAAWNWIRQSPSRGLEWLGRTYYRSKWYNDYAVSVKSRITINPDTSKN

QFSLQLNSVTPEDTAVYYCAREVTGDLEDAFDIWGQGTMVTVSSGGGGSG

GGGSGGGGSDIQMTQSPSSLSASVGDRVTITCRASQTIWSYLNWYQQRPG

KAPNLLIYAASSLQSGVPSRFSGRGSGTDFTLTISSLQAEDFATYYCQQS

YSIPQTFGQGTKLEIKGLAVSTISSFFPPGYQIYIWAPLAGTCGVLLLSL

VITLYCKRGRKKLLYIFKQPFMRPVQTTQEEDGCSCRFPEEEEGGCELRV

KFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYD

ALHMQALPPR.

V3-m971 (CD8α-CD8αTM-41BB.IC-CD3ζ.IC)
                                      (SEQ ID NO: 130)
MALPVTALLPLALLLHAARPQVQLQQSGPGLVKPSQTLSLTCAISGDSVS

SNSAAWNWIRQSPSRGLEWLGRTYYRSKWYNDYAVSVKSRITINPDTSKN

QFSLQLNSVTPEDTAVYYCAREVTGDLEDAFDIWGQGTMVTVSSGGGGSG

GGGSGGGGSDIQMTQSPSSLSASVGDRVTITCRASQTIWSYLNWYQQRPG

KAPNLLIYAASSLQSGVPSRFSGRGSGTDFTLTISSLQAEDFATYYCQQS

YSIPQTFGQGTKLEIKTTTPAPRPPTPAPTIASQPLSLRPEACRPAAGGA

VHTRGLDFACDIYIWAPLAGTCGVLLLSLVITLYCKRGRKKLLYIFKQPF

MRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR.

In a preferred embodiment the CD22 CAR of the
invention comprises the following sequence.
                                      (SEQ ID NO: 130)
MALPVTALLPLALLLHAARPQVQLQQSGPGLVKPSQTLSLTCAISGDSVS

SNSAAWNWIRQSPSRGLEWLGRTYYRSKWYNDYAVSVKSRITINPDTSKN

QFSLQLNSVTPEDTAVYYCAREVTGDLEDAFDIWGQGTMVTVSSGGGGSG

GGGSGGGGSDIQMTQSPSSLSASVGDRVTITCRASQTIWSYLNWYQQRPG

KAPNLLIYAASSLQSGVPSRFSGRGSGTDFTLTISSLQAEDFATYYCQQS

YSIPQTFGQGTKLEIKTTTPAPRPPTPAPTIASQPLSLRPEACRPAAGGA

VHTRGLDFACDIYIWAPLAGTCGVLLLSLVITLYCKRGRKKLLYIFKQPF

MRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR.
```

Sequences of CD22 CAR with a peptide signal from SEQ ID NO: 2, a TM domain from CD8α and a linker between the VH and VL domain:

(SEQ ID NO: 136)
METDTLLLWVLLLWVPGSTGEVQLVQSGGGVVRPGGSLRLPCAASGFTF
DDYGMSWVRQAPGKGLEWVSGINWNGGSTGYADSVKGRFTISRDNAKNS
LYLQMNSLRAEDTALYHCARGGDDAFDIWGQGTMVTVSSGGGGSGGGGS
GGGGSRIVMTQSPGTLSVSPGETATLSCRASQSFSNMLAWYQQKSGQPP
RLLIYGVSTRAAGVPARFSGSGSGTEFTLTISNLQSEDFAVYYCQQYGD
WPRYTFGQGTKVERKGLAVSTISSFFPPGYQIYIWAPLAGTCGVLLLSL
VITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKD
TYDALHMQALPPR (SEQ ID NO: 137)
METDTLLLWVLLLWVPGSTGEVQLVQSGGGVVRPGGSLRLPCAASGFTF
DDYGMSWVRQAPGKGLEWVSGINWNGGSTGYADSVKGRFTISRDNAKNS
LYLQMNSLRAEDTALYHCARGGDDAFDIWGQGTMVTVSSGGGGSGGGGS
GGGGSRIVMTQSPGTLSVSPGETATLSCRASQSFSNMLAWYQQKSGQPP
RLLIYGVSTRAAGVPARFSGSGSGTEFTLTISNLQSEDFAVYYCQQYGD
WPRYTFGQGTKVERKTTTPAPRPPTPAPTIASQPLSLRPEACRPAAGGA
VHTRGLDFACDIYIWAPLAGTCGVLLLSLVITLYCKRGRKKLLYIFKQP
FMRPVQTTQEEDGCSCRFPEEEEGGCELRVKFSRSADAPAYQQGQNQLY
NELNLGRREEYDVLDKRRGRDPEMGGKPRRKNPQEGLYNELQKDKMAEA
YSEIGMKGERRRGKGHDGLYQGLSTATKDTYDALHMQALPPR

M971 V1
(SEQ ID NO: 138)
METDTLLLWVLLLWVPGSTGQVQLQQSGPGLVKPSQTLSLTCAISGDSV
SSNSAAWNWIRQSPSRGLEWLGRTYYRSKWYNDYAVSVKSRITINPDTS
KNQFSLQLNSVTPEDTAVYYCAREVTGDLEDAFDIWGQGTMVTVSSGGG
GSGGGGSGGGGSDIQMTQSPSSLSASVGDRVTITCRASQTIWSYLNWYQ
QRPGKAPNLLIYAASSLQSGVPSRFSGRGSGTDFTLTISSLQAEDFATY
YCQQSYSIPQTFGQGTKLEIKGLAVSTISSFFPPGYQIYIWAPLAGTCG
VLLLSLVITLYCKRGRKKLLYIFKQPFMRPVQTTQEEDGCSCRFPEEEE
GGCELRVKFSRSADAPAYQQGQNQLYNELNLGRREEYDVLDKRRGRDPE
MGGKPRRKNPQEGLYNELQKDKMAEAYSEIGMKGERRRGKGHDGLYQGL
STATKDTYDALHMQALPPR

M971 V3
(SEQ ID NO: 139)
METDTLLLWVLLLWVPGSTGQVQLQQSGPGLVKPSQTLSLTCAISGDSV
SSNSAAWNWIRQSPSRGLEWLGRTYYRSKWYNDYAVSVKSRITINPDTS
KNQFSLQLNSVTPEDTAVYYCAREVTGDLEDAFDIWGQGTMVTVSSGGG
GSGGGGSGGGGSDIQMTQSPSSLSASVGDRVTITCRASQTIWSYLNWYQ
QRPGKAPNLLIYAASSLQSGVPSRFSGRGSGTDFTLTISSLQAEDFATY
YCQQSYSIPQTFGQGTKLEIKTTTPAPRPPTPAPTIASQPLSLRPEACR
PAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYQQ
GQNQLYNELNLGRREEYDVLDKRRGRDPEMGGKPRRKNPQEGLYNELQK
DKMAEAYSEIGMKGERRRGKGHDGLYQGLSTATKDTYDALHMQALPPR.

In one embodiment the present invention provides the following sequence:

(SEQ ID NO: 140)
QVQLQQSGPGLVKPSQTLSLTCAISGDSVSSNSAAWNWIRQSPSRGLEWL
GRTYYRSKWYNDYAVSVKSRITINPDTSKNQFSLQLNSVTPEDTAVYYCA
REVTGDLEDAFDIWGQGTMVTVSSGGGGSGGGGSGGGGSDIQMTQSPSSL
SASVGDRVTITCRASQTIWSYLNWYQQRPGKAPNLLIYAASSLQSGVPSR
FSGRGSGTDFTLTISSLQAEDFATYYCQQSYSIPQTFGQGTKLEIKTTTP
APRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEE
EEGGCELRVKFSRSADAPAYQQGQNQLYNELNLGRREEYDVLDKRRGRDP
EMGGKPRRKNPQEGLYNELQKDKMAEAYSEIGMKGERRRGKGHDGLYQGL
STATKDTYDALHMQALPPR.

In this CD22CAR the signal peptide is absent.

In one embodiment, the UCART22 of the present invention comprises a sequence of SEQ ID NO: 31

(SEQ ID NO: 31)
ATGGCTCTGCCCGTCACCGCTCTGCTGCTGCCACTGGCCCTGCTGCTGCA
CGCAGCAAGACCACAGGTGCAGCTGCAGCAGAGCGGCCCTGGCCTGGTGA
AGCCAAGCCAGACACTGTCCCTGACCTGCGCCATCAGCGGCGATTCCGTG
AGCTCCAACTCCGCCGCCTGGAATTGGATCAGGCAGTCCCCTTCTCGGGG
CCTGGAGTGGCTGGGAAGGACATACTATCGGTCTAAGTGGTACAACGATT
ATGCCGTGTCTGTGAAGAGCAGAATCACAATCAACCCTGACACCTCCAAG
AATCAGTTCTCTCTGCAGCTGAATAGCGTGACACCAGAGGACACCGCCGT
GTACTATTGCGCCAGGGAGGTGACCGGCGACCTGGAGGATGCCTTTGACA
TCTGGGGCCAGGGCACAATGGTGACCGTGTCTAGCGGAGGAGGAGGATCC
GGAGGAGGAGGATCTGGCGGCGGCGGCAGCGATATCCAGATGACACAGTC
CCCATCCTCTCTGAGCGCCTCCGTGGGCGACAGAGTGACAATCACCTGTA
GGGCCTCCCAGACCATCTGGTCTTACCTGAACTGGTATCAGCAGAGGCCC
GGCAAGGCCCCTAATCTGCTGATCTACGCAGCAAGCTCCCTGCAGAGCGG
AGTGCCATCCAGATTCTCTGGCAGGGGCTCCGGCACAGACTTCACCCTGA
CCATCTCTAGCCTGCAGGCCGAGGACTTCGCCACCTACTATTGCCAGCAG
TCTTATAGCATCCCCCAGACATTTGGCCAGGGCACCAAGCTGGAGATCAA
GACCACAACCCCAGCACCAAGGCCACCTACACCTGCACCAACCATCGCCT
CTCAGCCCCTGAGCCTGAGACCTGAGGCATGTAGGCCAGCAGCAGGAGGA
GCAGTCCATACAAGGGGTCTGGATTTTGCATGCGACATCTACATCTGGGC

-continued
```
ACCTCTGGCAGGAACATGTGGCGTGCTCCTGCTCAGCCTGGTCATCACCC
TGTACTGCAAGAGAGGCAGGAAGAAGCTGCTGTATATCTTCAAGCAGCCC
TTCATGCGCCCCGTGCAGACAACCCAGGAGGAGGATGGCTGCTCCTGTAG
GTTCCCAGAAGAGGAGGAGGGAGGATGTGAGCTGCGCGTGAAGTTTTCCC
GGTCTGCCGACGCACCTGCATACCAGCAGGGCCAGAACCAGCTGTATAAC
GAGCTGAATCTGGGCCGGAGAGAGGAGTACGATGTGCTGGACAAGAGGCG
CGGCAGAGATCCAGAGATGGGCGGCAAGCCCCGGAGAAAGAACCCTCAGG
AGGGCCTGTACAATGAGCTGCAGAAGGATAAGATGGCCGAGGCCTATTCT
GAGATCGGCATGAAGGGAGAGAGGCGCCGGGGCAAGGGACACGACGGACT
GTACCAGGGACTGAGCACAGCCACCAAGGATACCTATGACGCCCTGCATA
TGCAGGCACTGCCTCCAAGGTGA.
```

In one embodiment, the UCART22 of the present invention comprises a sequence of SEQ ID NO: 40 encoding for a CD22 CAR with a QR3.

(SEQ ID NO: 40)
```
ATGGCTCTGCCCGTCACCGCTCTGCTGCTGCCACTGGCCCTGCTGCTGC
ACGCCGCCAGACCCGGCGGAGGAGGCTCTTGCCCCTACAGCAACCCCAG
CCTGTGCTCTGGCGGCGGCGGCAGCGGAGGCGGCGGCTCCCAGGTGCAG
CTGCAGCAGAGCGGCCCCGGCCTGGTGAAGCCTAGCCAGACACTGTCCC
TGACCTGCGCAATCTCCGGCGACAGCGTGTCCGGAAACAGGGCCACATG
GAATTGGATCAGACAGTCTCCAAGCAGGGGCCTGGAGTGGCTGGGAAGG
ACCTACTATCGGTCCGCCTGGTACAACGACTATGCCGTGTCTGTGAAGG
GCCGCATCACATTCAACCCAGATACCAGCAAGAATCAGTTTTCCCTGCA
GCTGAATTCTGTGACACCCGAGGATACCGCCGTGTACTATTGCGCCAGA
GGCGAGAGCGGAGCAGCAGCAGACGCCTTCGATATCTGGGGCCAGGGCA
CCACAGTGACAGTGAGCGGAGGAGGAGGATCCGGCGGAGGAGGCTCTGG
CGGCGGCGGCAGCGACATCCAGCTGACCCAGAGCCCACCTTCCCTGTCT
GCCAGCGTGGGCGATCGCGTGACAATCACCTGTCGGGCCTCCCAGTCTA
TCAGCTCCTACCTGAACTGGTATCAGCAGAAGCCAGGCAAGGCCCCCAA
GCTGCTGATCTACGCAGCATCTAGCCTGCAGTCTGGAGTGCCAAGCAGA
TTCAGCGGATCCGGATTCGGCACAGACTTTACACTGACCATCTCCTCTC
TGCAGCCCGAGGATTTCGCCACCTACTATTGCCAGCAGTCTTATAGCAC
ACCTCAGACCTTTGGCCAGGGCACCAAGGTGGACATCAAGGGAAGTGGA
GGAGGAGGAAGTTGTCCCTACTCAAACCCATCTCTGTGCTCAGGAGGAG
GAGGAAGTGAACTGCCTACTCAGGGAACATTCAGCAACGTGTCCACCAA
TGTGAGCCCAGCAAAGCCTACCACAACCGCATGCCCATACTCTAACCCC
AGCCTGTGCACAACCACACCAGCACCCAGGCCCCCTACCCCTGCACCAA
CAATCGCCTCCCAGCCTCTGTCTCTGCGCCAGAGGCCTGCAGACCCGC
CGCCGGCGGAGCAGTGCACACACGGGCCTGGACTTTGCCTGTGATATC
TATATCTGGGCACCACTGGCCGGAACATGTGGCGTGCTGCTGCTGTCAC
TGGTCATTACACTGTACTGTAAGCGAGGCCGGAAGAAACTGCTGTATAT
```

-continued
```
TTTCAAACAGCCCTTTATGAGACCTGTGCAGACTACCCAGGAGGAAGAC
GGCTGCAGCTGTAGGTTCCCCGAGGAAGAGGAAGGCGGGTGTGAGCTGA
GGGTCAAGTTTAGCCGCTCCGCAGATGCCCCTGCTTACCAGCAGGGGCA
GAATCAGCTGTATAACGAGCTGAATCTGGGACGGAGAGAGGAATACGAC
GTGCTGGATAAAAGGCGCGGGAGAGACCCCGAAATGGGAGGCAAGCCAC
GACGGAAAAACCCCCAGGAGGGCCTGTACAATGAACTGCAGAAGGACAA
AATGGCAGAGGCCTATAGTGAAATCGGGATGAAGGGAGAGAGAAGGCGC
GGCAAAGGGCACGATGGCCTGTACCAGGGGCTGTCTACTGCCACCAAGG
ACACCTATGATGCTCTGCATATGCAGGCACTGCCTCCAAGGTGA
```

In a preferred embodiment the UCART22 of the present invention comprises a sequence of SEQ ID NO: 40 inserted into a human TRAC gene (such as in human TRAC gene Chromosome 14-NC_000014.9) and expresses at the cell surface an anti-CD22 CAR specific for the proximal part of CD22.

In a more preferred embodiment the UCART22 of the present invention comprises a sequence of SEQ ID NO: 20 inserted into a human TRAC gene (such as in human TRAC gene Chromosome 14-NC_000014.9) and expresses at the cell surface an anti-CD22 CAR specific for the distal part of CD22. (ANTI-CD22 CAR from HA22 with QR3 with the following sequence:

(SEQ ID NO: 93)
```
MALPVTALLLPLALLLHAARPEVQLVESGGGLVKPGGSLKLSCAASGFAF
SIYDMSWVRQTPEKRLEWVAYISSGGGTYYPDTVKGRFTISRDNAKNTLY
LQMSSLKSEDTAMYYCARHSGYGTHWGVLFAYWGQGTLVTVSAGGGGSGG
GGSGGGGSDIQMTQTTSSLSASLGDRVTISCRASQDISNYLNWYQQKPDG
TVKLLIYYTSILHSGVPSRFSGSGSGTDYSLTISNLEQEDFATYFCQQGN
TLPWTFGGGTKLEIKATTTPAPRPPTPAPTIASQPLSLRPEACRPAAGGA
VHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNE
LNLGRREEYDVLDKRRGRDPEMGGKPRRKNPQEGLYNELQKDKMAEAYSE
IGMKGERRRGKGHDGLYQGLSTATKDTYDALHMQALPPR
```

Encoded by the following sequence:

(SEQ ID NO: 94)
```
ATGGCTCTGCCCGTCACCGCTCTGCTGCTGCCACTGGCCCTGCTGCTGCA
CGCAGCAAGGCCTGAGGTGCAGCTGGTGGAATCCGGAGGAGGCCTGGTGA
AGCCTGGCGGCTCTCTGAAGCTGAGCTGTGCCGCCTCCGGCTTCGCCTTT
TCCATCTACGACATGTCTTGGGTGAGGCAGACCCCAGAGAAGCGCCTGGA
GTGGGTGGCCTATATCAGCTCCGGCGGCGGCACCTACTATCCCGACACAG
TGAAGGGCCGGTTCACCATCTCTAGAGATAACGCCAAGAATACACTGTAC
CTGCAGATGTCTAGCCTGAAGAGCGAGGATACCGCCATGTACTATTGCGC
AAGGCACTCCGGATACGGAACACACTGGGGCGTGCTGTTTGCCTATTGGG
GCCAGGGCACCCTGGTGACAGTGAGCGCCGGAGGAGGAGGAAGCGGCGGA
GGAGGCTCCGGCGGCGGCGGCTCTGACATCCAGATGACCCAGACCACATC
```

```
-continued
CTCTCTGAGCGCCTCCCTGGGCGACAGGGTGACAATCTCTTGTAGAGCCA

GCCAGGATATCTCCAACTACCTGAATTGGTATCAGCAGAAGCCTGATGGC

ACCGTGAAGCTGCTGATCTACTATACATCTATCCTGCACAGCGGAGTGCC

ATCCCGGTTCTCTGGAAGCGGATCCGGAACCGACTACTCTCTGACAATCA

GCAACCTGGAGCAGGAGGATTTCGCCACCTATTTTTGCCAGCAGGGCAAT

ACCCTGCCTTGGACATTTGGCGGCGGCACAAAGCTGGAGATCAAGGCCAC

CACAACCCCTGCACCAAGGCCACCAACACCAGCACCTACCATCGCATCTC

AGCCTCTGAGCCTGAGACCAGAGGCATGTAGGCCAGCAGCAGGAGGAGCA

GTGCACACAAGGGGACTGGATTTTGCCTGTGATATCTACATCTGGGCACC

TCTGGCAGGAACATGTGGCGTGCTCCTGCTCAGCCTGGTCATCACCCTGT

ACTGCAAGAGAGGCAGGAAGAAGCTGCTGTATATCTTCAAGCAGCCCTTC

ATGAGACCCGTGCAGACAACCCAGGAGGAGGACGGCTGCTCCTGTAGGTT

CCCAGAAGAGGAGGAGGGAGGATGTGAGCTGCGCGTGAAGTTTTCCCGGT

CTGCCGATGCACCTGCATACCAGCAGGGACAGAATCAGCTGTATAACGAG

CTGAATCTGGGCCGGAGAGAGGAGTACGACGTGCTGGATAAGAGGAGGGG

AAGGGACCCAGAGATGGGAGGCAAGCCTCGGAGAAAGAACCCACAGGAGG

GCCTGTACAATGAGCTGCAGAAGGACAAGATGGCCGAGGCCTATTCTGAG

ATCGGCATGAAGGGAGAGAGGCGCCGGGGCAAGGGACACGATGGCCTGTA

CCAGGGCCTGTCCACAGCCACCAAGGACACCTATGATGCCCTGCATATGC

AGGCACTGCCTCCAAGGTGA.
```

In one aspect, an anti-CD22 binding domain of the CD22 CAR of the invention is an anti-CD22 binding domain specific for the distal portion of CD22.

An anti-CD22 binding domain specific for the distal portion of CD22 may be expressed alone or with an anti-CD22 binding domain specific for the proximal portion of CD22.

In one aspect, the anti-CD22 binding domain of the CD22 CAR of the invention is an optimized anti-CD22 binding domain.

As used herein, "optimized" antibody (or scfv) refers to forms of antibodies (or scfv) that are chimeric immunoglobulins, immunoglobulin chains, or fragments thereof (such as Fv, Fab, Fab', F(ab')₂ or other antigen binding subsequences of antibodies) that contain minimal sequences derived from immunoglobulin. Preferably, antibodies are human immunoglobulins (recipient antibody) in which residues from a complementary determining region (CDR) are replaced by residues from a CDR to achieve the desired specificity, affinity, and capacity.

The donor CDR may undergo few amino acid changes that may significantly affect or alter the binding characteristics of the CD22 CAR of the invention. Indeed, one of the invention provided here is a CD22 CAR which binding to CD22-expressing cell (and cytolytoc activity) is maintained but the affinity is modified to reduce the intensity of the response (cytokine release).

Amino acid modifications are usually conservative modifications including amino acid substitutions, additions and deletions in said antibody fragment in said CAR and/or any of the other parts of said CAR molecule. Modifications can be introduced into an antibody, into an antibody fragment or in any of the other parts of the CAR molecule of the invention by standard techniques known in the art, such as site-directed mutagenesis, PCR-mediated mutagenesis or by employing optimized germline sequences.

In general, the optimized CAR will comprise substantially all of at least one, and typically two, variable domains, in which all or substantially all of the CDR regions correspond to the original human immunoglobulin.

Conservative amino acid substitutions mean substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

In a preferred embodiment, the present invention provides a anti-CD22 CAR having conservative sequence modifications (or an amino acid sequence change) as compared to the amino acid sequence of the polypeptide of SEQ ID NO: 64.

In a preferred embodiment, the present invention provides an anti-CD22 CAR having an amino acid sequence with 2 amino acid changes as compared to the amino acid sequence of the polypeptide of SEQ ID NO: 64.

In a preferred embodiment, the present invention provides an anti-CD22 CAR having an amino acid sequence with 3 amino acid changes as compared to the amino acid sequence of the polypeptide of SEQ ID NO: 64.

In a preferred embodiment, the present invention provides an anti-CD22 CAR having an amino acid sequence with 4 amino acid changes as compared to the amino acid sequence of the polypeptide of SEQ ID NO: 64

In a preferred embodiment, the present invention provides an anti-CD22 CAR having an amino acid sequence with 5 amino acid changes as compared to the amino acid sequence of the polypeptide of SEQ ID NO: 64, In a more preferred embodiment, the present invention provides an anti-CD22 CAR having an amino acid sequence with 5 amino acid changes as compared to the amino acid sequence of the polypeptide of SEQ ID NO: 64.

In a more preferred embodiment, the present invention provides an anti-CD22 CAR having an amino acid sequence with from 1 to 15 amino acid changes as compared to the amino acid sequence of the polypeptide of SEQ ID NO: 64

In a preferred embodiment, the sequence of an anti-CD22 CAR of the invention is modified by changing 1, 2, 3, 4, 5, 6, 7, 8, 9 or 10 amino acids as compared to the m971 CD22 CAR, to reduce the HAMA (human anti-mouse response), without affecting the binding capacity of said CAR to its target (CD22).

In a preferred embodiment, the present invention provides an anti-CD22 CAR having an amino acid sequence with at least 1 amino acid change as compared to the amino acid sequence of wt said at least 1 amino acid change having no impact or improving the binding and/or activity of said CD22 CAR in primary T cells.

Binding characteristics may be modified using adapted technique initially described in Mitchell Ho, Satoshi Nagata, and Ira Pastan. Isolation of anti-CD22 Fv with high affinity by Fv display on human cells *PNAS* 2006 103 (25) 9637-

9642; published ahead of print Jun. 8, 2006, doi:10.1073/pnas.0603653103 which is incorporated herein by reference.

Those optimized scfv also bear at least one mutations equivalent to mutations Pro-91-Thr-92 (PT) Gly-91-Ala-92 and Val-91-Phe-92.

In one embodiment the present invention provides an anti CD22 CAR comprising:

An extracellular domain comprising a signal peptide
a ligand binding-domain optionally optimized comprising a VH domain and a VL domain from a monoclonal anti-CD22 antibody having one of the following Pro-91-Thr-92 (PT), Gly-91-Ala-92, Val-91-Phe-92, mutations or equivalent,
a hinge, comprising a CD8 alpha ($\alpha$) hinge
  a CD8 alpha transmembrane domain and
  a cytoplasmic domain comprising a CD3 zeta signaling domain and a co-stimulatory domain from 4-1BB.

In a preferred embodiment the present invention provides an anti CD22 CAR as above wherein said monoclonal anti-CD22 antibody is from m971 antibody with hots spot in CDRs. Preferably, one of the following Pro-91-Thr-92 (PT), Gly-91-Ala-92, Val-91-Phe-92, mutations.

In a more preferred embodiment the present invention provides an isolated engineered (TCR and dCK KO) immune T cell comprising an anti CD22 CAR comprising An extracellular domain comprising,
a signal peptide, a ligand binding-domain comprising a VH domain and a VL domain from a monoclonal anti-CD22 antibody having at least one of the following Pro-91-Thr-92, Gly-91-Ala-92 mutation; Val-91-Phe-92 mutation,
a hinge, comprising a CD8 alpha (cc) hinge
  a CD8 alpha transmembrane domain and
  a cytoplasmic domain comprising a CD3 zeta signaling domain and a co-stimulatory domain from 4-1BB.

In a more preferred embodiment the present invention provides an isolated engineered (TCR and CD52 KO) immune T cell comprising an anti CD22 CAR comprising An extracellular domain comprising,
a signal peptide, a ligand binding-domain comprising a VH domain and a VL domain from a monoclonal anti-CD22 antibody having at least one of the following Pro-91-Thr-92, Gly-91-Ala-92 mutation; Val-91-Phe-92 mutation,
a hinge, comprising a CD8 alpha (cc) hinge
  a CD8 alpha transmembrane domain and
  a cytoplasmic domain comprising a CD3 zeta signaling domain and a co-stimulatory domain from 4-1BB.

In a more preferred embodiment the present invention provides an isolated engineered (TCR, CD52 and dCK KO) immune T cell comprising an anti CD22 CAR comprising:

An extracellular domain comprising,
a signal peptide, a ligand binding-domain comprising a VH domain and a VL domain from a monoclonal anti-CD22 antibody having at least one of the following Pro-91-Thr-92, Gly-91-Ala-92 mutation; Val-91-Phe-92 mutation,
a hinge, comprising a CD8 alpha (cc) hinge
  a CD8 alpha transmembrane domain and
  a cytoplasmic domain comprising a CD3 zeta signaling domain and a co-stimulatory domain from 4-1BB.
  In one aspect, the ANTI-CD22 CAR may be coexpressed at the cell surface with at least one, preferably two, more preferably three, monoclonal antibody (mAb)-specific epitopes, said mAb-specific epitope may be fused to a transmembrane domain of CD8. In one embodiment said mAb-specific epitope is an epitope recognized by rituximab, and/or from QBEND-10 and the peptide coexpressed with the cD22 CAR is RQR8.
  In another embodiment, at least one, preferably two, more preferably three, monoclonal antibody (mAb)-specific epitopes, may be inserted into the linker L of the scfv (binding the VH to the VL) specific for CD22 and/or into the hinge of the CD22 CAR.

Molecular antibody (mAb)-specific epitope, may be one of the following a mAb-specific epitope specifically recognized by an monoclonal antibody selected from ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably from rituximab (R) and/or from QBEND-10 (Q).

The epitope-specific mAb may be used for in vitro cell sorting and/or in vivo cell depletion of immune cells expressing a CD22.

In particular embodiments, the extracellular binding domain of the CD22 CAR of the invention may comprises one of the following sequences:

$V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-;
$(L)_x$-Epitope1-$(L)_x$-Epitope2-$(L)_x$-$V_1$-$L_1$-$V_2$-$(L)_x$-Epitope3-$(L)_x$-;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$-;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;
wherein,
V1 is VL, preferably of SEQ ID NO:12 and V2 is VH, preferably of SEQ ID NO:13 or V1 is VH and
V2 is VL;
L1 is a linker suitable to link the VH chain to the VL chain; preferably of SEQ ID NO:10
L is a linker comprising glycine and serine residues, and each occurrence of L in the extracellular binding domain can be identical or different to other occurrence of L in the same extracellular binding domain, and,
x is 0 or 1 and each occurrence of x is selected independently from the others; and,
Epitope 1, Epitope 2 and Epitope 3 are mAb-specific epitopes and can be identical or different.

In one embodiment, the extracellular binding domain comprises one of the following sequences $V_1$-$L_1$-$V_2$-L-Epitope1; $V_1$-$L_1$-$V_2$-L-Epitope1-L; $V_1$-$L_1$-$V_2$-L-Epitope1-L-Epitope2; $V_1$-$L_1$-$V_2$-L-Epitope1-L-Epitope2-L; $V_1$-$L_1$-$V_2$-L-Epitope1-L-Epitope2-L-Epitope3; $V_1$-$L_1$-$V_2$-L-Epitope1-L-Epitope2-L-Epitope3-L; $V_1$-$L_1$-$V_2$-Epitope1;

$V_1$-$L_1$-$V_2$-Epitope1-L; $V_1$-$L_1$-$V_2$-Epitope1-L-Epitope2; $V_1$-$L_1$-$V_2$-Epitope1-L-Epitope2-L;

$V_1$-$L_1$-$V_2$-Epitope1-L-Epitope2-L-Epitope3; $V_1$-$L_1$-$V_2$-Epitope1-L-Epitope2-L-Epitope3-L; Epitope1-$V_1$-$L_1$-$V_2$; Epitope1-L-$V_1$-$L_1$-$V_2$; L-Epitope1-$V_1$-$L_1$-$V_2$; L-Epitope1-L-$V_1$-$L_1$-$V_2$; Epitope1-L-Epitope2-$V_1$-$L_1$-$V_2$; Epitope1-L-Epitope2-L-$V_1$-$L_1$-$V_2$; L-Epitope1-L-Epitope2-$V_1$-$L_1$-$V_2$; L-Epitope1-L-Epitope2-L-$V_1$-$L_1$-$V_2$; Epitope1-L-Epitope2-L-Epitope3-$V_1$-$L_1$-$V_2$; Epitope1-L-Epitope2-L-Epitope3-L-$V_1$-$L_1$-$V_2$; L-Epitope1-L-Epitope2-L-Epitope3-$V_1$-$L_1$-$V_2$; L-Epitope1-L-Epitope2-L-Epitope3-L-$V_1$-$L_1$-$V_2$; $V_1$-L-Epitope1-L-$V_2$; L-Epitope1-L-$V_1$-L-Epitope2-L-$V_2$; $V_1$-L-Epitope1-L-$V_2$-L-Epitope2-L; $V_1$-L-Epitope1-L-$V_2$-L-Epitope2-L-Epitope3; $V_1$-L-Epitope1-L-$V_2$-L-Epitope2-Epitope3; $V_1$-L-Epitope1-L-$V_2$-L-Epitope2-L-Epitope3-Epitope4; L-Epitope1-L-$V_1$-L-Epitope2-L-$V_2$-L-Epitope3-L; Epitope1-L-$V_1$-L-Epitope2-L-$V_2$-L-Epitope3-L; L-Epitope1-L-$V_1$-L-Epitope2-L-$V_2$-L-Epitope3; L-Epitope1-L-$V_1$-$L_1$-$V_2$-L-Epitope2-L; L-Epitope1-L-$V_1$-$L_1$-$V_2$-L-Epitope2-L-Epitope3; L-Epitope1-L-$V_1$-$L_1$-$V_2$-L-Epitope2-Epitope3, or Epitope1-L-$V_1$-$L_1$-$V_2$-L-Epitope2-L-Epitope3-Epitope4 wherein $V_1$ is $V_L$ and $V_2$ is $V_H$ or $V_1$ is $V_H$ and $V_2$ is $V_L$; and VH, and VL are optimized VH and VL from m971.

$L_1$ is any linker suitable to link the $V_H$ chain to the $V_L$ chain; L is a linker comprising glycine and serine residues, and each occurrence of L in the extracellular binding domain can be identical or different to other occurrences of L in the same extracellular binding domain, and, Epitope 1, Epitope 2 and Epitope 3 are mAb-specific epitopes and can be identical or different.

$L_1$ is a linker comprising Glycine and/or Serine, preferably, $L_1$ is a linker comprising the amino acid sequence (Gly-Gly-Gly-Ser)$_n$ or (Gly-Gly-Gly-Gly-Ser)$_n$, where n is 1, 2, 3, 4 or 5 or a linker comprising the amino acid sequence $(Gly_4Ser)_4$ or $(Gly_4Ser)_3$ (SEQ ID NO: 10).

Similarly, L is a linker comprising Glycine and/or Serine, preferably L is a linker having an amino acid sequence selected from SGG, GGS, SGGS (SEQ ID NO: 101), SSGGS (SEQ ID NO: 102), GGGG (SEQ ID NO: 103), SGGGG (SEQ ID NO: 104), GGGGS (SEQ ID NO: 97), SGGGGS (SEQ ID NO: 105), GGGGGS (SEQ ID NO: 106), SGGGGGS (SEQ ID NO: 107), SGGGGG (SEQ ID NO: 108), GSGGGGS (SEQ ID NO: 109), GGGGGGGS (SEQ ID NO: 110), SGGGGGGG (SEQ ID NO: 111), SGGGGGGGS (SEQ ID NO: 112), and SGGGGSGGGGS (SEQ ID NO: 113), preferably L is a linker having an aminos acid sequence selected from SGGGG (SEQ ID NO: 104), GGGGS (SEQ ID NO: 97) and SGGGGS (SEQ ID NO: 105).

In a preferred embodiment, Epitope 1, Epitope 2, Epitope 3 and Epitope 4 are independently selected from mAb-specific epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably Epitope 1, Epitope 2, Epitope 3 and Epitope 4 are recognized by rituximab or QBEND-10.

Epitope 1, Epitope 2, Epitope 3 and Epitope 4 can be mAb-specific epitopes specifically recognized by one antibody listed in Table 5 below.

TABLE 5

| Antibody | Indication | Drug bank accession n° (or other n° if stated) | Target/ Antigen |
|---|---|---|---|
| Ibritumomab tiuxetan | Non-Hodgkin lymphoma (with yttrium-90 or indium-ill) | DB00078 | CD20 |
| Muromonab-CD3 | Transplant rejection | DB00075 | T cell CD3 Receptor |
| Tositumomab | Non-Hodgkin lymphoma | DB00081 | CD20 |
| Abciximab | Cardiovascular disease | DB00054 | inhibition of glycoprotein IIb/IIIa |
| Basiliximab | Transplant rejection | DB00074 | IL-2Rα receptor (CD25) |
| Brentuximab vedotin | Anaplastic large cell lymphoma | DB08870 | CD30 |
| Cetuximab | Colorectal cancer, Head and neck cancer | DB00002 | epidermal growth factor receptor |
| Infliximab | Several autoimmune disorders | DB00065 | inhibition of TNF-α signaling |
| Rituximab | Non-Hodgkin lymphoma | DB00073 | CD20 |
| Alemtuzumab | Chronic lymphocytic leukemia | DB00087 | CD52 |
| Bevacizumab | Colorectal cancer, Age related macular degeneration (off-label) | DB00112 | Vascular endothelial growth factor (VEGF) |
| Certolizumab pegol | Crohn's disease | DB08904 | inhibition of TNF-α signaling |
| Daclizumab | Transplant rejection | DB00111 | IL-2Rα receptor (CD25) |
| Eculizumab | Paroxysmal nocturnal hemoglobinuria | DB01257 | Complement system protein |
| Efalizumab | Psoriasis | DB00095 | CD11a |

TABLE 5-continued

| Antibody | Indication | Drug bank accession n° (or other n° if stated) | Target/ Antigen |
| --- | --- | --- | --- |
| Gemtuzumab | Acute myelogenous leukemia (with calicheamicin) | DB00056 | CD33 |
| Natalizumab | Multiple sclerosis and Crohn's disease | DB00108 | alpha-4 (α4) integrin |
| Omalizumab | mainly allergy-related asthma | DB00043 | immunoglobulin E (IgE) |
| Palivizumab | Respiratory Syncytial Virus | DB00110 | an epitope of the RSV F protein |
| Ranibizumab | Macular degeneration | DB01270 | Vascular endothelial growth factor A (VEGF-A) |
| Tocilizumab (or Atlizumab) | Rheumatoid arthritis | DB06273 | Anti- IL-6R |
| Trastuzumab | Breast cancer | DB00072 | ErbB2 |
| Vedolizumab | Crohn's disease, ulcerative colitis | CAS n°943609-66-3 | integrin $\alpha_4\beta_7$ |
| Adalimumab | Several auto-immune disorders | DB00051 | inhibition of TNF-α signaling |
| Belimumab | Systemic lupus erythematosus | DB08879 | inihibition of B-cell activating factor |
| Canakinumab | Cryopyrin-associated periodic syndrome (CAPS) | DB06168 | IL-Iβ |
| Denosumab | Postmenopausal osteoporosis, Solid tumor's bony metastases | DB06643 | RANK Ligand inhibitor |
| Golimumab | Rheumatoid arthritis, Psoriatic arthritis, and Ankylosing spondylitis | DB06674 | TNF-alpha inihibitor |
| Ipilimumab (MDX-101) | Melanoma | DB06186 | blocks CTLA-4 |
| Ofatumumab | Chronic lymphocytic leukemia | CAS n° 679818-59-8 | CD20 |
| Panitumumab | Colorectal cancer | DB01269 | epidermal growth factor receptor |
| Ustekinumab | Psoriatic Arthritis, Plaque Psoriasis | DB05679 | IL-12, IL-23 |
| Nivolumab | renal cell carcinoma, lung cancer, melanoma, and advanced or metastatic solid tumors | CAS n°946414-94-4 | PD-1 |

The mAb-specific epitope may therefore comprise one polypeptide selected from:

```
                                   (SEQ ID NO: 91)
CPYSNPSLC, (SEQ ID NO: 114)
NSELLSLINDMPITNDQKKLMSNN, (SEQ ID NO: 115)
CQFDLSTRRLKC, (SEQ ID NO: 116)
CQYNLSSRALKC, (SEQ ID NO: 117)
CVWQRWQKSYVC, (SEQ ID NO: 119)
SFVLNWYRMSPSNQTDKLAAFPEDR, (SEQ ID NO: 120)
SGTYLCGAISLAPKAQIKE,
```

-continued
```
                                   (SEQ ID NO: 92)
ELPTQGTFSNVSTNVSPAKPTTTA, (SEQ ID NO: 121)
GQNDTSQTSSPS.
```

TABLE 6

| Examples of antibody and mAb-specific epitope recognized by said antibody | |
| --- | --- |
| Antibody | mAb-specific epitope |
| Rituximab | |
| Mimotope | CPYSNPSLC (SEQ ID NO: 91) |
| Palivizumab | |
| Epitope | NSELLSLINDMPITNDQKKLMSNN (SEQ ID NO: 114) |

TABLE 6-continued

Examples of antibody and mAb-specific epitope recognized by said antibody

| Antibody | mAb-specific epitope |
|---|---|
| Cetuximab | |
| Mimotope 1 | CQFDLSTRRLKC (SEQ ID NO: 115) |
| Mimotope 2 | CQYNLSSRALKC (SEQ ID NO: 116) |
| Mimotope 3 | CVWQRWQKSYVC (SEQ ID NO: 117) |
| Mimotope 4 | CMWDRFSRWYKC (SEQ ID NO: 118) |
| Nivolumab | |
| Epitope 1 | SFVLNWYRMSPSNQTDKLAAFPEDR (SEQ ID NO: 119) |
| Epitope 2 | SGTYLCGAISLAPKAQIKE (SEQ ID NO: 120) |
| QBEND-10 | |
| Epitope | ELPTQGTFSNVSTNVSPAKPTTTA (SEQ ID NO: 92) |
| Alemtuzumab | |
| Epitope | GQNDTSQTSSPS (SEQ ID NO: 121) |

In a preferred embodiment, the mAb-specific epitope is a mAb-specific epitope having an amino acid sequence of ELPTQGTFSNVSTNVSPAKPTTTA (SEQ ID NO: 92) and/or CPYSNPSLC (SEQ ID NO: 91).

In a more preferred embodiment, the CD22 CAR of the invention comprises 3 mAb-specific epitopes having an amino acid sequence of CPYSNPSLC (SEQ ID NO: 91) (R) and one having an amino acid sequence of ELPTQGTFSNVSTNVSPAKPTTTA (SEQ ID NO: 92) (Q).

In one aspect, the present invention provides a CAR specific for CD22 comprising one of the following sequence SEQ ID NO: 46 to SEQ ID NO: 69, SEQ ID NO: 46 to SEQ ID NO: 55, SEQ ID NO: 56 to SEQ ID NO: 65, SEQ ID NO: 66 to SEQ ID NO: 69, preferably, SEQ ID NO: 49, SEQ ID NO: 52, SEQ ID NO: 54, SEQ ID NO: 55, preferably SEQ ID NO: 54, or SEQ ID NO: 59, SEQ ID NO: 62, SEQ ID NO:64, SEQ ID NO: 65, preferably, SEQ ID NO: 64, or SEQ ID NO: 66, SEQ ID NO: 67, SEQ ID NO: 68, SEQ ID NO: 69.

In preferred aspect, the present invention provides a CAR specific for CD22 comprising one of the following sequence: SEQ ID NO: 54, In preferred aspect, the present invention provides a CAR specific for CD22 comprising one of the following sequence: SEQ ID NO: 64, In preferred aspect, the present invention provides a CAR specific for CD22 comprising one of the following sequence: SEQ ID NO: 66, In preferred aspect, the present invention provides a CAR specific for CD22 comprising one of the following sequence: SEQ ID NO: 67, In preferred aspect, the present invention provides a CAR specific for CD22 comprising one of the following sequence: SEQ ID NO: 68, In preferred aspect, the present invention provides a CAR specific for CD22 comprising one of the following sequence: SEQ ID NO: 69, In one aspect, at least one sequence to which rituximab binds to (R) and/or a sequence to which QBEND-10 binds to (Q) may be inserted into the linker GGGGSGGGGSGGGGS and/or into the Hinge as previously described in (WO2016120216).

The RQR8 and method for preparing the same, are disclosed in WO2013153391A1.

In a particular embodiment, the CD22 CAR of the present invention is a single chain CAR (scCAR).

In a particular embodiment, the single chain anti-CD22 CAR of the invention comprises a scfv comprising any one of the (VH,VL) selected from (SEQ ID NO: 77 and SEQ ID NO: 78), from (SEQ ID NO: 83 and SEQ ID NO: 84), from (SEQ ID NO: 87 and SEQ ID NO: 88), from (SEQ ID NO: 89 and SEQ ID NO: 90), preferably from (SEQ ID NO: 87 and SEQ ID NO: 88) and at least one other binding domain, preferably specific for the distal part of CD22, alternatively for another B cell antigen, especially if expressed by B cells malignancies such as CD34, CD10, CD79a, CD20, IgD, CD5, CD23, CD19, STATS, CD3, CD30, BCMA.

In a particular embodiment, the CD22 CAR of the present invention is a multichain CAR (mcCAR). Multichain CD22 CARs are part of the present invention and may be produced as described in details in WO2014039523, which is incorporated herein by reference. In a particular embodiment, the $V_{H\ domain}$ and the $V_{L\ domain}$ of an immunoglobulin or a part of an immunoglobulin specific for CD22, may be carried by two different and isolated (non covalently bound) chains of a multichain CAR.

In a multichain version, the CD22 CAR of the invention comprises at least two, preferably 3 transmembrane domains (non covalently bound to each other) with at least one of the transmembrane domain comprising a scfv specific for CD22.

In a particular embodiment, the $V_{H\ domain}$ and the $V_{L\ domain}$ of an immunoglobulin specific for CD22, preferably from m971 may be carried by one chain of a multichain CAR.

Figure 2:
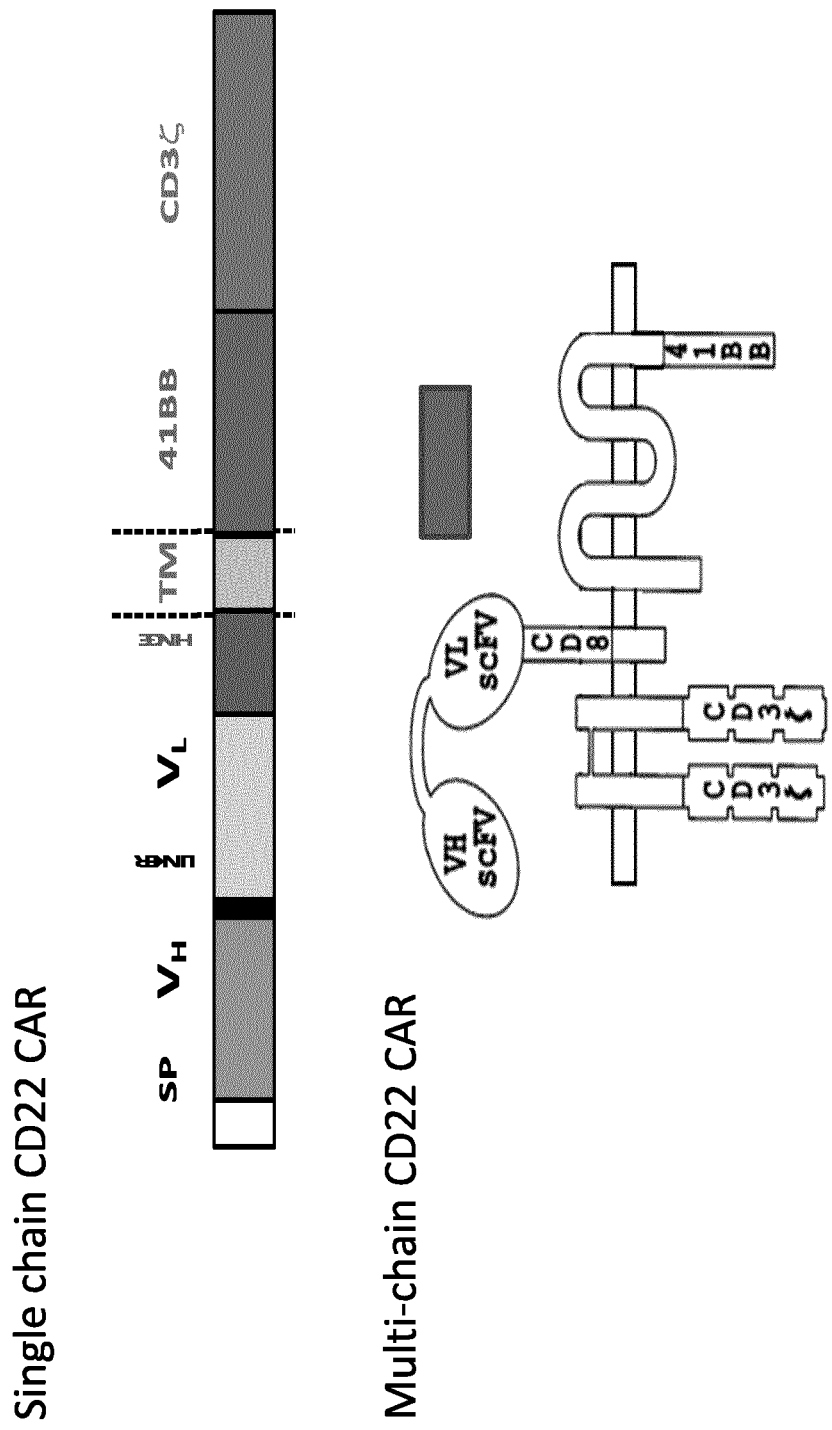
FIG. 2: Representation of a single chain and of a multi-chain CD22 CAR
Figure 3:
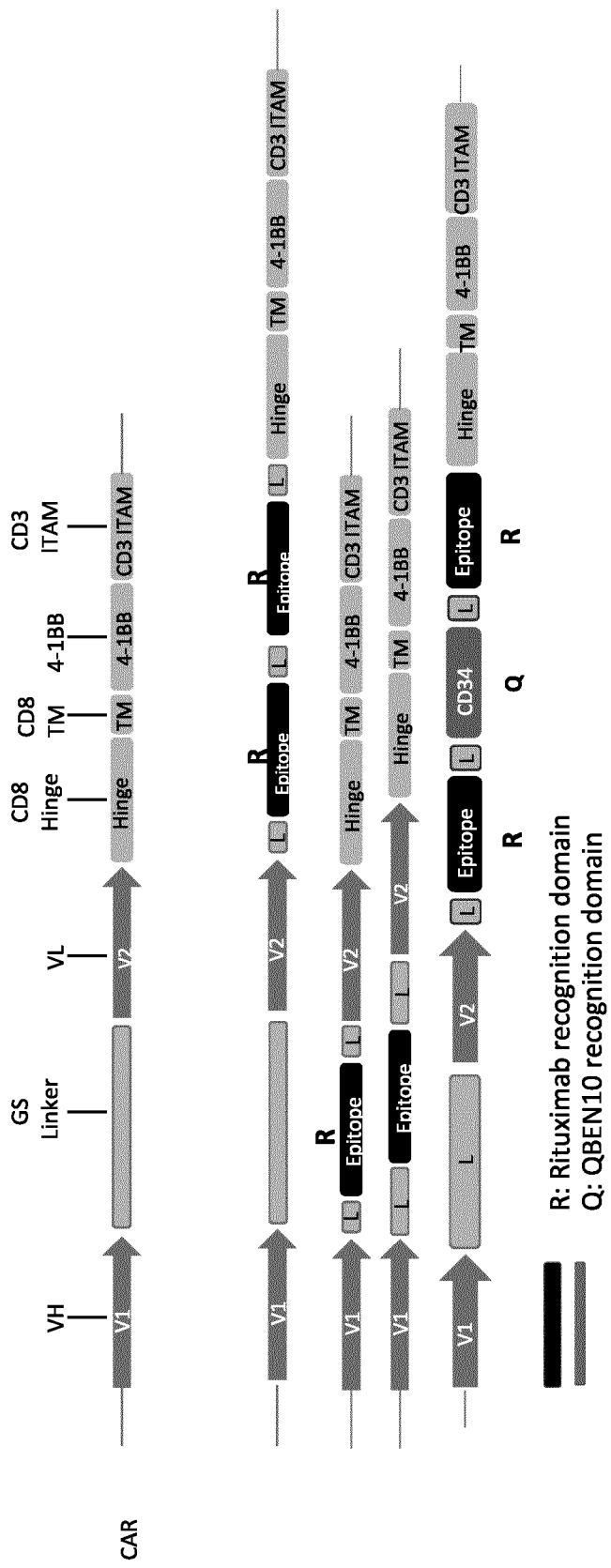
FIG. 3: Examples of CD22 CAR constructs of the invention comprising a safety switch.

An example of sc CD22CAR and of mc CD22CAR of the invention is provided FIG. 2.

In a particular embodiment, the $V_{H\ domain}$ and the $V_{L\ domain}$ of an immunoglobulin specific for CD22, preferably from m971 may be carried by one chain of a multichain CAR and the $V_H$ domain and the VL domain of another immunoglobulin specific for CD22, may be carried by another chain of the mc CAR.

Downregulation or mutation of target antigens is commonly observed in cancer cells, creating antigen-loss escape variants. Thus, to offset tumor escape and render immune cell more specific to target, the CD22 specific CAR according to the invention can comprise another extracellular ligand-binding domains, to simultaneously bind other elements in target thereby augmenting immune cell activation and function. In one embodiment, the extracellular ligand-binding domains can be placed in tandem on the same transmembrane polypeptide, and optionally can be separated by a linker.

In another embodiment, said different extracellular ligand-binding domains can be placed on different transmembrane polypeptides composing the multichain CAR. In another embodiment, the present invention relates to a population of CARs comprising different extracellular ligand binding domains, one of each is specific for CD22.

In one embodiment the extracellular binding domain specific for CD22 and the second extracellular binding domain are on the same scCAR, In another embodiment, the extracellular binding domain specific for CD22 and the second extracellular binding domain are on the same mc CAR and belong to the same or to two different and non covalently bound transmembrane domains of said mc CAR.

As other second extracellular binding domain may be any extracellular binding domain binding specific to an antigen associated (coexpressed—even temporarily) to CD22 on pathological cells, such as CD34, CD10, CD79a, CD20, IgD, CD5, CD23, CD19, STAT5, CD3, CD30, BCMA.

As other second extracellular binding domain expressed at the cell surface of the present UCART22, may be any extracellular binding domain binding specific to an antigen associated (coexpressed—even temporarily) to CD22 on pathological cells, such as CD19, CD20, CD30, glycosphingolipids, a major histocompatibility complex (MHC) molecule, an Ig, CD3, CD34, CD79, preferably CD79a, CD138, B7-1 (CD80), a major histocompatibility complex (MHC) molecule, BCMA (CD269, TNFRSF 17) or FLT-3.

The invention also provides related CD22 CAR nucleic acids, CD22 CAR recombinant expression vectors, engineered TCR KO cells comprising at least another edited gene endowed with the CD22 CAR, populations of said TCR KO cells endowed with a CD22 CAR, and pharmaceutical compositions relating to the CD22 CARs, protein, expression vector, engineered TCR KO CD52 KO cells expressing said CD22CAR of the invention.

The invention provides the following objects: a CD22 CAR of the invention-related nucleic acids,-recombinant expression vectors, engineered TCR KO cells comprising at least another edited gene endowed selected from a gene conferring resistance to hypoxia, a gene conferring resistance to alemtuzumab, to protease inhibitor, such as bortezomib, a gene conferring resistance to PNA (dCK) and endowed with a CD22 CAR, and related nucleic acid, populations of engineered TCR KO cells comprising at least another edited gene as below, endowed with said CD22 CAR and pharmaceutical compositions comprising said same objects as a medicament.

In particular embodiments any one of the above anti-CD22 CAR of the invention may comprise an apoptosis domain as described in PA 2017 70037, filed on 20 Jan. 2017 which is incorporated herein by reference.

In particular embodiments any one of the above UCART22 of the invention may comprise apoptosis CAR, as described in PA 2017 70037, filed on 20 Jan. 2017 which is incorporated herein by reference.

Polynucleotides, Vectors:

The present invention relates to polynucleotides, vectors encoding the above described CD22 CAR according to the invention.

A polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus or an adeno associated virus for introduction into a mammalian, preferably human host cell.

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)).

Accordingly the present invention provides a retroviral lentivirus vector coding CD22CAR of the invention linked by a peptide 2A.

The present invention provides a retroviral lentivirus vector coding CD22CAR (such as any SEQ ID NO:12 to NO:21 or SEQ ID NO 23 to SEQ ID NO 45) or a sequence having at least 80% identity with said sequence) of the invention linked by a peptide 2A and to a sequence coding a RQR8 motif.

By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

A vector allowing a CD22 CAR of the invention to be expressed in a cell is another object of the present invention. In a preferred embodiment, said vector allows a transient expression of the CD22 CAR of the invention. In a more preferred embodiment said vector allows a constitutive and stable expression of a CD22 CAR of the invention by insertion of the sequence coding said CD22 CAR into the genome of a cell.

The expression of a CD22 CAR of the invention and/or the survival of the cell expressing the CD22 CAR of the invention may be controlled using a gene under the control of an inducible promoter as described in (R. Kuhn, F. Schwenk, M. Aguet, K. Rajewsky. Inducible gene targeting in mice. Science 8 Sep. 1995: Vol. 269 no. 5229 pp. 1427-1429 DOI:10.1126/science.7660125, and cited references.

In one embodiment, a CD22 CAR is provided wherein the extracellular domain comprises at least two CD20 mimotopes of SEQ ID NO: 91 (CPYSNPSLC) located between the scfv domains and the hinge from human CD8alpha. Document Patent WO2016120216A1 discloses a method for preparing such constructions and is incorporated herein by reference.

In one embodiment, the present invention provides a vector comprising a sequence coding a CD22 CAR selected from SEQ ID NO: 21 to SEQ ID NO: 30, SEQ ID NO: 32 to SEQ ID NO: 45, preferably SEQ ID NO: 29 and SEQ ID NO: 40.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S.

Pat. No. 5,143,830). In a preferred embodiment the signal peptide comprises the amino acid sequence SEQ ID NO: 1 and SEQ ID NO.2.

In a more preferred embodiment, the signal peptide of the CAR of the invention comprises the amino acid sequence of SEQ ID NO: 1 from human CD8 alpha.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering Immune Cells Endowed with CD22 CARs:

The present invention encompasses a method for preparing immune cells expressing the CD22 CAR of the invention or UCART22 for immunotherapy comprising introducing ex-vivo into said immune cells a polynucleotide or a vector encoding one of the CD22 CAR of the invention, preferably of SEQ ID NO. 64 as previously described.

In a preferred embodiment, said polynucleotides are included into a vector in view of being stably expressed in the immune cells.

According to further embodiments, said method further comprises the step of genetically modifying said cell to make it more suitable for adoptive transfer, and/or for use with a drug affecting said immune cell survival, in particular for transplant (also called allograft, or homograft) alone or in combination with the drug for which the immune cell is made resistant In this later case, engineered cells may be initially isolated from a donor and used for a reinjection into the same donor in combination with a drug to which it is made resistant to.

For editing a gene, which means here modifying a gene, for example mutating a gene, deleting a gene, inserting a sequence in a gene, modifying the methylation of said gene (this includes the promotor of a gene), etc, methods described in PA201670503 are incorporated here by reference and illustrated in the examples below.

Methods described in MacLeod et al., Integration of a CD19 CAR into the TCR Alpha Chain Locus Streamlines Production of Allogeneic Gene-Edited CART Cells, Molecular Therapy (2017), incorporated herein by reference, are also a possible alternatives to the method used in the present invention for preparing a TCR KO CD22 CAR or a cell endowed with a CD22 CAR resistant to hypoxia by over expressing HIF-1alpha.

The method of the present invention is based on cellular homology-directed repair (HDR) mechanisms to "knock in" a CD22 CAR in the TRAC gene (encoding the TCR alpha subunit of the TCR) resulting in a more efficient product.

HDR with an exogenous DNA sequence has been described previously in T cells using short oligonucleotides paired with CRISPR/Cas9. Others have shown that adeno-associated virus (AAV) vectors can be used as a template in conjunction with a site-specific nuclease Crispr/Cas9 or MegaTAL to achieve gene insertion via HDR. In the present invention is provided a new method combining adeno-associated virus (AAV) vectors and TALEN to insert a CAR into the TCR gene.

Because TALEN are specific for a DNA sequence and allow integrating a sequence into a gene, preferably a TRAC gene, the present invention also provides an engineered immune cells comprising a sequence coding a CAR, preferably a CD22 CAR as described above located in a precise region of the TRAC gene determined by the TALEN used. The sequence in the TRAC gene of said engineered immune cell is unique due to the TALEN specificity.

Accordingly the present invention provides an engineered immune cell comprising the following sequence;

$(YYY)_n$-ZZZ-$(XXX)_m$.

with n is =1 to at least 10 and m is =1 to 100 preferably m is >100 and represents the number of base pair of the sequence to be integrated, more preferably, m is 300+/−50 nucleotides wherein ZZZ codes a self cleaving peptide, such as a peptide 2A, in frame with the TRAC encoding sequence, Y is A or T or G or C and flanking or comprising a sequence of the TRAC gene targeted by a TALEN comprising at least ttgtcccacagATATC (SEQ ID NO: 141), preferably ttgtcccacagATATCCAG (SEQ ID NO: 142) and $(XXX)_n$ is A or T or G or C and part of an exogenous sequence to be inserted into the TRAC gene, preferably a sequence encoding a CAR, more preferably a sequence encoding a CD22 CAR.

In one embodiment the TRAC gene is deleted and the inserted gene is expressed under the control of the TRAC promotor.

Additional or alternative sequences, such as IRES internal ribosome entry site; maybe interposed between the TALEN target and XXX.

In the present invention, the TALEN target is SEQ ID NO: 21 and an example of gene to be inserted is any one of the anti-CD22 CAR of the invention of SEQ ID NO: 21 to SEQ ID NO: 30, SEQ ID NO: 32 to SEQ ID NO: 45, SEQ ID NO: 31.

In one embodiment the sequence clived by said TALEN is AGAACCCTGACCCTG (SEQ ID NO: 143). The sequence AGAACCCTGACCCTG (SEQ ID NO: 143) may be conserved at least in part (see FIG. 10) in the engineered cell of the invention, depending on the insert sequence. In one embodiment the sequence or part of the sequence is conserved and it is used as a signature of the product.

The present invention provides an engineered immune cell comprising a TRAC gene comprising at least a ATC sequence, an exogenous sequence, any one of the sequences of SEQ ID NO: 21 to SEQ ID NO: 45, preferably of SEQ ID NO: 40, A sequence coding for the flowing protein (Primary (citable) accession number: Q16665)

Adoptive cell transfer is the transfer of cells into a patient. The cells may have originated from the patient him- or herself and then been altered before being transferred back (syngenic transfer) or, they may have come from another individual. The cells are most commonly derived from the immune system, with the goal of transferring improved immune functionality and characteristics along with the cells back to the patient. Transferring autologous cells, or cells from the patient, minimizes graft-versus-host disease (GVHD) or tissue or organ rejection.

In one embodiment, the step of genetically modifying (engineering) said immune cell takes place before the step of introducing the polynucleotides or vectors encoding one of the CD22 CAR of the invention into said cells. According to a first aspect, the immune cell can be made less allogeneic, for instance, by inactivating at least one gene expressing one or more component of T-cell receptor (TCR) as described in WO 2013/176915, which can be combined with the inactivation of a gene encoding or regulating HLA expression such as β2m gene as described in WO2008102199 or in WO2015136001 or in WO2016201047 which are all incorporated herein by reference. Accordingly, the risk of graft versus host syndrome and the risk of graft rejection are significantly reduced.

According to another aspect, the immune cells of the invention can be further genetically engineered to improve the resistance of engineered immune cells to an immunosuppressive drug or a chemotherapy treatment, which are used as standard care for treating CD22 positive malignant cells as disclosed in WO201575195 which is incorporated herein by reference.

Resistance to Campath (Alemtuzumab)

In one preferred embodiment, the genes which can be inactivated to confer drug resistance to the T-cell is a glucocorticoid receptor (GR) and CD52. Genes are inactivated to make the cells resistant to these treatments and give them a competitive advantage over patient's own T-cells not endowed with specific CD22 CARs.

The inactivation of the CD52 and TRAC gene in the engineered immune cell according to the invention is performed using a TALE nuclease or a CRISPR CAS9 system.

In one more preferred embodiment, the gene which can be inactivated to confer drug resistance to the T-cell is the CD52 in TCR KO immune T cells endowed with a CD22 CAR.

In one preferred embodiment, the gene which can be inactivated to confer drug resistance to the T-cell is a glucocorticoid receptor (GR).

Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblasic leukemia.

Resistance to Purine Nucleotide Analogs by Deletion of Human Deoxycytidine Kinase (dCK) Gene.

In one preferred embodiment, the gene which can be inactivated to confer drug resistance to the T-cell is the human deoxycytidine kinase (dCK) gene. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA. Their triphosphate forms and particularly clofarabine triphosphate compete with ATP for DNA synthesis, acts as proapoptotic agent and are potent inhibitors of ribonucleotide reductase (RNR) which is involved in trinucleotide production.

The inactivation of the dCK gene in the engineered immune cell according to the invention is mediated by a TALE nuclease or a CRISPR CAS9 system. To achieve this goal, several pairs of dCK TALE-nuclease have been designed, assembled at the polynucleotide level and validated by sequencing. Examples of TALE-nuclease pairs which can be used according to the present invention are depicted in PCT/EP2014/075317.

This dCK inactivation in engineered immune cells of the invention confers resistance to purine nucleoside analogs (PNAs) such as clofarabine and fludarabine.

In another preferred embodiment, the dCK inactivation in engineered immune cells of the invention is combined with an inactivation of TRAC genes rendering these double knock out (KO) (TCR or TRAC KO and dCK KO) cells both resistant to drug such as clofarabine and less allogeneic.

In another preferred embodiment, the CD52 inactivation in engineered immune cells of the invention is combined with an inactivation of TRAC gene rendering these double knock out (KO) (TCR or TRAC KO and CD52 KO) cells both resistant to drug such as CAMPATH (alemtuzumab) and less allogeneic.

This double feature is particularly useful for a therapeutic goal, allowing "off-the-shelf" allogeneic cells (UCART22) for immunotherapy in conjunction with chemotherapy to treat patients with cancer in need thereof. This double KO inactivation dCK/TRAC or CD52/TRAC can be performed simultaneously or sequentially. One example of TALE-nuclease dCK/TRAC pairs which gave success in the invention is described in PCT/EP2014/075317, in particular, the target sequences in the 2 loci (dCK and TRAC). Document PCT/EP2014/075317 is incorporated herein in its entirety.

The present invention provides a primary T cells expressing a CD22 CAR of SEQ ID NO.64, wherein, wherein the CD52 and TRAC genes are inactivated by deletion for their use in the treatment of CLL, ALL, preferably their aggressive, relapsing refractory forms, optionally in lymphodepleted patients, more preferably relapsing refractory forms of B-ALL.

According to a further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 7.

The present invention also provides a primary T cells expressing a CD22 CAR of SEQ ID NO.64, wherein the CD52, TRAC and dCK genes were deleted.

In another embodiment the present invention also provides a primary T cells expressing a CD22 CAR that were made resistant to hypoxia.

The present invention also provides a primary T cells expressing a CD22 CAR of SEQ ID NO.64, wherein the CD52, TRAC and dCK genes were deleted and sequences of HIF-1a were inserted to make cells resistant to hypoxia.

Making Engineered Cells Resistant to Hypoxia

In particular embodiments, the expression and cytolytic activity of CD22 CART cell of the invention is maintained, or the expression of CD22 CART cell induced and the activity maintained under low oxygen condition (hypoxia), (as compared to normal oxygen condition 20% 02 vs 1 to 5% 02) and said cell still target and destroy tumor cells when embedded into tissues.

Examples of hypoxia-inducible CAR in T cell are described in WO2013123061 or in Juillerat, A. et al. (An oxygen sensitive self-decision making engineered CAR T-cell, Sci. Rep. 7, 39833; doi: 10.1038/srep39833 (2017)), both incorporated by reference. A synthetic promoter specific for the OxiTF driving the expression of the CD22 CAR was constructed. The OxiTF is designed to activate a synthetic genetic element encoding a CD22 CAR. Upon CD22-expressing tumor encounter, engineered T cells can detect a decrease in oxygen level (as compared to the mean level of 02 in the blood) and trigger the expression of the CD22 CAR. Cell surface exposure of CD22 CAR enables the recognition of tumor antigen under hypoxia that eventually triggers T cells activation and proliferation via the activation and co-stimulatory domains present within said CD22 CAR. Ultimately, tumor antigen expressing cells are lysed by the UCART22 of the invention.

In the present invention, immune cells may be also engineered to remain efficient under low 02 condition (low oxygen concentration means 1-5%) by overexpressing at least one, preferably all of the following factors: Oct3, Oct4, Sox2, Klf4 and c-Myc, or by editing a HIF-1a factor.

In the present invention, an oxygen sensitive CD22 single chain CAR-expressing engineered cell and a hypoxia resistant CD22 CAR-expressing engineered cell were constructed and tested successfully.

Because CD22 is mainly expressed on CD22-expressing B cell malignancies, which are "liquid" tumors" and therefore are not supposed to create hypoxia in contrast to solid tumor, it was not expected that a CD22 CAR engineered immune cells resistant to hypoxia would be more efficient than CD22 CAR engineered immune cells which are not resistant to hypoxia against B-ALL from patient. In fact, the UCART22 of the invention reaching the nested cancer cells clustered or homing in tissues may be able to lyse these cells.

Other genes may be edited in the UCART22 of the present invention such as those listed in Table 7.

In a preferred embodiment said method of further engineering the immune cells involves introducing into said T cells polynucleotides, in particular mRNAs, encoding specific rare-cutting endonuclease to selectively inactivate the genes, as those mentioned above, by DNA cleavage.

In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice and preferred for producing of the engineered immune cells on a large scale with a constant turn-over.

Delivery Methods

The different methods described above involve introducing a CD22 CAR of the invention into a cell. As non-limiting examples, said CD22 CAR can be introduced as a transgene encoded by one plasmid vector of the invention. Said plasmid vector encoding a CD22 CAR of the invention can also contain a selection marker which provides for identification and/or selection of cells which received said vector.

TABLE 7

List of genes encoding immune checkpoint proteins that may be inactivated according to the present invention in the CD22 CAR engineered T cells of the invention

| | Pathway | Genes that can be inactivated In the pathway |
|---|---|---|
| Co-inhibitory receptors | CTLA4(CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HM0X2 |
| | IL6 signalling | IL6R, IL6ST |
| Prevention of TCR signalling | | CSK, PAG1 SIT1 |
| Induced Treg Transcription factors controlling exhaustion | induced Treg transcription factors controlling exhaustion | FOXP3 PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

In bold are the preferred gene inactivated in the UCART of the invention

The present invention provides isolated engineered immune T cells expressing a CD22 CAR of SEQ ID NO.64, wherein, the dCK and/or CD52 and TRAC genes are edited, that is, inactivated by deletion, for their use in the treatment of CLL, ALL, preferably their aggressive, relapsing refractory forms, in lymphodepleted patients.

The present invention provides isolated engineered immune T cells expressing a CD22 CAR of SEQ ID NO.64, wherein the CD52 and TRAC genes are inactivated by deletion, for their use in the treatment of relapsing refractory forms of BALL, in lymphodepleted patients.

A Method allowing a CD22 CAR according to the invention to be introduced and then expressed into an isolated immune cell was described elsewhere, for example in WO2013126720 or in WO2015121454 which are incorporated herein by reference in entirety.

Polypeptides corresponding to the CD22 CAR of the invention may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, such as lentiviruses, adenoviruses, adeno associated virus), liposome and the like. For example, transient transformation methods include for example microinjection, electroporation or particle bombardment. Said polynucleotides may be included in vectors, more particularly plasmids or virus, in view of being expressed in cells.

Methods for preparing a vector allowing the CD22 CAR of the invention to be introduced and then expressed into an isolated T cell were described elsewhere, for example in WO2013126720 which is incorporated herein by reference.

Engineered Immune Cells (UCART 22)

An engineered immune cell endowed with a CD22 CAR of the invention (UCART 22) is another object of the present invention.

Preferably said immune cell is an isolated immune cell, more preferably an isolated immune T cell, more preferably an isolated primary immune T cell.

"A primary immune cell" according to the invention means a "cell originating from a tissue such as a blood sample or from peripheral blood mononuclear cells (PBMCs) and that may be in culture for a few passages, eventually frozen before use, said primary immune cell has a limited capacity of division (Raulf-Heimsoth M. T cell—primary culture from peripheral blood. Methods Mol Med. 2008; 138:17-30. doi: 10.1007/978-1-59745-366-0) as compared to a transformed or cancerous cell.

An immune cell according to the invention is preferably an immune T or NK cell. Accordingly, an engineered immune cell according the invention is isolated from a blood sample, is a primary cell and derived from an immune T cell selected from inflammatory T-lymphocytes, cytotoxic T-lymphocytes, regulatory T-lymphocytes or helper T-lymphocytes, Natural Killer T-cell, preferably from cytotoxic T-lymphocytes and further engineered.

Engineered means that primary immune cells are modified so that they will be endowed with a CD22 CAR and at least one gene is edited, preferably said cells are modified so that they will be endowed with a CD22 CAR and will neither express a TCR nor die in the presence of purine nucleotide analogs.

In other word, engineered immune cells means a TCR KO isolated immune T cells comprising at least one other edited gene, expressing CD22 CAR.

In a particular embodiment, engineered means that primary immune cells are modified so that they will be endowed with a CD22 CAR, preferably said cells are modified so that they will be endowed with a CD22 CAR and will not die in the presence of purine nucleotide analogs '1 to 5 micromol/L) or in the presence of alemtuzumab (50 microgram/mL) (Valton et al., Molecular Therapy vol. 23 no. 9, 1507-1518 September 2015).

Preferably, said T cell is endowed with a CD22 CAR of SEQ ID NO. 64.

More preferably, said T cell is endowed with a CD22 CAR of SEQ ID NO. 64 and comprises at least one sequence of SEQ ID NO. 40.

The present invention provides a primary immune T cell expressing a CD22 CAR of the invention and exhibiting a CTL and/or degranulating activity towards a CD22-expressing cell.

The present invention also provides a primary T cell expressing a CD22 CAR of the invention for lysing a CD22-expressing cell, in particular a CD22-expressing cancerous cell.

Preferably T cells endowed with a CD22 CAR of SEQ ID NO. 64 of the invention are efficient in the treatment of relapsed/refractory/aggressive ALL or CLL.

The present invention also relates to isolated cells or cell lines susceptible to be obtained by said method to engineer cells. In particular said isolated cell comprises at least one CD22 CAR of the invention as described above. In another embodiment, said isolated cell comprises more than one CAR; each one comprising a different extracellular ligand binding domain. In particular, said isolated cell comprises exogenous polynucleotide sequence encoding CAR. Genetically modified immune cells of the present invention are activated and can proliferate independently of antigen binding mechanisms.

In the scope of the present invention is also encompassed an isolated immune cell, preferably an isolated immune T cell (T-cell), more preferably an engineered isolated immune T cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, a killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes.

Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a engineered T-cell according to the method described. Modified cells resistant to an immunosuppressive treatment and susceptible to be obtained by the previous method are encompassed in the scope of the present invention.

As a preferred embodiment, the present invention provides T-cells or a population of T-cells endowed with a CD22 CAR of the invention as described above, that do not express functional TCR and that a reactive towards CD22 positive cells, for their adoptive transfer into patients.

As a more preferred embodiment the present invention provides T-cells or a population of T-cells endowed with a CD22 CAR as described above, that do not express functional TCR and that were made resistant to chemotherapy, in particular to purine nucleotide analogues (PNAs).

According to a preferred embodiment of the invention, the immune cells endowed with an CD22 CAR are engineered to be resistant to chemotherapy drugs, in particular to purine nucleotide analogues (PNAs), making them suitable for cancer treatments combining adoptive immunotherapy and chemotherapy.

Purine nucleotide analogues enter chemotherapy compositions for many cancer treatments. It is used as a standard of care against leukemia or lymphoma. The most widely used PNAs are clofarabine, fludarabine and cytarabine alone or in combination. PNAs are metabolized by enzymes having deoxycytidine kinase (dCK) activity [EC 2.7.1.74] into mono, -di and tri-phosphate PNA. Their tri-phosphate forms and particularly clorofarabine triphosphate compete with ATP for DNA synthesis, acts as pro-apoptotic agent and are potent inhibitors of ribonucleotide reductase (RNR), which is involved in trinucleotide production.

The present invention thus includes a method of producing ex-vivo immune cells, preferably primary T-cells expressing no TCR, which are resistant to a purine analogue drug and that can target CD22 positive malignant cells.

A Method for preparing a UCART22 according to the invention can be also that disclosed in WO 2013176915 or in WO 2014191128 which are incorporated herein by reference in entirety.

A method for preparing a UCART22 comprises the following steps:
(a) Providing an immune cell from a donor, preferably an isolated T cell or an isolated population of T cells,
(b) introducing into said immune cell (preferably by transfection or transduction) a nucleic acid sequence encoding a rare-cutting endonuclease specifically targeting
   a gene expressing an enzyme having deoxycytidine kinase activity (dcK-EC 2.7.1.74), in particular the human deoxycytidine kinase gene (NCBI Gene ID: 1633) and/or
   a gene coding one of the TCR subunit alpha and/or beta, preferably alpha, and/or
(c) expressing said endonuclease into said immune cells to obtain targeted inactivation of said gene(s);
(d) Expanding the engineered immune cells obtained in step c), optionally in the presence of a purine analogue drug;
(e) Introducing into said immune cell a polynucleotide coding CD22 CAR of the invention, preferably of SEQ ID NO:40.

In a preferred embodiment, the present invention includes a method of producing ex-vivo immune cells, preferably primary T-cells expressing no TCR, which are resistant to a purine analogue drug and that can target CD22 positive malignant cells. Said method comprises the following steps:
Providing an immune cell from a donor, preferably an isolated T cell (or an isolated population of T cells)
Introducing into said immune cell a CD22 CAR of the invention, preferably of SEQ ID selected from SEQ ID NO: 64.
Expanding the engineered immune cells obtained in step b)
(d) introducing into said immune cell (by transfection or transduction) a nucleic acid sequence encoding a rare-cutting endonuclease specifically targeting
a gene expressing an enzyme having deoxycytidine kinase activity (dcK-EC 2.7.1.74), in particular the human deoxycytidine kinase gene (NCBI Gene ID: 1633) and/or a gene expressing one of the TCR subunit alpha or beta,
(e) expressing said endonuclease into said immune cells to obtain targeted inactivation of said gene(s);
(f) Expanding the engineered immune cells obtained in step e), optionally in the presence of a purine analogue drug.

The method of producing ex-vivo immune cells, preferably primary T-cells expressing no TCR, which are resistant to a purine analogue drug and that can target CD22 positive malignant cells optionally comprises another step of introducing into said immune cell (by transfection or transduction) a nucleic acid sequence encoding a rare-cutting endonuclease specifically targeting one of the gene cited in Table 7, preferably PD-1, CD279 and more preferably PDCD1 (PD-1, CD279) or CTLA4 (CD152).

The present inventors have successfully created CD22 CAR expressing primary T cells resistant to purine nucleotide analogues (dCK-KO), more particularly to clorofarabine and/or fludarabine, by mediating the inactivation (deletion) of dcK gene expression into said cells particularly by using nucleases, in particular TAL-nucleases.

Transfection of the T-cells using mRNA encoding specific TAL-nuclease directed against dCK genes, preferably by using electroporation as described in WO2013176915, induced a significant resistance to the drugs, while maintaining T-cells cytotoxic activity towards CD22 bearing cells.

The present application also provides a TCR-KO, CD22 CAR (preferably of SEQ ID NO 64) primary T-cells, which expression of deoxycytidine kinase has been repressed or inactivated (dCK-KO) for the treatment of leukemia or lymphoma, preferably of their aggressive, resistant, relapsing form; more preferably B-ALL.

According to a preferred embodiment of the invention, the immune cells endowed with an CD22 CAR are engineered to be resistant to chemotherapy drugs, in particular to alemtuzumab (CAMPATH), making them suitable for cancer treatments combining adoptive immunotherapy and chemotherapy.

Alemtuzumab is used for many cancer treatments. It is used as a standard of care against leukemia or lymphoma, in particular in the treatment of chronic lymphocytic leukemia (CLL), cutaneous T-cell lymphoma (CTCL) and T-cell lymphoma. It is known under the trade names Campath, Mab-Campath and Campath-1H. It is also used in some conditioning regimens for bone marrow transplantation, kidney transplantation and islet cell transplantation.

It is a monoclonal antibody that binds to CD52, a protein present on the surface of mature lymphocytes, but not on the stem cells from which these lymphocytes are derived. After treatment with alemtuzumab, these CD52-bearing lymphocytes are targeted for destruction.

Alemtuzumab is also used as second-line therapy for CLL. It was approved by the US Food and Drug Administration for CLL patients who have been treated with alkylating agents and who have failed fludarabine therapy.

The present invention thus includes a method of producing ex-vivo UCART22, thus expressing no TCR, that are resistant to alemtuzumab.

A method for preparing a UCART22 CD52 KO comprises the following steps:
(a) Providing an immune cell from a donor, preferably an isolated T cell or an isolated population of T cells, (b) introducing into said immune cell (preferably by transfection or transduction) a nucleic acid sequence encoding a rare-cutting endonuclease specifically targeting
- a gene coding one of the TCR subunit alpha and/or beta, preferably alpha, and/or
- a gene coding the CD52, (c) expressing said endonuclease into said immune cells to obtain targeted inactivation of said gene(s);

(d) Expanding the engineered immune cells obtained in step c), optionally in the presence of alemtuzumab, (e) Introducing into said immune cell a CD22 CAR of the invention, preferably of SEQ ID NO:40.

In a preferred embodiment, the present invention includes a method of producing ex-vivo immune cells, preferably primary T-cells expressing no TCR, which are resistant to alemtuzumab and that can target CD22 positive malignant cells. Said method comprises the following steps:
- Providing an immune cell from a donor, preferably an isolated T cell (or an isolated population of T cells)
- Introducing into said immune cell a CD22 CAR of the invention, preferably of SEQ ID NO: 40.
- Expanding the engineered immune cells obtained in step b)
- (d) introducing into said immune cell (by transfection or transduction) a nucleic acid sequence encoding a rare-cutting endonuclease specifically targeting
- a gene expressing CD52 and a gene expressing one of the TCR subunit alpha or beta,
- (e) expressing said endonuclease into said immune cells to obtain targeted inactivation of said gene(s);
- (f) Expanding the engineered immune cells obtained in step e), optionally in the presence of a purine analogue drug.

In one embodiment, a method for preparing a UCART22 comprises the following steps:

(a) Providing an immune cell from a donor, preferably an isolated T cell or an isolated population of T cells, (b) introducing into said immune cell (preferably by transfection or transduction)
- a nucleic acid sequence encoding a rare-cutting endonuclease specifically targeting a gene coding one of the TCR subunit alpha and/or beta, preferably alpha, and
- a nucleic acid encoding a sequence to be inserted, preferably coding HIF-1alpha, (c) Expressing said endonuclease into said immune cells to obtain targeted insertion of said sequence to be inserted, (d) Expanding the engineered immune cells obtained in step c), optionally in the presence of low 02 concentration (5% 02, preferably 1% 02);

(e) Introducing into said immune cell a CD22 CAR of the invention, preferably of SEQ ID SEQ ID NO:40.

In a preferred embodiment, the present invention includes a method of producing ex-vivo immune cells, preferably primary T-cells expressing no TCR, which are resistant to a hypoxia and that can target CD22 positive malignant cells. Said method comprises the following steps:
- Providing an immune cell from a donor, preferably an isolated T cell (or an isolated population of T cells)
- Introducing into said immune cell a CD22 CAR of the invention, preferably of SEQ ID NO: 40.
- Expanding the engineered immune cells obtained in step b)
- (d) introducing into said immune cell (preferably by transfection or transduction)
  - a nucleic acid sequence encoding a rare-cutting endonuclease specifically targeting a gene coding one of the TCR subunit alpha and/or beta, preferably alpha, and
  - a nucleic acid encoding a sequence to be inserted coding HIF-1alpha,
- (e) expressing said endonuclease into said immune cells to obtain targeted insertion of said gene(s);
- (f) Expanding the engineered immune cells obtained in step e), optionally in the presence of low 02 concentration (5% 02, preferably 1% 02);

The method of producing ex-vivo immune cells, preferably primary T-cells expressing no TCR, which are resistant to either a purine analogue drug, alemtuzumab or hypoxia and that can target CD22 positive malignant cells optionally comprises another step of introducing into said immune cell (by transfection or transduction) a nucleic acid sequence encoding a rare-cutting endonuclease specifically targeting one of the gene cited in Table 7, preferably (PD-1, CD279) and more preferably PDCD1 (PD-1, CD279) and CTLA4 (CD152).

The present inventors have successfully created CD22 CAR expressing primary T cells resistant to purine nucleotide analogues (dCK-KO), more particularly to clorofarabine and/or fludarabine, by mediating the inactivation (deletion) of dcK gene expression into said cells particularly by using nucleases, in particular TAL-nucleases.

Transfection of the T-cells using mRNA encoding specific TAL-nuclease directed against dCK genes, preferably by using electroporation as described in WO2013176915, induced a significant resistance to the drugs, while maintaining T-cells cytotoxic activity towards CD22 bearing cells.

The same method applies to deletion of human CD52 using specific TALEN as described by the present inventors.

The present application also provides a TCR-KO, CD22 CAR (preferably of SEQ ID NO 64) primary T-cells, which expression of deoxycytidine kinase has been repressed or inactivated (dCK-KO) for the treatment of leukemia or lymphoma, preferably of their aggressive, resistant, relapsing form; more preferably relapsing B-ALL.

Such cells are "universal" T cells (or UCART).

In one embodiment, the present application provides a CD22 CAR (preferably of SEQ ID NO 64) primary T-cells, which expression of deoxycytidine kinase has been repressed or inactivated (dCK-KO) for the treatment of leukemia or lymphoma, preferably of their aggressive, resistant, relapsing form; more preferably relapsing B-ALL after autologous transfer.

In one embodiment, the present application provides a CD22 CAR (preferably of SEQ ID NO 64) primary T-cells, which expression of CD52 has been repressed or inactivated (CD52-KO) for the treatment of leukemia or lymphoma, preferably of their aggressive, resistant, relapsing form; more preferably relapsing B-ALL after autologous transfer.

In one embodiment, the present application provides a CD22 CAR (preferably of SEQ ID NO 64) primary T-cells, which expression of HIF-1Alpha has been increased by insertion of the coding sequence into the TRAC sequence without knocking out the TCR.

for the treatment of leukemia or lymphoma, preferably of their aggressive, resistant, relapsing form; more preferably relapsing B-ALL after autologous transfer In one embodiment, the present application provides a CD22 CAR (preferably of SEQ ID NO 64) primary T-cells, which expression of deoxycytidine kinase and CD52 have been repressed or inactivated (dCK- and CD52KO) for the treatment of leukemia or lymphoma, preferably of their aggressive, resistant, relapsing form; more preferably relapsing B-ALL after autologous transfer. In one embodiment, the present application provides a CD22 CAR (preferably of SEQ ID NO 64) primary T-cells, which expression of deoxycytidine kinase and CD52 have been repressed or inactivated (dCK- and CD52KO) and the expression of HIF-1alpha increased by insertion of the HIF1alpha coding sequence into the TRAC sequence without knocking out the TCR, for the treatment of leukemia or lymphoma, preferably of their aggressive, resistant, relapsing form; more preferably relapsing B-ALL after autologous transfer.

The method of producing ex-vivo immune cells, preferably primary T-cells expressing no TCR, which are resistant to a purine analogue drug and/or to alemtuzumab and/or to hypoxia, that can target CD22 positive malignant cells optionally comprises another step of introducing into said immune cell (by transfection or transduction) a nucleic acid sequence encoding a rare-cutting endonuclease specifically targeting one of the gene cited in Table 7, preferably PD-1, CD279 and more preferably PDCD1 (PD-1, CD279) or CTLA4 (CD152).

The present inventors have successfully created CD22 CAR expressing primary T cells resistant to purine nucleotide analogues (dCK-KO), more particularly to clorofarabine and/or fludarabine, by mediating the inactivation (deletion) of dcK gene expression into said cells particularly by using nucleases, in particular TAL-nucleases.

The present inventors have successfully created CD22 CAR expressing primary T cells resistant to hypoxia, by a targeted insertion of the HIF-1alpha gene into said cells particularly by using nucleases, in particular TAL-nucleases.

Transfection of the T-cells using mRNA encoding specific TAL-nuclease directed against dCK genes, preferably by using electroporation as described in WO2013176915, induced a significant resistance to the drugs, while maintaining T-cells cytotoxic activity towards CD22 bearing cells.

The present application also provides a TCR-KO, CD22 CAR (preferably of SEQ ID NO 64) primary T-cells, resistant to hypoxia for the treatment of leukemia or lymphoma, preferably of their aggressive, resistant, relapsing form; more preferably B-ALL.

The UCART 22 is provided as a medicament, thus a therapeutically efficient amount of UCART 22 is provided as a medicament.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Pharmaceutical Composition

A pharmaceutical composition comprising an engineered (TRAC KO) or (TRAC and CD52 KO) immune T cell expressing a CD22 CAR of the invention (preferably of SEQ ID NO: 64) and a pharmaceutically acceptable vehicle is another object of the present invention.

A pharmaceutical composition comprising an engineered (TRAC KO) or (TRAC and dCK KO) immune T cell expressing a CD22 CAR of the invention (preferably of SEQ ID NO: 64) and a pharmaceutically acceptable vehicle is another object of the present invention.

In another embodiment the present invention provides a composition comprising the UCART22 of the present invention (as any one of the above embodiments) with a compound of the family of the bryostatin compounds, preferably bryostatin-1.

Bryostatins are a group of macrolide lactones from bryozoan, Bugula neritina. The structure of bryostatin 1 was determined in 1980's. To date 20 different bryostatins have been isolated; further, certain analogs of bryostatin have been referred to as "bryologs". Bryostatins are potent modulators of protein kinase C. (Wender, Paul A., Jeremy L. Baryza, Chad E. Bennett, F. Christopher Bi, Stacey E. Brenner, Michael O. Clarke, Joshua C. Horan, Cindy Kan, Emmanuel Lacote, Blaise Lippa, Peter G. Nell, and, and Tim M. Turner. The Practical Synthesis of a Novel and Highly Potent Analogue of Bryostatin. Journal of the American Chemical Society 2002 124 (46), 13648-13649 DOI: 10.1021/ja027509+).

Examples of bryostatin compounds suitable to be compibed with the UCART22 of the invention and methods for preparing these compounds are described in WO2001040214A1 or in EP2737904A2, WO1997034598 incorporated here by reference.

An example of a dose of bryostatin-1 that may be used in combination with the UCART22 of the present invention is as previously described in Varterasian ML1, Mohammad R M, Shurafa M S, Hulburd K, Pemberton P A, Rodriguez D H, Spadoni V, Eilender D S, Murgo A, Wall N, Dan M, Al-Katib A M. Phase II trial of bryostatin 1 in patients with relapsed low-grade non-Hodgkin's lymphoma and chronic lymphocytic leukemia. Clin Cancer Res. 2000 March; 6(3): 825-8.

An engineered (TRAC and dCK KO or TRAC and CD52 KO) immune T cell expressing a CD22 CAR of the invention (preferably of SEQ ID NO: 64) [an UCART22] or a pharmaceutical composition comprising said UCART22 is provided as a medicament. An engineered (TRAC and dCK KO or TRAC and CD52 KO) immune T cell expressing a CD22 CAR of the invention (preferably of SEQ ID NO: 64) [an UCART22] for use in the treatment of cancer or to attenuate inflammation is another object of the present invention.

An engineered (TRAC and dCK KO or TRAC and CD52 KO) immune T cell expressing a CD22 CAR of the invention (preferably of SEQ ID NO: 64) [an UCART22] for use in the treatment of ALL, CLL, relapse refractory aggressive forms of CLL or ALL is another object of the present invention.

An engineered (TRAC and dCK KO or TRAC and CD52 KO) immune T cell expressing a CD22 CAR of the invention (preferably of SEQ ID NO: 64) [an UCART22] for use in the treatment of a CD19 relapse cancer, preferably a CD19 relapse B-ALL is provided.

In another embodiment, hypoxia resistant, engineered (TRAC and dCK KO or TRAC and CD52 KO) immune T cell expressing a CD22 CAR of the invention (preferably of SEQ ID NO: 64) [an UCART22] or a pharmaceutical composition comprising said UCART22 is provided as a medicament.

In another embodiment, hypoxia resistant, engineered (TRAC and dCK KO or TRAC and CD52 KO) immune T cell expressing a CD22 CAR of the invention (preferably of SEQ ID NO: 64) [an UCART22] for use in the treatment of cancer or to attenuate inflammation is another object of the present invention.

In another embodiment hypoxia resistant, engineered (TRAC and dCK KO or TRAC and CD52 KO) immune T cell expressing a CD22 CAR of the invention (preferably of SEQ ID NO: 64) [an UCART22] for use in the treatment of ALL, CLL, relapse refractory aggressive forms of CLL or ALL is another object of the present invention.

In another embodiment hypoxia resistant, engineered (TRAC and dCK KO or TRAC and CD52 KO) immune T cell expressing a CD22 CAR of the invention (preferably of SEQ ID NO: 64) [an UCART22] for use in the treatment of a CD19 relapse cancer, preferably a CD19 relapse B-ALL is provided.

In another embodiment, isolated cell obtained by the different methods of the present invention or cell line derived from said isolated cell can be used as a medicament. In another embodiment, said medicament can be used for treating cancer, particularly for the treatment of B-cell lymphomas and leukemia in a patient in need thereof. In another embodiment, said isolated cell according to the invention or cell line derived from said isolated cell can be used in the manufacture of a medicament for treatment of a cancer in a patient in need thereof.

The present invention encompasses autologous transfer of engineered cells. In that case cells are isolated from one donor, a human donor, engineered and then transferred to the initial donor in need thereof.

In this particular embodiment, cells may be engineered for example to be resistant to a drug such as alemtuzumab (campath) and/or dCK and optionally to be resistant to hypoxia.

Therapeutic Applications

The term "cancer" refers to a disease characterized by the uncontrolled growth of one or several types of cells.

Examples of cancers are described herein and, include but are not limited to liquid tumors or hematological cancer.

A hematological cancer according to the present invention may be selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22-expressing hematological cancer, more preferably a relapse or refractory CD22-expressing hematological cancer, even more preferably an aggressive form of said CD22-related hematological cancer.

In a preferred embodiment, a relapsed or refractory CD22-expressing hematological cancer is relapsed and/or refractory CD22 expressing or positive B-ALL.

Accordingly, a therapeutically effective amount of UCART 22 according to any one of the embodiments described above or a therapeutically effective amount of the pharmaceutical composition as described above is provided for use as a medication for treating a patient suffering a relapsed and/or refractory CD22 expressing or positive B-ALL.

In another embodiment a therapeutically effective amount of UCART 22 according to any one of the embodiments described above or a therapeutically effective amount of the pharmaceutical composition as described above is provided for use as a medication for treating a patient suffering a CD22 positive hematological cancer selected from leukemia and lymphoma, hairy cell leukemia, any of acute lymphocytic cancer, acute lymphocytic leukemia (ALL), acute myeloid leukemia, chronic lymphocytic leukemia, B-chronic lymphocytic leukemia, chronic myeloid cancer, Hodgkin lymphoma, non-Hodgkin lymphoma, and Burkitt's lymphoma, multiple myeloma.

In another embodiment a therapeutically effective amount of UCART 22 according to any one of the embodiments described above or a therapeutically effective amount of the pharmaceutical composition as described above is provided for use as a medication for treating a patient suffering a CD22 positive cancer selected from alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, cancer of the gallbladder, cancer of the pleura, cancer of the nose, cancer of the nasal cavity, cancer of the middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), hypopharynx cancer, kidney cancer, larynx cancer, liver cancer, lung cancer (e.g., non-small cell lung carcinoma), malignant mesothelioma, mastocytoma, melanoma, nasopharynx cancer, ovarian cancer, pancreatic cancer, peritoneum cancer, omentum cancer, mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer.

Other Examples of CD22-mediated cancers are described herein and, include but are not limited to liver cancer, lung cancer (e.g., non-small cell lung carcinoma), ovarian cancer, pancreatic cancer, thyroid cancer, and urothelial cancer.

In a particular embodiment, the object of the present invention is provided for the treatment of aggressive forms of these cancers, defined as growing at least 2 times faster than the general mean of growth of such cancers in the population.

In one embodiment the objects of the present invention are used in the treatment of leukemia during the accelerated phase of the treatment.

In a particular embodiment, the object of the present invention is provided for the treatment of Refractory/Relapsed Diffuse Large B-Cell Non-Hodgkin's Lymphoma—Breast metastasis in lung-Triple cancer consisting of chronic lymphocytic leukemia with bladder and prostate carcinoma.

Preferably, the cancer is a hematological malignancy (e.g., leukemia or lymphoma, including but not limited to Hodgkin lymphoma, non-Hodgkin lymphoma, chronic lymphocytic leukemia, acute lymphocytic cancer, acute myeloid leukemia, B-chronic lymphocytic leukemia, hairy cell leukemia, acute lymphocytic leukemia (ALL), and Burkitt's lymphoma).

More preferably, the cancer is characterized by the expression of CD22, more preferably, the cancer is characterized by the expression of CD22 by cancerous cells, even more preferably by overexpression of CD22 by cancer cells.

In one embodiment said cancer cells are a relapsed refractory CD19 negative cancer cells.

In one embodiment said cancer cells are a relapsed refractory CD22 expressing cancer cells.

In a preferred embodiment said cancer cells are a relapsed refractory CD19 negative CD22 positive expressing B-ALL.

B-cell ALL comprises:

Early precursor B (early pre-B) ALL (also called pro-B ALL)
Common ALL
Pre-B ALL
Mature B-cell ALL also called Burkitt leukemia or Non-Hodgkin Lymphoma in Children.

The term "disease associated with expression of CD22" as used herein includes, but is not limited to, a disease associated with expression of CD22 or condition linked to the activity of cells which express CD22 including, tumor cells of various cancers such as, e.g., a CD22 expressing B-ALL.

Cellular destruction by lyse is one of the mechanisms whereby the CD22 CAR T cells of the invention acts against CD22-expressing cells, reducing or eliminating tumors, facilitating infiltration of immune cells of the hosts to the tumor site, and enhancing/extending anti-tumor responses.

In another aspect, the present invention relies on methods for treating patients in need thereof, said method comprising at least one of the following steps:
providing an UCART22 of the invention
Administrating said transformed immune cells to said patient, In one embodiment, said UCART22 cells of the invention can undergo robust in vivo T cell expansion and can persist for an extended amount of time in the host.

In another aspect, the present invention provides methods for treating patients in need thereof, said method comprising at least one of the following steps:
Conditioning a patient suffering a cancer
providing an UCART22 of the invention
Administrating said transformed immune cells to said patient,
Conditioning includes lymphodepletion, or any appropriate conditioning a skilled person, preferably also a Medical Doctor, will recognize as determinant for curing said patient.
In a preferred embodiment said method further comprises a step of bone marrow transplantation.

In one embodiment, said UCART22 cells of the invention can undergo robust in vivo T cell expansion and can persist for an extended amount of time in the host.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In one embodiment, survival of said T cells of the invention in the host is controlled using an anti CD20 (rituximab) and/or QBEND-10 treatment.

Subject

Compositions and methods of the present invention may be used to treat a subject who has been characterized as having pathological cells or tissues expressing CD22, or is suspected of having pathological cells or tissues expressing CD22. For example, subjects benefiting from treatment according to the invention include subjects with B-ALL or CLL, refractory BALL, relapse B-ALL.

In a preferred embodiment the patients are children suffering BALL, relapsed BALL, refractory BALL.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

Accordingly, the present invention provides a pharmaceutical composition comprising a therapeutically active amount of UCART22 for the treatment of children suffering BALL, relapsed BALL, refractory BALL.

The present invention also provides a pharmaceutical composition comprising a UCART22 and a pharmaceutically acceptable excipient for the treatment of children suffering BALL, relapsed BALL, refractory BALL.

In a preferred embodiment, a pharmaceutical composition comprises the UCART22 of the invention and a compound of the bryostatin family, preferably bryostatin-1 and a pharmaceutically acceptable excipient for the treatment of children suffering BALL, relapsed BALL, refractory BALL.

According to a preferred embodiment of the invention, said treatment can be administrated into patients undergoing an immunosuppressive treatment, (conditioning treatment), more preferably a lymphodepletion. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment or lymphodepletion should help the selection and expansion of the T-cells according to the invention within the patient and destruction of CD22 cancerous cells.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses, preferably several successive doses (redosing) to avoid escaping (relapsed cells). In another embodiment, said effective amount of cells are administrated as a single dose or in to doses. In another embodiment, said effective amount of cells are administrated as more than one dose over a period time.

Timing of administration is within the judgment of managing physician and depends on the clinical condition of the patient.

The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

The present UCART22 are design to be efficient but for being not to active and limit cytokine storm. In case of overresponding patients, the present invention may be combined with adequate medication for preventing of blocking cytokine storm such as anti IL-6 drugs.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, alemtuzumab, anti-CD3 antibodies or other antibody therapies, cytoxin, fludarabine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p7056 kinase that is important for growth factor induced signaling (rapamycin) (Henderson, Naya et al. 1991; Liu, Albers et al. 1992; Bierer, Hollander et al. 1993).

In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., RITUXAN® or QBEND-10. For example, in one embodiment, subjects may undergo standard treatment with high dose chemotherapy followed by peripheral blood cell transplantation. In certain embodiments, following the transplant, subjects receive an infusion of the expanded immune cells of the present invention. In an additional embodiment, expanded cells are administered before or following surgery.

In another embodiment, following the transplant, subjects receive an agent that react with CD20, e.g., RITUXAN® (rituximab), preferably with an agent that reacts with CD22 and CD20.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against CD22 antigen and can comprise as non-limiting example the amino acid sequences: SEQ ID NO: 46 to 69, preferably SEQ ID NO.54 or SEQ ID NO.64, more preferably SEQ ID NO.64.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Custom-made TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracr RNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses, in particular aav6), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. CD28 is excluded from this list. A co-stimulatory ligand also encompasses, inter alia, an antibody that specifically binds with a co-stimulatory molecule present on a T cell, such as but not limited to, CD27, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans, preferably human. In one embodiment patients are Patients with aggressive, or refractory or relapsing ALL, or, aggressive, refractory, relapsing CLL.

A mammal is any warm-blooded vertebrate of the class Mammalia, preferably a human.

"Suicide domain or switches," or safety on-and-off switches" means a domain usually a cell surface domain recognized by a molecule, protein, chemical, antibody for immunoselecting expressing cells and eventually controlling their functioning and survival.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

General Methods
Screening and Selection of CAR
Primary T-Cell Cultures

T cells were purified from Buffy coat samples provided by EFS (Etablissement Francais du Sang, Paris, France) using Ficoll gradient density medium. The PBMC layer was recovered. T cells were activated in X-Vivo™-15 medium (Lonza) supplemented with 20 ng/mL Human IL-2, 5% Human, and Dynabeads Human T activator CD3/CD28 at a bead:cell ratio 1:1 (Life Technologies).

CAR mRNA Transfection

Transfections of CAR mRNAs encoding each CAR constructs were done at Day 4 or Day 11 after T-cell purification and activation. Cells were immediately diluted in X-Vivo™-15 media and incubated at 37° C. with 5% CO2. IL-2 was added 2h after electroporation at 20 ng/mL.

T-Cell Transduction

Vectors coding a CD22 CAR are introduced into T cells as previously described.

CAR detection at the surface of T-cells is performed using a recombinant protein consisting on the extracellular domain of the human CD22 protein (whole protein, distal portion of CD22 or proximal portion of CD22) fused together with a murine IgG1 Fc fragment. Binding of this protein to the CAR molecule is detected with a PE-conjugated secondary antibody (Jackson Immunoresearch) targeting the mouse Fc portion of the protein, and analyzed by flow cytometry.

Inactivation of Specific Gene(s) in Primary T Cells

Inactivation of specific gene(s) in primary T cells may be performed before preferably after CD22 CAR introduction into cells using endonucleases such as TAL endonuclease, optionally Crispr Cas 9 endonucleases, designed accordingly. At least one gene is inactivated, one, two or three genes may be inactivated in one step or in several successive step. In a preferred embodiment two genes are inactivated, preferably TCRalpha gene and a gene which deletion confers resistance to a drug selected from purine nucleotide analogues, alemtuzumab, platines (cisplatine or carboplatine), anti-topoisomerase I (Irinotecan), anti-topoisomerase II (Etoposide), Methotrexate (folic acid analogs), preferably purine nucleotide analogues, alemtuzumab.

In general, heterodimeric nuclease, in particular TALE-Nuclease targeting two long sequences (called half targets) separated by a spacer within a target gene is designed and produced.

Each TALE-nuclease construct may be cloned in an appropriate mammalian expression vector. mRNA encoding TALE-nuclease cleaving a targeted genomic sequence may be synthesized from plasmid carrying the coding sequence downstream a promoter. Purified T cells preactivated with anti-CD3/CD28 coated beads are used and transfected with each of the 2 mRNAs encoding both half TALE-nucleases. Cells may be reactivated with soluble anti-CD28 to measure cell proliferation for various times and the activation marker CD25 detected to assess the activation state of the cells.

Degranulation Assay (CD107a Mobilization)

Cells were incubated in 96-well plates, together with an equal amount of cells expressing various levels of the targeted protein (CD22). Co-cultures were maintained for 6 hours at 37° C. with 5% $CO_2$. CD107a staining was done during cell stimulation, by the addition of a fluorescent anti-CD107a antibody at the beginning of the co-culture, together with an anti-CD49d, anti-CD28, and 1× Monensin solution, as a control. After the 6h incubation period, cells were stained with a fixable viability dye and fluorochrome-conjugated anti-CD8 and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection.

IFN Gamma Release Assay 24 h after mRNA transfection, CD22 CAR expressing T-cells were incubated together with cell lines expressing various levels of the targeted protein for 24 hours at 37° C. The supernatants were recovered and IFN gamma detection in the cell culture supernatants was done by ELISA assay.

Cytotoxicity Assay

Cells were incubated together with target cells (expressing different levels of CD22) or (negative control) cells. Target and control cells were labelled with fluorescent intracellular dyes (CFSE or Cell Trace Violet) before co-culturing them with CAR+ T-cells. The co-cultures were incubated for 4 hours at 37° C. After this incubation period, cells were labelled with a fixable viability dye and analyzed by flow cytometry. Viability of each cellular population (target cells or negative control cells) was determined and the % of specific cell lysis was calculated. Cytotoxicity assays were carried out 48h after mRNA transfection.

Anti-Tumor Mouse Model

Immuno deficient mice are implanted with tumor cells (CD22 BALL from patients) or with targeted protein expressing-Luciferase cells into the flank. Subsequently, cells were implanted into mouse brains. Serial transplantation into further generations of mice continues the maintenance of in vivo xenograft cell lines. Optionally, mice received an anti-cancer treatment before/or together with injection with CAR+ T-cells (alemtuzumab and/or flu). Mice are then iv injected (either 2 or 7 days after injection of the tumor cell line) with different doses of CAR+ T-cells to be tested, or with T-cells that were not expressing CD22CAR. Bioluminescent signals are determined at the day of T-cell injection (D0), at D7, 14, 21, 28 and 40 after T-cell injection in order to follow tumoral progression in the different animals.

In this model, the anti-CD22 CAR of the invention completely cleared the CD22+ cancer cells ($1\times10^6$ cells and $5\times10^6$ cells).

Phase I dose-escalation study to evaluate the safety, expansion and persistence of allogeneic CD22 CART (UCART22) in patients with relapsed or refractory or MRD+CD22+ B-cell acute lymphoblastic leukemia (B-ALL).

Background and Rationale

With the current multi-drug chemotherapy regimens, long term survival is seen in >80% of childhood acute lymphoblastic leukemia (ALL) and in approximately 40% of adult ALL. (1) Further intensification of chemotherapy has not proved to be effective. (2) There has been significant advancement in our understanding of the biology of ALL in the last few years which provides an opportunity for 'targeted therapy'. (3, 4)

Relapse/refractory ALL remains a challenging disease. Post-relapse therapies will lead to a second CR (CR2) in 30-40% of patients with a 5-year OS of only around 10%. In the largest report of relapsed adult ALL patients to date, Fielding and colleagues analyzed the outcomes of relapsed adult ALL patients who were treated on the MRC UKALLXII/ECOG E2993 trial. (5) Of the 1508 evaluable patients, 1372 (91%) achieved CR1 of whom 609 (44% of the CR1 patients) relapsed at a median of 11 months. The 5-year OS was only 7% for the relapsed patients. The median OS for the relapsed patients was 5.5 months. Tavernier and colleagues reported outcomes of 421 ALL patients who experienced first relapse treated on the French LALA-94 trial. (6) A CR2 was achieved in 44% patients with a median DFS of 5.2 months and median OS of 6.3 months. Oriol and colleagues reported the outcomes of 263 ALL patients in first relapse treated on 4 consecutive PETHEMA trials. (7) CR2 was achieved in 45% of patients, a rate similar to the French LALA trials. The median OS was after relapse was 4.5 months with a 5-year OS of 10%.

CD22 expression occurs in >90% of patients with ALL, and is a valid therapeutic target. Cellular therapies such as chimeric antigen receptor (CAR) T cell therapies are increasingly being used to treat patients with hematologic malignancies. (8-16) In patients with relapsed acute lymphoblastic leukemia (ALL), a very high complete response rate (80-90%) have been reported with autologous CD19-CART cells. (12) Similarly, response rate of 40-50% is seen in patients with relapsed chronic lymphocytic leukemia (CLL) undergoing autologous CD19 CART therapies. (9)

The present study evaluates allogeneic CART cells directed to CD22 in patients with relapsed and/or refractory CD22 B-ALL.

Objectives

Primary Objectives

To evaluate the safety and tolerability of allogeneic CD22 CART and to determine the maximum tolerated dose (MTD)

Secondary Objectives

To determine the efficacy of allogeneic CD22 CART

To determine the incidence of GVHD

Exploratory Objectives

To determine the expansion, phenotype, trafficking and persistence of infused CART cells Inclusion Criteria 1. Relapsed or refractory CD22-positive ALL (For expansion phase: patients with MRD+ disease are allowed)
2. Patients aged years
3. ECOG performance status
4. Normal organ function including bilirubin mg/dl, ALT/AST <3×ULN, and creatinine mg/dl
5. Left Ventricle Ejection Fraction (LVEF) 40%

Exclusion Criteria

1. Patient is pregnant or breastfeeding
2. Patients with uncontrolled active infections
3. Isolated extramedullary relapse (i.e. testicular, CNS)
4. Known active CNS leukemia. Note: Patients with history of CNS disease that has been effectively treated will be eligible provided that they have been in CNS remission >4 weeks before enrollment
5. Active hepatitis B or active hepatitis C
6. HIV infection
7. Active GVHD requiring systemic steroid therapy. Steroid therapy for physiologic replacement is acceptable.
8. Received a DLI within 4 weeks of CD22 CART infusion
9. Allo-SCT within 60 days of CD22 CART infusion Description of Study This is Phase I study. There are 2 phases to this trial. Dose escalation, and Dose expansion.

Patients receive CD22 allogeneic CART after receiving lymphodepletion chemotherapy.

Dose-escalation: Four dose levels are studied in a standard 3×3 design. A total of 9-18 patients are be enrolled.

TABLE 8

| Dose Level | UCART22 cells/kg |
|---|---|
| −1 | $1 \times 10^4$ |
| 1 (Starting dose) | $1 \times 10^5$ |
| 2 | $1 \times 10^6$ |
| 3 | $5 \times 10^6$ |

Once the R2PD level is identified, dose-expansion starts.
A total of 20 patients are then enrolled (10 R/R ALL; 10 MRD+ post-SCT).
Total sample size: 29-38 patients

TABLE 9

| Number of Patients with DLT at a Dose Level | Decision |
|---|---|
| 0 of 3 | Escalate and evaluate in 3 subsequent patients. |
| 1 of 3 | Enroll 3 additional subjects at this dose level. |
| >/=2 of 3 | The MTD has been exceeded. Dose escalation will stop and this level will be declared the maximum administered dose. Evaluate 3 additional patients at the prior dose level if only three were treated at that dose previously. |
| 1 of 6 | Escalate dose and evaluate in 3 subsequent patients. |
| </=1 out of 6 at the Highest Dose Below the Maximum Administered Dose | This is the MTD. |
| >/=2 of 6 | The MTD has been exceeded. Dose escalation will stop and this level will be declared the maximum administered dose. Evaluate 3 additional patients at the prior dose level if only three were treated at that dose previously. |

REFERENCES

1. Inaba H, Greaves M, Mullighan C G. Acute lymphoblastic leukaemia. Lancet. 2013; 381(9881):1943-55.
2. Faderl S, Thomas D A, O'Brien S, Ravandi F, Garcia-Manero G, Borthakur G, et al. Augmented hyper-CVAD based on dose-intensified vincristine, dexamethasone, and asparaginase in adult acute lymphoblastic leukemia salvage therapy. Clin Lymphoma Myeloma Leuk. 2011; 11(1):54-9.
3. Mullighan C G. Genome sequencing of lymphoid malignancies. Blood. 2013; 122(24):3899-907.
4. Mullighan C G. Genomic characterization of childhood acute lymphoblastic leukemia. Semin Hematol. 2013; 50(4):314-24.
5. Fielding A K, Richards S M, Chopra R, Lazarus H M, Litzow M R, Buck G, et al. Outcome of 609 adults after relapse of acute lymphoblastic leukemia (ALL); an MRC UKALL12/ECOG 2993 study. Blood. 2007409(3):944-50.
6. Tavernier E, Boiron J M, Huguet F, Bradstock K, Vey N, Kovacsovics T, et al. Outcome of treatment after first relapse in adults with acute lymphoblastic leukemia initially treated by the LALA-94 trial. Leukemia: official journal of the Leukemia Society of America, Leukemia Research Fund, U. K. 2007; 21(9):1907-14.
7. Oriol A, Vives S, Hernandez-Rivas J M, Tormo M, Heras I, Rivas C, et al. Outcome after relapse of acute lymphoblastic leukemia in adult patients included in four consecutive risk-adapted trials by the PETHEMA Study Group. Haematologica. 2010; 95(4):589-96.
8. Kochenderfer J N, Wilson W H, Janik J E, Dudley M E, Stetler-Stevenson M, Feldman S A, et al. Eradication of B-lineage cells and regression of lymphoma in a patient treated with autologous T cells genetically engineered to recognize CD19. Blood. 2010; 116(20):4099-102.
9. Porter D L, Levine B L, Kalos M, Bagg A, June C H. Chimeric antigen receptor-modified T cells in chronic lymphoid leukemia. N Engl J Med. 2011; 365(8):725-33.
10. Brentjens R J, Davila M L, Riviere I, Park J, Wang X, Cowell L G, et al. CD19-targeted T cells rapidly induce molecular remissions in adults with chemotherapy-refractory acute lymphoblastic leukemia. Sci Transl Med. 2013; 5(177):177ra38.
11. Grupp S A, Kalos M, Barrett D, Aplenc R, Porter D L, Rheingold S R, et al. Chimeric antigen receptor-modified T cells for acute lymphoid leukemia. N Engl J Med. 2013; 368(16):1509-18.
12. Maude S L, Teachey D T, Porter D L, Grupp S A. CD19-targeted chimeric antigen receptor T-cell therapy for acute lymphoblastic leukemia. Blood. 2015; 125(26): 4017-23.
13. Park J H, Geyer M B, Brentjens R J. CD19-targeted CAR T-cell therapeutics for hematologic malignancies: interpreting clinical outcomes to date. Blood. 2016; 127 (26):3312-20.
14. Lee D W, Kochenderfer J N, Stetler-Stevenson M, Cui Y K, Delbrook C, Feldman S A, et al. T cells expressing CD19 chimeric antigen receptors for acute lymphoblastic leukaemia in children and young adults: a phase 1 dose-escalation trial. Lancet. 2015; 385(9967):517-28.
15. Kochenderfer J N, Dudley M E, Kassim S H, Somerville R P, Carpenter R O, Stetler-Stevenson M, et al. Chemotherapy-refractory diffuse large B-cell lymphoma and indolent B-cell malignancies can be effectively treated with autologous T cells expressing an anti-CD19 chimeric antigen receptor. J Clin Oncol. 2015; 33(6):540-9.
16. Kebriaei P, Singh H, Huls M H, Figliola M J, Bassett R, Olivares S, et al. Phase I trials using Sleeping Beauty to generate CD19-specific CART cells. J Clin Invest. 2016; 126(9):3363-76.

Results

Example 1: Proliferation of TCR Alpha Inactivated Cells Expressing a CD22-CAR

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 10.

TABLE 10

TAL-nucleases targeting TCR alpha gene

| Target | Target sequence | Repeat sequence | Half TALE-nuclease |
|---|---|---|---|
| TRAC_T01 | TTGTCCCACAGATATCC Agaaccctgaccctg | Repeat TRAC_ T01-L | TRAC_T01-L TALEN (SEQ ID NO: 19) |
| | CCGTGTACCAGCTGAGA (SEQ ID NO: 70) | Repeat TRAC_ T01-R | TRAC_T01-R TALEN (SEQ ID NO: 20) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with anti-CD3/CD28 coated beads were transfected with each of the 2 mRNAs encoding both half TRAC T01 TALE-nucleases. 48 hours post-transfection, different groups of T cells from the same donor were respectively transduced with a lentiviral vector encoding one of the CD22 CAR previously described. 2 days post-transduction, $CD3_{NEG}$ cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. Increased proliferation in TCR alpha inactivated cells expressing the CD22 CARs, especially when reactivated with anti-CD28, was observed compared to non-transduced cells.

To investigate whether the human T cells expressing the CD22 CAR display activated state, the expression of the activation marker CD25 are analyzed by FACS 7 days post transduction. The purified cells transduced with the lentiviral vector encoding CD22 CAR assayed for CD25 expression at their surface in order to assess their activation in comparison with the non-transduced cells. Increased CD25 expression is expected both in CD28 reactivation or no reactivation conditions.

Safe engineering of UCART cells was checked as described in ASGCT 2017. Brian W. Busser, Sonal Temburni, Aymeric Duclert, Philippe Duchateau and Laurent Poirot.

Genome-wide Analysis of TALEN® Activity in Primary Cells

Example 2: CD22 CAR-T

Development of engineered CAR T-cells targeting CD22, for the treatment of refractory, relapsing or aggressive ALL or CLL.

CD22 CARs:

CD22 CARs were designed and prepared using different VH and VL for preparing new scfv. The m971 scfv is derived from 971 antibody (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B-cell precursor acute lymphoblastic leukemia. Blood. 2013 Feb. 14; 121(7):1165-74. doi: 10.1182/blood-2012-06-438002. Epub 2012 Dec. 14).

The general CARs architecture (V3) was constructed with the 41BB costimulatory domain, the CD3ζ activation domain, the CD8α transmembrane domain and a hinge, CD8α hinge. Constructions comprising a FcγRIIIα-hinge (V1) correspond to (SEQ-ID NO:3) were also made. Constructs were inserted into a vector (retrovirus lentiviral vector) for stable expression and screening of designed CARs Wt CD22 CARs was m971-V3 CAR (SEQ ID NO.18) also CAR number 16.

CAR 17 recognizes the distal part of CD22 and is from HA22.

Sequences were also optimized for CD22 binding and the treatment of ALL and CLL, preferably their refractory relapsing and aggressive forms.

CAR Expression

CD22 CARs were introduced into primary T cells 5 days after activation by anti-CD3CD28 coated beads and IL-2. CAR expression was assessed by flow cytometry. All CARs were expressed at the cell surface.

Activity towards CD22+ transformed cell lines and refractory or relapsed CD22+ B ALL from patients.

To test the functionality of the anti-CD22 CARs, B Cell expressing CD22 (ALL lines REH, SEM, NALM6-GL, KOPN8, Daudi, Raji, and on K562 were used (see Haso et al., 2013, 2013; Blood: 121 (7): 1165-1174 for experimental details). Refractory and relapsed CD22+ B ALL were obtained from patients.

As expected, all cells expressing CD22 were positively stained and targeted by the CD22 CAR of the invention, with an increased activity or equivalent (degranulation and CTL) when using variants or m971 derived CD22 CAR expressing cells of the invention as compared to wt CD22 m971 CAR. Surprisingly particular variants were slightly less active in lysing target cells and inducing IFNgamma as compared to wt CD22 CAR (HA22, scfv against the distal part of CD22) and CD22 CAR derived from m971.

Degranulation Assay

To validate the CD22 CAR constructs a degranulation assay was performed on target cells with T cells expressing the CD22 CARs of the invention. The CART degranulation was evaluated by flow cytometry. The read-out is the CD107a expression at the T cell plasma membrane after 5 hours incubation with target cells. The results showed that the CARs m971- and variants were able to degranulate CD22 expressing cells as compared to previous CD22 CART cells.

Cytotoxicity Assay

Figure 6:
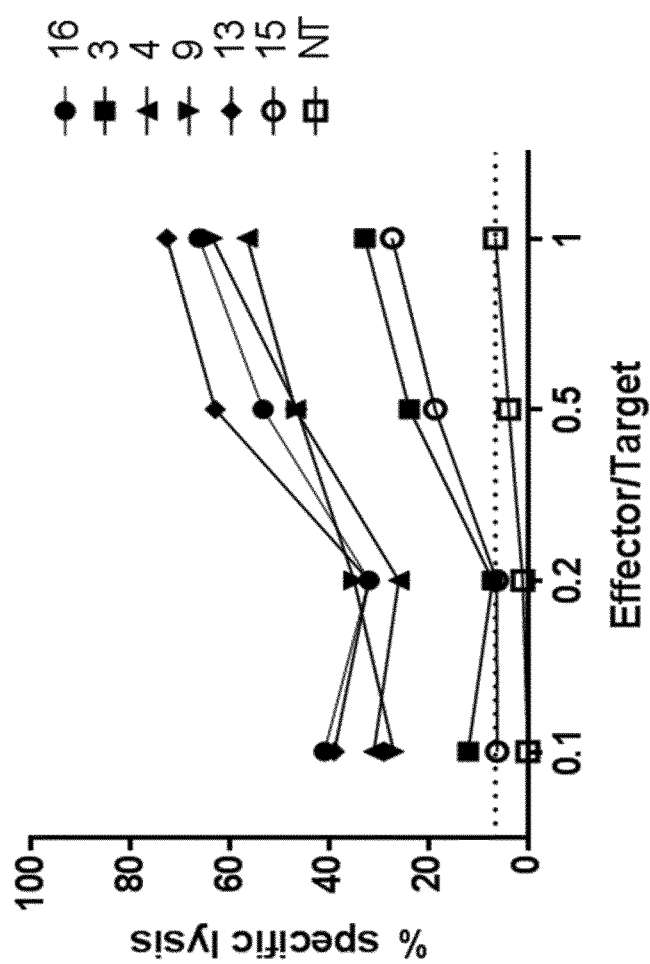
FIG. 6: Cytolytic activity of T cells expressing the CARs specific for CD22 of the invention at various effector/target ratios.

A cytotoxicity assay was performed on these same target cells with T cells expressing CD22 CARs of the invention. CD22 CARs, showed a strong specific lysis of CD22 cells (FIG. 6).

Interferon Gamma Assay

Interestingly, variants induced less amount of IFNgamma as compared to m971 derived CAR.

Resistance to Hypoxia and/or Drugs

Engineered cells of the invention were not significantly affected (survival and CTL activity) in the presence of alemtuzumab (50 microgramme/mL), or PNA (flu) as compared to non engineered cells which died 48 hours following addition of the drug in the cell culture, or following culture condition under hypoxia (less than 5%, preferably less than 1% 02).

Tests performed under low 02 condition (<5% or <1%) generated similar results and confirmed that UCART22 with increase HIF-1a expression can survive, express CD22 CAR and be active under hypoxia.

Similar results (survival, CTL activity) were obtained in mice treated with campath (50 microgramme/mL) confirming the resistance of UCART22 to drugs. The possibility for the UCART22 cells of the invention to reach cancer cells nested in tissues or to reach cancer cells making clusters in vivo is suggested, as the amount of cancer cells "recovering" or "escaping" the treatment with UCART22 was much less (about 15% decrease) than in mice treated with UCART22 non resistant to 02. It seems therefore that a local hypoxia created by liquid tumors may prevent immune cells to fight them.

Examples of CD22 CAR Polypeptide Sequences:

Framed sequences correspond to preferred VH and VL sequences. VH and VL may be swapped (modification in hot spot) to improve CAR efficiency as described above

```
v1-m972 (FcγRIIIα-CD8αTM-41BB.IC-CD3ζ.IC) (Control not part of the invention)
                                                                    (SEQ ID NO: 127)
MALPVTALLPLALLLHAARPEVQLVQSGGGVVRPGGSLRLPCAASGFTFDDYGMSWVRQAPGKGLEWVSGINW

NGGSTGYADSVKGRFTISRDNAKNSLYLQMNSLRAEDTALYHCARGGDDAFDIWGQGTMVTVSSGGGGSGGGG

SGGGGSRIVMTQSPGTLSVSPGETATLSCRASQSFSNMLAWYQQKSGQPPRLLIYGVSTRAAGVPARFSGSGSGTE

FTLTISNLQSEDFAVYYCQQYGDWPRYTFGQGTKVERKGLAVSTISSFFPPGYQIYIWAPLAGTCGVLLLSLVITLYCK

RGRKKLLYIFKQPFMRPVQTTQEEDGCSCRFPEEEEGGCELRVKFSRSADAPAYQQGQNQLYNELNLGRREEYDVL

DKRRGRDPEMGGKPRRKNPQEGLYNELQKDKMAEAYSEIGMKGERRRGKGHDGLYQGLSTATKDTYDALHMQA

LPPR

V3-m972 (CD8α-CD8αTM-41BB.IC-CD3ζ.IC) (control not part of the invention)
                                                                    (SEQ ID NO: 128)
MALPVTALLPLALLLHAARPEVQLVQSGGGVVRPGGSLRLPCAASGFTFDDYGMSWVRQAPGKGLEWVSGINW

NGGSTGYADSVKGRFTISRDNAKNSLYLQMNSLRAEDTALYHCARGGDDAFDIWGQGTMVTVSSGGGGSGGGG

SGGGGSRIVMTQSPGTLSVSPGETATLSCRASQSFSNMLAWYQQKSGQPPRLLIYGVSTRAAGVPARFSGSGSGTE

FTLTISNLQSEDFAVYYCQQYGDWPRYTFGQGTKVERKTTTPAPRPPTPAPTIASQPLSLRPEACRPAAGGAVHTRG

LDFACDIYIWAPLAGTCGVLLLSLVITLYCKRGRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQEGLYNELQKDKMAEAYSEIGMKGER

RRGKGHDGLYQGLSTATKDTYDALHMQALPPR v1-m971 (FcγRIIIα-CD80αTM-41BB.IC-CD3ζ.IC)
                                                                    (SEQ ID NO: 129)
MALPVTALLPLALLLHAARPQVQLQQSGPGLVKPSQTLSLTCAISGDSVSSNSAAWNWIRQSPSRGLEWLGRTYYR

SKWYNDYAVSVKSRITINPDTSKNQFSLQLNSVTPEDTAVYYCAREVTGDLEDAFDIWGQGTMVTVSSGGGGSGG

GGSGGGGSDIQMTQSPSSLSASVGDRVTITCRASQTIWSYLNWYQQRPGKAPNLLIYAASSLQSGVPSRFSGRGSG

TDFTLTISSLQAEDFATYYCQQSYSIPQTFGQGTKLEIKGLAVSTISSFFPPGYQIYIWAPLAGTCGVLLLSLVITLYCKRG

RKKLLYIFKQPFMRPVQTTQEEDGCSCRFPEEEEGGCELRVKFSRSADAPAYQQGQNQLYNELNLGRREEYDVLDK
```

-continued

RRGRDPEMGGKPRRKNPQEGLYNELQKDKMAEAYSEIGMKGERRRGKGHDGLYQGLSTATKDTYDALHMQALP

PR v3-m971 (CD8α-CD8αTM-41BB.IC-CD3ζ.IC)

(SEQ ID NO: 130)

MALPVTALLPLALLLHAARPQVQLQQSGPGLVKPSQTLSLTCAISGDSVSSNSAAWNWIRQSPSRGLEWLGRTYYR

SKWYNDYAVSVKSRITINPDTSKNQFSLQLNSVTPEDTAVYYCAREVTGDLEDAFDIWGQGTMVTVSSGGGGSGG

GGSGGGGSDIQMTQSPSSLSASVGDRVTITCRASQTIWSYLNWYQQRPGKAPNLLIYAASSLQSGVPSRFSGRGSG

TDFTLTISSLQAEDFATYYCQQSYSIPQTFGQGTKLEIKTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKDKMAEAYSEIGMKGERR

RGKGHDGLYQGLSTATKDTYDALHMQALPPR

Production of New CD22 CAR and of UCART 22 Cells 10 new ScFv directed against the proximal region of CD22 protein and a scfv directed against the distal portion of CD22 (SEQ ID NO: 31) were identified and produced as previously described.

Alignment sequences of 10 new anti CD22 antibodies of the invention and comparison with that of m971 allowed to identify at least one difference between the 10 new scfv of the invention and m971 that resides in the CDR3 of VL chain. Thus, the 6th amino acid of the CDR3 is a T in all the new antibodies whereas it is an I in m971 (CDR3 of m971: QQSYSIPQT (SEQ ID NO: 144)) whereas the CDR3 of all new scfv have a T in 6th position of the CDR3. XXXXXTXXX.

The 10 corresponding CARs (SEQ ID NO: 46 to SEQ ID NO: 55), optionally comprising a QR3 (SEQ ID NO: 56 to SEQ ID NO: 65) or a R2 (SEQ ID NO: 66 SEQ ID NO: 67 SEQ ID NO: 68 and SEQ ID NO: 69) were constructed using the following single chain CAR structure.

A signal peptide (of SEQ ID NO:1), a scfv comprising a VH, a spacer (SEQ ID NO:10), a VL—a CD8alpha hinge (SEQ ID NO:4)- and a CD8alpha Trans Membrane domain (TM) (SEQ ID NO:6)—an intracellular domain from 4-1BB and an intracellular domain from CD3 zeta (SEQ ID NO: 7 and SEQ ID NO: 8), as previously described for example in (WO2013059593).

For this purpose, 10 viral vectors encoding the 10 corresponding CARS 1 to 10 (SEQ ID NO: 21 to SEQ ID NO:30) were cloned.

SEQ ID NO:31 corresponds to the sequence of an anti-CD22 CAR with a scfv binding to the distal part of CD22.

SEQ ID NO:32 to SEQ ID NO:41 corresponds to the sequences of the 10 CARs of the present invention comprising QR3.

SEQ ID NO:42 to SEQ ID NO:45 corresponds to the sequences of the 4 preferred CARs (CAR 4, 7, 9 and 10 with a R2).

SEQ ID NO:71 and SEQ ID NO:72 correspond to a VH and VL of CAR 1, respectively.

SEQ ID NO:73 and SEQ ID NO:74 correspond to a VH and VL of CAR 2, respectively.

SEQ ID NO:75 and SEQ ID NO:76 correspond to VH and VL of CAR 3.

SEQ ID NO:77 and SEQ ID NO:78 correspond to VH and VL of CAR 4 (preferred).

SEQ ID NO:79 and SEQ ID NO:80 correspond to VH and VL of CAR 5.

SEQ ID NO:81 and SEQ ID NO:82 correspond to VH and VL of CAR 6.

SEQ ID NO:83 and SEQ ID NO:84 correspond to VH and VL of CAR 7 (more preferred).

SEQ ID NO:85 and SEQ ID NO:86 correspond to VH and VL of CAR 8.

SEQ ID NO:87 and SEQ ID NO:88 correspond to VH and VL of CAR 9 (more preferred).

SEQ ID NO:89 and SEQ ID NO:90 (preferred) correspond to a VH and VL of CAR 10, respectively.

The constructions were amplified using transformed Stbl3 E. Coli for maxiprep DNA production.

The plasmids were sequenced using the Sanger method for sequences verification. 293T cells were then transfected with the different plasmids encoding the different CARs along with reagents allowing replicative deficient viral particles to be prepared. Supernatants were harvested 48h later and concentrated by ultracentrifugation. Titration was performed using Jurkat T cells inoculated with different quantities (µl) of viral supernatant. Viral titers obtained are reported in Table 11.

Table 11 represents the viral titer obtained for each of the polynucleotide vector preparations.

TABLE 11

|  | Titer (TU/mL) |
| --- | --- |
| CAR1 | 3.69E+08 |
| CAR2 | 2.32E+08 |
| CAR3 | 2.90E+08 |
| CAR4 | 3.13E+08 |
| CAR7 | 3.29E+08 |
| CAR8 | 2.48E+08 |
| CAR9 | 3.29E+08 |
| CAR12 | 2.83E+08 |
| CAR13 | 2.70E+08 |
| CAR15 | 2.31E+08 |

The numbers in Table 11, left column, and in Figures are the original numbers of the clones; they correspond to CARs 1 to 10 in the legend of the sequence listing (without safety switch).

The preferred CARs of the invention are CAR clones 4, 9, 13 and 15, preferably CAR clone 13, that is to say CAR 4, 7, 9 and 10, preferably CAR 9.

Figure 7:
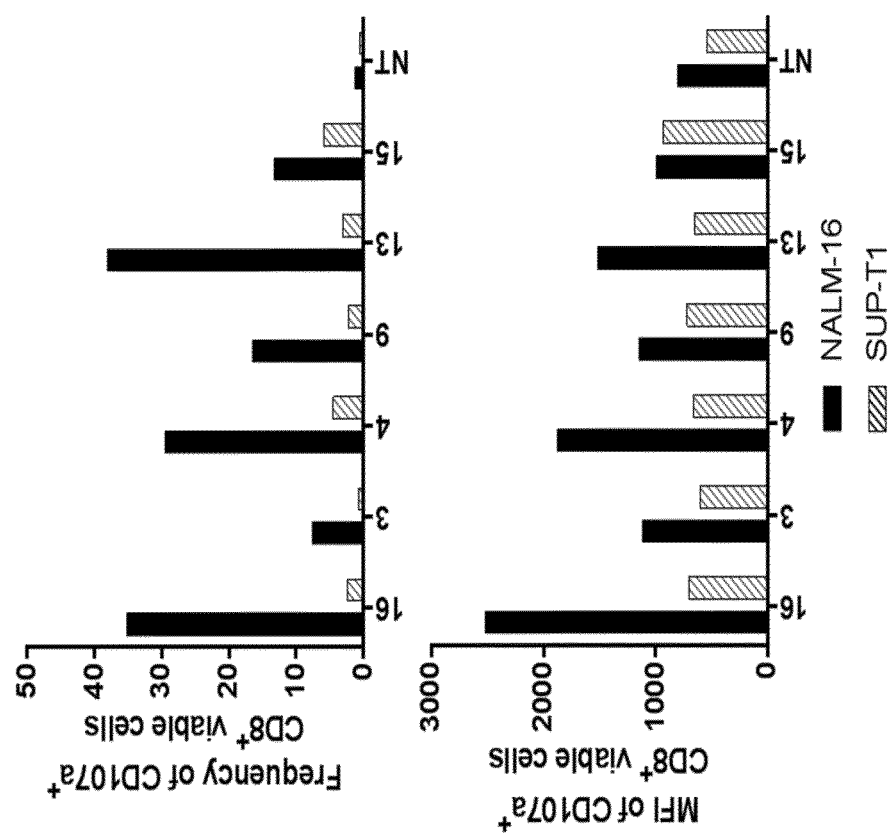
FIG. 7: degranulation activity of CARs specific for CD22 of the invention as measured by CD107a expression
Figure 8:
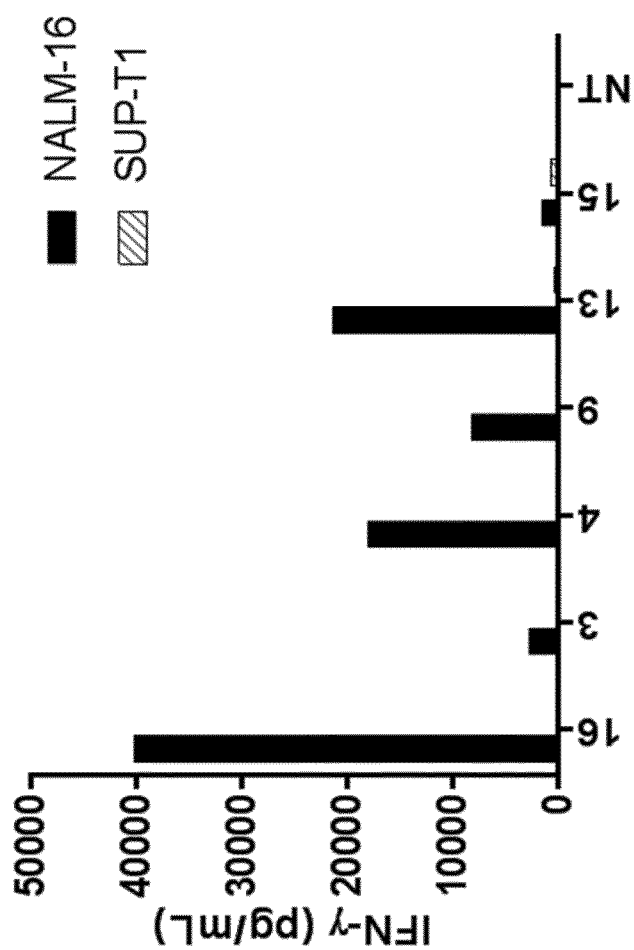
FIG. 8: Expression of interferon gamma in co culture of T cells expressing the CARs specific for CD22 of the invention with target cells

CAR prepared with m971 is the number 16 in FIGS. 7 and 8.

Figure 5:
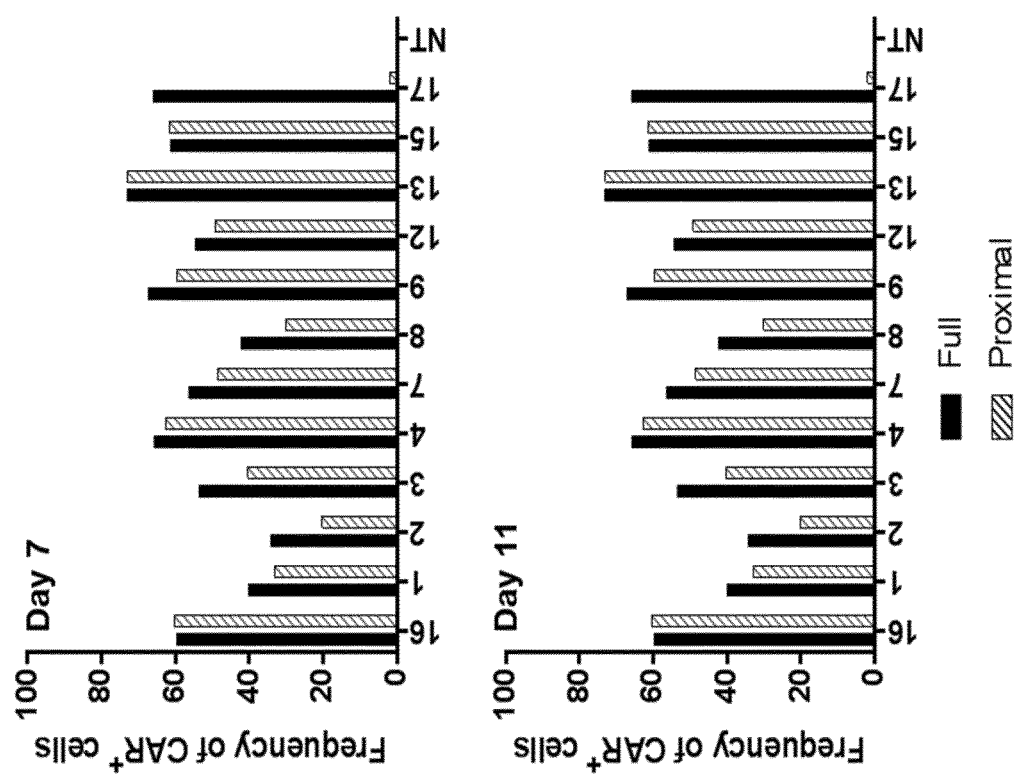
FIG. 5: Cell surface expression of the CARs specific for CD22 of the invention using a full or a distal recombinant CD22 protein.

CAR prepared with HA22 (against the distal part of the CD22 protein is the number 17 (FIG. 5).

The expression and activity of the 10 ScFv in a single chain chimeric antigen receptor was then analyzed. PBMCs were thawed and activated using Transact human T activator CD3/CD28 beads.

Figure 4:
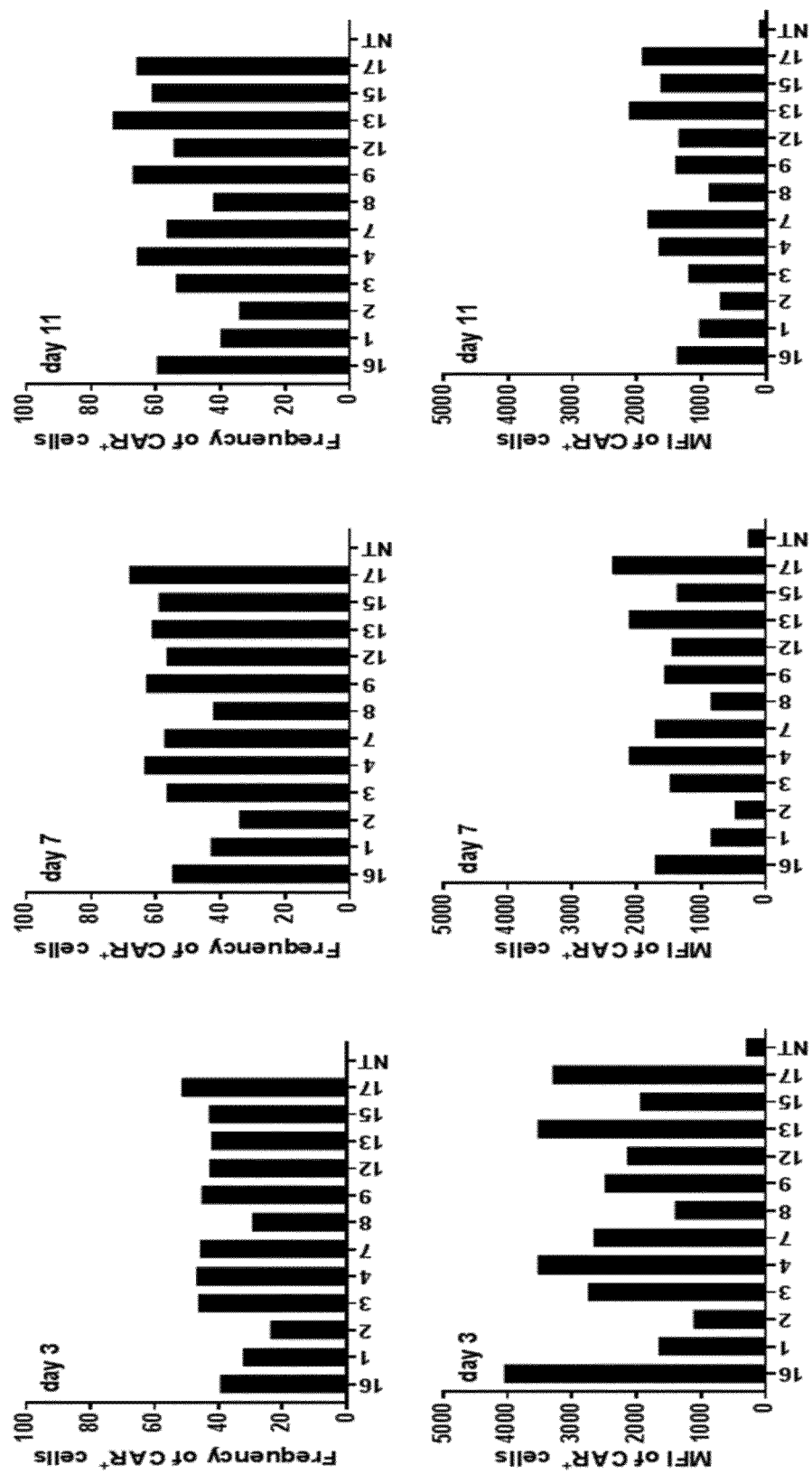
FIG. 4: Cell surface expression of the 10 new CARs specific for CD22 of the invention

3 days after activation, 1 million T cells were transduced or not using the tool CAR (m971 scfv) (CAR 16 in the figure) or the 10 CARS at a MOI of 5 the CAR binding to the distal part of CD22 was also used (CAR 17 in the figure). Cells were then immediately diluted in X-Vivo-15 media supplemented by 20 ng/ml IL-2 and 5% CTS™ Immune Cell SR and diluted at $1 \times 10^6$ cells/ml and kept in culture at 37° C. in the presence of 5% CO2. At day 3, 7 and 11 post-transduction, cell viability, CD4 and CD8 phenotypes, CAR positive cells frequency were assessed by flow cytometry (FIG. 4).

Then, CAR positive cells frequency (% of CAR-expressing cells over the total number of cells) was assessed by flow cytometry using a recombinant CD22 protein corresponding to the membrane proximal domain of CD22 or a recombinant CD22 protein corresponding to the whole extracellular domain of CD22 (FIG. 5).

9 days post-transduction, cytolytic (FIG. 6) activity of anti-CD22 CAR$^+$ T cells was assessed in a flow-based cytotoxicity assay after an overnight coculture with antigen presenting cells at 37° C. in the presence of 5% CO2.

CART and target cells were cocultured in X-Vivo-15 medium at effector (CAR$^+$): target ratios of 0.1:1, 0.2:1, 0.5:1 and 1:1. Culture medium was supplemented with 5% CTS™ Immune Cell SR. To distinguish positive (NALM-16) and negative (SUP-T1) tumor cell lines, NALM-16 target cells were stained with CFSE while SUP-T1 were stained with the CellTrace violet proliferation marker. At the end of the coculture, cell viability was measured and the percentage of specific lysis was calculated after normalization to non-specific target cell lysis.

At the same time point, the degranulation activity of CART cells was measured using a flow-based degranulation assay (FIG. 7).

CART and target cells were cocultured in X-Vivo-15 medium at effector (CAR$^+$):target ratios of 2:1. At the end of the coculture, cell viability was measured and the degranulation activity as represented by CD107a expression was determined by flow cytometry on CD8 CART cells.

As a last test of CART cells activity, we evaluated the ability of CART cells to secrete IFN-γ following coculture with irradiated antigen presenting cells for 24h. CAR$^+$ T cells IFN-γ secretion capacity towards antigen presenting cells (NALM-16) was assessed in an ELISA immunoassay. 50000 CART cells were cocultured for 24 hours with 50000 antigen presenting cells (NALM-16). IFN-γ secretion was measured using the Quantikine® ELISA Human IFN-γ Immunoassay KIT, R&D Systems (FIG. 8).

Figure 9:
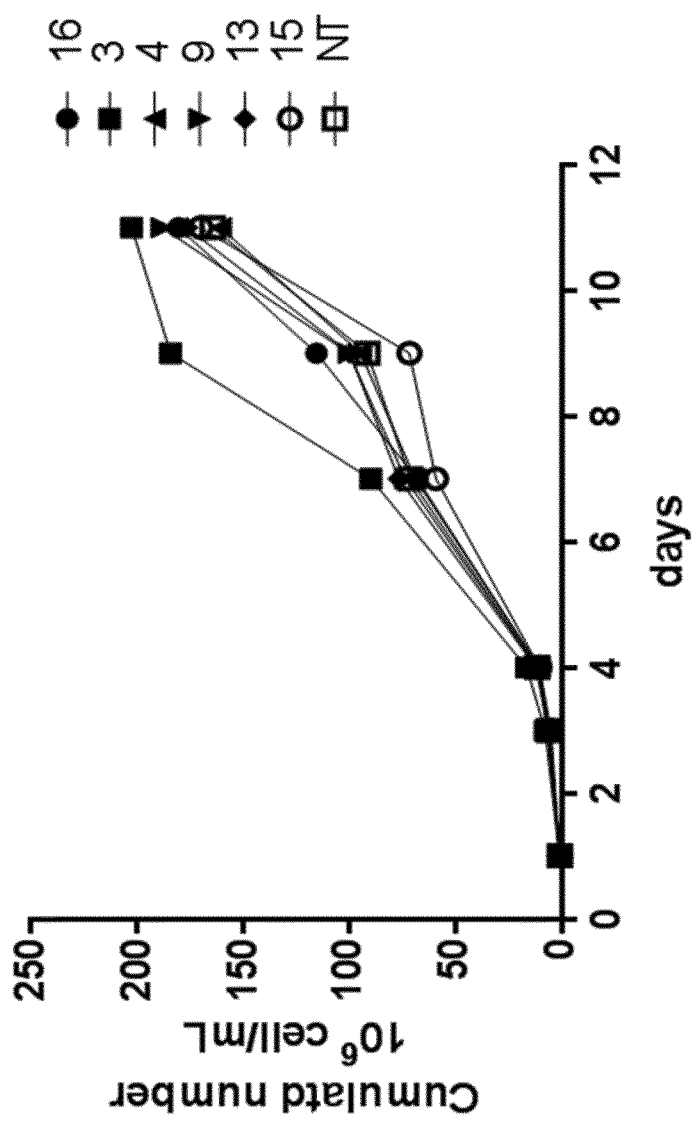
FIG. 9: Proliferation of control (NT) and anti-CD22 CAR expressing cells

The number of anti-CD22 CART cells was assessed at every cell passage (FIG. 9). Following up on this first screen, the 4 more potent anti-CD22 CARs were designed with a suicide switch, either R2 or QR3 as previously described in WO2016120216.

CAR Comprising mAb-Specific Epitopes were Prepared

Constructs (polynucleotides) comprising a CAR with QR3 were prepared (SEQ ID NO: 56 to SEQ ID NO: 65) corresponding to peptide sequences SEQ ID NO: 32 to SEQ ID NO: 41.

Constructs (polynucleotides) comprising a CAR with R2 were prepared SEQ ID NO: 42, SEQ ID NO: 43, SEQ ID NO: 44 to SEQ ID NO: 45 corresponding to sequences SEQ ID NO: 66, SEQ ID NO: 67, SEQ ID NO: 68 and SEQ ID NO: 69, respectively.

The binding of all anti-CD22 CARs tested was positive regardless of the recombinant protein used either proximal domain of CD22 or the full length recombinant CD22 protein.

The binding of three out of 10 anti-CD22 CARs (numbered 4,13,15) to the CD22 proteins was comparable to that measured for the tool CAR (16). As expected a CAR specific for the distal portion of the CD22 protein (17) did not bind the proximal portion of the CD22 protein.

6 different anti-CD22 CARs were used for further experiments. Anti-CD22 CARs were then selected based on their binding to recombinant CD22 protein as compared to the binding of the tool CAR m971.

The cytolytic capacity of CAR$^+$ T cells was evaluated using antigen presenting cells (NALM-16) as a target in a flow-based cytotoxicity assay. For this purpose, cell viability was measured after an overnight coculture of target cells with CART cells at an effector/target ratio set at 1:1, 0.5:1, 0.2:1 or 0.1:1. (FIG. 6).

The results show that all CAR selected are cytotoxic with CARs 3, 4, 9, 13 and 15 slightly more active ie cytotoxic in vitro, the levels of cytotoxic activity being similar to the level of cytotoxicity of the m971 tool CAR (CAR16), for anti-CD22 CAR numbered 4, 9 and 13 and slightly lower for anti-CD22 CAR numbered 3 and 15.

CAR$^+$ T cells degranulation capacity towards antigen presenting cells (NALM-16) was assessed in a flow-based degranulation assay (FIG. 7). The upper histograms represent the frequencies of CD107a$^+$CD8$^+$ viable cells while the lower histograms represent the MFI of CD107$^+$ cells on CD8$^+$ viable cells (FIG. 7).

When considering CD8 positive CART cells, a degranulation activity (20 to 40% of CD107a expression) for CART cells numbered 3, 4, 9, 13 and 15 was detectable. Importantly, the MFI of CD107a on CD8$^+$ CART cells is attenuated for anti-CD22 CAR numbered 3, and 15.

CAR$^+$ T cells IFN-γ secretion capacities towards antigen presenting cells (NALM-16) were assessed in an ELISA immunoassay (FIG. 8).

The results show that the anti-CD22 CARs tested express a detectable amount of IFN-γ upon coculture with irradiated antigen presenting cells for 24 h as compared to cell without anti-CD22 CAR (NT), especially CARs 4, 9 and 13, and the level is lower than that detected for the tool CAR 16 (FIG. 8).

Activated T cells transduced with the different CAR lentiviral particles were passed every other day. 1 day post-transduction the cells were harvested and the CAR expression was assessed by flow cytometry on viable T cells using a recombinant biotinylated CD22 protein in combination with a marker of cell viability.

The results show that there is no major difference in terms of CART cell expansion between all the CARs tested (FIG. 9).

Figure 10:
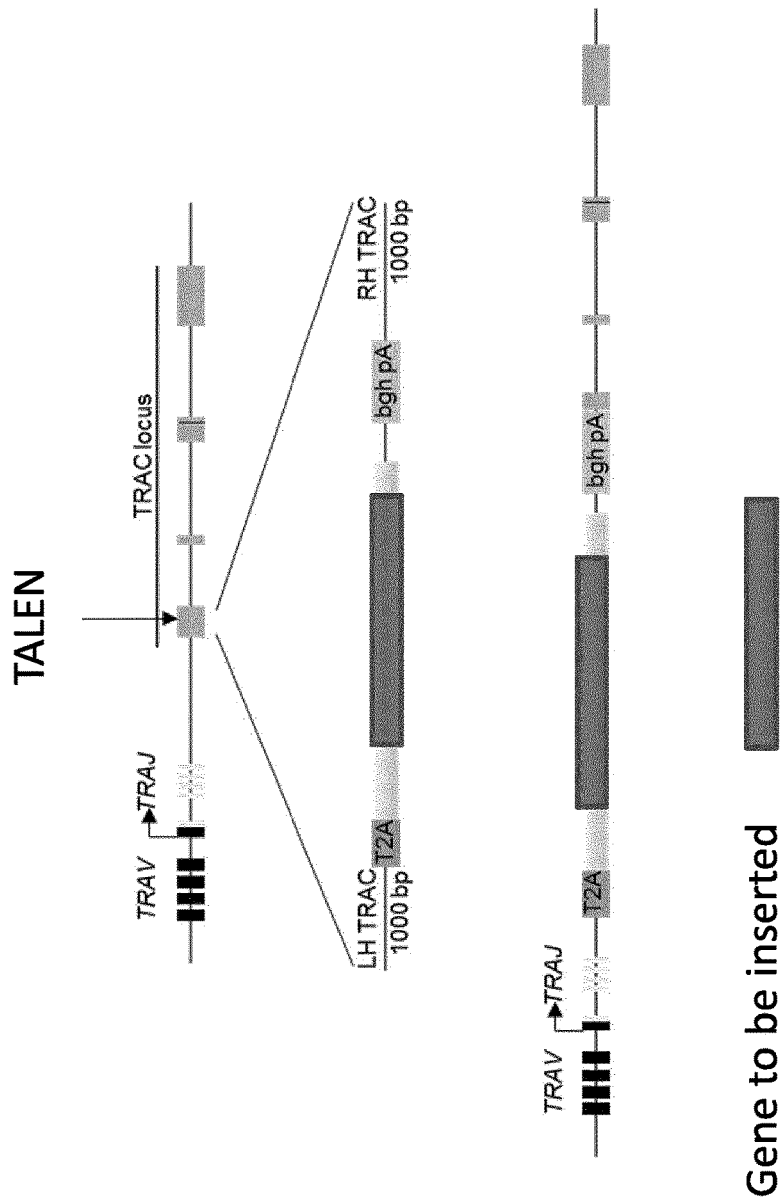
FIG. 10: Strategy for inserting the CARs specific for CD22 of the invention into and in frame with a TCR locus

TALEN-targeted CAR gene integration into the TRAC locus (FIG. 10). The top panel represents the TRAC locus. The middle panel represents the rAAV6 containing the CAR cassette flanked by 1000 bp homology arms and the bottom panel the edited TRAC locus.

Production of CD22 UCART cells by INSERTING in frame a CD22 CAR into the TRAC locus with a TALEN®

FIG. 10: General Strategy to insert a gene into the TRAC gene using TALEN.

To disrupt the TRAC locus and place the CD22-specific CAR- or HIF_1alpha or any other sequence) under its transcriptional control (TRAC-CAR) we used a TRAC TALEN® targeting the first exon of TRAC locus and an adeno-associated virus (AAV) vector repair matrix encoding a self-cleaving T2A peptide followed by the CAR cDNA. Other method allow an integration into this gene but in another locus (MacLeod et al., Integration of a CD19 CAR into the TCR Alpha Chain Locus Streamlines Production of Allogeneic Gene-Edited CAR T Cells, Molecular Therapy (2017), Eyquem J, Mansilla-Soto J, Giavridis T, van der Stegen S J, Hamieh M, Cunanan K M, Odak A, Gonen M, Sadelain M, Targeting a CAR to the TRAC locus with CRISPR/Cas9 enhances tumour rejection. Nature. 2017 Mar. 2; 543(7643):113-117. doi: 10.1038/nature21405. Epub 2017 Feb. 22).

Figure 11:
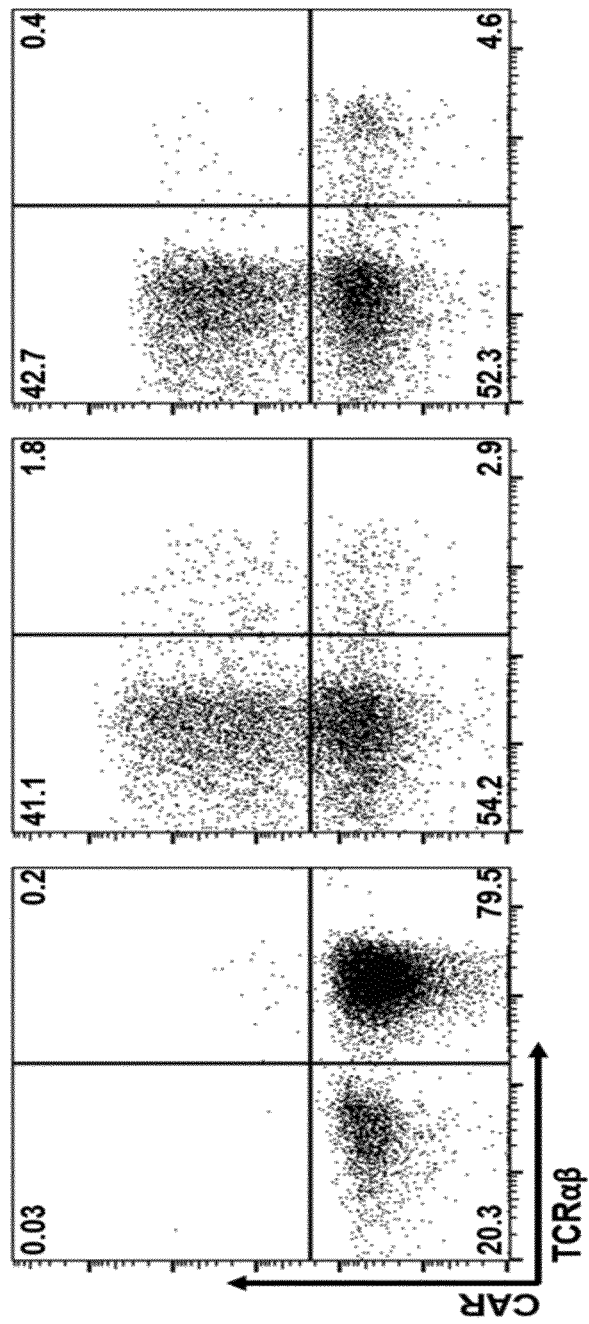
FIG. 11: Expression of anti-CD22 CAR and TCR alpha beta in cells in which the anti-CD22 CAR gene of the invention was inserted into the TRAC gene using AAV6 and TALEN®

PBMCs were thawed and activated using Transact human T activator CD3/CD28 beads. 3 days after their activation, T cells were passed to be transfected 4 hours later at the earliest. T cells were then transfected by electrotransfer of 1 µg of mRNA encoding TRAC TALEN per million cells using an AgilePulse system (Harvard Apparatus) into a 0.4 cm cuvette. Following electroporation, cells were immediately diluted in X-Vivo-15 media supplemented by 20 ng/ml IL-2 and 5% CTS™ Immune Cell SR at the concentration of 4×106 cells/mL and incubated in 12 well-plates (500 µl per well) at 37° C. in the presence of 5% CO2. Recombinant AAV6 donor vector manufactured by Sirion was added to the culture 1.5 h after electroporation at the multiplicity of infection of 3×104 vg/cell. Subsequently, cells were cultured overnight at 30° C. in X-Vivo-15 media supplemented by 20 ng/ml IL-2 and 5% CTS™ Immune Cell SR and cultured back in the standard conditions starting from the day after (37° C., 1×106 cells/mL, X-Vivo-15 media supplemented by 20 ng/ml IL-2 and 5% CTS™ Immune Cell SR). Cells were then expanded in the standard conditions and passed every 2 to 3 days. 4 days after transfection/transduction TRAC knock-out and CAR expression were assessed by flow cytometry (FIG. 11).

TCR and CAR expressions were assessed by flow cytometry on viable T cells using CD4, CD8, TCRαβ mAb, CD22 recombinant protein (full length) in combination with a marker of cell viability. The frequency of positive cells is indicated in each panel. D4, D7 and D11 correspond to the day post-transduction.

The present invention encompassed a cell comprising a gene with any one of sequences selected from of SEQ ID NO: 21 to 30, 32, 33, 34, 35, 36, 37, 38, 39, 40 to 41 and 42, 43, 44 to 45 inserted into the TRAC gene.

The present invention encompassed a cell comprising a gene with any one of sequences selected from of SEQ ID NO: 17, SEQ ID NO: 18, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, to SEQ ID NO: 41 and SEQ ID NO: 42, SEQ ID NO: 43, SEQ ID NO: 44, to SEQ ID NO: 45 inserted into the TRAC gene and a deletion in the CD52 gene, dCK gene, GR gene.

The binding of all anti-CD22 CARs tested was positive regardless of the recombinant protein used either proximal domain of CD22 or the full length recombinant CD22 protein.

The binding of three out of 10 anti-CD22 CARs (numbered 4,13,15) to the CD22 proteins was comparable to that measured for the tool CAR (16). As expected a CAR specific for the distal portion of the CD22 protein (17) did not bind the proximal portion of the CD22 protein.

```
CAR16
                                                          (SEQ ID NO: 31)
ATGGCTCTGCCCGTCACCGCTCTGCTGCTGCCACTGGCCCTGCTGCTGCACGCAGCAAGACCACAGGT

GCAGCTGCAGCAGAGCGGCCCTGGCCTGGTGAAGCCAAGCCAGACACTGTCCCTGACCTGCGCCATCA

GCGGCGATTCCGTGAGCTCCAACTCCGCCGCCTGGAATTGGATCAGGCAGTCCCCTTCTCGGGGCCTG

GAGTGGCTGGGAAGGACATACTATCGGTCTAAGTGGTACAACGATTATGCCGTGTCTGTGAAGAGCAG

AATCACAATCAACCCTGACACCTCCAAGAATCAGTTCTCTCTGCAGCTGAATAGCGTGACACCAGAGG

ACACCGCCGTGTACTATTGCGCCAGGGAGGTGACCGGCGACCTGGAGGATGCCTTTGACATCTGGGGC

CAGGGCACAATGGTGACCGTGTCTAGCGGAGGAGGAGGATCCGGAGGAGGAGGATCTGGCGGCGGCGG

CAGCGATATCCAGATGACACAGTCCCCATCCTCTCTGAGCGCCTCCGTGGGCGACAGAGTGACAATCA

CCTGTAGGGCCTCCCAGACCATCTGGTCTTACCTGAACTGGTATCAGCAGAGGCCCGGCAAGGCCCCT

AATCTGCTGATCTACGCAGCAAGCTCCCTGCAGAGCGGAGTGCCATCCAGATTCTCTGGCAGGGCTC

CGGCACAGACTTCACCCTGACCATCTCTAGCCTGCAGGCCGAGGACTTCGCCACCTACTATTGCCAGC

AGTCTTATAGCATCCCCCAGACATTTGGCCAGGGCACCAAGCTGGAGATCAAGACCACAACCCCAGCA

CCAAGGCCACCTACACCTGCACCAACCATCGCCTCTCAGCCCCTGAGCCTGAGACCTGAGGCATGTAG

GCCAGCAGCAGGAGGAGCAGTCCATACAAGGGGTCTGGATTTTGCATGCGACATCTACATCTGGGCAC

CTCTGGCAGGAACATGTGGCGTGCTCCTGCTCAGCCTGGTCATCACCCTGTACTGCAAGAGAGGCAGG

AAGAAGCTGCTGTATATCTTCAAGCAGCCCTTCATGCGCCCCGTGCAGACAACCCAGGAGGAGGATGG

CTGCTCCTGTAGGTTCCCAGAAGAGGAGGAGGGAGGATGTGAGCTGCGCGTGAAGTTTTCCCGGTCTG

CCGACGCACCTGCATACCAGCAGGGCCAGAACCAGCTGTATAACGAGCTGAATCTGGGCCGGAGAGAG

GAGTACGATGTGCTGGACAAGAGGCGCGGCAGAGATCCAGAGATGGGCGGCAAGCCCCGGAGAAAGAA

CCCTCAGGAGGGCCTGTACAATGAGCTGCAGAAGGATAAGATGGCCGAGGCCTATTCTGAGATCGGCA
```

-continued
TGAAGGGAGAGAGGCGCCGGGGCAAGGGACACGACGGACTGTACCAGGGACTGAGCACAGCCACCAAG

GATACCTATGACGCCCTGCATATGCAGGCACTGCCTCCAAGGTGA

CAR1 (SEQ ID NO: 21)
ATGGCTCTGCCCGTCACCGCTCTGCTGCTGCCACTGGCCCTGCTGCTGCACGCAGCCAGACCCCAGGT

GCAGCTGCAGCAGAGCGGCCCTGGCCTGGTGAAGCCATCTCAGACACTGAGCCTGACCTGCGCCATCT

CTGGCGACAGCGTGAGCTCCAACTCTGCCGCCTGGAATTGGATCAGACAGTCCCCATCTAGGGGCCTG

GAGTGGCTGGGACGCACATACTATCGGTCCACCTGGTACAACGACTATGCCGTGTCCGTGAAGTCTCG

CATCACAATCAACCCCGATACCTCTAAGAATCAGTTCAGCCTGCAGCTGAATTCCGTGACACCTGAGG

ACACCGCCGTGTACTATTGCGCCAGAGAGGTGAGCGGCACATCCGCCTTTGATATCTGGGGCCAGGGC

ACAATGGTGACCGTGTCTGGAGGAGGAGGAAGCGGAGGAGGAGGATCCGGCGGCGGCGGCTCTGACAT

CCAGATGACCCAGAGCCCTTCTAGCCTGAGCGCCTCCGTGGGCGATCGCGTGACAATCACCTGTCGGG

CCTCTCAGAGCATCTCCTCTTACCTGAACTGGTATCAGCAGAAGCCCGGCAAGGCCCCTAAGCTGCTG

ATCTACGCAGCAAGCTCCCTGCAGTCCGGAGTGCCATCTCGGTTCTCCGGCTCTGGCAGCGGCACAGA

CTTTACACTGACCATCTCTAGCCTGCAGCCTGAGGATTTCGCCACCTACTATTGCCAGCAGTCCTATT

CTACACCACTGACCTTTGGCGGCGGCACCAAGCTGGAGATCAAGACCACAACCCCAGCACCCAGACCC

CCTACACCTGCACCAACCATCGCAAGCCAGCCACTGTCCCTGCGCCCTGAGGCATGTAGGCCAGCAGC

AGGAGGAGCAGTGCACACCAGGGGCCTGGACTTCGCCTGCGATATTTACATCTGGGCACCACTGGCAG

GAACATGTGGCGTGCTGCTCCTGAGCCTGGTCATCACCCTGTACTGCAAGAGAGGCAGGAAGAAGCTG

CTGTATATCTTCAAGCAGCCCTTCATGCGGCCCGTGCAGACAACCCAGGAGGAGGACGGCTGCTCCTG

TAGGTTCCCAGAAGAGGAGGAGGGCGGCTGTGAGCTGAGAGTGAAGTTTAGCAGGTCCGCCGATGCAC

CAGCATACCAGCAGGGACAGAATCAGCTGTATAACGAGCTGAATCTGGGCCGGAGAGAGGAGTACGAC

GTGCTGGATAAGAGGAGGGGAAGGGATCCTGAGATGGGAGGCAAGCCCCGGAGAAAGAACCCTCAGGA

GGGCCTGTACAATGAGCTGCAGAAGGACAAGATGGCCGAGGCCTATAGCGAGATCGGCATGAAGGGAG

AGAGGCGCCGGGGCAAGGGACACGATGGCCTGTACCAGGGCCTGTCCACAGCCACCAAGGACACCTAT

GATGCCCTGCATATGCAGGCACTGCCTCCAAGGTGA

CAR2 (Seq ID NO: 22)
ATGGCTCTGCCCGTCACCGCTCTGCTGCTGCCACTGGCCCTGCTGCTGCACGCAGCCAGACCCCAGGT

GCAGCTGCAGCAGAGCGGCCCTGGCCTGGTGAAGCCATCCCAGACCCTGTCTCTGACATGCGCCATCA

GCGGCGACTCCGTGAGCTCCAACTCTGCCGCCTGGAATTGGATCAGACAGTCCCCATCTAGGGGCCTG

GAGTGGCTGGGAAGGACCTACTATCGGTCCAAGTGGTACAACGACTATGCCGTGTCTGTGAAGAGCCG

CATCACCATCAACCCCGATACATCCAAGAATCAGTTCTCTCTGCAGCTGAATAGCGTGACCCCTGAGG

ACACAGCCGTGTACTATTGCGCCAGAGCCTCTATGACCGGCGGCTACAGCTATGGCGACGCCTTTGAT

ATCTGGGGCCAGGGCACACTGGTGACCGTGTCCGGCGGCGGCGGCTCTGGAGGAGGAGGAAGCGGAGG

AGGAGGATCCGCCATCCGCATGACACAGAGCCCTTCTAGCCTGAGCGCCTCCGTGGGCGATCGCGTGA

CAATCACCTGTCGGGCCTCTCAGAGCATCTCCTCTTACCTGAACTGGTATCAGCAGAAGCCCGGCAAG

GCCCCTAAGCTGCTGATCTACGCAGCAAGCTCCCTGCAGAGCGGAGTGCCATCCCGGTTCTCCGGATC

TGGAAGCGGAACCGACTTTTCCCTGACAATCTCTAGCCTGCAGCCTGAGGATTCCGCCACCTACTATT

GCCAGCAGACATATTCTACCCCACTGACATTCGGCCAGGGCACAAAGGTGGAGATCAAGACCACAACC

CCAGCACCCAGACCCCCTACCCCTGCACCAACAATCGCCTCTCAGCCCCTGAGCCTGCGCCCTGAGGC

ATGTAGGCCAGCAGCAGGAGGAGCAGTGCACACCAGGGGCCTGGACTTTGCCTGCGATATTTACATCT

GGGCACCACTGGCAGGAACCTGTGGCGTGCTGCTCCTGAGCCTGGTCATCACCCTGTACTGCAAGAGA

```
GGCAGGAAGAAGCTGCTGTATATCTTCAAGCAGCCCTTCATGCGGCCCGTGCAGACAACCCAGGAGGA

GGACGGCTGCTCCTGTAGGTTCCCAGAAGAGGAGGAGGGCGGCTGTGAGCTGAGAGTGAAGTTTTCCA

GGTCTGCCGATGCACCAGCATACCAGCAGGGACAGAATCAGCTGTATAACGAGCTGAATCTGGGCCGG

AGAGAGGAGTACGACGTGCTGGATAAGAGGAGGGGACGGGATCCTGAGATGGGAGGCAAGCCCCGGAG

AAAGAACCCTCAGGAGGGCCTGTACAATGAGCTGCAGAAGGACAAGATGGCCGAGGCCTATAGCGAGA

TCGGCATGAAGGGAGAGAGGCGCCGGGGCAAGGGACACGATGGCCTGTACCAGGGCCTGTCCACAGCC

ACCAAGGACACCTATGATGCCCTGCATATGCAGGCACTGCCTCCAAGGTGA

CAR3
                                                                    (Seq ID NO: 23)
ATGGCTCTGCCCGTCACCGCTCTGCTGCTGCCACTGGCCCTGCTGCTGCACGCAGCCAGACCCCAGGT

GCAGCTGCAGCAGAGCGGCCCTGGCCTGGTGGAGCCAAGCCAGACACTGTCCCTGACCTGCGCCATCT

CTGGCGACAGCGTGAGCTCCGATTCCGTGGCCTGGAACTGGATCAGGCAGTCTCCAAGCCGGGGCCTG

GAGTGGCTGGGCAGAACATACTATAGGTCTACCTGGTACAATGACTATGCCGGCTCCGTGAAGTCTCG

CATCACAATCAACCCCGATACCAGCAAGAATCAGTTCTCCCTGCAGCTGACATCTGTGACCCCTGAGG

ACACAGCCGTGTACTATTGCACCAGATCCAGGCACAACACATTTCGGGGAATGGACGTGTGGGGACAG

GGAACCACAGTGACCGTGAGCGGAGGAGGAGGATCCGGCGGAGGAGGCTCTGGAGGAGGAGGAAGCGA

CATCGTGATGACCCAGAGCCCTTCTAGCCTGTCCGCCTCTGTGGGCGATAGAGTGACAATCACCTGTA

GGGCCTCCCAGACCATCTCCTCTTACCTGAACTGGTATCAGCAGAAGCCCGGCAAGGCCCCTAAGCTG

CTGATCTACGACGCAAGCTCCCTGCAGTCTGGAGTGCCAAGCAGATTCAGCGGCTCCGGCTCTGGCAC

CGACTTTACACTGACCATCAATTCCCTGCAGCCTGAGGATTTCGCCACATACTATTGCCAGCAGTCTT

ATACCACACCAATCACATTTGGCCAGGGCACCCGCCTGGAGATCAAGACCACAACCCCAGCACCCAGA

CCCCCTACACCTGCACCAACCATCGCATCCCAGCCACTGTCTCTGCGGCCCGAGGCATGTAGGCCAGC

AGCAGGAGGAGCAGTGCACACCAGGGGCCTGGACTTCGCCTGCGATATTTACATCTGGGCACCACTGG

CAGGAACCTGTGGCGTGCTGCTCCTGAGCCTGGTCATCACCCTGTACTGCAAGCGCGGCCGGAAGAAG

CTGCTGTATATCTTCAAGCAGCCCTTCATGCGGCCCGTGCAGACAACCCAGGAGGAGGACGGCTGCTC

CTGTAGGTTCCCAGAAGAGGAGGAGGGAGGATGTGAGCTGAGGGTGAAGTTTAGCCGGTCCGCCGATG

CACCAGCATACCAGCAGGGCCAGAATCAGCTGTATAACGAGCTGAATCTGGGCCGGAGAGAGGAGTAC

GACGTGCTGGATAAGAGGAGGGGAAGGGATCCTGAGATGGGAGGCAAGCCCCGGAGAAAGAACCCTCA

GGAGGGCCTGTACAATGAGCTGCAGAAGGACAAGATGGCCGAGGCCTATTCTGAGATCGGCATGAAGG

GAGAGAGGCGCCGGGGCAAGGGACACGATGGCCTGTACCAGGGCCTGAGCACAGCCACCAAGGACACC

TATGATGCCCTGCATATGCAGGCACTGCCTCCAAGGTGA

CAR4
                                                                    (SEQ ID NO: 24)
ATGGCTCTGCCCGTCACCGCTCTGCTGCTGCCACTGGCCCTGCTGCTGCACGCAGCCAGACCCCAGGT

GCAGCTGCAGCAGAGCGGCCCTGGCCTGGTGGAGCCAAGCCAGACACTGTCCCTGACCTGCGCCATCT

CTGGCGACAGCGTGAGCTCCAACAGCGCCGCATGGAATTGGATCAGGCAGTCCCCATCTCGGGGCCTG

GAGTGGCTGGGCAGAACATACTATAGGTCCACCTGGTACAACGACTATGCCGGCTCCGTGAAGTCTCG

CATCACAATCAACCCCGATACCAGCAAGAATCAGTTCTCCCTGCAGCTGACATCTGTGACCCCTGAGG

ACACAGCCGTGTACTATTGCACCAGAAGCAGGCACAATACATTTCGGGGAATGGACGTGTGGGGACAG

GGCACACTGGTGACCGTGAGCGGAGGAGGAGGATCCGGCGGAGGAGGCTCTGGCGGCGGCGGCAGCGA

CATCCAGCTGACCCAGTCCCCTTCTAGCCTGAGCGCCTCCGTGGGCGATAGAGTGACAATCACCTGTA

GGGCCTCTCAGAGCATCTCCTCTTACCTGAACTGGTATCAGCAGAAGCCCGGCAAGGCCCCTAAGCTG

CTGATCTACGCAGCAAGCTCCCTGCAGTCTGGAGTGCCAAGCAGATTCTCCGGCTCTGGCAGCGGCAC
```

-continued
CGACTTTACACTGACCATCTCTAGCCTGCAGCCTGAGGATTTCGCCACATACTATTGCCAGCAGTCCT
ATTCTACACCACTGACCTTTGGCGGCGGCACCAAGGTGGAGATCAAGACCACAACCCCAGCACCCAGA
CCCCCTACACCTGCACCAACCATCGCATCCCAGCCACTGTCTCTGCGGCCCGAGGCATGTAGGCCAGC
AGCAGGAGGAGCAGTGCACACCAGGGGCCTGGACTTCGCCTGCGATATCTACATTTGGGCACCACTGG
CAGGAACCTGTGGCGTGCTGCTCCTGAGCCTGGTCATCACCCTGTACTGCAAGCGCGGCCGGAAGAAG
CTGCTGTATATCTTCAAGCAGCCCTTCATGCGGCCCGTGCAGACAACCCAGGAGGAGGACGGCTGCTC
CTGTCGGTTCCCAGAAGAGGAGGAGGAGGATGTGAGCTGAGGGTGAAGTTTAGCCGGTCCGCCGATG
CACCAGCATACCAGCAGGGCCAGAATCAGCTGTATAACGAGCTGAATCTGGGCCGGAGAGAGGAGTAC
GACGTGCTGGATAAGAGGAGGGGAAGGGATCCTGAGATGGGAGGCAAGCCCCGGAGAAAGAACCCTCA
GGAGGGCCTGTACAATGAGCTGCAGAAGGACAAGATGGCCGAGGCCTATTCCGAGATCGGCATGAAGG
GAGAGAGGCGCCGGGGCAAGGGACACGATGGCCTGTACCAGGGCCTGTCTACAGCCACCAAGGACACC
TATGATGCCCTGCATATGCAGGCACTGCCTCCAAGGTGA CAR7 5
(SEQ ID NO: 25)
ATGGCTCTGCCCGTCACCGCTCTGCTGCTGCCACTGGCCCTGCTGCTGCACGCAGCCAGACCCCAGGT
GCAGCTGCAGCAGAGCGGCCCTGGCCTGGTGGAGCCAAGCCAGACCCTGTCCCTGACATGCGCCATCT
CTGGCGACAGCGTGAGCTCCGATTCTGTGGCCTGGAACTGGATCAGGCAGAGCCCAAGCCGGGGCCTG
GAGTGGCTGGGCAGAACCTACTATAGGTCCACATGGTACAATGACTATGCCGGCTCCGTGAAGTCTCG
GATCACCATCAACCCCGATACATCCAAGAATCAGTTCTCTCTGCAGCTGAACAGCGTGACCCCTGAGG
ACACAGCCGTGTACTATTGCGCCAGAGACAGGAATGGCATGGACGTGTGGGCCAGGGAACCATGGTG
ACAGTGTCCGGAGGAGGCGGCTCTGGAGGAGGAGGAAGCGGAGGAGGAGGATCCGACATCGTGATGAC
CCAGAGCCCTTCTAGCCTGTCTGCCAGCGTGGGCGATAGAGTGACAATCACCTGTAGGGCCTCCCAGT
CTATCTCCTCTTACCTGAACTGGTATCAGCAGAAGCCCGGCAAGGCCCCTAAGCTGCTGATCTACGAT
GCCTCTAATCTGGAGACAGGCGTGCCAAGCAGATTCAGCGGCTCCGGCTCTGGCACAGACTTCACCTT
CACCATCACATCCCTGCAGCCTGAGGATTTCGCCACCTACTATTGCCAGCAGTCTTATACCACACCAC
TGACCTTTGGCGGCGGCACAAAGGTGGAGATCAAGACCACAACCCCAGCACCCAGACCCCCTACCCCT
GCACCAACAATCGCCTCTCAGCCCCTGAGCCTGCGGCCCGAGGCCTGTAGGCCAGCAGCAGGAGGAGC
AGTGCACACCAGGGGCCTGGACTTTGCCTGCGATATTTACATCTGGGCACCACTGGCAGGAACCTGTG
GCGTGCTGCTCCTGAGCCTGGTCATCACCCTGTACTGCAAGCGCGGCCGGAAGAAGCTGCTGTATATC
TTCAAGCAGCCCTTCATGCGGCCCGTGCAGACAACCCAGGAGGAGGACGGCTGCTCCTGTCGGTTCCC
AGAAGAGGAGGAGGAGGATGTGAGCTGAGGGTGAAGTTTAGCCGGTCCGCCGATGCACCAGCATACC
AGCAGGGACAGAACCAGCTGTATAACGAGCTGAATCTGGGCCGGAGAGAGGAGTACGACGTGCTGGAT
AAGAGGAGGGGACGGGACCCTGAGATGGGAGGCAAGCCCCGGAGAAAGAACCCTCAGGAGGGCCTGTA
CAATGAGCTGCAGAAGGACAAGATGGCCGAGGCCTATAGCGAGATCGGCATGAAGGGAGAGAGGCGCC
GGGGCAAGGGACACGATGGCCTGTACCAGGGCCTGTCCACCGCCACAAAGGACACCTATGATGCCCTG
CATATGCAGGCACTGCCTCCAAGGTGA CAR8 6
(SEQ ID NO: 26)
ATGGCTCTGCCCGTCACCGCTCTGCTGCTGCCACTGGCCCTGCTGCTGCACGCAGCCCGCCCTCAGGT
GCAGCTGCAGCAGTCCGGCCCAGGCCTGGTGAAGCCATCCCAGACACTGTCTCTGACCTGCGCCATCA
GCGGCGACTCCGTGAGCTCCTCTAGCGCCGCCTGGAACTGGATCAGACAGTCTCCTAGCAGGGGCCTG
GAGTGGCTGGGAAGGACCTACTATCGGTCCGCCTGGTACAATGACTATGCCGTGTCTGTGAAGAGCAG
AATCACAATCAACCCCGATACCTCCAAGAATCAGTTCTCTCTGCAGCTGAACAGCGTGACACCTGAGG -continued ATACCGCCGTGTACTATTGCGCCAGAGAGAGCGTGCTGCTGGACGGAATGGACGTGTGGGGAAGGGGA
ACCACAGTGACAGTGTCCGGAGGAGGCGGCTCTGGAGGAGGAGGAAGCGGAGGAGGAGGATCCGCCAT
CAGGATGACACAGTCCCCATCTACCCTGAGCGCCTCCGTGGGCGACCGCGTGACAATCACCTGTCGGG
CCTCTCAGAGCATCTCCACCTACCTGAATTGGTATCAGCAGAAGGCCGGCAAGGCCCCAAGACTGCTG
ATCCACGATGCATCCTCTCTGCAGAGCGGAGTGCCATCCAGGTTCTCTGGAAGCGGATCCGGCACAGA
CTTTACACTGACCATCAGCTCCCTGCAGCCTGAGGATTTCGCCACCTACTATTGCCAGCAGTCTTACA
GCACACCACTGACCTTTGGCGGCGGCACAAAGGTGGAGATCAAGACCACAACCCCAGCACCCAGACCC
CCTACACCTGCACCAACCATCGCCTCTCAGCCTCTGAGCCTGCGCCCAGAGGCATGTAGGCCAGCAGC
AGGAGGAGCAGTGCACACCAGAGGCCTGGACTTTGCCTGCGATATTTATATCTGGGCACCTCTGGCAG
GAACATGTGGCGTGCTGCTCCTGAGCCTGGTCATCACCCTGTACTGCAAGAGAGGCAGGAAGAAGCTG
CTGTATATCTTCAAGCAGCCCTTTATGCGCCCTGTGCAGACAACCCAGGAGGAGGACGGCTGCAGCTG
TCGGTTCCCAGAAGAGGAGGAGGGCGGCTGTGAGCTGAGAGTGAAGTTTTCCAGGTCTGCCGATGCAC
CAGCATACCAGCAGGGACAGAACCAGCTGTATAACGAGCTGAATCTGGGCCGGAGAGAGGAGTACGAC
GTGCTGGATAAGAGGAGGGGAAGGGACCCCGAGATGGGAGGCAAGCCTCGGAGAAAGAACCCACAGGA
GGGCCTGTACAATGAGCTGCAGAAGGACAAGATGGCCGAGGCCTATTCTGAGATCGGCATGAAGGGAG
AGAGGCGCCGGGGCAAGGGACACGATGGCCTGTACCAGGGCCTGAGCACAGCCACCAAGGACACCTAT
GATGCCCTGCATATGCAGGCACTGCCTCCAAGGTGA CAR9 7
(SEQ ID NO: 27)
ATGGCTCTGCCCGTCACCGCTCTGCTGCTGCCACTGGCCCTGCTGCTGCACGCAGCCAGACCCCAGGT
GCAGCTGCAGCAGAGCGGCCCTGGCCTGGTGCAGCCATCCCAGACACTGTCTCTGACCTGCGTGATCA
GCGGCGACTCCGTGAGCTCCAACTCTGCCACATGGAATTGGATCAGACAGAGCCCATCCAGGGGCCTG
GAGTGGCTGGGACGCACCTACTATCGGAGCAAGTGGTACAACGACTATGCCGTGTCTGTGAAGAGCAG
AATCACAATCAACCCCGATACCTCTAAGAATCAGTTCAGCCTGCAGCTGAATTCCGTGACACCTGAGG
ATACCGCCGTGTACTATTGCGCCAGGGACGGCGATGGAGGAAGCTACTATGACTACTATTACTATGGC
ATGGACGTGTGGGGCCAGGGCACCACAGTGACAGTGTCTGGAGGAGGAGGAAGCGGAGGAGGAGGATC
CGGCGGCGGCGGCTCTGACATCCAGCTGACACAGTCCCCTTCTAGCCTGTCTACCAGCGTGGGCGATC
GCGTGACAATCACCTGTCGGGCCTCCCAGTCTATCAGCACCTACCTGAACTGGTATCAGCAGAAGCCC
GGCAAGGCCCCTAAGCTGCTGATCTACGCAGCAAGCAATCTGCAGTCCGGAGTGCCATCTCGCTTCTC
CGGCTCTGGCAGCGGCACAGACTTTACACTGACCATCTCCTCTCTGCAGCCTGAGGATTTCGCCACCT
ACTTTTGCCAGCAGTCCTATACCACACCAATCACATTCGGCCAGGGCACCAGACTGGAGATCAAGACC
ACAACCCCAGCACCCAGGCCCCCTACACCTGCACCAACCATCGCAAGCCAGCCACTGTCCCTGCGCCC
TGAGGCATGTAGGCCAGCAGCAGGAGGAGCAGTGCACACCAGAGGCCTGGACTTTGCCTGCGATATTT
ACATCTGGGCACCACTGGCAGGAACATGTGGCGTGCTGCTCCTGAGCCTGGTCATCACCCTGTACTGC
AAGAGAGGCAGGAAGAAGCTGCTGTATATCTTCAAGCAGCCCTTCATGCGGCCCGTGCAGACAACCCA
GGAGGAGGACGGCTGCTCTTGTCGGTTCCCAGAAGAGGAGGAGGGCGGCTGTGAGCTGAGAGTGAAGT
TTTCCAGGTCTGCCGATGCACCAGCATACCAGCAGGGACAGAACCAGCTGTATAACGAGCTGAATCTG
GGCCGGAGAGAGGAGTACGACGTGCTGGATAAGAGGAGGGGACGGGACCCTGAGATGGGAGGCAAGCC
CCGGAGAAAGAACCCTCAGGAGGGCCTGTACAATGAGCTGCAGAAGGACAAGATGGCCGAGGCCTATA
GCGAGATCGGCATGAAGGGAGAGAGGCGCCGGGGCAAGGGACACGATGGCCTGTACCAGGGCCTGTCC
ACAGCCACCAAGGACACCTATGATGCCCTGCATATGCAGGCACTGCCTCCAAGGTGA -continued

CAR12 8

(SEQ ID NO: 28)
ATGGCTCTGCCCGTCACCGCTCTGCTGCTGCCACTGGCCCTGCTGCTGCACGCAGCCAGACCCCAGGT

GCAGCTGCAGCAGTCCGGCCCTGGCCTGGTGAAGCCATCTCAGACACTGAGCCTGACCTGCGCCATCT

CCGGCGACTCTGTGAGCTCCAACTCCGCCGCCTGGAATTGGATCAGACAGAGCCCATCCAGGGGCCTG

GAGTGGCTGGGACGCACCTACTATCGGAGCGCCTGGTACAACGACTATGCCGTGAGCGTGAAGTCCAG

AATCACAATCAACCCCGATACCTCTAAGAATCAGTTCAGCCTGCAGCTGTCTAGCGTGACACCTGAGG

ATACCGCCGTGTACTATTGCGCCAGGGACGTGGAGGGCTTTGATTACTGGGGCCAGGGCACACTGGTG

ACCGTGTCCGGCGGCGGCGGCTCTGGAGGAGGAGGAAGCGGAGGAGGAGGATCCGACATCGTGATGAC

ACAGACCCCTTCCTCTCTGTCTGCCAGCGTGGGCGATCGCGTGACAATCACCTGTCGGGCCTCCCAGT

CTATCAGCTCCTACCTGAATTGGTATCAGCAGAAGCCCGGCAAGGCCCCTAAGCTGCTGATCTACGCA

GCATCTAGCCTGCAGTCCGGAGTGCCATCTCGCTTCAGCGGATCCGGCTCTGGCACAGACTTTACACT

GACCATCTCCTCTCTGCAGCCTGAGGATTTCGCCACCTACTATTGCCAGCAGAGCTATTCCACACCAA

TCACCTTTGGCCAGGGCACAAGACTGGAGATCAAGACCACAACCCCAGCACCCAGGCCCCCTACACCT

GCACCAACCATCGCAAGCCAGCCACTGTCCCTGCGCCCTGAGGCATGTAGGCCAGCAGCAGGAGGAGC

AGTGCACACCAGAGGCCTGGACTTCGCCTGCGATATTTACATCTGGGCACCACTGGCAGGAACATGTG

GCGTGCTGCTCCTGAGCCTGGTCATCACCCTGTACTGCAAGAGAGGCAGGAAGAAGCTGCTGTATATC

TTCAAGCAGCCCTTCATGCGGCCCGTGCAGACAACCCAGGAGGAGGACGGCTGCAGCTGTCGGTTCCC

AGAAGAGGAGGAGGGCGGCTGTGAGCTGAGAGTGAAGTTTTCTAGGAGCGCCGATGCACCAGCATACC

AGCAGGGACAGAACCAGCTGTATAACGAGCTGAATCTGGGCCGGAGAGAGGAGTACGACGTGCTGGAT

AAGAGGAGGGGACGGGACCCTGAGATGGGAGGCAAGCCCCGGAGAAAGAACCCTCAGGAGGGCCTGTA

CAATGAGCTGCAGAAGGACAAGATGGCCGAGGCCTATTCTGAGATCGGCATGAAGGGAGAGAGGCGCC

GGGGCAAGGGACACGATGGCCTGTACCAGGGCCTGAGCACAGCCACCAAGGACACCTATGATGCCCTG

CATATGCAGGCACTGCCTCCAAGGTGA

CAR13 9

(SEQ ID NO: 29)
ATGGCTCTGCCCGTCACCGCTCTGCTGCTGCCTCTGGCCCTGCTGCTGCACGCAGCCCGCCCACAGGT

GCAGCTGCAGCAGAGCGGCCCCGGCCTGGTGAAGCCTAGCCAGACACTGTCCCTGACCTGCGCAATCT

CCGGCGACAGCGTGTCCGGAAACAGGGCCACATGGAATTGGATCAGACAGTCTCCAAGCAGGGGCCTG

GAGTGGCTGGGAAGGACCTACTATCGGTCCGCCTGGTACAACGACTATGCCGTGTCTGTGAAGGGCCG

CATCACATTCAACCCAGATACCAGCAAGAATCAGTTTTCCCTGCAGCTGAATTCTGTGACACCCGAGG

ATACCGCCGTGTACTATTGCGCCAGAGGCGAGAGCGGAGCAGCAGCAGACGCCTTCGATATCTGGGGC

CAGGGCACCACAGTGACAGTGAGCGGAGGAGGAGGATCCGGCGGAGGAGGCTCTGGCGGCGGCGGCAG

CGACATCCAGCTGACCCAGAGCCCACCTTCCCTGTCTGCCAGCGTGGGCGATCGCGTGACAATCACCT

GTCGGGCCTCCCAGTCTATCAGCTCCTACCTGAACTGGTATCAGCAGAAGCCAGGCAAGGCCCCCAAG

CTGCTGATCTACGCAGCATCTAGCCTGCAGTCTGGAGTGCCAAGCAGATTCAGCGGATCCGGATTCGG

CACAGACTTTACACTGACCATCTCCTCTCTGCAGCCCGAGGATTTCGCCACCTACTATTGCCAGCAGT

CTTATAGCACACCTCAGACCTTTGGCCAGGGCACCAAGGTGGACATCAAGACCACAACCCCTGCACCA

AGACCACCAACACCAGCACCTACCATCGCATCCCAGCCACTGTCTCTGCGCCCCGAGGCATGTAGGCC

TGCAGCAGGCGGCGCCGTGCACACCAGGGGCCTGGACTTTGCCTGCGATATTTACATCTGGGCACCTC

TGGCAGGAACATGTGGCGTGCTGCTCCTGAGCCTGGTCATCACCCTGTACTGCAAGAGAGGCAGGAAG

AAGCTGCTGTATATCTTCAAGCAGCCCTTCATGCGGCCCGTGCAGACAACCCAGGAGGAGGACGGCTG

CTCCTGTAGGTTCCCTGAAGAGGAGGAGGGCGGCTGTGAGCTGAGAGTGAAGTTTTCCAGGTCTGCCG

```
ATGCACCAGCATACCAGCAGGGACAGAATCAGCTGTATAACGAGCTGAATCTGGGCCGGAGAGAGGAG

TACGACGTGCTGGATAAGAGGAGGGGACGGGATCCCGAGATGGGAGGCAAGCCACGGAGAAAGAACCC

CCAGGAGGGCCTGTACAATGAGCTGCAGAAGGACAAGATGGCCGAGGCCTATTCTGAGATCGGCATGA

AGGGAGAGAGGCGCCGGGGCAAGGGACACGATGGCCTGTACCAGGGCCTGTCCACAGCCACCAAGGAC

ACCTATGATGCCCTGCATATGCAGGCACTGCCTCCAAGGTGA
```

CAR15_10
(SEQ ID NO: 30)
```
ATGGCTCTGCCCGTCACCGCTCTGCTGCTGCCACTGGCCCTGCTGCTGCACGCAGCCAGACCCCAGGT

GCAGCTGGTGCAGAGCGGAGCAGAGGTGAAGAAGCCTGGCGCCAGCGTGAAGGTGTCCTGCAAGGCCT

CTGGCTACACATTCACCAGCTACTATATGCACTGGGTGCGGCAGGCCCCTGGCCAGGGCCTGGAGTGG

ATGGGCATCATCAACCCATCCGGCGGCTCCACCTCTTACGCCCAGAAGTTTCAGGGCAGAGTGACAAT

GACCAGGGACACAAGCACCTCCACAGTGTATATGGAGCTGAGCTCCCTGAGATCCGAGGATACAGCCG

TGTACTATTGCGCCAGGGAGGACTCTGGAAGCGGAGCCTTCGATATCTGGGGCCAGGGCACCCTGGTG

ACAGTGTCTGGAGGAGGAGGAAGCGGAGGAGGAGGATCCGGCGGCGGCGGCTCTGAGATCGTGCTGAC

CCAGTCTCCACTGAGCCTGCCAGTGACACCTGGCGAGCCAGCCTCCATCTCTTGTCGCTCTAGCCGGT

CCCTGCTGTCTTACCACGGCTACAATTATCTGGACTGGTATCTGCAGAAGCAGGCCAGAGCCCCCAG

CTGCTGATCTTCGTGGGATCCAACAGGGCCCCTGGCGTGCCTGACCGGTTCAGCGGATCCGGATCTGG

AACCGACTTCACCCTGAACATCTCTAGAGTGGAGGCCGAGGATGTGGGCGTGTACTATTGCATGCAGA

GCCTGCAGACCCCAAGAACATTTGGCCAGGGCACCAAGGTGGAGATCAAGACCACAACCCCAGCACCC

AGGCCCCCTACCCCTGCACCAACAATCGCAAGCCAGCCACTGTCCCTGCGCCCTGAGGCATGTAGGCC

AGCAGCAGGAGGAGCAGTGCACACCAGGGGCCTGGACTTTGCCTGCGATATCTACATTTGGGCACCAC

TGGCAGGAACCTGTGGCGTGCTGCTCCTGAGCCTGGTCATCACCCTGTACTGCAAGAGAGGCAGGAAG

AAGCTGCTGTATATCTTCAAGCAGCCTTTTATGCGCCCAGTGCAGACAACCCAGGAGGAGGACGGCTG

CTCCTGTAGGTTCCCAGAAGAGGAGGAGGAGGATGTGAGCTGAGAGTGAAGTTTAGCAGGTCCGCCG

ATGCACCTGCATACCAGCAGGGACAGAACCAGCTGTATAACGAGCTGAATCTGGGCCGGAGAGAGGAG

TACGACGTGCTGGATAAGAGGAGGGGACGGGACCCCGAGATGGGAGGCAAGCCCGGAGAAAGAACCC

TCAGGAGGGCCTGTACAATGAGCTGCAGAAGGACAAGATGGCCGAGGCCTATTCCGAGATCGGCATGA

AGGGAGAGAGGCGCCGGGGCAAGGGACACGATGGCCTGTACCAGGGCCTGTCTACCGCCACAAAGGAC

ACCTATGATGCCCTGCATATGCAGGCACTGCCTCCAAGGTGA
```

CAR1_QR3
(SEQ ID NO: 32)
```
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCTGGCCTGGTGAAGCCATCTCAGACACTGAGCCTGACCTGC

GCCATCTCTGGCGACAGCGTGAGCTCCAACTCTGCCGCCTGGAATTGGATCAGACAGTCCCCATCTAG

GGGCCTGGAGTGGCTGGGACGCACATACTATCGGTCCACCTGGTACAACGACTATGCCGTGTCCGTGA

AGTCTCGCATCACAATCAACCCCGATACCTCTAAGAATCAGTTCAGCCTGCAGCTGAATTCCGTGACA

CCTGAGGACACCGCCGTGTACTATTGCGCCAGAGAGGTGAGCGGCACATCCGCCTTTGATATCTGGGG

CCAGGGCACAATGGTGACCGTGTCTGGAGGAGGAGGAAGCGGAGGAGGAGGATCCGGCGGCGGCGGCT

CTGACATCCAGATGACCCAGAGCCCTTCTAGCCTGAGCGCCTCCGTGGGCGATCGCGTGACAATCACC

TGTCGGGCCTCTCAGAGCATCTCCTCTTACCTGAACTGGTATCAGCAGAAGCCCGGCAAGGCCCCTAA

GCTGCTGATCTACGCAGCAAGCTCCCTGCAGTCCGGAGTGCCATCTCGGTTCTCCGGCTCTGGCAGCG

GCACAGACTTTACACTGACCATCTCTAGCCTGCAGCCTGAGGATTTCGCCACCTACTATTGCCAGCAG
```

-continued

TCCTATTCTACACCACTGACCTTTGGCGGCGGCACCAAGCTGGAGATCAAGGGAAGTGGAGGAGGAGG

AAGTTGTCCCTATTCAAACCCATCCCTGTGCAGCGGAGGAGGAGGAAGCGAACTGCCTACTCAGGGAA

CATTCAGCAACGTGTCCACCAATGTGAGCCCAGCAAAGCCTACCACAACCGCATGCCCATACTCTAAC

CCCAGCCTGTGCACAACCACACCAGCACCCAGGCCCCCTACCCCTGCACCAACAATCGCCTCCCAGCC

TCTGTCTCTGCGGCCAGAGGCCTGCAGACCCGCCGCCGGCGGAGCAGTGCACACGGGGCCTGGACT

TTGCCTGTGATATCTATATCTGGGCCCCACTGGCTGGAACATGTGGCGTGCTGCTGCTGTCACTGGTC

ATTACCCTGTACTGTAAGCGAGGCCGGAAGAAACTGCTGTATATTTTCAAACAGCCCTTTATGAGACC

TGTGCAGACTACCCAGGAGGAAGACGGCTGCAGCTGTAGGTTCCCCGAGGAAGAGGAAGGCGGGTGTG

AGCTGAGGGTCAAGTTTAGCCGCTCCGCAGATGCCCCTGCTTACCAGCAGGGGCAGAATCAGCTGTAT

AACGAGCTGAATCTGGGACGGAGAGAGGAATACGACGTGCTGGATAAAAGGCGCGGGAGAGACCCCGA

AATGGGAGGCAAGCCACGACGGAAAAACCCCAGGAGGGCCTGTACAATGAACTGCAGAAGGACAAAA

TGGCAGAGGCCTATAGTGAAATCGGGATGAAGGGAGAGAGAAGGCGCGGCAAAGGGCACGATGGCCTG

TACCAGGGGCTGTCTACTGCCACCAAGGACACCTATGATGCTCTGCATATGCAGGCACTGCCTCCAAG

GTGA

CAR2_QR3

(SEQ ID NO: 33)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCTGGCCTGGTGAAGCCATCCCAGACCCTGTCTCTGACATGC

GCCATCAGCGGCGACTCCGTGAGCTCCAACTCTGCCGCCTGGAATTGGATCAGACAGTCCCCATCTAG

GGGCCTGGAGTGGCTGGGAAGGACCTACTATCGGTCCAAGTGGTACAACGACTATGCCGTGTCTGTGA

AGAGCCGCATCACCATCAACCCCGATACATCCAAGAATCAGTTCTCTCTGCAGCTGAATAGCGTGACC

CCTGAGGACACAGCCGTGTACTATTGCGCCAGAGCCTCTATGACCGGCGGCTACAGCTATGGCGACGC

CTTTGATATCTGGGGCCAGGGCACACTGGTGACCGTGTCCGGCGGCGGCGGCTCTGGAGGAGGAGGAA

GCGGAGGAGGAGGATCCGCCATCCGCATGACACAGAGCCCTTCTAGCCTGAGCGCCTCCGTGGGCGAT

CGCGTGACAATCACCTGTCGGGCCTCTCAGAGCATCTCCTCTTACCTGAACTGGTATCAGCAGAAGCC

CGGCAAGGCCCCTAAGCTGCTGATCTACGCAGCAAGCTCCCTGCAGAGCGGAGTGCCATCCCGGTTCT

CCGGATCTGGAAGCGGAACCGACTTTTCCCTGACAATCTCTAGCCTGCAGCCTGAGGATTCCGCCACC

TACTATTGCCAGCAGACATATTCTACCCCACTGACATTCGGCCAGGGCACAAAGGTGGAGATCAAGGG

CAGTGGAGGAGGAGGAAGTTGTCCCTACTCTAACCCAAGCCTGTGCAGTGGAGGAGGAGGAAGTGAAC

TGCCTACCCAGGGAACATTCAGCAACGTGTCCACCAATGTGAGCCCAGCAAAGCCTACCACAACCGCA

TGCCCATACTCTAACCCCAGCCTGTGCACAACCACACCAGCACCCAGGCCCCCTACCCCTGCACCAAC

AATCGCCTCCCAGCCTCTGTCTCTGCGGCCAGAGGCCTGCAGACCCGCCGCCGGCGGAGCAGTGCACA

CACGGGGCCTGGACTTTGCCTGTGATATCTATATCTGGGCACCACTGGCCGGAACATGTGGCGTGCTG

CTGCTGTCACTGGTCATTACACTGTATTGTAAGCGAGGCCGGAAGAAACTGCTGTATATTTTCAAACA

GCCCTTTATGAGACCTGTGCAGACTACCCAGGAGGAAGACGGCTGCAGCTGTAGGTTCCCCGAGGAAG

AGGAAGGCGGGTGTGAGCTGAGGGTCAAGTTTAGCCGCTCCGCAGATGCCCCTGCTTACCAGCAGGGG

CAGAATCAGCTGTATAACGAGCTGAATCTGGGACGGAGAGAGGAATACGACGTGCTGGATAAAAGGCG

CGGGAGAGACCCCGAAATGGGAGGCAAGCCACGACGGAAAAACCCCAGGAGGGCCTGTACAATGAAC

TGCAGAAGGACAAAATGGCAGAGGCCTATAGTGAAATCGGGATGAAGGGAGAGAGAAGGCGCGGCAAA

GGGCACGATGGCCTGTACCAGGGGCTGTCTACTGCCACCAAGGACACCTATGATGCTCTGCATATGCA

GGCACTGCCTCCAAGGTGA

CAR3_QR3

(SEQ ID NO: 34)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCTGGCCTGGTGGAGCCAAGCCAGACACTGTCCCTGACCTGC

GCCATCTCTGGCGACAGCGTGAGCTCCGATTCCGTGGCCTGGAACTGGATCAGGCAGTCTCCAAGCCG

GGGCCTGGAGTGGCTGGGCAGAACATACTATAGGTCTACCTGGTACAATGACTATGCCGGCTCCGTGA

AGTCTCGCATCACAATCAACCCCGATACCAGCAAGAATCAGTTCTCCCTGCAGCTGACATCTGTGACC

CCTGAGGACACAGCCGTGTACTATTGCACCAGATCCAGGCACAACACATTTCGGGGAATGGACGTGTG

GGGACAGGGAACCACAGTGACCGTGAGCGGAGGAGGAGGATCCGGCGGAGGAGGCTCTGGAGGAGGAG

GAAGCGACATCGTGATGACCCAGAGCCCTTCTAGCCTGTCCGCCTCTGTGGGCGATAGAGTGACAATC

ACCTGTAGGGCCTCCCAGACCATCTCCTCTTACCTGAACTGGTATCAGCAGAAGCCCGGCAAGGCCCC

TAAGCTGCTGATCTACGACGCAAGCTCCCTGCAGTCTGGAGTGCCAAGCAGATTCAGCGGCTCCGGCT

CTGGCACCGACTTTACACTGACCATCAATTCCCTGCAGCCTGAGGATTTCGCCACATACTATTGCCAG

CAGTCTTATACCACACCAATCACATTTGGCCAGGGCACCCGCCTGGAGATCAAGGGAAGCGGCGGCGG

CGGCTCATGCCCTTATTCAAACCCATCTCTGTGCTCAGGAGGAGGAGGAAGCGAACTGCCTACTCAGG

GAACATTCAGCAACGTGTCCACCAATGTGAGCCCAGCAAAGCCTACCACAACCGCATGCCCATACTCT

AACCCCAGCCTGTGCACAACCACACCAGCACCCAGGCCCCCTACCCCTGCACCAACAATCGCCTCCCA

GCCTCTGTCTCTGCGGCCAGAGGCCTGCAGACCCGCCGCCGGCGGAGCAGTGCACACACGGGGCCTGG

ACTTTGCCTGTGATATCTATATCTGGGCACCACTGGCTGGAACATGTGGCGTGCTGCTGCTGTCACTG

GTCATTACACTGTATTGCAAGCGAGGCCGGAAGAAACTGCTGTATATTTTCAAACAGCCCTTTATGAG

ACCTGTGCAGACTACCCAGGAGGAAGACGGCTGCAGCTGTAGGTTCCCCGAGGAAGAGGAAGGCGGGT

GTGAGCTGAGGGTCAAGTTTAGCCGCTCCGCAGATGCCCCTGCTTACCAGCAGGGGCAGAATCAGCTG

TATAACGAGCTGAATCTGGACGGAGAGAGGAATACGACGTGCTGGATAAAAGGCGCGGGAGAGACCC

CGAAATGGAGGCAAGCCACGACGGAAAAACCCCCAGGAGGGCCTGTACAATGAACTGCAGAAGGACA

AAATGGCAGAGGCCTATAGTGAAATCGGGATGAAGGGAGAGAGAAGGCGCGGCAAAGGGCACGATGGC

CTGTACCAGGGGCTGTCTACTGCCACCAAGGACACCTATGATGCTCTGCATATGCAGGCACTGCCTCC

AAGGTGA

CAR4_QR3

(SEQ ID NO: 35)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCTGGCCTGGTGGAGCCAAGCCAGACACTGTCCCTGACCTGC

GCCATCTCTGGCGACAGCGTGAGCTCCAACAGCGCCGCATGGAATTGGATCAGGCAGTCCCCATCTCG

GGGCCTGGAGTGGCTGGGCAGAACATACTATAGGTCCACCTGGTACAACGACTATGCCGGCTCCGTGA

AGTCTCGCATCACAATCAACCCCGATACCAGCAAGAATCAGTTCTCCCTGCAGCTGACATCTGTGACC

CCTGAGGACACAGCCGTGTACTATTGCACCAGAAGCAGGCACAATACATTTCGGGGAATGGACGTGTG

GGGACAGGGCACACTGGTGACCGTGAGCGGAGGAGGAGGATCCGGCGGAGGAGGCTCTGGCGGCGGCG

GCAGCGACATCCAGCTGACCCAGTCCCCTTCTAGCCTGAGCGCCTCCGTGGGCGATAGAGTGACAATC

ACCTGTAGGGCCTCTCAGAGCATCTCCTCTTACCTGAACTGGTATCAGCAGAAGCCCGGCAAGGCCCC

TAAGCTGCTGATCTACGCAGCAAGCTCCCTGCAGTCTGGAGTGCCAAGCAGATTCTCCGGCTCTGGCA

GCGGCACCGACTTTACACTGACCATCTCTAGCCTGCAGCCTGAGGATTTCGCCACATACTATTGCCAG

CAGTCCTATTCTACACCACTGACCTTTGGCGGCGGCACCAAGGTGGAGATCAAGGGAAGCGGCGGCGG

-continued

CGGAAGTTGTCCATATTCAAACCCAAGTCTGTGCAGCGGCGGAGGAGGAAGCGAACTGCCTACTCAGG

GAACCTTCAGCAACGTGTCCACCAATGTGAGCCCAGCAAAGCCTACCACAACCGCATGCCCATACTCT

AACCCCAGCCTGTGCACAACCACACCAGCACCCAGGCCCCCTACCCCTGCACCAACAATCGCCTCCCA

GCCTCTGTCTCTGCGGCCAGAGGCCTGCAGACCCGCCGCCGGCGGAGCAGTGCACACACGGGGCCTGG

ACTTTGCCTGTGATATCTATATCTGGGCACCACTGGCCGGAACATGTGGCGTGCTGCTGCTGTCACTG

GTCATTACACTGTACTGTAAGCGAGGCCGGAAGAAACTGCTGTATATTTTCAAACAGCCCTTTATGAG

ACCTGTGCAGACTACCCAGGAGGAAGACGGCTGCAGCTGTAGGTTCCCCGAGGAAGAGGAAGGCGGGT

GTGAGCTGAGGGTCAAGTTTAGCCGCTCCGCAGATGCCCCTGCTTACCAGCAGGGGCAGAATCAGCTG

TATAACGAGCTGAATCTGGGACGGAGAGAGGAATACGACGTGCTGGATAAAAGGCGCGGGAGAGACCC

CGAAATGGGAGGCAAGCCACGACGGAAAAACCCCCAGGAGGGCCTGTACAATGAACTGCAGAAGGACA

AAATGGCAGAGGCCTATAGTGAAATCGGGATGAAGGGAGAGAGAAGGCGCGGCAAAGGGCACGATGGC

CTGTACCAGGGGCTGTCTACTGCCACCAAGGACACCTATGATGCTCTGCATATGCAGGCACTGCCTCC

AAGGTGA

CAR7_QR3

(SEQ ID NO: 36)

ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCTGGCCTGGTGGAGCCAAGCCAGAGACCCGTCCCTGACATGC

GCCATCTCTGGCGACAGCGTGAGCTCCGATTCTGTGGCCTGGAACTGGATCAGGCAGAGCCCAAGCCG

GGGCCTGGAGTGGCTGGGCAGAACCTACTATAGGTCCACATGGTACAATGACTATGCCGGCTCCGTGA

AGTCTCGGATCACCATCAACCCCGATACATCCAAGAATCAGTTCTCTCTGCAGCTGAACAGCGTGACC

CCTGAGGACACAGCCGTGTACTATTGCGCCAGAGACAGGAATGGCATGGACGTGTGGGGCCAGGGAAC

CATGGTGACAGTGTCCGGAGGAGGCGGCTCTGGAGGAGGAGGAAGCGGAGGAGGAGGATCCGACATCG

TGATGACCCAGAGCCCTTCTAGCCTGTCTGCCAGCGTGGGCGATAGAGTGACAATCACCTGTAGGGCC

TCCCAGTCTATCTCCTCTTACCTGAACTGGTATCAGCAGAAGCCCGGCAAGGCCCCTAAGCTGCTGAT

CTACGATGCCTCTAATCTGGAGACAGGCGTGCCAAGCAGATTCAGCGGCTCCGGCTCTGGCACAGACT

TCACCTTCACCATCACATCCCTGCAGCCTGAGGATTTCGCCACCTACTATTGCCAGCAGTCTTATACC

ACACCACTGACCTTTGGCGGCGGCACAAAGGTGGAGATCAAGGGAAGCGGAGAGGAGGAAGTTGTCC

CTATTCAAATCCATCACTGTGCAGCGGAGGAGGAGGAAGCGAACTGCCTACTCAGGGAACCTTCAGCA

ACGTGTCCACCAATGTGAGCCCAGCAAAGCCTACCACAACCGCATGCCCATACTCTAACCCCAGCCTG

TGCACAACCACACCAGCACCCAGGCCCCCTACCCCTGCACCAACAATCGCCTCCCAGCCTCTGTCTCT

GCGGCCAGAGGCCTGCAGACCCGCCGCCGGCGGAGCAGTGCACACACGGGGCCTGGACTTTGCCTGTG

ATATCTATATCTGGGCACCACTGGCTGGAACATGCGCGTGCTGCTGCTGTCACTGGTCATCACACTG

TACTGTAAGCGAGGCCGGAAGAAACTGCTGTATATTTTCAAACAGCCCTTTATGAGACCTGTGCAGAC

TACCCAGGAGGAAGACGGCTGCAGCTGTAGGTTCCCCGAGGAAGAGGAAGGCGGGTGTGAGCTGAGGG

TCAAGTTTAGCCGCTCCGCAGATGCCCCTGCTTACCAGCAGGGGCAGAATCAGCTGTATAACGAGCTG

AATCTGGGACGGAGAGAGGAATACGACGTGCTGGATAAAAGGCGCGGGAGAGACCCCGAAATGGGAGG

CAAGCCACGACGGAAAAACCCCCAGGAGGGCCTGTACAATGAACTGCAGAAGGACAAAATGGCAGAGG

CCTATAGTGAAATCGGGATGAAGGGAGAGAGAAGGCGCGGCAAAGGGCACGATGGCCTGTACCAGGGG

CTGTCTACTGCCACCAAGGACACCTATGATGCTCTGCATATGCAGGCACTGCCTCCAAGGTGA

-continued

CAR8_QR3
(SEQ ID NO: 37)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGTCCGGCCCAGGCCTGGTGAAGCCATCCCAGACACTGTCTCTGACCTGC

GCCATCAGCGGCGACTCCGTGAGCTCCTCTAGCGCCGCCTGGAACTGGATCAGACAGTCTCCTAGCAG

GGGCCTGGAGTGGCTGGGAAGGACCTACTATCGGTCCGCCTGGTACAATGACTATGCCGTGTCTGTGA

AGAGCAGAATCACAATCAACCCCGATACCTCCAAGAATCAGTTCTCTCTGCAGCTGAACAGCGTGACA

CCTGAGGATACCGCCGTGTACTATTGCGCCAGAGAGAGCGTGCTGCTGGACGGAATGGACGTGTGGGG

AAGGGGAACCACAGTGACAGTGTCCGGAGGAGGCGGCTCTGGAGGAGGAGGAAGCGGAGGAGGAGGAT

CCGCCATCAGGATGACACAGTCCCCATCTACCCTGAGCGCCTCCGTGGGCGACCGCGTGACAATCACC

TGTCGGGCCTCTCAGAGCATCTCCACCTACCTGAATTGGTATCAGCAGAAGGCCGGCAAGGCCCCAAG

ACTGCTGATCCACGATGCATCCTCTCTGCAGAGCGGAGTGCCATCCAGGTTCTCTGGAAGCGGATCCG

GCACAGACTTTACACTGACCATCAGCTCCCTGCAGCCTGAGGATTTCGCCACCTACTATTGCCAGCAG

TCTTACAGCACACCACTGACCTTTGGCGGCGGCACAAAGGTGGAGATCAAGGGAAGCGGGGGAGGAGG

ATCTTGCCCATATTCAAACCCATCACTGTGCTCAGGAGGAGGAGGAAGCGAACTGCCTACTCAGGGAA

CTTTCAGCAACGTGTCCACCAATGTGAGCCCAGCAAAGCCTACCACAACCGCATGCCCATACTCTAAC

CCCAGCCTGTGCACAACCACACCAGCACCCAGGCCCCCTACCCCTGCACCAACAATCGCCTCCCAGCC

TCTGTCTCTGCGGCCAGAGGCCTGCAGACCCGCCGCCGGCGGAGCAGTGCACACGGGGCCTGGACT

TTGCCTGTGATATCTATATCTGGGCACCACTGGCCGGAACATGTGGCGTGCTGCTGCTGTCACTGGTC

ATTACACTGTACTGTAAGCGAGGCCGGAAGAAACTGCTGTATATTTTCAAACAGCCCTTTATGAGACC

TGTGCAGACTACCCAGGAGGAAGACGGCTGCAGCTGTAGGTTCCCCGAGGAAGAGGAAGGCGGGTGTG

AGCTGAGGGTCAAGTTTAGCCGCTCCGCAGATGCCCCTGCTTACCAGCAGGGGCAGAATCAGCTGTAT

AACGAGCTGAATCTGGGACGGAGAGAGGAATACGACGTGCTGGATAAAAGGCGCGGGAGAGACCCCGA

AATGGGAGGCAAGCCACGACGGAAAAACCCCCAGGAGGGCCTGTACAATGAACTGCAGAAGGACAAAA

TGGCAGAGGCCTATAGTGAAATCGGGATGAAGGGAGAGAGAAGGCGCGGCAAAGGGCACGATGGCCTG

TACCAGGGGCTGTCTACTGCCACCAAGGACACCTATGATGCTCTGCATATGCAGGCACTGCCTCCAAG

GTGA

CAR9_QR3
(SEQ ID NO: 38)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCTGGCCTGGTGCAGCCATCCCAGACACTGTCTCTGACCTGC

GTGATCAGCGGCGACTCCGTGAGCTCCAACTCTGCCACATGGAATTGGATCAGACAGAGCCCATCCAG

GGGCCTGGAGTGGCTGGGACGCACCTACTATCGGAGCAAGTGGTACAACGACTATGCCGTGTCTGTGA

AGAGCAGAATCACAATCAACCCCGATACCTCTAAGAATCAGTTCAGCCTGCAGCTGAATTCCGTGACA

CCTGAGGATACCGCCGTGTACTATTGCGCCAGGGACGGCGATGGAGGAAGCTACTATGACTACTATTA

CTATGGCATGGACGTGTGGGGCCAGGGCACCACAGTGACAGTGTCTGGAGGAGGAGGAAGCGGAGGAG

GAGGATCCGGCGGCGGCGGCTCTGACATCCAGCTGACACAGTCCCCTTCTAGCCTGTCTACCAGCGTG

GGCGATCGCGTGACAATCACCTGTCGGGCCTCCCAGTCTATCAGCACCTACCTGAACTGGTATCAGCA

GAAGCCCGGCAAGGCCCCTAAGCTGCTGATCTACGCAGCAAGCAATCTGCAGTCCGGAGTGCCATCTC

GCTTCTCCGGCTCTGGCAGCGGCACAGACTTTACACTGACCATCTCCTCTCTGCAGCCTGAGGATTTC

GCCACCTACTTTTGCCAGCAGTCCTATACCACACCAATCACATTCGGCCAGGGCACCAGACTGGAGAT

-continued

CAAGGGAAGTGGAGGAGGAGGAAGTTGCCCTTACTCTAACCCAAGTCTGTGCTCAGGAGGCGGAGGAA

GCGAACTGCCTACTCAGGGAACATTCAGCAACGTGTCCACCAATGTGAGCCCAGCAAAGCCTACCACA

ACCGCATGCCCATACTCTAACCCCAGCCTGTGCACAACCACACCAGCACCCAGGCCCCCTACCCCTGC

ACCAACAATCGCCTCCCAGCCTCTGTCTCTGCGGCCAGAGGCCTGCAGACCCGCCGCCGGCGGAGCAG

TGCACACACGGGGCCTGGACTTTGCCTGTGATATCTATATCTGGGCACCACTGGCTGGAACATGCGGA

GTGCTGCTGCTGTCACTGGTCATTACACTGTACTGTAAGCGAGGCCGGAAGAAACTGCTGTATATTTT

CAAACAGCCCTTTATGAGACCTGTGCAGACTACCCAGGAGGAAGACGGCTGCAGCTGTAGGTTCCCCG

AGGAAGAGGAAGGCGGGTGTGAGCTGAGGGTCAAGTTTAGCCGCTCCGCAGATGCCCCTGCTTACCAG

CAGGGGCAGAATCAGCTGTATAACGAGCTGAATCTGGGACGGAGAGAGGAATACGACGTGCTGGATAA

AAGGCGCGGGAGAGACCCCGAAATGGGAGGCAAGCCACGACGGAAAAACCCCCAGGAGGGCCTGTACA

ATGAACTGCAGAAGGACAAAATGGCAGAGGCCTATAGTGAAATCGGGATGAAGGGAGAGAGAAGGCGC

GGCAAAGGGCACGATGGCCTGTACCAGGGGCTGTCTACTGCCACCAAGGACACCTATGATGCTCTGCA

TATGCAGGCACTGCCTCCAAGGTGA

CAR12_QR3

(SEQ ID NO: 39)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGTCCGGCCCTGGCCTGGTGAAGCCATCTCAGACACTGAGCCTGACCTGC

GCCATCTCCGGCGACTCTGTGAGCTCCAACTCCGCCGCCTGGAATTGGATCAGACAGAGCCCATCCAG

GGGCCTGGAGTGGCTGGGACGCACCTACTATCGGAGCGCCTGGTACAACGACTATGCCGTGAGCGTGA

AGTCCAGAATCACAATCAACCCCGATACCTCTAAGAATCAGTTCAGCCTGCAGCTGTCTAGCGTGACA

CCTGAGGATACCGCCGTGTACTATTGCGCCAGGGACGTGGAGGGCTTTGATTACTGGGGCCAGGGCAC

ACTGGTGACCGTGTCCGGCGGCGGCGGCTCTGGAGGAGGAGGAAGCGGAGGAGGAGGATCCGACATCG

TGATGACACAGACCCCTTCCTCTCTGTCTGCCAGCGTGGGCGATCGCGTGACAATCACCTGTCGGGCC

TCCCAGTCTATCAGCTCCTACCTGAATTGGTATCAGCAGAAGCCCGGCAAGGCCCCTAAGCTGCTGAT

CTACGCAGCATCTAGCCTGCAGTCCGGAGTGCCATCTCGCTTCAGCGGATCCGGCTCTGGCACAGACT

TTACACTGACCATCTCCTCTCTGCAGCCTGAGGATTTCGCCACCTACTATTGCCAGCAGAGCTATTCC

ACACCAATCACCTTTGGCCAGGGCACAAGACTGGAGATCAAGGGAAGCGGGGGAGGAGGATCATGTCC

ATACTCTAACCCATCACTGTGCTCTGGAGGAGGAGGAAGCGAACTGCCTACTCAGGGAACCTTCAGCA

ACGTGTCCACCAATGTGAGCCCAGCAAAGCCTACCACAACCGCATGCCCATACTCTAACCCCAGCCTG

TGCACAACCACACCAGCACCCAGGCCCCCTACCCCTGCACCAACAATCGCCTCCCAGCCTCTGTCTCT

GCGGCCAGAGGCCTGCAGACCCGCCGCCGGCGGAGCAGTGCACACACGGGGCCTGGACTTTGCCTGTG

ATATCTATATCTGGGCACCACTGGCTGGAACATGCGCGTGCTGCTGCTGTCACTGGTCATTACACTG

TATTGTAAGCGAGGCCGGAAGAAACTGCTGTATATTTTCAAACAGCCCTTTATGAGACCTGTGCAGAC

TACCCAGGAGGAAGACGGCTGCAGCTGTAGGTTCCCCGAGGAAGAGGAAGGCGGGTGTGAGCTGAGGG

TCAAGTTTAGCCGCTCCGCAGATGCCCCTGCTTACCAGCAGGGGCAGAATCAGCTGTATAACGAGCTG

AATCTGGGACGGAGAGAGGAATACGACGTGCTGGATAAAAGGCGCGGGAGAGACCCCGAAATGGGAGG

CAAGCCACGACGGAAAAACCCCCAGGAGGGCCTGTACAATGAACTGCAGAAGGACAAAATGGCAGAGG

CCTATAGTGAAATCGGGATGAAGGGAGAGAGAAGGCGCGGCAAAGGGCACGATGGCCTGTACCAGGGG

CTGTCTACTGCCACCAAGGACACCTATGATGCTCTGCATATGCAGGCACTGCCTCCAAGGTGA

-continued

CAR13_QR3
(SEQ ID NO: 40)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCCGGCCTGGTGAAGCCTAGCCAGACACTGTCCCTGACCTGC

GCAATCTCCGGCGACAGCGTGTCCGGAAACAGGGCCACATGGAATTGGATCAGACAGTCTCCAAGCAG

GGGCCTGGAGTGGCTGGGAAGGACCTACTATCGGTCCGCCTGGTACAACGACTATGCCGTGTCTGTGA

AGGGCCGCATCACATTCAACCCAGATACCAGCAAGAATCAGTTTTCCCTGCAGCTGAATTCTGTGACA

CCCGAGGATACCGCCGTGTACTATTGCGCCAGAGGCGAGAGCGGAGCAGCAGCAGACGCCTTCGATAT

CTGGGGCCAGGGCACCACAGTGACAGTGAGCGGAGGAGGAGGATCCGGCGGAGGAGGCTCTGGCGGCG

GCGGCAGCGACATCCAGCTGACCCAGAGCCCACCTTCCCTGTCTGCCAGCGTGGGCGATCGCGTGACA

ATCACCTGTCGGGCCTCCCAGTCTATCAGCTCCTACCTGAACTGGTATCAGCAGAAGCCAGGCAAGGC

CCCCAAGCTGCTGATCTACGCAGCATCTAGCCTGCAGTCTGGAGTGCCAAGCAGATTCAGCGGATCCG

GATTCGGCACAGACTTTACACTGACCATCTCCTCTCTGCAGCCCGAGGATTTCGCCACCTACTATTGC

CAGCAGTCTTATAGCACACCTCAGACCTTTGGCCAGGGCACCAAGGTGGACATCAAGGGAAGTGGAGG

AGGAGGAAGTTGTCCCTACTCAAACCCATCTCTGTGCTCAGGAGGAGGAGGAAGTGAACTGCCTACTC

AGGGAACATTCAGCAACGTGTCCACCAATGTGAGCCCAGCAAAGCCTACCACAACCGCATGCCCATAC

TCTAACCCCAGCCTGTGCACAACCACACCAGCACCCAGGCCCCCTACCCCTGCACCAACAATCGCCTC

CCAGCCTCTGTCTCTGCGGCCAGAGGCCTGCAGACCCGCCGCCGGCGGAGCAGTGCACACACGGGCC

TGGACTTTGCCTGTGATATCTATATCTGGGCACCACTGGCCGGAACATGTGGCGTGCTGCTGCTGTCA

CTGGTCATTACACTGTACTGTAAGCGAGGCCGGAAGAAACTGCTGTATATTTTCAAACAGCCCTTTAT

GAGACCTGTGCAGACTACCCAGGAGGAAGACGGCTGCAGCTGTAGGTTCCCCGAGGAAGAGGAAGGCG

GGTGTGAGCTGAGGGTCAAGTTTAGCCGCTCCGCAGATGCCCCTGCTTACCAGCAGGGGCAGAATCAG

CTGTATAACGAGCTGAATCTGGGACGGAGAGAGGAATACGACGTGCTGGATAAAAGGCGCGGGAGAGA

CCCCGAAATGGGAGGCAAGCCACGACGGAAAAACCCCCAGGAGGGCCTGTACAATGAACTGCAGAAGG

ACAAAATGGCAGAGGCCTATAGTGAAATCGGGATGAAGGGAGAGAGAAGGCGCGGCAAAGGGCACGAT

GGCCTGTACCAGGGGCTGTCTACTGCCACCAAGGACACCTATGATGCTCTGCATATGCAGGCACTGCC

TCCAAGGTGA

CAR15_QR3
(SEQ ID NO: 41)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGGTGCAGAGCGGAGCAGAGGTGAAGAAGCCTGGCGCCAGCGTGAAGGTGTCCTGC

AAGGCCTCTGGCTACACATTCACCAGCTACTATATGCACTGGGTGCGGCAGGCCCCTGGCCAGGGCCT

GGAGTGGATGGGCATCATCAACCCATCCGGCGGCTCCACCTCTTACGCCCAGAAGTTTCAGGGCAGAG

TGACAATGACCAGGGACACAAGCACCTCCACAGTGTATATGGAGCTGAGCTCCCTGAGATCCGAGGAT

ACAGCCGTGTACTATTGCGCCAGGGAGGACTCTGGAAGCGGAGCCTTCGATATCTGGGGCCAGGGCAC

CCTGGTGACAGTGTCTGGAGGAGGAGGAAGCGGAGGAGGAGGATCCGGCGGCGGCGGCTCTGAGATCG

TGCTGACCCAGTCTCCACTGAGCCTGCCAGTGACACCTGGCGAGCCAGCCTCCATCTCTTGTCGCTCT

AGCCGGTCCCTGCTGTCTTACCACGGCTACAATTATCTGGACTGGTATCTGCAGAAGCCAGGCCAGAG

CCCCCAGCTGCTGATCTTCGTGGGATCCAACAGGGCCCCTGGCGTGCCTGACCGGTTCAGCGGATCCG

GATCTGGAACCGACTTCACCCTGAACATCTCTAGAGTGGAGGCCGAGGATGTGGGCGTGTACTATTGC

ATGCAGAGCCTGCAGACCCCAAGAACATTTGGCCAGGGCACCAAGGTGGAGATCAAGGGAAGCGGCGG

-continued

AGGCGGAAGTTGTCCCTACTCAAACCCAAGTCTGTGCTCAGGAGGAGGAGGAAGCGAACTGCCTACTC

AGGGAACATTCAGCAACGTGTCCACCAATGTGAGCCCAGCAAAGCCTACCACAACCGCATGCCCATAC

TCTAACCCCAGCCTGTGCACAACCACACCAGCACCCAGGCCCCCTACCCCTGCACCAACAATCGCCTC

CCAGCCTCTGTCTCTGCGGCCAGAGGCCTGCAGACCCGCCGCCGGCGGAGCAGTGCACACACGGGGCC

TGGACTTTGCCTGTGATATCTATATCTGGGCACCACTGGCCGGAACATGCGGAGTCCTGCTGCTGTCA

CTGGTCATTACACTGTACTGTAAGCGAGGCCGGAAGAAACTGCTGTATATTTTCAAACAGCCCTTTAT

GAGACCTGTGCAGACTACCCAGGAGGAAGACGGCTGCAGCTGTAGGTTCCCCGAGGAAGAGGAAGGCG

GGTGTGAGCTGAGGGTCAAGTTTAGCCGCTCCGCAGATGCCCCTGCTTACCAGCAGGGGCAGAATCAG

CTGTATAACGAGCTGAATCTGGGACGGAGAGAGGAATACGACGTGCTGGATAAAAGGCGCGGGAGAGA

CCCCGAAATGGGAGGCAAGCCACGACGGAAAAACCCCCAGGAGGGCCTGTACAATGAACTGCAGAAGG

ACAAAATGGCAGAGGCCTATAGTGAAATCGGGATGAAGGGAGAGAGAAGGCGCGGCAAAGGGCACGAT

GGCCTGTACCAGGGGCTGTCTACTGCCACCAAGGACACCTATGATGCTCTGCATATGCAGGCACTGCC

TCCAAGGTGA

CAR4_R2

(SEQ ID NO: 42)
ATGGCTCTGCCCGTCACCGCTCTGCTGCTGCCCCTGGCCCTGCTGCTGCACGCCGCCCGGCCTCAGGT

GCAGCTGCAGCAGAGCGGCCCTGGCCTGGTGGAGCCAAGCCAGACACTGTCCCTGACCTGCGCCATCT

CTGGCGACAGCGTGAGCTCCAACAGCGCCGCATGGAATTGGATCAGGCAGTCCCCATCTCGGGGCCTG

GAGTGGCTGGGCAGAACATACTATAGGTCCACCTGGTACAACGACTATGCCGGCTCCGTGAAGTCTCG

CATCACAATCAACCCCGATACCAGCAAGAATCAGTTCTCCCTGCAGCTGACATCTGTGACCCCTGAGG

ACACAGCCGTGTACTATTGCACCAGAAGCAGGCACAATACATTTCGGGGAATGGACGTGTGGGGACAG

GGCACACTGGTGACCGTGAGCGGAGGAGGAGGATCCGGCGGAGGAGGCTCTGGCGGCGGCGGCAGCGA

CATCCAGCTGACCCAGTCCCCTTCTAGCCTGAGCGCCTCCGTGGGCGATAGAGTGACAATCACCTGTA

GGGCCTCTCAGAGCATCTCCTCTTACCTGAACTGGTATCAGCAGAAGCCCGGCAAGGCCCCTAAGCTG

CTGATCTACGCAGCAAGCTCCCTGCAGTCTGGAGTGCCAAGCAGATTCTCCGGCTCTGGCAGCGGCAC

CGACTTTACACTGACCATCTCTAGCCTGCAGCCTGAGGATTTCGCCACATACTATTGCCAGCAGTCCT

ATTCTACACCACTGACCTTTGGCGGCGGCACCAAGGTGGAGATCAAGTCTGACCCCGGAAGTGGCGGC

GGCGGAAGTTGCCCTTATTCAAATCCATCCCTGTGCTCTGGCGGCGGAGGAAGTTGTCCTTATAGCAA

CCCCAGCCTGTGCTCCGGAGGAGGAGGCAGCACCACAACCCCAGCACCCAGGCCCCCTACACCTGCAC

CAACCATCGCCTCTCAGCCACTGAGCCTGCGCCCTGAGGCCTGCAGACCAGCCGCCGGCGGAGCAGTG

CACACACGGGGCCTGGACTTCGCCTGTGATATCTACATCTGGGCACCACTGGCCGGAACATGTGGCGT

GCTGCTGCTGTCACTGGTCATTACACTGTACTGTAAGCGAGGCCGGAAGAAACTGCTGTATATTTTCA

AACAGCCCTTTATGAGACCTGTGCAGACTACCCAGGAGGAAGACGGCTGCAGCTGTAGGTTCCCCGAG

GAAGAGGAAGGCGGGTGTGAGCTGAGGGTCAAGTTTAGCCGCTCCGCAGATGCCCCTGCTTACCAGCA

GGGGCAGAATCAGCTGTATAACGAGCTGAATCTGGGACGGAGAGAGGAATACGACGTGCTGGATAAAA

GGCGCGGGAGAGACCCCGAAATGGGAGGCAAGCCACGACGGAAAAACCCCCAGGAGGGCCTGTACAAT

GAACTGCAGAAGGACAAAATGGCAGAGGCCTATAGTGAAATCGGGATGAAGGGAGAGAGAAGGCGCGG

CAAAGGGCACGATGGCCTGTACCAGGGGCTGTCTACTGCCACCAAGGACACCTATGATGCTCTGCATA

TGCAGGCACTGCCTCCAAGGTGA

CAR9_R2

(SEQ ID NO: 43)
ATGGCTCTGCCCGTCACCGCTCTGCTGCTGCCCCTGGCCCTGCTGCTGCACGCCGCCCGGCCTCAGGT

GCAGCTGCAGCAGAGCGGCCCTGGCCTGGTGCAGCCATCCCAGACACTGTCTCTGACCTGCGTGATCA

-continued

GCGGCGACTCCGTGAGCTCCAACTCTGCCACATGGAATTGGATCAGACAGAGCCCATCCAGGGGCCTG

GAGTGGCTGGGACGCACCTACTATCGGAGCAAGTGGTACAACGACTATGCCGTGTCTGTGAAGAGCAG

AATCACAATCAACCCCGATACCTCTAAGAATCAGTTCAGCCTGCAGCTGAATTCCGTGACACCTGAGG

ATACCGCCGTGTACTATTGCGCCAGGGACGGCGATGGAGGAAGCTACTATGACTACTATTACTATGGC

ATGGACGTGTGGGGCCAGGGCACCACAGTGACAGTGTCTGGAGGAGGAGGAAGCGGAGGAGGAGGATC

CGGCGGCGGCGGCTCTGACATCCAGCTGACACAGTCCCCTTCTAGCCTGTCTACCAGCGTGGGCGATC

GCGTGACAATCACCTGTCGGGCCTCCCAGTCTATCAGCACCTACCTGAACTGGTATCAGCAGAAGCCC

GGCAAGGCCCCTAAGCTGCTGATCTACGCAGCAAGCAATCTGCAGTCCGGAGTGCCATCTCGCTTCTC

CGGCTCTGGCAGCGGCACAGACTTTACACTGACCATCTCCTCTCTGCAGCCTGAGGATTTCGCCACCT

ACTTTTGCCAGCAGTCCTATACCACACCAATCACATTCGGCCAGGGCACCAGACTGGAGATCAAGAGC

GACCCCGGCAGTGGAGGAGGAGGCTCTTGTCCCTACTCTAACCCATCTCTGTGCAGTGGCGGAGGAGG

CTCTTGCCCTTATTCCAACCCCAGCCTGTGCTCCGGAGGAGGAGGCAGCACCACAACCCCAGCACCCA

GGCCCCCTACACCTGCACCAACCATCGCCTCTCAGCCACTGAGCCTGCGGCCTGAGGCCTGCAGACCA

GCCGCCGGCGGAGCAGTGCACACACGGGGCCTGGACTTCGCCTGTGATATCTACATCTGGGCACCACT

GGCCGGAACATGTGGCGTGCTGCTGCTGTCACTGGTCATTACACTGTACTGTAAGCGAGGCCGGAAGA

AACTGCTGTATATTTTCAAACAGCCCTTTATGAGACCTGTGCAGACTACCCAGGAGGAAGACGGCTGC

AGCTGTAGGTTCCCCGAGGAAGAGGAAGGCGGGTGTGAGCTGAGGGTCAAGTTTAGCCGCTCCGCAGA

TGCCCCTGCTTACCAGCAGGGGCAGAATCAGCTGTATAACGAGCTGAATCTGGGACGGAGAGAGGAAT

ACGACGTGCTGGATAAAAGGCGCGGGAGAGACCCCGAAATGGGAGGCAAGCCACGACGGAAAAACCCC

CAGGAGGGCCTGTACAATGAACTGCAGAAGGACAAAATGGCAGAGGCCTATAGTGAAATCGGGATGAA

GGGAGAGAGAAGGCGCGGCAAAGGGCACGATGGCCTGTACCAGGGGCTGTCTACTGCCACCAAGGACA

CCTATGATGCTCTGCATATGCAGGCACTGCCTCCAAGGTGA

CAR13_R2

(SEQ ID NO: 44)

ATGGCTCTGCCCGTCACCGCTCTGCTGCTGCCCCTGGCCCTGCTGCTGCACGCCGCCCGGCCTCAGGT

GCAGCTGCAGCAGAGCGGCCCCGGCCTGGTGAAGCCTAGCCAGACACTGTCCCTGACCTGCGCAATCT

CCGGCGACAGCGTGTCCGGAAACAGGGCCACATGGAATTGGATCAGACAGTCTCCAAGCAGGGGCCTG

GAGTGGCTGGGAAGGACCTACTATCGGTCCGCCTGGTACAACGACTATGCCGTGTCTGTGAAGGGCCG

CATCACATTCAACCCAGATACCAGCAAGAATCAGTTTTCCCTGCAGCTGAATTCTGTGACACCCGAGG

ATACCGCCGTGTACTATTGCGCCAGAGGCGAGAGCGGAGCAGCAGCAGACGCCTTCGATATCTGGGGC

CAGGGCACCACAGTGACAGTGAGCGGAGGAGGAGGATCCGGCGGAGGAGGCTCTGGCGGCGGCGGCAG

CGACATCCAGCTGACCCAGAGCCCACCTTCCCTGTCTGCCAGCGTGGGCGATCGCGTGACAATCACCT

GTCGGGCCTCCCAGTCTATCAGCTCCTACCTGAACTGGTATCAGCAGAAGCCAGGCAAGGCCCCCAAG

CTGCTGATCTACGCAGCATCTAGCCTGCAGTCGGAGTGCCAAGCAGATTCAGCGGATCCGGATTCGG

CACAGACTTTACACTGACCATCTCCTCTCTGCAGCCCGAGGATTTCGCCACCTACTATTGCCAGCAGT

CTTATAGCACACCTCAGACCTTTGGCCAGGGCACCAAGGTGGACATCAAGAGCGACCCCGGAAGCGGA

GGAGGAGGAAGTTGTCCCTACTCAAACCCTAGCCTGTGTAGCGGCGGCGGAGGATCTTGTCCCTATTC

TAACCCCAGCCTGTGCTCCGGAGGAGGAGGCAGCACCACAACCCCAGCACCCAGGCCCCCTACACCTG

CACCAACCATCGCCTCTCAGCCACTGAGCCTGCGGCCTGAGGCCTGCAGACCAGCCGCCGGCGGAGCA

GTGCACACACGGGGCCTGGACTTCGCCTGTGATATCTACATCTGGGCACCACTGGCTGGAACATGCGG

AGTGCTGCTGCTGTCACTGGTCATTACACTGTACTGTAAGCGAGGCCGGAAGAAACTGCTGTATATTT

TCAAACAGCCCTTTATGAGACCTGTGCAGACTACCCAGGAGGAAGACGGCTGCAGCTGTAGGTTCCCC

```
GAGGAAGAGGAAGGCGGGTGTGAGCTGAGGGTCAAGTTTAGCCGCTCCGCAGATGCCCTGCTTACCA

GCAGGGGCAGAATCAGCTGTATAACGAGCTGAATCTGGGACGGAGAGAGGAATACGACGTGCTGGATA

AAAGGCGCGGGAGAGACCCCGAAATGGGAGGCAAGCCACGACGGAAAAACCCCAGGAGGGCCTGTAC

AATGAACTGCAGAAGGACAAAATGGCAGAGGCCTATAGTGAAATCGGGATGAAGGGAGAGAGAAGGCG

CGGCAAAGGGCACGATGGCCTGTACCAGGGGCTGTCTACTGCCACCAAGGACACCTATGATGCTCTGC

ATATGCAGGCACTGCCTCCAAGGTGA
```

CAR15_R2

(SEQ ID NO: 45)
```
ATGGCTCTGCCCGTCACCGCTCTGCTGCTGCCCCTGGCCCTGCTGCTGCACGCCGCCCGGCCTCAGGT

GCAGCTGGTGCAGAGCGGAGCAGAGGTGAAGAAGCCTGGCGCCAGCGTGAAGGTGTCCTGCAAGGCCT

CTGGCTACACATTCACCAGCTACTATATGCACTGGGTGCGGCAGGCCCCTGGCCAGGGCCTGGAGTGG

ATGGGCATCATCAACCCATCCGGCGGCTCCACCTCTTACGCCCAGAAGTTTCAGGGCAGAGTGACAAT

GACCAGGGACACAAGCACCTCCACAGTGTATATGGAGCTGAGCTCCCTGAGATCCGAGGATACAGCCG

TGTACTATTGCGCCAGGGAGGACTCTGGAAGCGGAGCCTTCGATATCTGGGGCCAGGGCACCCTGGTG

ACAGTGTCTGGAGGAGGAGGAAGCGGAGGAGGAGGATCCGGCGGCGGCGGCTCTGAGATCGTGCTGAC

CCAGTCTCCACTGAGCCTGCCAGTGACACCTGGCGAGCCAGCCTCCATCTCTTGTCGCTCTAGCCGGT

CCCTGCTGTCTTACCACGGCTACAATTATCTGGACTGGTATCTGCAGAAGCCAGGCCAGAGCCCCCAG

CTGCTGATCTTCGTGGGATCCAACAGGGCCCCTGGCGTGCCTGACCGGTTCAGCGGATCCGGATCTGG

AACCGACTTCACCCTGAACATCTCTAGAGTGGAGGCCGAGGATGTGGGCGTGTACTATTGCATGCAGA

GCCTGCAGACCCCAAGAACATTTGGCCAGGGCACCAAGGTGGAGATCAAGAGCGACCCCGGAAGCGGC

GGAGGAGGAAGTTGTCCCTATTCTAACCCATCTCTGTGCAGCGGCGGCGGAGGAAGTTGTCCTTATTC

AAACCCCAGCCTGTGCTCCGGAGGAGGAGGCAGCACCACAACCCCAGCACCCAGGCCCCCTACACCTG

CACCAACCATCGCCTCTCAGCCACTGAGCCTGCGGCCTGAGGCCTGCAGACCAGCCGCCGGCGGAGCA

GTGCACACACGGGGCCTGGACTTCGCCTGTGATATCTACATCTGGGCACCACTGGCTGGAACATGCGG

CGTGCTGCTGCTGTCACTGGTCATTACACTGTACTGTAAGCGAGGCCGGAAGAAACTGCTGTATATTT

TCAAACAGCCCTTTATGAGACCTGTGCAGACTACCCAGGAGGAAGACGGCTGCAGCTGTAGGTTCCCC

GAGGAAGAGGAAGGCGGGTGTGAGCTGAGGGTCAAGTTTAGCCGCTCCGCAGATGCCCTGCTTACCA

GCAGGGGCAGAATCAGCTGTATAACGAGCTGAATCTGGGACGGAGAGAGGAATACGACGTGCTGGATA

AAAGGCGCGGGAGAGACCCCGAAATGGGAGGCAAGCCACGACGGAAAAACCCCAGGAGGGCCTGTAC

AATGAACTGCAGAAGGACAAAATGGCAGAGGCCTATAGTGAAATCGGGATGAAGGGAGAGAGAAGGCG

CGGCAAAGGGCACGATGGCCTGTACCAGGGGCTGTCTACTGCCACCAAGGACACCTATGATGCTCTGC

ATATGCAGGCACTGCCTCCAAGGTGA
```

CAR1 polypeptide (SEQ ID NO: 46)
```
MALPVTALLLPLALLLHAARPQVQLQQSGPGLVKPSQTLSLTCAISGDSVSSNSAAWNWIRQSPSRGL

EWLGRTYYRSTWYNDYAVSVKSRITINPDTSKNQFSLQLNSVTPEDTAVYYCAREVSGTSAFDIWGQG

TMVTVSGGGSGGGGSGGGGSDIQMTQSPSSLSASVGDRVTITCRASQSISSYLNWYQQKPGKAPKLL

IYAASSLQSGVPSRFSGSGSGTDFTLTISSLQPEDFATYYCQQSYSTPLTFGGGTKLEIKTTTPAPRP

PTPAPTIASQPLSLRPEACRPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYQQGQNQLYNELNLGRREEYD

VLDKRRGRDPEMGGKPRRKNPQEGLYNELQKDKMAEAYSEIGMKGERRRGKGHDGLYQGLSTATKDTY

DALHMQALPPR
```

-continued

CAR2 polypeptide
(SEQ ID NO: 47)
MALPVTALLLPLALLLHAARPQVQLQQSGPGLVKPSQTLSLTCAISGDSVSSNSAAWNWIRQSPSRGL

EWLGRTYYRSKWYNDYAVSVKSRITINPDTSKNQFSLQLNSVTPEDTAVYYCARASMTGGYSYGDAFD

IWGQGTLVTVSGGGGSGGGGSGGGGSAIRMTQSPSSLSASVGDRVTITCRASQSISSYLNWYQQKPGK

APKLLIYAASSLQSGVPSRFSGSGSGTDFSLTISSLQPEDSATYYCQQTYSTPLTFGQGTKVEIKTTT

PAPRPPTPAPTIASQPLSLRPEACRPAAGGAVHTRGLDFACDIYIWAPLAGTCGVLLLSLVITLYCKR

GRKKLLYIFKQPFMRPVQTTQEEDGCSCRFPEEEEGGCELRVKFSRSADAPAYQQGQNQLYNELNLGR

REEYDVLDKRRGRDPEMGGKPRRKNPQEGLYNELQKDKMAEAYSEIGMKGERRRGKGHDGLYQGLSTA

TKDTYDALHMQALPPR

CAR3 polypeptide
(SEQ ID NO: 48)
MALPVTALLLPLALLLHAARPQVQLQQSGPGLVEPSQTLSLTCAISGDSVSSDSVAWNWIRQSPSRGL

EWLGRTYYRSTWYNDYAGSVKSRITINPDTSKNQFSLQLTSVTPEDTAVYYCTRSRHNTFRGMDVWGQ

GTTVTVSGGGGSGGGGSGGGGSDIVMTQSPSSLSASVGDRVTITCRASQTISSYLNWYQQKPGKAPKL

LIYDASSLQSGVPSRFSGSGSGTDFTLTINSLQPEDFATYYCQQSYTTPITFGQGTRLEIKTTTPAPR

PPTPAPTIASQPLSLRPEACRPAAGGAVHTRGLDFACDIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQGLSTATKDT

YDALHMQALPPR

CAR4 polypeptide
(SEQ ID NO: 49)
MALPVTALLLPLALLLHAARPQVQLQQSGPGLVEPSQTLSLTCAISGDSVSSNSAAWNWIRQSPSRGL

EWLGRTYYRSTWYNDYAGSVKSRITINPDTSKNQFSLQLTSVTPEDTAVYYCTRSRHNTFRGMDVWGQ

GTLVTVSGGGGSGGGGSGGGGSDIQLTQSPSSLSASVGDRVTITCRASQSISSYLNWYQQKPGKAPKL

LIYAASSLQSGVPSRFSGSGSGTDFTLTISSLQPEDFATYYCQQSYSTPLTFGGGTKVEIKTTTPAPR

PPTPAPTIASQPLSLRPEACRPAAGGAVHTRGLDFACDIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQGLSTATKDT

YDALHMQALPPR

CAR7 polypeptide
(SEQ ID NO: 50)
MALPVTALLLPLALLLHAARPQVQLQQSGPGLVEPSQTLSLTCAISGDSVSSDSVAWNWIRQSPSRGL

EWLGRTYYRSTWYNDYAGSVKSRITINPDTSKNQFSLQLNSVTPEDTAVYYCARDRNGMDVWGQGTMV

TVSGGGGSGGGGSGGGGSDIVMTQSPSSLSASVGDRVTITCRASQSISSYLNWYQQKPGKAPKLLIYD

ASNLETGVPSRFSGSGSGTDFTFTITSLQPEDFATYYCQQSYTTPLTFGGGTKVEIKTTTPAPRPPTP

APTIASQPLSLRPEACRPAAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDAL

HMQALPPR

CAR8 polypeptide
(SEQ ID NO: 51)
MALPVTALLLPLALLLHAARPQVQLQQSGPGLVKPSQTLSLTCAISGDSVSSSSAAWNWIRQSPSRGL

EWLGRTYYRSAWYNDYAVSVKSRITINPDTSKNQFSLQLNSVTPEDTAVYYCARESVLLDGMDVWGRG

TTVTVSGGGGSGGGGSGGGGSAIRMTQSPSTLSASVGDRVTITCRASQSISTYLNWYQQKAGKAPRLL

IHDASSLQSGVPSRFSGSGSGTDFTLTISSLQPEDFATYYCQQSYSTPLTFGGGTKVEIKTTTPAPRP

PTPAPTIASQPLSLRPEACRPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYQQGQNQLYNELNLGRREEYD

VLDKRRGRDPEMGGKPRRKNPQEGLYNELQKDKMAEAYSEIGMKGERRRGKGHDGLYQGLSTATKDTY

DALHMQALPPR

CAR9 polypeptide (SEQ ID NO: 52)

MALPVTALLLPLALLLHAARPQVQLQQSGPGLVQPSQTLSLTCVISGDSVSSNSATWNWIRQSPSRGL

EWLGRTYYRSKWYNDYAVSVKSRITINPDTSKNQFSLQLNSVTPEDTAVYYCARDGDGGSYYDYYYYG

MDVWGQGTTVTVSGGGGSGGGGSGGGGSDIQLTQSPSSLSTSVGDRVTITCRASQSISTYLNWYQQKP

GKAPKLLIYAASNLQSGVPSRFSGSGSGTDFTLTISSLQPEDFATYFCQQSYTTPITFGQGTRLEIKT

TTPAPRPPTPAPTIASQPLSLRPEACRPAAGGAVHTRGLDFACDIYIWAPLAGTCGVLLLSLVITLYC

KRGRKKLLYIFKQPFMRPVQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGMKGERRRGKGHDGLYQGLS

TATKDTYDALHMQALPPR

CAR12 polypeptide (SEQ ID NO: 53)

MALPVTALLLPLALLLHAARPQVQLQQSGPGLVKPSQTLSLTCAISGDSVSSNSAAWNWIRQSPSRGL

EWLGRTYYRSAWYNDYAVSVKSRITINPDTSKNQFSLQLSSVTPEDTAVYYCARDVEGFDYWGQGTLV

TVSGGGGSGGGGSGGGGSDIVMTQTPSSLSASVGDRVTITCRASQSISSYLNWYQQKPGKAPKLLIYA

ASSLQSGVPSRFSGSGSGTDFTLTISSLQPEDFATYYCQQSYSTPITFGQGTRLEIKTTTPAPRPPTP

APTIASQPLSLRPEACRPAAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDAL

HMQALPPR

CAR13 polypeptide (SEQ ID NO: 54)

MALPVTALLLPLALLLHAARPQVQLQQSGPGLVKPSQTLSLTCAISGDSVSGNRATWNWIRQSPSRGL

EWLGRTYYRSAWYNDYAVSVKGRITFNPDTSKNQFSLQLNSVTPEDTAVYYCARGESGAAADAFDIWG

QGTTVTVSGGGGSGGGGSGGGGSDIQLTQSPPSLSASVGDRVTITCRASQSISSYLNWYQQKPGKAPK

LLIYAASSLQSGVPSRFSGSGSGFGTDFTLTISSLQPEDFATYYCQQSYSTPQTFGQGTKVDIKTTTPAP

RPPTPAPTIASQPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQLYNELNLGRREE

YDVLDKRRGRDPEMGGKPRRKNPQEGLYNELQKDKMAEAYSEIGMKGERRRGKGHDGLYQGLSTATKD

TYDALHMQALPPR

CAR15 polypeptide (SEQ ID NO: 55)

MALPVTALLLPLALLLHAARPQVQLVQSGAEVKKPGASVKVSCKASGYTFTSYYMHWVRQAPGQGLEW

MGIINPSGGSTSYAQKFQGRVTMTRDTSTSTVYMELSSLRSEDTAVYYCAREDSGSGAFDIWGQGTLV

TVSGGGGSGGGGSGGGGSEIVLTQSPLSLPVTPGEPASISCRSSRSLLSYHGYNYLDWYLQKPGQSPQ

LLIFVGSNRAPGVPDRFSGSGSGTDFTLNISRVEAEDVGVYYCMQSLQTPRTFGQGTKVEIKTTTPAP

RPPTPAPTIASQPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQLYNELNLGRREE

YDVLDKRRGRDPEMGGKPRRKNPQEGLYNELQKDKMAEAYSEIGMKGERRRGKGHDGLYQGLSTATKD

TYDALHMQALPPR

-continued

CAR1_QR3 polypeptide
(SEQ ID NO: 56)
MALPVTALLLPLALLLHAARPGGGGSCPYSNPSLCSGGGGSGGGGSQVQLQQSGPGLVKPSQTLSLTC
AISGDSVSSNSAAWNWIRQSPSRGLEWLGRTYYRSTWYNDYAVSVKSRITINPDTSKNQFSLQLNSVT
PEDTAVYYCAREVSGTSAFDIWGQGTMVTVSGGGGSGGGGSGGGGSDIQMTQSPSSLSASVGDRVTIT
CRASQSISSYLNWYQQKPGKAPKLLIYAASSLQSGVPSRFSGSGSGTDFTLTISSLQPEDFATYYCQQ
SYSTPLTFGGGTKLEIKGSGGGGSCPYSNPSLCSGGGGSELPTQGTFSNVSTNVSPAKPTTTACPYSN
PSLCTTTPAPRPPTPAPTIASQPLSLRPEACRPAAGGAVHTRGLDFACDIYIWAPLAGTCGVLLLSLV
ITLYCKRGRKKLLYIFKQPFMRPVQTTQEEDGCSCRFPEEEEGGCELRVKFSRSADAPAYQQGQNQLY
NELNLGRREEYDVLDKRRGRDPEMGGKPRRKNPQEGLYNELQKDKMAEAYSEIGMKGERRRGKGHDGL
YQGLSTATKDTYDALHMQALPPR CAR2_QR3 polypeptide
(SEQ ID NO: 57)
MALPVTALLLPLALLLHAARPGGGGSCPYSNPSLCSGGGGSGGGGSQVQLQQSGPGLVKPSQTLSLTC
AISGDSVSSNSAAWNWIRQSPSRGLEWLGRTYYRSKWYNDYAVSVKSRITINPDTSKNQFSLQLNSVT
PEDTAVYYCARASMTGGYSYGDAFDIWGQGTLVTVSGGGGSGGGGSGGGGSAIRMTQSPSSLSASVGD
RVTITCRASQSISSYLNWYQQKPGKAPKLLIYAASSLQSGVPSRFSGSGSGTDFSLTISSLQPEDSAT
YYCQQTYSTPLTFGQGTKVEIKGSGGGGSCPYSNPSLCSGGGGSELPTQGTFSNVSTNVSPAKPTTTA
CPYSNPSLCTTTPAPRPPTPAPTIASQPLSLRPEACRPAAGGAVHTRGLDFACDIYIWAPLAGTCGVL
LLSLVITLYCKRGRKKLLYIFKQPFMRPVQTTQEEDGCSCRFPEEEEGGCELRVKFSRSADAPAYQQG
QNQLYNELNLGRREEYDVLDKRRGRDPEMGGKPRRKNPQEGLYNELQKDKMAEAYSEIGMKGERRRGK
GHDGLYQGLSTATKDTYDALHMQALPPR CAR3_QR3 polypeptide
(SEQ ID NO: 58)
MALPVTALLLPLALLLHAARPGGGGSCPYSNPSLCSGGGGSGGGGSQVQLQQSGPGLVEPSQTLSLTC
AISGDSVSSDSVAWNWIRQSPSRGLEWLGRTYYRSTWYNDYAGSVKSRITINPDTSKNQFSLQLTSVT
PEDTAVYYCTRSRHNTFRGMDVWGQGTTVTVSGGGGSGGGGSGGGGSDIVMTQSPSSLSASVGDRVTI
TCRASQTISSYLNWYQQKPGKAPKLLIYDASSLQSGVPSRFSGSGSGTDFTLTINSLQPEDFATYYCQ
QSYTTPITFGQGTRLEIKGSGGGGSCPYSNPSLCSGGGGSELPTQGTFSNVSTNVSPAKPTTTACPYS
NPSLCTTTPAPRPPTPAPTIASQPLSLRPEACRPAAGGAVHTRGLDFACDIYIWAPLAGTCGVLLLSL
VITLYCKRGRKKLLYIFKQPFMRPVQTTQEEDGCSCRFPEEEEGGCELRVKFSRSADAPAYQQGQNQL
YNELNLGRREEYDVLDKRRGRDPEMGGKPRRKNPQEGLYNELQKDKMAEAYSEIGMKGERRRGKGHDG
LYQGLSTATKDTYDALHMQALPPR CAR4_QR3 polypeptide
(SEQ ID NO: 59)
MALPVTALLLPLALLLHAARPGGGGSCPYSNPSLCSGGGGSGGGGSQVQLQQSGPGLVEPSQTLSLTC
AISGDSVSSNSAAWNWIRQSPSRGLEWLGRTYYRSTWYNDYAGSVKSRITINPDTSKNQFSLQLTSVT
PEDTAVYYCTRSRHNTFRGMDVWGQGTLVTVSGGGGSGGGGSGGGGSDIQLTQSPSSLSASVGDRVTI
TCRASQSISSYLNWYQQKPGKAPKLLIYAASSLQSGVPSRFSGSGSGTDFTLTISSLQPEDFATYYCQ
QSYSTPLTFGGGTKVEIKGSGGGGSCPYSNPSLCSGGGGSELPTQGTFSNVSTNVSPAKPTTTACPYS
NPSLCTTTPAPRPPTPAPTIASQPLSLRPEACRPAAGGAVHTRGLDFACDIYIWAPLAGTCGVLLLSL
VITLYCKRGRKKLLYIFKQPFMRPVQTTQEEDGCSCRFPEEEEGGCELRVKFSRSADAPAYQQGQNQL
YNELNLGRREEYDVLDKRRGRDPEMGGKPRRKNPQEGLYNELQKDKMAEAYSEIGMKGERRRGKGHDG
LYQGLSTATKDTYDALHMQALPPR -continued CAR7_QR3 polypeptide
(SEQ ID NO: 60)
MALPVTALLLPLALLLHAARPGGGGSCPYSNPSLCSGGGGSGGGGSQVQLQQSGPGLVEPSQTLSLTC
AISGDSVSSDSVAWNWIRQSPSRGLEWLGRTYYRSTWYNDYAGSVKSRITINPDTSKNQFSLQLNSVT
PEDTAVYYCARDRNGMDVWGQGTMVTVSGGGGSGGGGSGGGGSDIVMTQSPSSLSASVGDRVTITCRA
SQSISSYLNWYQQKPGKAPKLLIYDASNLETGVPSRFSGSGSGTDFTFTITSLQPEDFATYYCQQSYT
TPLTFGGGTKVEIKGSGGGGSCPYSNPSLCSGGGGSELPTQGTFSNVSTNVSPAKPTTTACPYSNPSL
CTTTPAPRPPTPAPTIASQPLSLRPEACRPAAGGAVHTRGLDFACDIYIWAPLAGTCGVLLLSLVITL
YCKRGRKKLLYIFKQPFMRPVQTTQEEDGCSCRFPEEEEGGCELRVKFSRSADAPAYQQGQNQLYNEL
NLGRREEYDVLDKRRGRDPEMGGKPRRKNPQEGLYNELQKDKMAEAYSEIGMKGERRRGKGHDGLYQG
LSTATKDTYDALHMQALPPR CAR8_QR3 polypeptide
(SEQ ID NO: 61)
MALPVTALLLPLALLLHAARPGGGGSCPYSNPSLCSGGGGSGGGGSQVQLQQSGPGLVKPSQTLSLTC
AISGDSVSSSSAAWNWIRQSPSRGLEWLGRTYYRSAWYNDYAVSVKSRITINPDTSKNQFSLQLNSVT
PEDTAVYYCARESVLLDGMDVWGRGTTVTVSGGGGSGGGGSGGGGSAIRMTQSPSTLSASVGDRVTIT
CRASQSISTYLNWYQQKAGKAPRLLIHDASSLQSGVPSRFSGSGSGTDFTLTISSLQPEDFATYYCQQ
SYSTPLTFGGGTKVEIKGSGGGGSCPYSNPSLCSGGGGSELPTQGTFSNVSTNVSPAKPTTTACPYSN
PSLCTTTPAPRPPTPAPTIASQPLSLRPEACRPAAGGAVHTRGLDFACDIYIWAPLAGTCGVLLLSLV
ITLYCKRGRKKLLYIFKQPFMRPVQTTQEEDGCSCRFPEEEEGGCELRVKFSRSADAPAYQQGQNQLY
NELNLGRREEYDVLDKRRGRDPEMGGKPRRKNPQEGLYNELQKDKMAEAYSEIGMKGERRRGKGHDGL
YQGLSTATKDTYDALHMQALPPR CAR9_QR3 polypeptide
(SEQ ID NO: 62)
MALPVTALLLPLALLLHAARPGGGGSCPYSNPSLCSGGGGSGGGGSQVQLQQSGPGLVQPSQTLSLTC
VISGDSVSSNSATWNWIRQSPSRGLEWLGRTYYRSKWYNDYAVSVKSRITINPDTSKNQFSLQLNSVT
PEDTAVYYCARDGDGGSYYDYYYYGMDVWGQGTTVTVSGGGGSGGGGSGGGGSDIQLTQSPSSLSTSV
GDRVTITCRASQSISTYLNWYQQKPGKAPKLLIYAASNLQSGVPSRFSGSGSGTDFTLTISSLQPEDF
ATYFCQQSYTTPITFGQGTRLEIKGSGGGGSCPYSNPSLCSGGGGSELPTQGTFSNVSTNVSPAKPTT
TACPYSNPSLCTTTPAPRPPTPAPTIASQPLSLRPEACRPAAGGAVHTRGLDFACDIYIWAPLAGTCG
VLLLSLVITLYCKRGRKKLLYIFKQPFMRPVQTTQEEDGCSCRFPEEEEGGCELRVKFSRSADAPAYQ
QGQNQLYNELNLGRREEYDVLDKRRGRDPEMGGKPRRKNPQEGLYNELQKDKMAEAYSEIGMKGERRR
GKGHDGLYQGLSTATKDTYDALHMQALPPR CAR12_QR3 polypeptide
(SEQ ID NO: 63)
MALPVTALLLPLALLLHAARPGGGGSCPYSNPSLCSGGGGSGGGGSQVQLQQSGPGLVKPSQTLSLTC
AISGDSVSSNSAAWNWIRQSPSRGLEWLGRTYYRSAWYNDYAVSVKSRITINPDTSKNQFSLQLSSVT
PEDTAVYYCARDVEGFDYWGQGTLVTVSGGGGSGGGGSGGGGSDIVMTQTPSSLSASVGDRVTITCRA
SQSISSYLNWYQQKPGKAPKLLIYAASSLQSGVPSRFSGSGSGTDFTLTISSLQPEDFATYYCQQSYS
TPITFGQGTRLEIKGSGGGGSCPYSNPSLCSGGGGSELPTQGTFSNVSTNVSPAKPTTTACPYSNPSL
CTTTPAPRPPTPAPTIASQPLSLRPEACRPAAGGAVHTRGLDFACDIYIWAPLAGTCGVLLLSLVITL
YCKRGRKKLLYIFKQPFMRPVQTTQEEDGCSCRFPEEEEGGCELRVKFSRSADAPAYQQGQNQLYNEL
NLGRREEYDVLDKRRGRDPEMGGKPRRKNPQEGLYNELQKDKMAEAYSEIGMKGERRRGKGHDGLYQG
LSTATKDTYDALHMQALPPR -continued CAR13_QR3 polypeptide
(SEQ ID NO: 64)
MALPVTALLLPLALLLHAARPGGGGSCPYSNPSLCSGGGGSGGGGSQVQLQQSGPGLVKPSQTLSLTC
AISGDSVSGNRATWNWIRQSPSRGLEWLGRTYYRSAWYNDYAVSVKGRITFNPDTSKNQFSLQLNSVT
PEDTAVYYCARGESGAAADAFDIWGQTTVTVSGGGGSGGGGSGGGGSDIQLTQSPPSLSASVGDRVT
ITCRASQSISSYLNWYQQKPGKAPKLLIYAASSLQSGVPSRFSGSGFGTDFTLTISSLQPEDFATYYC
QQSYSTPQTFGQGTKVDIKGSGGGGSCPYSNPSLCSGGGGSELPTQGTFSNVSTNVSPAKPTTTACPY
SNPSLCTTTPAPRPPTPAPTIASQPLSLRPEACRPAAGGAVHTRGLDFACDIYIWAPLAGTCGVLLLS
LVITLYCKRGRKKLLYIFKQPFMRPVQTTQEEDGCSCRFPEEEEGGCELRVKFSRSADAPAYQQGQNQ
LYNELNLGRREEYDVLDKRRGRDPEMGGKPRRKNPQEGLYNELQKDKMAEAYSEIGMKGERRRGKGHD
GLYQGLSTATKDTYDALHMQALPPR CAR15_QR3 polypeptide
(SEQ ID NO: 65)
MALPVTALLLPLALLLHAARPGGGGSCPYSNPSLCSGGGGSGGGGSQVQLVQSGAEVKKPGASVKVSC
KASGYTFTSYYMHWVRQAPGQGLEWMGIINPSGGSTSYAQKFQGRVTMTRDTSTSTVYMELSSLRSED
TAVYYCAREDSGSGAFDIWGQGTLVTVSGGGGSGGGGSGGGGSEIVLTQSPLSLPVTPGEPASISCRS
SRSLLSYHGYNYLDWYLQKPGQSPQLLIFVGSNRAPGVPDRFSGSGSGTDFTLNISRVEAEDVGVYYC
MQSLQTPRTFGQGTKVEIKGSGGGGSCPYSNPSLCSGGGGSELPTQGTFSNVSTNVSPAKPTTTACPY
SNPSLCTTTPAPRPPTPAPTIASQPLSLRPEACRPAAGGAVHTRGLDFACDIYIWAPLAGTCGVLLLS
LVITLYCKRGRKKLLYIFKQPFMRPVQTTQEEDGCSCRFPEEEEGGCELRVKFSRSADAPAYQQGQNQ
LYNELNLGRREEYDVLDKRRGRDPEMGGKPRRKNPQEGLYNELQKDKMAEAYSEIGMKGERRRGKGHD
GLYQGLSTATKDTYDALHMQALPPR CAR4_R2 polypeptide
(SEQ ID NO: 66)
MALPVTALLLPLALLLHAARPQVQLQQSGPGLVEPSQTLSLTCAISGDSVSSNSAAWNWIRQSPSRGL
EWLGRTYYRSTWYNDYAGSVKSRITINPDTSKNQFSLQLTSVTPEDTAVYYCTRSRHNTFRGMDVWGQ
GTLVTVSGGGGSGGGGSGGGGSDIQLTQSPSSLSASVGDRVTITCRASQSISSYLNWYQQKPGKAPKL
LIYAASSLQSGVPSRFSGSGSGTDFTLTISSLQPEDFATYYCQQSYSTPLTFGGGTKVEIKSDPGSGG
GGSCPYSNPSLCSGGGGSCPYSNPSLCSGGGGSTTTPAPRPPTPAPTIASQPLSLRPEACRPAAGGAV
HTRGLDFACDIYIWAPLAGTCGVLLLSLVITLYCKRGRKKLLYIFKQPFMRPVQTTQEEDGCSCRFPE
EEEGGCELRVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR CAR9_R2 polypeptide
(SEQ ID NO: 67)
MALPVTALLLPLALLLHAARPQVQLQQSGPGLVQPSQTLSLTCVISGDSVSSNSATWNWIRQSPSRGL
EWLGRTYYRSKWYNDYAVSVKSRITINPDTSKNQFSLQLNSVTPEDTAVYYCARDGDGGSYYDYYYYG
MDVWGQGTTVTVSGGGGSGGGGSGGGGSDIQLTQSPSSLSTSVGDRVTITCRASQSISTYLNWYQQKP
GKAPKLLIYAASNLQSGVPSRFSGSGSGTDFTLTISSLQPEDFATYFCQQSYTTPITFGQGTRLEIKS
DPGSGGGGSCPYSNPSLCSGGGGSCPYSNPSLCSGGGGSTTTPAPRPPTPAPTIASQPLSLRPEACRP
AAGGAVHTRGLDFACDIYIWAPLAGTCGVLLLSLVITLYCKRGRKKLLYIFKQPFMRPVQTTQEEDGC
SCRFPEEEEGGCELRVKFSRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDALHMQALPPR CAR13_R2 polypeptide
(SEQ IDSEQ ID NO: 68)
MALPVTALLLPLALLLHAARPQVQLQQSGPGLVKPSQTLSLTCAISGDSVSGNRATWNWIRQSPSRGL
EWLGRTYYRSAWYNDYAVSVKGRITFNPDTSKNQFSLQLNSVTPEDTAVYYCARGESGAAADAFDIWG -continued

QGTTVTVSGGGGSGGGGSGGGGSDIQLTQSPPSLSASVGDRVTITCRASQSISSYLNWYQQKPGKAPK

LLIYAASSLQSGVPSRFSGSGFGTDFTLTISSLQPEDFATYYCQQSYSTPQTFGQGTKVDIKSDPGSG

GGGSCPYSNPSLCSGGGGSCPYSNPSLCSGGGGSTTTPAPRPPTPAPTIASQPLSRPEACRPAAGGA

VHTRGLDFACDIYIWAPLAGTCGVLLLSLVITLYCKRGRKKLLYIFKQPFMRPVQTTQEEDGCSCRFP

EEEEGGCELRVKFSRSADAPAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQALPPR

CAR15_R2 polypeptide (SEQ ID NO: 69)
MALPVTALLLPLALLLHAARPQVQLVQSGAEVKKPGASVKVSCKASGYTFTSYYMHWVRQAPGQGLEW

MGIINPSGGSTSYAQKFQGRVTMTRDTSTSTVYMELSSLRSEDTAVYYCAREDSGSGAFDIWGQGTLV

TVSGGGGSGGGGSGGGGSEIVLTQSPLSLPVTPGEPASISCRSSRSLLSYHGYNYLDWYLQKPGQSPQ

LLIFVGSNRAPGVPDRFSGSGSGTDFTLNISRVEAEDVGVYYCMQSLQTPRTFGQGTKVEIKSDPGSG

GGGSCPYSNPSLCSGGGGSCPYSNPSLCSGGGGSTTTPAPRPPTPAPTIASQPLSRPEACRPAAGGA

VHTRGLDFACDIYIWAPLAGTCGVLLLSLVITLYCKRGRKKLLYIFKQPFMRPVQTTQEEDGCSCRFP

EEEEGGCELRVKFSRSADAPAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQALPPR (SEQ ID NO: 70)
RGATCCTCTTGTCCCACAGATATCCAGAACCCTGACCCTGCCGRGTACCAGCTGAGAG

A

Nucleic sequence of the preferred anti-CD22 CAR (AD4)

(SEQ ID NO: 29)
ATGGCTCTGCCCGTCACCGCTCTGCTGCTGCCTCTGGCCCTGCTGCTGCACGCAGCCCGCCCACAGGT

GCAGCTGCAGCAGAGCGGCCCCGGCCTGGTGAAGCCTAGCCAGACACTGTCCCTGACCTGCGCAATCT

CCGGCGACAGCGTGTCCGGAAACAGGGCCACATGGAATTGGATCAGACAGTCTCCAAGCAGGGGCCTG

GAGTGGCTGGGAAGGACCTACTATCGGTCCGCCTGGTACAACGACTATGCCGTGTCTGTGAAGGGCCG

CATCACATTCAACCCAGATACCAGCAAGAATCAGTTTTCCCTGCAGCTGAATTCTGTGACACCCGAGG

ATACCGCCGTGTACTATTGCGCCAGAGGCGAGAGCGGAGCAGCAGCAGACGCCTTCGATATCTGGGGC

CAGGGCACCACAGTGACAGTGAGCGGAGGAGGAGGATCCGGCGGAGGAGGCTCTGGCGGCGGCGGCAG

CGACATCCAGCTGACCCAGAGCCCACCTTCCCTGTCTGCCAGCGTGGGCGATCGCGTGACAATCACCT

GTCGGGCCTCCCAGTCTATCAGCTCCTACCTGAACTGGTATCAGCAGAAGCCAGGCAAGGCCCCCAAG

CTGCTGATCTACGCAGCATCTAGCCTGCAGTCTGGAGTGCCAAGCAGATTCAGCGGATCCGGATTCGG

CACAGACTTTACACTGACCATCTCCTCTCTGCAGCCCGAGGATTTCGCCACCTACTATTGCCAGCAGT

CTTATAGCACACCTCAGACCTTTGGCCAGGGCACCAAGGTGGACATCAAGACCACAACCCCTGCACCA

AGACCACCAACACCAGCACCTACCATCGCATCCCAGCCACTGTCTCTGCGCCCCGAGGCATGTAGGCC

TGCAGCAGGCGGCGCCGTGCACACCAGGGGCCTGGACTTTGCCTGCGATATTTACATCTGGGCACCTC

TGGCAGGAACATGTGGCGTGCTGCTCCTGAGCCTGGTCATCACCCTGTACTGCAAGAGAGGCAGGAAG

AAGCTGCTGTATATCTTCAAGCAGCCCTTCATGCGGCCCGTGCAGACAACCCAGGAGGAGGACGGCTG

CTCCTGTAGGTTCCCTGAAGAGGAGGAGGGCGGCTGTGAGCTGAGAGTGAAGTTTTCCAGGTCTGCCG

ATGCACCAGCATACCAGCAGGGACAGAATCAGCTGTATAACGAGCTGAATCTGGGCCGGAGAGAGGAG

TACGACGTGCTGGATAAGAGGAGGGGACGGGATCCCGAGATGGGAGGCAAGCCACGGAGAAAGAACCC

CCAGGAGGGGCCTGTACAATGAGCTGCAGAAGGACAAGATGGCCGAGGCCTATTCTGAGATCGGCATGA

AGGGAGAGAGGCGCCGGGGCAAGGGACACGATGGCCTGTACCAGGGCCTGTCCACAGCCACCAAGGAC

ACCTATGATGCCCTGCATATGCAGGCACTGCCTCCAAGGTGA

-continued

Amino acid sequence of the preferred anti-CD22 CAR (AD4)
(SEQ ID NO: 54)
MALPVTALLLPLALLLHAARPQVQLQQSGPGLVKPSQTLSLTCAISGDSVSGNRATWNWIRQSPSRGL

EWLGRTYYRSAWYNDYAVSVKGRITFNPDTSKNQFSLQLNSVTPEDTAVYYCARGESGAAADAFDIWG

QGTTVTVSGGGGSGGGGSGGGGSDIQLTQSPPSLSASVGDRVTITCRASQSISSYLNWYQQKPGKAPK

LLIYAASSLQSGVPSRFSGSGFGTDFTLTISSLQPEDFATYYCQQSYSTPQTFGQGTKVDIKTTTPAP

RPPTPAPTIASQPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQLYNELNLGRREE

YDVLDKRRGRDPEMGGKPRRKNPQEGLYNELQKDKMAEAYSEIGMKGERRRGKGHDGLYQGLSTATKD

TYDALHMQALPPR

Nucleic sequence of the preferred QR3 anti-CD22 CAR (AD4)
(SEQ ID NO: 40)
ATGGCTCTGCCCGTCACCGCTCTGCTGCTGCCACTGGCCCTGCTGCTGCACGCCGCCAGACCCGGCGG

AGGAGGCTCTTGCCCCTACAGCAACCCCAGCCTGTGCTCTGGCGGCGGCGGCAGCGGAGGCGGCGGCT

CCCAGGTGCAGCTGCAGCAGAGCGGCCCCGGCCTGGTGAAGCCTAGCCAGACACTGTCCCTGACCTGC

GCAATCTCCGGCGACAGCGTGTCCGGAAACAGGGCCACATGGAATTGGATCAGACAGTCTCCAAGCAG

GGGCCTGGAGTGGCTGGGAAGGACCTACTATCGGTCCGCCTGGTACAACGACTATGCCGTGTCTGTGA

AGGGCCGCATCACATTCAACCCAGATACCAGCAAGAATCAGTTTTCCCTGCAGCTGAATTCTGTGACA

CCCGAGGATACCGCCGTGTACTATTGCGCCAGAGGCGAGAGCGGAGCAGCAGCAGACGCCTTCGATAT

CTGGGGCCAGGGCACCACAGTGACAGTGAGCGGAGGAGGAGGATCCGGCGGAGGAGGCTCTGGCGGCG

GCGGCAGCGACATCCAGCTGACCCAGAGCCCACCTTCCCTGTCTGCCAGCGTGGGCGATCGCGTGACA

ATCACCTGTCGGGCCTCCCAGTCTATCAGCTCCTACCTGAACTGGTATCAGCAGAAGCCAGGCAAGGC

CCCCAAGCTGCTGATCTACGCAGCATCTAGCCTGCAGTCTGGAGTGCCAAGCAGATTCAGCGGATCCG

GATTCGGCACAGACTTTACACTGACCATCTCCTCTCTGCAGCCCGAGGATTTCGCCACCTACTATTGC

CAGCAGTCTTATAGCACACCTCAGACCTTTGGCCAGGGCACCAAGGTGGACATCAAGGGAAGTGGAGG

AGGAGGAAGTTGTCCCTACTCAAACCCATCTCTGTGCTCAGGAGGAGGAGGAAGTGAACTGCCTACTC

AGGGAACATTCAGCAACGTGTCCACCAATGTGAGCCCAGCAAAGCCTACCACAACCGCATGCCCATAC

TCTAACCCCAGCCTGTGCACAACCACACCAGCACCCAGGCCCCCTACCCCTGCACCAACAATCGCCTC

CCAGCCTCTGTCTCTGCGGCCAGAGGCCTGCAGACCCGCCGCCGGCGGAGCAGTGCACACACGGGCC

TGGACTTTGCCTGTGATATCTATATCTGGGCACCACTGGCCGGAACATGTGGCGTGCTGCTGCTGTCA

CTGGTCATTACACTGTACTGTAAGCGAGGCCGGAAGAAACTGCTGTATATTTTCAAACAGCCCTTTAT

GAGACCTGTGCAGACTACCCAGGAGGAAGACGGCTGCAGCTGTAGGTTCCCCGAGGAAGAGGAAGGCG

GGTGTGAGCTGAGGGTCAAGTTTAGCCGCTCCGCAGATGCCCCTGCTTACCAGCAGGGGCAGAATCAG

CTGTATAACGAGCTGAATCTGGGACGGAGAGAGGAATACGACGTGCTGGATAAAAGGCGCGGGAGAGA

CCCCGAAATGGAGGCAAGCCACGACGGAAAAACCCCCAGGAGGGCCTGTACAATGAACTGCAGAAGG

ACAAAATGGCAGAGGCCTATAGTGAAATCGGGATGAAGGGAGAGAGAAGGCGCGGCAAAGGGCACGAT

GGCCTGTACCAGGGGCTGTCTACTGCCACCAAGGACACCTATGATGCTCTGCATATGCAGGCACTGCC

TCCAAGGTGA

Amino acid sequence of the preferred QR3 anti-CD22 CAR (AD4)
(SEQ ID NO: 64)
MALPVTALLLPLALLLHAARPGGGGSCPYSNPSLCSGGGGSGGGGSQVQLQQSGPGLVKPSQTLSLTC

AISGDSVSGNRATWNWIRQSPSRGLEWLGRTYYRSAWYNDYAVSVKGRITFNPDTSKNQFSLQLNSVT

PEDTAVYYCARGESGAAADAFDIWGQGTTVTVSGGGGSGGGGSGGGGSDIQLTQSPPSLSASVGDRVT

ITCRASQSISSYLNWYQQKPGKAPKLLIYAASSLQSGVPSRFSGSGFGTDFTLTISSLQPEDFATYYC

QQSYSTPQTFGQGTKVDIKGSGGGGSCPYSNPSLCSGGGGSELPTQGTFSNVSTNVSPAKPTTTACPY

SNPSLCTTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAEAYSEIGMKGERRRGKGHD

GLYQGLSTATKDTYDALHMQALPPR

Nucleic sequence of the more preferred R2 anti-CD22 CAR
(SEQ ID NO: 44)
ATGGCTCTGCCCGTCACCGCTCTGCTGCTGCCCCTGGCCCTGCTGCTGCACGCCGCCCGGCCTCAGGT

GCAGCTGCAGCAGAGCGGCCCCGGCCTGGTGAAGCCTAGCCAGACACTGTCCCTGACCTGCGCAATCT

CCGGCGACAGCGTGTCCGGAAACAGGGCCACATGGAATTGGATCAGACAGTCTCCAAGCAGGGGCCTG

GAGTGGCTGGGAAGGACCTACTATCGGTCCGCCTGGTACAACGACTATGCCGTGTCTGTGAAGGGCCG

CATCACATTCAACCCAGATACCAGCAAGAATCAGTTTTCCCTGCAGCTGAATTCTGTGACACCCGAGG

ATACCGCCGTGTACTATTGCGCCAGAGGCGAGAGCGGAGCAGCAGCAGACGCCTTCGATATCTGGGGC

CAGGGCACCACAGTGACAGTGAGCGGAGGAGGAGGATCCGGCGGAGGAGGCTCTGGCGGCGGCGGCAG

CGACATCCAGCTGACCCAGAGCCCACCTTCCCTGTCTGCCAGCGTGGGCGATCGCGTGACAATCACCT

GTCGGGCCTCCCAGTCTATCAGCTCCTACCTGAACTGGTATCAGCAGAAGCCAGGCAAGGCCCCCAAG

CTGCTGATCTACGCAGCATCTAGCCTGCAGTCTGGAGTGCCAAGCAGATTCAGCGGATCCGGATTCGG

CACAGACTTTACACTGACCATCTCCTCTCTGCAGCCCGAGGATTTCGCCACCTACTATTGCCAGCAGT

CTTATAGCACACCTCAGACCTTTGGCCAGGGCACCAAGGTGGACATCAAGAGCGACCCCGGAAGCGGA

GGAGGAGGAAGTTGTCCCTACTCAAACCCTAGCCTGTGTAGCGGCGGCGGAGGATCTTGTCCCTATTC

TAACCCCAGCCTGTGCTCCGGAGGAGGAGGCAGCACCACAACCCCAGCACCCAGGCCCCCTACACCTG

CACCAACCATCGCCTCTCAGCCACTGAGCCTGCGGCCTGAGGCCTGCAGACCAGCCGCCGGCGGAGCA

GTGCACACACGGGGCCTGGACTTCGCCTGTGATATCTACATCTGGGCACCACTGGCTGGAACATGCGG

AGTGCTGCTGCTGTCACTGGTCATTACACTGTACTGTAAGCGAGGCCGGAAGAAACTGCTGTATATTT

TCAAACAGCCCTTTATGAGACCTGTGCAGACTACCCAGGAGGAAGACGGCTGCAGCTGTAGGTTCCCC

GAGGAAGAGGAAGGCGGGTGTGAGCTGAGGGTCAAGTTTAGCCGCTCCGCAGATGCCCCTGCTTACCA

GCAGGGCAGAATCAGCTGTATAACGAGCTGAATCTGGGACGGAGAGAGGAATACGACGTGCTGGATA

AAAGGCGCGGGAGAGACCCCGAAATGGGAGGCAAGCCACGACGGAAAAACCCCCAGGAGGGCCTGTAC

AATGAACTGCAGAAGGACAAAATGGCAGAGGCCTATAGTGAAATCGGGATGAAGGGAGAGAGAAGGCG

CGGCAAAGGGCACGATGGCCTGTACCAGGGGCTGTCTACTGCCACCAAGGACACCTATGATGCTCTGC

ATATGCAGGCACTGCCTCCAAGGTGA

Amino acid sequence of the more preferred R2 anti-CD22 CAR
(SEQ ID NO: 68)
MALPVTALLLPLALLLHAARPQVQLQQSGPGLVKPSQTLSLTCAISGDSVSGNRATWNWIRQSPSRGL

EWLGRTYYRSAWYNDYAVSVKGRITFNPDTSKNQFSLQLNSVTPEDTAVYYCARGESGAAADAFDIWG

QGTTVTVSGGGGSGGGGSGGGGSDIQLTQSPPSLSASVGDRVTITCRASQSISSYLNWYQQKPGKAPK

LLIYAASSLQSGVPSRFSGSGFGTDFTLTISSLQPEDFATYYCQQSYSTPQTFGQGTKVDIKSDPGSG

GGGSCPYSNPSLCSGGGGSCPYSNPSLCSGGGGSTTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGCSCRFP

EEEEGGCELRVKFSRSADAPAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQALPPR

TALEN-targeted CAR gene integration into the TRAC locus. The top panel represents the TRAC locus. The middle panel represents the rAAV6 containing the CAR cassette flanked by 1000 bp homology arms and the bottom panel the edited TRAC locus.

3 days after activation, T cells were transfected or not by electrotransfer of 1 μg of mRNA encoding TRAC TALEN per million cells. 1.5 h later, rAAV6 donor vector was added or not to the culture at the multiplicity of infection of $3\times10^4$ vg/cell. TCR and CAR expressions were assessed by flow cytometry on viable T cells using CD4, CD8, TCRαβ mAb, CD22 recombinant protein (full length) in combination with a live/dead cell marker. The frequency of positive cells is indicated in each panel.

The results show that the integration of the CAR at the TRAC locus is highly efficient since the frequency of CAR$^+$ TCR$^-$ cells reached more than 42% (FIG. 11).

Total cells or CAR$^+$ T cells cytolytic capacities towards antigen presenting cells (Daudi or Raji) were assessed in a flow-based cytotoxicity assay. The cell viability was measured after 4h or after an overnight coculture with CART cells at effector/target ratios set at 10:1, 5:1, 2:1 and 1:1 or 1:1, 0.5:1, 0.2:1 and 0.1:1 respectively.

Figure 12:
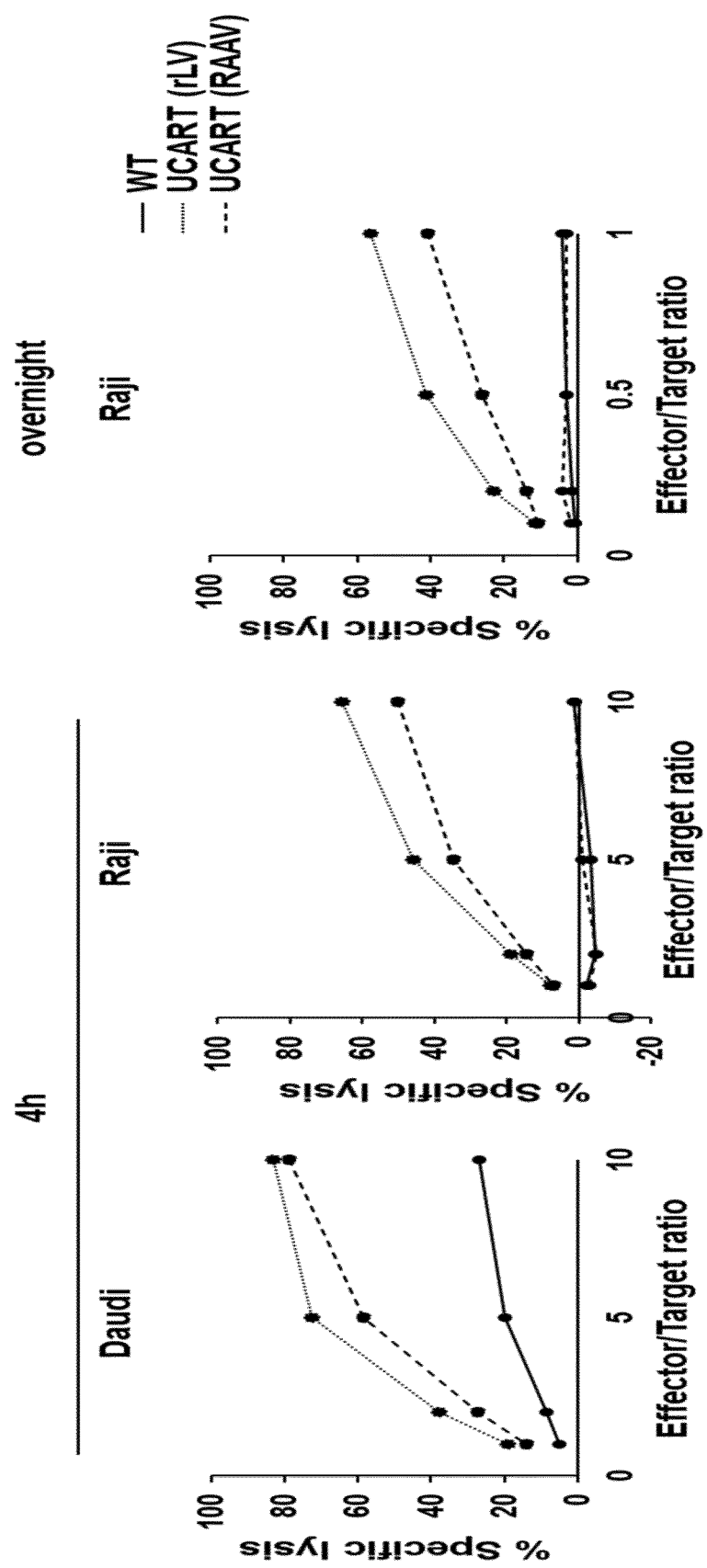
FIG. 12: Cytolytic activity of cells in which the anti-CD22 CAR of the invention was inserted into the TCR as compared to the cytolytic activity of cells prepared by previous method

The results show that the cytolytic activity of these cells was comparable to that of UCART22 obtained by other method (classical transduction) (FIG. 12).

3 days after activation, T cells were transfected or not by electrotransfer of 1 μg of each mRNA encoding TRAC and CD52 TALEN per million cells. 1.5h later, rAAV6 donor vector was added or not to the culture at the multiplicity of infection of $3\times10^4$ vg/cell. TCR, CD52 and CAR expressions were assessed by flow cytometry on viable T cells using CD4, CD8, TCRαβ mAb, CD22 recombinant protein (full length) in combination with a live/dead cell marker. The frequency of positive cells is indicated in each panel.

Figure 13:
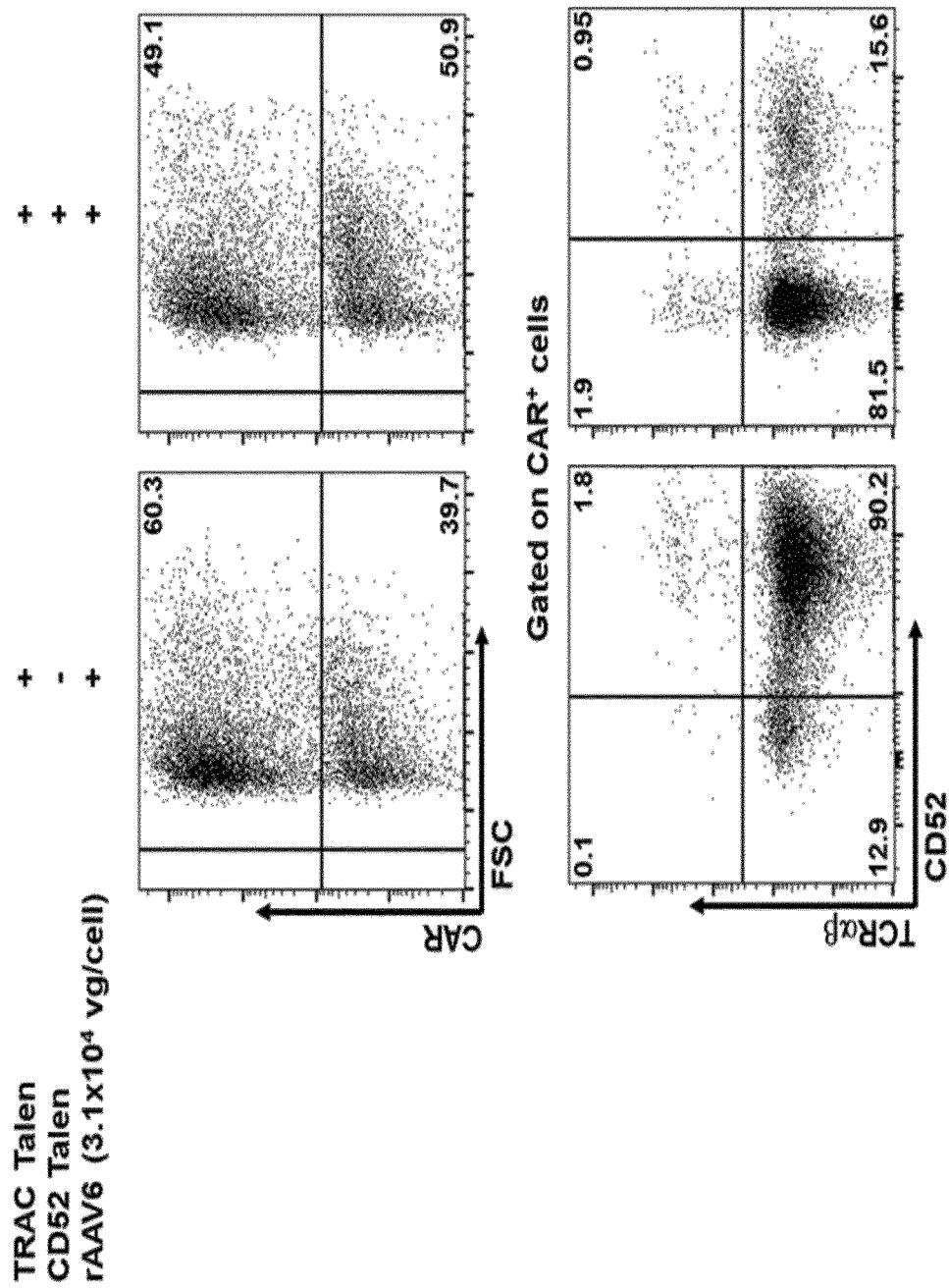
FIG. 13: Parallel inactivation of CD52 gene and inactivation by insertion of the TRAC gene in anti-CD22 CAR expressing cells.

The results (FIG. 13) show that this 2-in-1 strategy of TCR KO and CAR KI can be extended to the use of more than one TALEN. The integration of the CAR at the TRAC locus is highly efficient since the frequency of CAR$^+$ TCR$^-$ cells reached more than 47%. Importantly, no CAR expression was detected at the CD52 locus when T cells were transfected only with 1 μg of mRNA encoding CD52 TALEN. More than 80% of the population of CAR$^+$ T cells is knocked-out for both TCRαβ and CD5

Clinical Settings

The first clinical data obtained show that UCAR T cells significantly reduce relapse and refractory ALL in vivo and in vitro, with no or very mild (grade 1) GVHD and mild to no uncontrolled cytokine storm. Such treatment is to be less "toxic" than autologous CD22 CART and can be controlled in patients using rituximab and/or QBEND-10. This correlates with their capacity to induce IFNgamma.

Cells persists in human long enough to be active (over a month) and can be depleted using QBEND-10. The first data from clinical study confirmed the efficiency of UCART22 (allogeneic cells directed against CD22 cancer cells) of the invention for the treatment of relapsing/refractory forms of ALL using the object of the present invention as claimed.

In one arm UCART 22 and UCART19 were injected successively to "sieve" or tamed relapse cells and then to clear the rest of cancer cells in two or three windows of immunodepletion.

REFERENCES

Andris-Widhopf, J., Steinberger, P., Fuller, R., Rader, C., & Barbas, C. F. (2011). Generation of human scFv antibody libraries: PCR amplification and assembly of light- and heavy-chain coding sequences. Cold Spring Harbor protocols, 2011(9).Arimondo, P. B., C. J. Thomas, et al. (2006). "Exploring the cellular activity of camptothecin-triple-helix-forming oligonucleotide conjugates." Mol Cell Biol 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." Rna 13(6): 803-10.

Bierer, B. E., G. Hollander, et al. (1993). "Cyclosporin A and FK506: molecular mechanisms of immunosuppression and probes for transplantation biology." Curr Opin Immunol 5(5): 763-73.

Boch, J., H. Scholze, et al. (2009). "Breaking the code of DNA binding specificity of TAL-type III effectors." Science 326(5959): 1509-12.

Choulika, A., A. Perrin, et al. (1995). "Induction of homologous recombination in mammalian chromosomes by using the I-SceI system of Saccharomyces cerevisiae." Mol Cell Biol 15(4): 1968-73.

Christian, M., T. Cermak, et al. (2010). "Targeting DNA double-strand breaks with TAL effector nucleases." Genetics 186(2): 757-61.

Cong, L., F. A. Ran, et al. (2013). "Multiplex genome engineering using CRISPR/Cas systems." Science 339 (6121): 819-23.

Cros, E. et al. (2004)."Problems related to resistance to cytarabine in acute myeloid leukemia". Leukemia & Lymphoma. 45(6):1123-1132.

Deltcheva, E., K. Chylinski, et al. (2011). "CRISPR RNA maturation by trans-encoded small RNA and host factor RNase III." Nature 471(7340): 602-7.

Donnelly, M. and G. Elliott (2001). "Nuclear localization and shuttling of herpes simplex virus tegument protein VP13/14." J Virol 75(6): 2566-74.

Doronina, V. A., C. Wu, et al. (2008). "Site-specific release of nascent chains from ribosomes at a sense codon." Mol Cell Biol 28(13): 4227-39.

Eisenschmidt, K., T. Lanio, et al. (2005). "Developing a programmed restriction endonuclease for highly specific DNA cleavage." Nucleic Acids Res 33(22): 7039-47.

Gardin, C. et al. (2007). "Postremission treatment of elderly patients with acute myeloid leukemia in first complete remission after intensive induction chemotherapy:results of the multicenter randomized Acute Leukemia French Association (ALFA) 9803 trial". Blood. 109(12):5129-5135.

Garneau, J. E., M. E. Dupuis, et al. (2010). "The CRISPR/ Cas bacterial immune system cleaves bacteriophage and plasmid DNA." Nature 468(7320): 67-71.

Gasiunas, G., R. Barrangou, et al. (2012). "Cas9-crRNA ribonucleoprotein complex mediates specific DNA cleavage for adaptive immunity in bacteria." Proc Natl Acad Sci USA 109(39): E2579-86.

Henderson, D. J., I. Naya, et al. (1991). "Comparison of the effects of FK-506, cyclosporin A and rapamycin on IL-2 production." Immunology 73(3): 316-21.

Jena, B., G. Dotti, et al. (2010). "Redirecting T-cell specificity by introducing a tumor-specific chimeric antigen receptor." Blood 116(7): 1035-44.

Jinek, M., K. Chylinski, et al. (2012). "A programmable dual-RNA-guided DNA endonuclease in adaptive bacterial immunity." Science 337(6096): 816-21.

June, C. H. et al. (2011). "T Cells with Chimeric Antigen Receptors Have Potent Antitumor Effects and Can Establish Memory in Patients with Advanced Leukemia". Sci. Transl. Med. 3(95):ra73.

Kalish, J. M. and P. M. Glazer (2005). "Targeted genome modification via triple helix formation." Ann NY Acad Sci 1058: 151-61.

Li, T., S. Huang, et al. (2011). "TAL nucleases (TALNs): hybrid proteins composed of TAL effectors and FokI DNA-cleavage domain." Nucleic Acids Res 39(1): 359-72.

Liu, J., M. W. Albers, et al. (1992). "Inhibition of T cell signaling by immunophilin-ligand complexes correlates with loss of calcineurin phosphatase activity." Biochemistry 31(16): 3896-901.

Lonial S, Mitsiades C. S., Richardson P. G., (2011) "Treatment options for relapsed and refractory multiple myeloma". Clin Cancer Res. 17:1264-77.

Mali, P., L. Yang, et al. (2013). "RNA-guided human genome engineering via Cas9." Science 339(6121): 823-6.

Moscou, M. J. and A. J. Bogdanove (2009). "A simple cipher governs DNA recognition by TAL effectors." Science 326(5959): 1501.

Paques, F. and P. Duchateau (2007). "Meganucleases and DNA double-strand break-induced recombination: perspectives for gene therapy." Curr Gene Ther 7(1): 49-66.

Park, T. S., S. A. Rosenberg, et al. (2011). "Treating cancer with genetically engineered T cells." Trends Biotechnol 29(11): 550-7.

Peipp, M., D. Saul, et al. (2004). "Efficient eukaryotic expression of fluorescent scFv fusion proteins directed against CD antigens for FACS applications." J Immunol Methods 285(2): 265-80.

Perrin, A., M. Buckle, et al. (1993). "Asymmetrical recognition and activity of the I-SceI endonuclease on its site and on intron-exon junctions." Embo J 12(7): 2939-47.

Pingoud, A. and G. H. Silva (2007). "Precision genome surgery." Nat Biotechnol 25(7): 743-4.

Porteus, M. H. and D. Carroll (2005). "Gene targeting using zinc finger nucleases." Nat Biotechnol 23(8): 967-73.

Rouet, P., F. Smih, et al. (1994). "Introduction of double-strand breaks into the genome of mouse cells by expression of a rare-cutting endonuclease." Mol Cell Biol 14(12): 8096-106.

Sorek, R., C. M. Lawrence, et al. (2013). "CRISPR-mediated Adaptive Immune Systems in Bacteria and Archaea." Annu Rev Biochem.

Stoddard, B. L. (2005). "Homing endonuclease structure and function." Q Rev Biophys 38(1): 49-95.

Van De Donk, N. W. C. J., Kamps S., Mutis, T., Lokhorst, H. M. (2012) "Monoclonal antibody-based therapy as a new treatment strategy in multiple myeloma". Leukemia. 26:199-213.

Van Meir, E. G., Hadjipanayis, C. G., Norden, A. D., Shu, H. K., Wen, P., and Olson, J. J. (2010) "The Avenue to a Cure for Malignant Glioma" CA Cancer J Clin. 60(3): 166-193.

---

The invention claimed is:

1. A Chimeric Antigen Receptor (CAR) specific for CD22 (Anti-CD22 CAR) comprising:
   i) at least one extracellular domain comprising an antigen binding domain specific for CD22, and a hinge domain comprising an FcRIIIα, a CD8α, an IgG1, an IgG4, or a PD1 hinge;
   ii) a transmembrane domain;
   iii) an intracellular signaling domain comprising a CD3zeta signaling domain comprising an amino acid sequence having at least 95% identity with SEQ ID NO: 9; and
   iv) at least one monoclonal antibody (mAb)-specific epitope(s) selected from the following sequences: CPYSNPSLC (SEQ ID NO: 91), NSELLSLINDMPITNDQKKLMSNN (SEQ ID NO: 114), CQFDLSTRRLKC (SEQ ID NO: 115), CQYNLSSRALKC (SEQ ID NO: 116), CVWQRWQKSYVC (SEQ ID NO: 117), SFVLNWYRMSPSNQTDKLAAFPEDR (SEQ ID NO: 119), SGTYLCGAISLAPKAQIKE (SEQ ID NO: 120), ELPTQGTFSNVSTNVSPAKPTTTA (SEQ ID NO: 92), and GQNDTSQTSSPS (SEQ ID NO: 121);
   wherein said antigen binding domain specific for CD22 comprises a single chain variable fragment (scFv) specific for CD22, said scFv comprising a heavy chain variable (VH) region and a light chain variable (VL) region comprising one of the following combinations of sequences, respectively:

SEQ ID NO: 71 and SEQ ID NO: 72; SEQ ID NO: 73 and SEQ ID NO: 74; SEQ ID NO: 75 and SEQ ID NO: 76; SEQ ID NO: 77 and SEQ ID NO: 78; SEQ ID NO: 79 and SEQ ID NO: 80; SEQ ID NO: 81 and SEQ ID NO: 82; SEQ ID NO: 83 and SEQ ID NO: 84; SEQ ID NO: 85 and SEQ ID NO: 86; SEQ ID NO: 87 and SEQ ID NO: 88; or SEQ ID NO: 89 and SEQ ID NO: 90.

2. The Anti-CD22 CAR of claim 1, wherein the hinge domain comprises a CD8α hinge.

3. The Anti-CD22 CAR of claim 1, wherein said intracellular signaling domain further comprises a 4-1BB signaling domain.

4. The Anti-CD22 CAR of claim 1, wherein the at least one monoclonal antibody (mAb)-specific epitope(s) of (iv) comprises:
   (i) two mAb-specific epitopes, each having an amino acid sequence of CPYSNPSLC (SEQ ID NO: 91), or
   (ii) three mAb-specific epitopes, each having an amino acid sequence of CPYSNPSLC (SEQ ID NO: 91), and one mAb-specific epitope having an amino acid sequence of ELPTQGTFSNVSTNVSPAKPTTTA (SEQ ID NO: 92).

5. The Anti-CD22 CAR of claim 1, wherein the Anti-CD22 CAR is a single-chain CAR or a multi-chain CAR, further comprising:
   an additional scFv specific for one of CD19, CD20, CD30, a major histocompatibility complex (MHC) molecule, an Immunoglobulin (Ig), CD3, CDS, CD34, or CD79.

6. A polynucleotide encoding the Anti-CD22 CAR of claim 1.

7. An immune cell comprising the Anti-CD22 CAR of claim 1.

8. The immune cell of claim 7, comprising an inactivation of a TRAC (T Cell Receptor Alpha Constant) gene (UCART22).

9. The immune cell of claim 7, wherein the immune cell is a human immune cell, a human immune T cell, or an engineered human immune T cell.

10. The immune cell of claim 7, further comprising at least one additional alteration of a gene selected from the group consisting of a β2 Microglobulin (B2M), an Aryl hydrocarbon receptor (AHR), a Transforming growth factor β receptor (TGF receptor), an Interleukin 10 receptor (IL-10 R), a Programmed cell death protein 1, and a combination thereof.

11. The immune cell of claim 8, wherein the Anti-CD22 CAR is a multi-chain CAR comprising an additional scFv specific for CD19.

12. A population of cells comprising the immune cell of claim 8.

13. A pharmaceutical composition comprising the population of cells of claim 12, and a pharmaceutically acceptable excipient.

14. A method for treating a subject having received the pharmaceutical composition of claim 13, the method comprising administering at least one monoclonal antibody (mAb) to the subject at a dose allowing binding of said UCART22 with the at least one mAb.

15. The method of claim 14, wherein the at least one mAb is QBEND-10 or rituximab.

16. A method for treating a subject having a hematological cancer or a relapsing refractory hematological cancer selected from lymphoma, Hodgkin lymphoma, non-Hodgkin lymphoma, leukemia, multiple myeloma, B-chronic lymphocytic leukemia, hairy cell leukemia, acute lymphocytic leukemia (ALL), Burkitt's lymphoma, acute lymphocytic cancer, and acute myeloid leukemia, the method comprising administering the pharmaceutical composition of claim 13.

17. The method of claim 16, wherein the method further comprises treating relapsed or refractory CD22-expressing B-cell ALL or relapsed or refractory CD19-expressing B-cell ALL.

18. A kit comprising the immune cell of claim 8 and an immune cell comprising an Anti-CD19 CAR and comprising an inactivation of a TRAC (T Cell Receptor Alpha Constant) gene (UCART19) for successive or concomitant administration to a subject in need thereof.

19. A method comprising administering the UCART19 and the UCART22 of claim 18 wherein:
   (i) the UCART19 is administered first at least once, twice or several times, and then the UCART22 is administered alone or with the UCART19 at least once, twice or several times; or
   (ii) the UCART22 is administered first at least once, twice or several times, and then the UCART19 is administered alone or with the UCART22 at least once, twice or several times.

20. The method of claim 19, further comprising a lymphodepleting treatment, administered before administration of the UCART19 or the UCART22.

* * * * *

UNITED STATES PATENT AND TRADEMARK OFFICE
CERTIFICATE OF CORRECTION

PATENT NO. : 11,690,873 B2
APPLICATION NO. : 16/498276
DATED : July 4, 2023
INVENTOR(S) : Cecile Schiffer-Mannioui, Philippe Duchateau and Anne-Sophie Gautron Page 1 of 1

It is certified that error appears in the above-identified patent and that said Letters Patent is hereby corrected as shown below:

In the Claims

Claim 5, Column 357, Line 29 reads:
"CDS"
Whereas it should read:
--CD5--

Signed and Sealed this
Twenty-first Day of November, 2023

Katherine Kelly Vidal
*Director of the United States Patent and Trademark Office*